United States Patent
Lian et al.

(10) Patent No.: US 12,356,990 B2
(45) Date of Patent: Jul. 15, 2025

(54) PYRIDAZINOL COMPOUND, DERIVATIVE THEREOF, PREPARATION METHOD THEREFOR, HERBICIDAL COMPOSITION AND USE THEREOF

(71) Applicant: QINGDAO KINGAGROOT CHEMICAL COMPOUND CO., LTD., Shandong (CN)

(72) Inventors: Lei Lian, Shandong (CN); Rongbao Hua, Shandong (CN); De Zhao, Shandong (CN); Xuegang Peng, Shandong (CN); Qi Cui, Shandong (CN)

(73) Assignee: QINGDAO KINGAGROOT CHEMICAL COMPOUND CO., LTD., Shandong (CN)

( * ) Notice: Subject to any disclaimer, the term of this patent is extended or adjusted under 35 U.S.C. 154(b) by 691 days.

(21) Appl. No.: 17/634,486

(22) PCT Filed: Aug. 15, 2020

(86) PCT No.: PCT/CN2020/109408
§ 371 (c)(1),
(2) Date: Feb. 10, 2022

(87) PCT Pub. No.: WO2021/032033
PCT Pub. Date: Feb. 25, 2021

(65) Prior Publication Data
US 2022/0354120 A1    Nov. 10, 2022

(30) Foreign Application Priority Data

Aug. 16, 2019 (CN) .......................... 201910759709.2

(51) Int. Cl.
| | | |
|---|---|---|
| A01N 43/58 | (2006.01) | |
| A01N 25/32 | (2006.01) | |
| A01N 43/56 | (2006.01) | |

(52) U.S. Cl.
CPC ............. *A01N 43/58* (2013.01); *A01N 25/32* (2013.01); *A01N 43/56* (2013.01)

(58) Field of Classification Search
CPC ......... A01N 43/56; A01N 43/58; A01N 25/32
See application file for complete search history.

(56) References Cited

U.S. PATENT DOCUMENTS

| | | | |
|---|---|---|---|
| 5,362,708 A | 11/1994 | Kores et al. | |
| 2021/0032229 A1* | 2/2021 | Lian | ........................ A01N 43/70 |
| 2022/0312770 A1* | 10/2022 | Lian | ..................... C07D 401/10 |

FOREIGN PATENT DOCUMENTS

| | | |
|---|---|---|
| CN | 106316962 A | 1/2017 |
| CN | 110878081 A | 3/2020 |
| WO | WO 01/16129 A1 | 3/2001 |
| WO | WO 2019/148850 A1 | 8/2019 |
| WO | WO 2019/148851 A1 | 8/2019 |
| WO | WO 2019149260 A1 | 8/2019 |

OTHER PUBLICATIONS

China National Intellectual Property Administration, First Office Action in counterpart Chinese Patent Application No. 202010821759.1, mailed on Dec. 10, 2021.
World Intellectual Property Organization, International Search Report and Written Opinion in counterpart International Patent Application No. PCT/CN2020/109408, mailed on Oct. 19, 2020.

* cited by examiner

*Primary Examiner* — Johann R Richter
*Assistant Examiner* — Danielle Johnson
(74) *Attorney, Agent, or Firm* — Leydig, Voit & Mayer, Ltd.

(57) ABSTRACT

The present invention belongs to the technical field of pesticides, and in particular relates to a pyridazinol compound, a derivative thereof, a preparation method therefor, a herbicidal composition and the use thereof. The pyridazinol compound is as represented by general formula I,

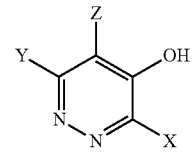

wherein X represents

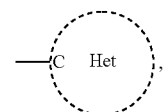

and the ring is an unsubstituted or substituted aryl or unsubstituted or substituted heterocyclyl containing a carbon atom at the 1-position; Y represents haloalkyl; and Z represents halogen, cyano, hydroxy, etc. The derivative refers to an agriculturally acceptable derivative of the hydroxyl group at the 4-position of the pyridazine ring in the general formula I, including a salt, an ester, an oxime, a hydroxylamine and an ether derivative, etc. The compound, the derivative thereof and the composition thereof have good herbicidal activity and crop safety.

16 Claims, No Drawings

PYRIDAZINOL COMPOUND, DERIVATIVE THEREOF, PREPARATION METHOD THEREFOR, HERBICIDAL COMPOSITION AND USE THEREOF

CROSS-REFERENCE TO RELATED APPLICATIONS

This patent application is the U.S. National Stage of International Patent Application No. PCT/CN2020/109408, filed Aug. 15, 2020, which claims the benefit of Chinese Patent Application No. 201910759709.2, filed Aug. 16, 2019, which are each incorporated by reference.

TECHNICAL FIELD

The present invention belongs to the technical field of pesticides, and in particular relates to a pyridazinol compound, a derivative thereof, a preparation method therefor, a herbicidal composition and the use thereof.

BACKGROUND ART

Weed control is a vital part in achieving high-efficiency agriculture. At present, various herbicides are available in the market, such as pyridazine photosystem II inhibitor herbicides: pyridate

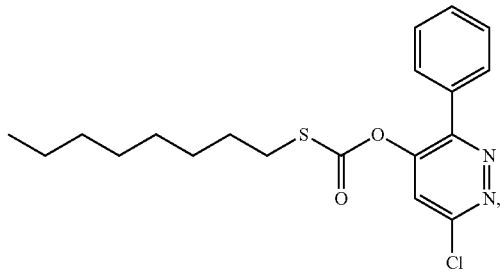 [SMILES: CCCCCCCCSC(=O)Oc1cc(Cl)nnc1-c1ccccc1]

pyridazinol

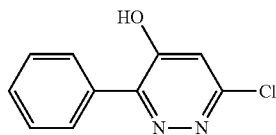 [SMILES: Oc1cc(Cl)nnc1-c1ccccc1]

and the like, which inhibit photosynthesis by blocking electron transport and conversion of light energy. Since the continuous expansion of the market, the resistance of weeds, the service life of herbicides and the economical efficiency of herbicides as well as the increasing attention on environmental protection, it is in great demand of constantly research of scientists for developing new herbicides with high-efficiency, safety, economical efficiency and different mechanism of action.

CONTENTS OF THE INVENTION

In order to solve the above problems in the prior art, the present invention provides a pyridazinol compound, a derivative thereof, a preparation method therefor, a herbicidal composition and the use thereof. The compound, the derivative thereof and the composition thereof have good herbicidal activity and crop safety.

The technical solution adopted by the present invention is as follows:

A pyridazinol compound of Formula I or a derivative thereof:

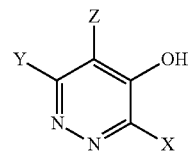

wherein, X represents

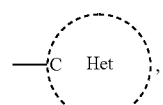

and the ring is an unsubstituted or substituted aryl or unsubstituted or substituted heterocyclyl containing a carbon atom at the 1-position;

Y represents haloalkyl;

Z represents halogen, cyano, hydroxyl; alkyl, alkenyl, alkynyl, cycloalkyl, alkoxy, alkylsulfanyl, alkylsulfoxide or alkylsulfonyl with or without halogen; amino which is unsubstituted or substituted by one or two groups selected from alkyl, alkylcarbonyl, alkylaminocarbonyl, dialkylaminocarbonyl and phenyl; or aryl, heterocyclyl, aryloxy or heterocyclyloxy, each of which is unsubstituted or substituted;

the "substituted aryl or substituted heterocyclyl" and "aryl, heterocyclyl, aryloxy or heterocyclyloxy, each of which is substituted" refer to being respectively substituted by at least one of the following groups: halogen, nitro, cyano, thiocyano, cyanoalkyl, sulfhydryl, hydroxy, hydroxyalkyl, carboxyl, formyl, azide, trialkylsilyl, dialkylphosphono; heterocyclyl, heterocyclylalkyl, aryl or arylalkyl, each of which is unsubstituted or substituted; alkyl, alkenyl, alkynyl, cycloalkyl, cycloalkenyl, cycloalkylalkyl, cycloalkenylalkyl, alkyl-substituted cycloalkyl, OR", SR", -alkyl-OR", —O-alkyl-OR", -alkyl-SR", COR", -alkyl-COR", —O-alkyl-COR", COOR", -alkyl-COOR", —O-alkyl-COOR", COSR", SOR", $SO_2R"$, —O—$SO_2R"$, -alkyl-$SO_2R"$, OCOR", -alkyl-OCOR" or SCOR" with or without halogen; amino, aminocarbonyl, aminocarbonylalkyl or aminosulfonyl, each of which is unsubstituted or substituted by one or two groups selected from R", COR", COOR", $SO_2R"$, -alkyl-$SO_2R"$ and OR", wherein each of the group contains or does not contain a halogen; or any two adjacent carbon atoms in the ring are connected with —$CH_2CH_2CH_2$—, —$OCH_2CH_2$—, —$OCH_2O$—, —$OCH_2CH_2O$— or —CH=CH—CH=CH— group to form a fused ring;

R" each independently represents alkyl, alkenyl, alkynyl, cycloalkyl, cycloalkylalkyl, cycloalkenyl, cycloalkenylalkyl; or heterocyclyl, heterocyclylalkyl, aryl or arylalkyl, each of which is unsubstituted or substituted.

In another embodiment, X represents

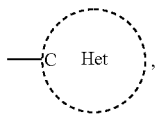

and the ring is an aryl or heterocyclyl containing a carbon atom at the 1-position;

Y represents haloalkyl;

Z represents halogen, cyano, hydroxy, formyl, aryl, heterocyclyl; alkyl, alkenyl, alkynyl, cycloalkyl, OR", SR", SOR" or SO$_2$R" with or without halogen; or amino which is unsubstituted or substituted by one or two groups selected from R", COR", CON(R")$_2$, COOR", SO$_2$R", -alkyl-SO$_2$R" and OR", wherein each of the group contains or does not contain a halogen;

the "aryl", "heterocyclyl", "aryloxy" and "heterocyclyloxy" are respectively unsubstituted or substituted by at least one of the following groups: halogen, nitro, cyano, thiocyano, cyanoalkyl, sulfhydryl, hydroxy, hydroxyalkyl, carboxyl, carboxyalkyloxy, formyl, azide, trialkylsilyl, dialkylphosphono; heterocyclyl, heterocyclylalkyl, aryl or arylalkyl, each of which is unsubstituted or substituted; alkyl, alkenyl, alkynyl, cycloalkyl, cycloalkenyl, cycloalkylalkyl, cycloalkenylalkyl, alkyl-substituted cycloalkyl, OR", SR", -alkyl-OR", —O-alkyl-OR", -alkyl-SR", COR", -alkyl-COR", —O-alkyl-COR", COOR", -alkyl-COOR", —O-alkyl-COOR", COSR", SOR", SO$_2$R", —O—SO$_2$R", -alkyl-SO$_2$R", OCOR", -alkyl-OCOR" or SCOR" with or without halogen; amino, aminocarbonyl, aminocarbonylalkyl or aminosulfonyl, each of which is unsubstituted or substituted by one or two groups selected from R", COR", CON(R")$_2$, COOR", SO$_2$R", -alkyl-SO$_2$R" and OR", wherein each of the group contains or does not contain a halogen; or any two adjacent carbon atoms in the ring are connected with —CH$_2$CH$_2$CH$_2$—, —OCH$_2$CH$_2$—, —OCH$_2$O—, —OCH$_2$CH$_2$O— or —CH=CH—CH=CH— group to form a fused ring, wherein each of the group contains or does not contain a halogen;

R" each independently represents alkyl, alkenyl, alkynyl, cycloalkyl, cycloalkylalkyl, cycloalkenyl, cycloalkenylalkyl; or heterocyclyl, heterocyclylalkyl, aryl or arylalkyl, each of which is unsubstituted or substituted.

Preferably, X represents

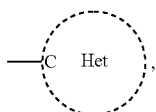

and the ring is an unsubstituted or substituted aryl or unsubstituted or substituted heterocyclyl containing a carbon atom at the 1-position;

Y represents halo C1-C8 alkyl;

Z represents halogen, cyano, hydroxyl; C1-C8 alkyl, C2-C8 alkenyl, C2-C8 alkynyl, C3-C8 cycloalkyl, C1-C8 alkoxy, C1-C8 alkylsulfanyl, C1-C8 alkylsulfoxide or C1-C8 alkylsulfonyl with or without halogen; amino which is unsubstituted or substituted by one or two groups selected from C1-C8 alkyl, C1-C8 alkylcarbonyl, C1-C8 alkylaminocarbonyl, di-C1-C8 alkylaminocarbonyl and phenyl; or aryl, heterocyclyl, aryloxy or heterocyclyloxy, each of which is unsubstituted or substituted;

the "substituted aryl or substituted heterocyclyl" and "aryl, heterocyclyl, aryloxy or heterocyclyloxy, each of which is substituted" refer to being respectively substituted by at least one of the following groups: halogen, nitro, cyano, thiocyano, cyano C1-C8 alkyl, sulfhydryl, hydroxy, hydroxy C1-C8 alkyl, carboxyl, formyl, azide, tri-C1-C8 alkylsilyl, di-C1-C8 alkylphosphono; heterocyclyl, heterocyclyl C1-C8 alkyl, aryl or aryl C1-C8 alkyl, each of which is unsubstituted or substituted; C1-C8 alkyl, C2-C8 alkenyl, C2-C8 alkynyl, C3-C8 cycloalkyl, C3-C8 cycloalkenyl, C3-C8 cycloalkyl C1-C8 alkyl, C3-C8 cycloalkenyl C1-C8 alkyl, C1-C8 alkyl-substituted C3-C8 cycloalkyl, OR", SR", —(C1-C8)alkyl-OR", —O—(C1-C8)alkyl-OR", —(C1-C8)alkyl-SR", COR", —(C1-C8)alkyl-COR", —O—(C1-C8)alkyl-COR", COOR", —(C1-C8)alkyl-COOR", —O—(C1-C8)alkyl-COOR", COSR", SOR", SO$_2$R", —O—SO$_2$R", —(C1-C8)alkyl-SO$_2$R", OCOR", —(C1-C8)alkyl-OCOR" or SCOR" with or without halogen; amino, aminocarbonyl, aminocarbonyl C1-C8 alkyl or aminosulfonyl, each of which is unsubstituted or substituted by one or two groups selected from R", COR", COOR", SO$_2$R", —(C1-C8)alkyl-SO$_2$R" and OR", wherein each of the group contains or does not contain a halogen; or any two adjacent carbon atoms in the ring are connected with —CH$_2$CH$_2$CH$_2$—, —OCH$_2$CH$_2$—, —OCH$_2$O—, —OCH$_2$CH$_2$O— or —CH=CH—CH=CH— group to form a fused ring;

R" each independently represents C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl; or heterocyclyl, heterocyclyl C1-C8 alkyl, aryl or aryl C1-C8 alkyl, each of which is unsubstituted or substituted.

In another embodiment, X represents

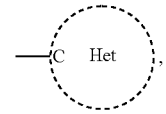

and the ring is an aryl or heterocyclyl containing a carbon atom at the 1-position;

Y represents halo C1-C8 alkyl;

Z represents halogen, cyano, hydroxy, formyl, aryl, heterocyclyl; C1-C8 alkyl, C2-C8 alkenyl, C2-C8 alkynyl, C3-C8 cycloalkyl, OR", SR", SOR" or SO$_2$R" with or without halogen; or amino which is unsubstituted or substituted by one or two groups selected from R", COR", CON(R")$_2$, COOR", SO$_2$R", —(C1-C8)alkyl-SO$_2$R" and OR", wherein each of the group contains or does not contain a halogen;

the "aryl", "heterocyclyl", "aryloxy" and "heterocyclyloxy" are respectively unsubstituted or substituted by at least one of the following groups: halogen, nitro, cyano, thiocyano, cyano C1-C8 alkyl, sulfhydryl, hydroxy, hydroxy C1-C8 alkyl, carboxyl, carboxyalkyloxy, formyl, azide, tri-C1-C8 alkylsilyl, di-C1-C8 alkylphosphono; heterocyclyl, heterocyclyl C1-C8 alkyl, aryl or aryl C1-C8 alkyl, each of which is unsubstituted or substituted; C1-C8 alkyl, C2-C8 alkenyl, C2-C8 alkynyl, C3-C8 cycloalkyl, C3-C8 cycloalkenyl, C3-C8 cycloalkyl C1-C8 alkyl, C3-C8 cycloalkenyl C1-C8 alkyl, C1-C8 alkyl-substituted C3-C8 cycloalkyl, OR", SR", —(C1-C8)alkyl-OR", —O—(C1-C8)alkyl-OR", —(C1-C8)alkyl-SR", COR", —(C1-C8)alkyl-COR", —O—(C1-C8)alkyl-COR", COOR", —(C1-C8)alkyl-COOR", —O—(C1-C8)alkyl-COOR", COSR", SOR", SO$_2$R", —O—SO$_2$R", —(C1-C8)alkyl-SO$_2$R", OCOR", —(C1-C8)alkyl-OCOR" or SCOR" with or without halogen; amino, aminocarbonyl, aminocarbonyl C1-C8 alkyl or aminosulfonyl, each of which is unsubstituted or substituted by one or two groups selected from R", COR", CON(R")$_2$, COOR", SO$_2$R", —(C1-C8)alkyl-SO$_2$R" and OR", wherein each of the group contains or does not contain a halogen; or any two adjacent carbon atoms in the ring are connected with —CH$_2$CH$_2$CH$_2$—, —OCH$_2$CH$_2$—, —OCH$_2$O—, —OCH$_2$CH$_2$O— or —CH=CH—CH=CH— group to form a fused ring, wherein each of the group contains or does not contain a halogen;

R" each independently represents C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl; or heterocyclyl, heterocyclyl C1-C8 alkyl, aryl or aryl C1-C8 alkyl, each of which is unsubstituted or substituted by at least one group selected from halogen, cyano, C1-C8 alkyl, halo C1-C8 alkyl, C2-C8 alkenyl and C1-C8 alkoxy.

More preferably, X represents

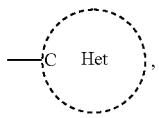

and the ring is an unsubstituted or substituted aryl or unsubstituted or substituted heterocyclyl containing a carbon atom at the 1-position;

Y represents halo C1-C6 alkyl;

Z represents halogen, cyano, hydroxyl; C1-C6 alkyl, C2-C6 alkenyl, C2-C6 alkynyl, C3-C6 cycloalkyl, C1-C6 alkoxy, C1-C6 alkylsulfanyl, C1-C6 alkylsulfoxide or C1-C6 alkylsulfonyl with or without halogen; amino which is unsubstituted or substituted by one or two groups selected from C1-C6 alkyl, C1-C6 alkylcarbonyl, C1-C6 alkylaminocarbonyl, di-C1-C6 alkylaminocarbonyl and phenyl; or aryl, heterocyclyl, aryloxy or heterocyclyloxy, each of which is unsubstituted or substituted;

the "substituted aryl or substituted heterocyclyl" and "aryl, heterocyclyl, aryloxy or heterocyclyloxy, each of which is substituted" refer to being respectively substituted by at least one (1, 2, 3, 4 or 5) of the following groups: halogen, nitro, cyano, thiocyano, cyano C1-C6 alkyl, sulfhydryl, hydroxy, hydroxy C1-C6 alkyl, carboxyl, formyl, azide, tri-C1-C6 alkylsilyl, di-C1-C6 alkylphosphono; heterocyclyl, heterocyclyl C1-C6 alkyl, aryl or aryl C1-C6 alkyl, each of which is unsubstituted or substituted; C1-C6 alkyl, C2-C6 alkenyl, C2-C6 alkynyl, C3-C6 cycloalkyl, C3-C6 cycloalkenyl, C3-C6 cycloalkyl C1-C6 alkyl, C3-C6 cycloalkenyl C1-C6 alkyl, C1-C6 alkyl-substituted C3-C6 cycloalkyl, OR", SR", —(C1-C6)alkyl-OR", —O—(C1-C6)alkyl-OR", —(C1-C6)alkyl-SR", COR", —(C1-C6)alkyl-COR", —O—(C1-C6)alkyl-COR", COOR", —(C1-C6)alkyl-COOR", —O—(C1-C6)alkyl-COOR", COSR", SOR", SO$_2$R", —O—SO$_2$R", —(C1-C6)alkyl-SO$_2$R", OCOR", —(C1-C6)alkyl-OCOR" or SCOR" with or without halogen; amino, aminocarbonyl, aminocarbonyl C1-C6 alkyl or aminosulfonyl, each of which is unsubstituted or substituted by one or two groups selected from R", COR", COOR", SO$_2$R", —(C1-C6)alkyl-SO$_2$R" or OR", wherein each of the group contains or does not contain a halogen; or any two adjacent carbon atoms in the ring are connected with —CH$_2$CH$_2$CH$_2$—, —OCH$_2$CH$_2$—, —OCH$_2$O—, —OCH$_2$CH$_2$O— or —CH=CH—CH=CH— group to form a fused ring;

R" each independently represents C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl; or heterocyclyl, heterocyclyl C1-C6 alkyl, aryl or aryl C1-C6 alkyl, each of which is unsubstituted or substituted.

In another embodiment, X represents

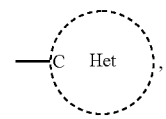

and the ring is an aryl or heterocyclyl containing a carbon atom at the 1-position;

Y represents halo C1-C6 alkyl;

Z represents halogen, cyano, hydroxy, formyl, aryl, heterocyclyl; C1-C6 alkyl, C2-C6 alkenyl, C2-C6 alkynyl, C3-C6 cycloalkyl, OR", SR", SOR" or SO$_2$R" with or without halogen; or amino which is unsubstituted or substituted by one or two groups selected from R", COR", CON(R")$_2$, COOR", SO$_2$R", —(C1-C6)alkyl-SO$_2$R" and OR", wherein each of the group contains or does not contain a halogen;

the "aryl", "heterocyclyl", "aryloxy" and "heterocyclyloxy" are respectively unsubstituted or substituted by 1-5 (1, 2, 3, 4 or 5) of the following groups: halogen, nitro, cyano, thiocyano, cyano C1-C6 alkyl, sulfhydryl, hydroxy, hydroxy C1-C6 alkyl, carboxyl, carboxyalkyloxy, formyl, azide, tri-C1-C6 alkylsilyl, di-C1-C6 alkylphosphono; heterocyclyl, heterocyclyl C1-C6 alkyl, aryl or aryl C1-C6 alkyl, each of which is unsubstituted or substituted; C1-C6 alkyl, C2-C6 alkenyl, C2-C6 alkynyl, C3-C6 cycloalkyl, C3-C6 cycloalkenyl, C3-C6 cycloalkyl C1-C6 alkyl, C3-C6 cycloalkenyl C1-C6 alkyl, C1-C6 alkyl-substituted C3-C6 cycloalkyl, OR", SR", —(C1-C6)alkyl-OR", —O—(C1-C6)alkyl-OR", —(C1-C6)alkyl-SR", COR", —(C1-C6)alkyl-COR", —O—(C1-C6)alkyl-COR", COOR", —(C1-C6)alkyl-COOR", —O—(C1-C6)alkyl-COOR", COSR", SOR", SO$_2$R", —O—SO$_2$R", —(C1-C6)alkyl-SO$_2$R", OCOR", —(C1-C6)alkyl-OCOR" or SCOR" with or without halogen; amino, aminocarbonyl, aminocarbonyl C1-C6 alkyl or aminosulfonyl, each of which is unsubstituted or substituted by one or two groups selected from R", COR", CON(R")$_2$, COOR", SO$_2$R", —(C1-C6)alkyl-SO$_2$R" and OR", wherein each of the group contains or does not contain a halogen; or any two adjacent carbon atoms in the ring are connected with —CH$_2$CH$_2$CH$_2$—, —OCH$_2$CH$_2$—, —OCH$_2$O—, —OCH₂CH₂O— or —CH=CH—CH=CH— group to form a fused ring, wherein each of the group contains or does not contain a halogen;

R" each independently represents C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl; or heterocyclyl, heterocyclyl C1-C6 alkyl, aryl or aryl C1-C6 alkyl, each of which is unsubstituted or substituted by 1~5 (1, 2, 3, 4 or 5) groups selected from halogen, cyano, C1-C6 alkyl, halo C1-C6 alkyl, C2-C6 alkenyl and C1-C6 alkoxy.

More preferably, X represents

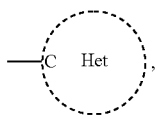

the ring is phenyl,

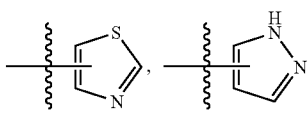

or

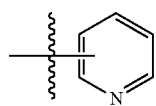

containing a carbon atom at the 1-position, which is respectively unsubstituted or substituted;

Y represents trifluoromethyl or pentafluoroethyl;

Z represents C1-C6 alkyl, C2-C6 alkenyl, C3-C6 cycloalkyl, C1-C6 alkoxy; or amino which is unsubstituted or substituted by one or two groups selected from C1-C6 alkyl;

the "phenyl,

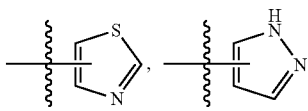

or

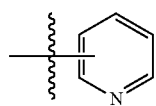

which is respectively substituted" refers to being respectively substituted by 1-2 groups selected from fluorine, chlorine, bromine, cyano, C1-C6 alkyl and halo C1-C6 alkyl.

In another embodiment, X represents

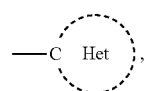

the ring is phenyl,

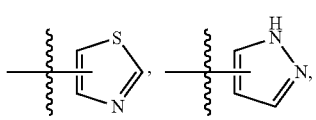

or

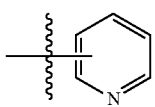

containing a carbon atom at the 1-position, which is respectively unsubstituted or substituted by 1~3 (1, 2 or 3) groups selected from fluorine, chlorine, bromine, cyano, C1-C6 alkyl, C2-C6 alkenyl, halo C1-C6 alkyl, or any two adjacent carbon atoms in the ring are connected with —OCH₂O— group to form a fused ring, wherein the —OCH₂O— group contains or does not contain a halogen;

Y represents trifluoromethyl or pentafluoroethyl;

Z represents halogen, cyano, hydroxy, formyl, aryl, heterocyclyl, C1-C6 alkyl, halo C1-C6 alkyl, C2-C6 alkenyl, C2-C6 alkynyl, C3-C6 cycloalkyl, C1-C6 alkoxy, halo C1-C6 alkoxy, aryloxy, heterocyclyloxy, C1-C6 alkylsulfanyl, C1-C6 alkylsulfoxide, C1-C6 alkylsulfonyl; or amino which is unsubstituted or substituted by one or two groups selected from C1-C6 alkyl, C1-C6 alkylcarbonyl, C1-C6 alkylaminocarbonyl, C1-C6 alkoxycarbonyl, C3-C6 cycloalkyloxycarbonyl, C1-C6 alkylsulfonyl, aryl and aryl C1-C2 alkyl;

the "aryl" is phenyl which is unsubstituted or substituted by 1-3 (1, 2 or 3) groups selected from fluorine, cyano and C1-C6 alkoxy; the "heterocyclyl" is

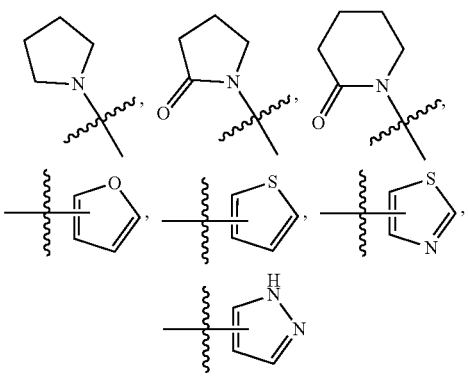

or

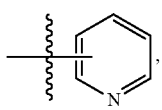

each of which is unsubstituted or substituted by 1-3 (1, 2 or 3) groups selected from C1-C6 alkyl.

In the definition of the compound represented by the above Formula and all of the following structural formulas, the technical terms used, whether used alone or used in compound word, represent the following substituents: an alkyl having more than two carbon atoms may be linear or branched. For example, the alkyl in the compound word "-alkyl-OR''" may be —CH$_2$—, —CH$_2$CH$_2$—, —CH(CH$_3$)—, —C(CH$_3$)$_2$—, and the like. The alkyl is, for example, C$_1$ alkyl: methyl; C$_2$ alkyl: ethyl; C$_3$ alkyl: propyl such as n-propyl or isopropyl; C$_4$ alkyl: butyl such as n-butyl, isobutyl, tert-butyl or 2-butyl; C$_5$ alkyl: pentyl such as n-pentyl; C$_6$ alkyl: hexyl such as n-hexyl, isohexyl and 1,3-dimethylbutyl. Similarly, the alkenyl is, for example, allyl, 1-methylprop-2-en-1-yl, 2-methylprop-2-en-1-yl, but-2-en-1-yl, butyl-3-en-1-yl, 1-methylbut-3-en-1-yl and 1-methylbut-2-en-1-yl. The alkynyl is, for example, propargyl, but-2-yn-1-yl, but-3-yn-1-yl, 1-methylbut-3-yn-1-yl. At least one (for example, 1, 2 or 3) multiple bonds may be placed at any position of each unsaturated group. The cycloalkyl is a carbocyclic saturated ring system having, for example, three to six carbon atoms, such as cyclopropyl, cyclobutyl, cyclopentyl or cyclohexyl. Similarly, the cycloalkenyl is monocycloalkenyl having, for example, three to six carbon ring members, such as cyclopropenyl, cyclobutenyl, cyclopentenyl, and cyclohexenyl, wherein double bond can be at any position. Halogen is fluorine, chlorine, bromine or iodine.

Unless otherwise specified, the "aryl" of the present invention includes, for example, phenyl, naphthyl,

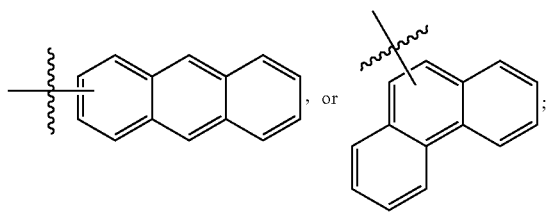

the "heterocyclyl" not only includes,

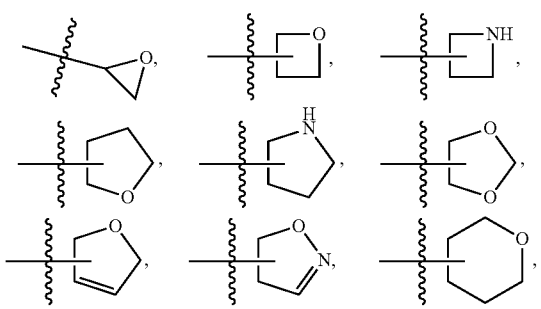

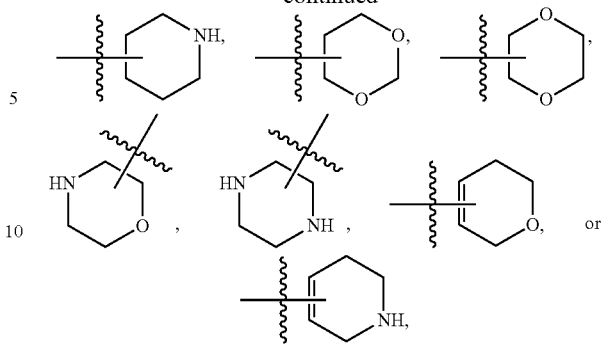

which has for example 0, 1 or 2 oxo groups; but also includes "heteroaryl" (also called "aromatic heterocycly"), which is an aromatic cyclic group having, for example, 3 to 6 (for example, 3, 4, 5 or 6) ring atoms and which may also be fused with a benzo ring, and 1 to 4 (for example, 1, 2, 3 or 4) heteroatoms of the ring are selected from the group consisting of oxygen, nitrogen and sulfur. For example,

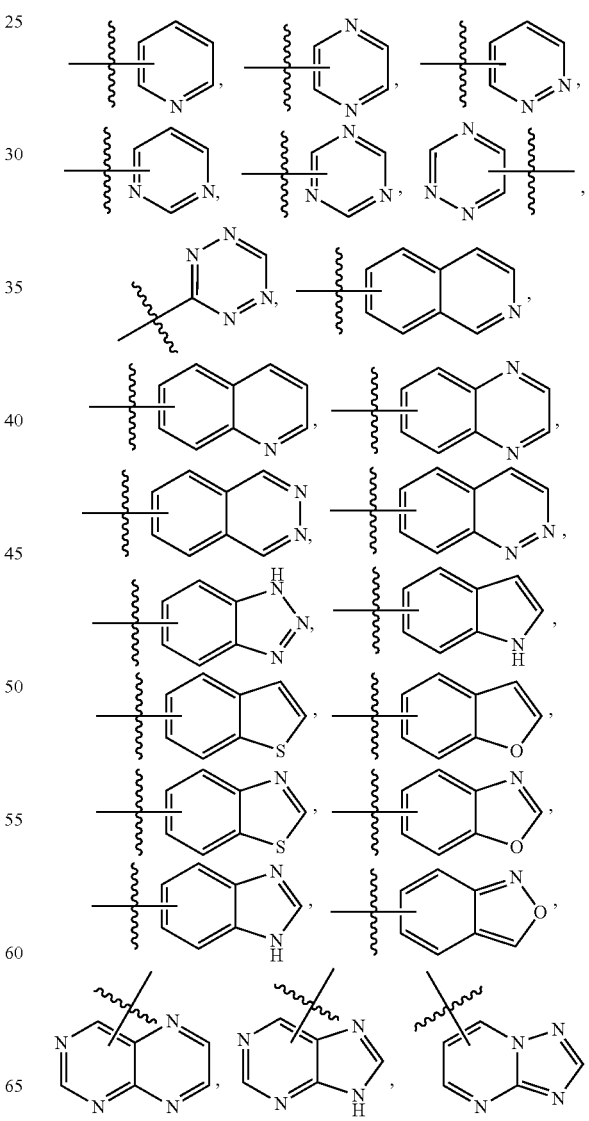

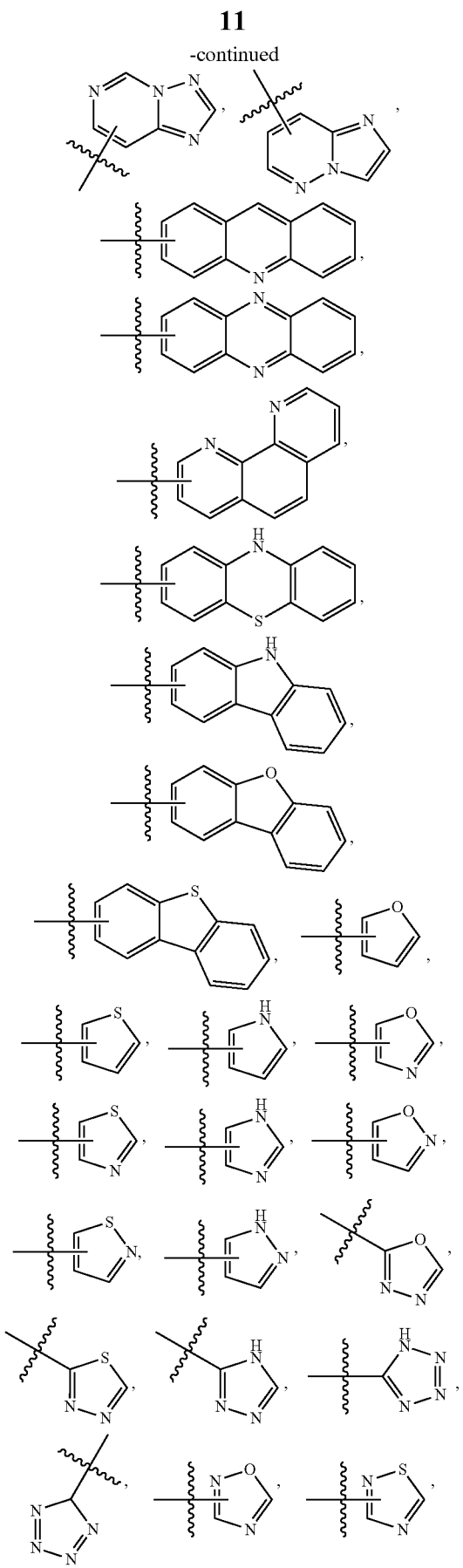

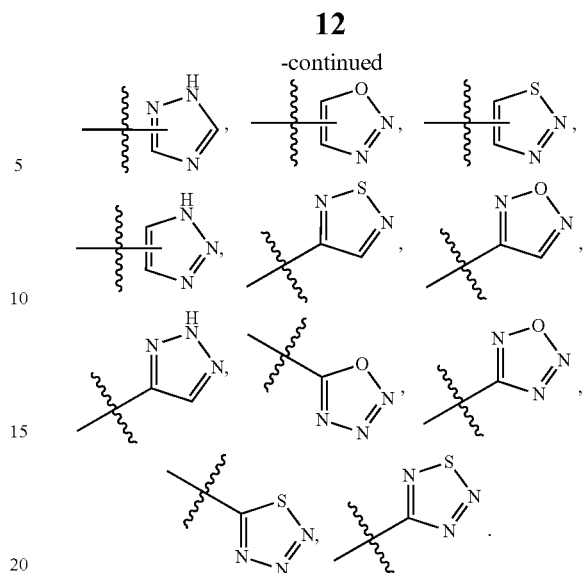

or

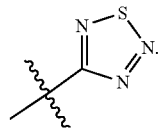 [SMILES: *c1nnsn1]

If a group is substituted by a group, which should be understood to mean that the group is substituted by one or more groups, which are same or different groups, selected from the mentioned groups. In addition, the same or different substitution characters contained in the same or different substituents are independently selected, and may be the same or different. This is also applicable to ring systems formed with different atoms and units. Meanwhile, the scope of the claims will exclude those compounds chemically unstable under standard conditions known to those skilled in the art.

In addition, unless specifically defined, the term occurring before or after multiple juxtaposed substituents (separated by "," or "or") in the present invention has a limiting effect on each of the substituents, such as the term "with or without halogen" in "alkyl, alkenyl, alkynyl, cycloalkyl, OR″, SR″, SOR″ or SO$_2$R″ with or without halogen" has a limiting effect on each of the following groups "alkyl", "alkenyl", "alkynyl", "cycloalkyl", "OR″", "SR″", "SOR″" and "SO$_2$R″"; "alkylamino" refers to an amino group that is mono- or di-substituted by an alkyl group, and other substituted amino groups have similar definitions; a group (including heterocyclyl, aryl, etc.) without being specified a linking site may be attached at any site, including a C or N site; if it is substituted, the substituent may be substituted at any site as long as it comply with the valence bond theory. For example, if the heteroaryl

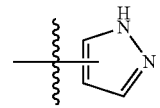

is substituted with one methyl, it can be

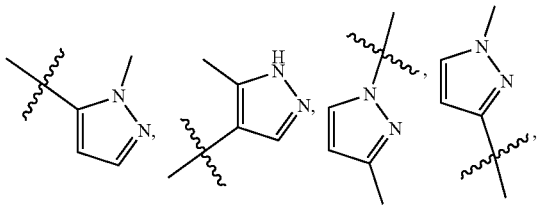

etc.

Depending on the property of substituents and the linkage manner thereof, the compound of Formula I and its derivatives may exist as a stereoisomer. For example, if a compound has one or more asymmetric carbon atoms, it may has enantiomers and diastereomers, in this case, the present invention also includes a mixture of one kind of optically active material and a plurality of kinds of optically active material in an arbitrary ratio. The stereoisomer can be obtained from the mixtures obtained in the preparation by conventional separation methods, for example by chromatographic separation. The stereoisomer may also be prepared selectively by using stereoselective reactions and using optically active starting materials and/or auxiliaries. The present invention also relates to all stereoisomers and mixtures thereof which are included in the general Formula I and a derivative thereof but are not specifically defined.

In the present invention, the derivative

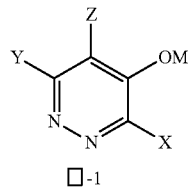

□-1 refers to an agriculturally acceptable derivative of the hydroxyl group at the 4-position of the pyridazine ring in the general formula I, including a salt, an ester, an oxime, a hydroxylamine, and an ether derivative, etc.

The agriculturally acceptable salt is a salt commonly used in agricultural chemicals, for example, the pyridazaine compound or the derivative may be processed into an alkali metal salt, an alkaline earth metal salt or an amine salt, or, when a basic moiety is present in the molecule, it can be processed into, for example, a sulfate, a hydrochloride, a nitrate, a phosphate, etc. When these salts are used as herbicides in agriculture or horticulture, they are also included in the present invention. In the present invention, the "alkali metal salt" may be, for example, a sodium salt, a potassium salt or a lithium salt, preferably a sodium salt or a potassium salt. In the present invention, the "alkaline earth metal salt" may be, for example, a calcium salt or a magnesium salt, preferably a calcium salt. In the present invention, the "amine salt" may be, for example, a secondary alkylamine salt, a tertiary alkylamine salt or a quaternary alkylammonium salt; a primary alkanolamine salt, a secondary alkanolamine salt, a tertiary alkanolamine salt or a quaternary alkanoammonium salt; a primary alkylalkanolamine salt, a secondary alkylalkanolamine salt, a tertiary alkylalkanolamine salt or a quaternary alkylalkanolammonium salt; or a primary alkoxyalkanolamine salt, a secondary alkoxyalkanolamine salt, a tertiary alkoxyalkanolamine salt or a quaternary alkoxyalkanolammonium salt, preferably, wherein the alkyl, alkanol and alkoxy are independently saturated and independently contain 1-4 carbon atoms, more preferably, ethanolamine salt, dimethylethanolamine salt, triethanolamine salt, dimethylamine salt, triethylamine salt, isopropylamine salt, choline salt or diglycolamine salt.

Solvates of the compounds of the invention are also included in the invention.

The ester derivative is formed by bonding an acyl group (including carbonyl, thiocarbonyl, sulfoxide, sulfonyl, phosphoryl, thiophosphoryl, etc.) to the oxygen atom of the hydroxyl group at the 4-position of the pyridazine ring. For example, the group may be (thio)formyl, C1~C18 alkyl (thio)carbonyl, wherein the (thio)formyl, or C1~C18 alkyl (thio)carbonyl is optionally substituted by a substituent [the substituent is one or more same or different substituents selected from halogen, amino, C3~C8 cycloalkyl, C1~C8 alkoxy, C1~C8 alkylsulfanyl, C1~C8 alkoxycarbonyl, C1~C8 alkylcarbonyloxy, C1~C8 alkylcarbonyl, and C2~C8 alkenyloxycarbonyl optionally substituted by a substituent {the substituent is 1~3 same or different substituents selected from C3~C8 cycloalkyl, cyano, and benzoyl optionally substituted by a substituent (the substituent is 1~3 same or different substituents selected from halogen, C1~C8 alkyl, C1~C8 haloalkyl, C1~C8 alkoxycarbonyl, nitro and C1~C8 alkylsulfonyl)}, hydroxy(methyl)phosphinyl, C3~C8 cycloalkenyloxycarbonyl optionally substituted by a substituent {the substituent is 1~2 same or different substituents selected from oxo and benzoyl optionally substituted by a substituent (the substituent is 1~3 same or different substituents selected from halogen atom, C1~C8 alkyl, C1~C8 haloalkyl, C1~C8 alkoxycarbonyl, nitro and C1~C8 alkylsulfonyl)}, 5- or 6-membered heterocyclyloxycarbonyl optionally substituted by a substituent {the ring of the heterocyclyl contains one nitrogen atom, oxygen atom or sulfur atom, and may further contain one or two nitrogen atoms, the substituent is 1~3 same or different substituents selected from halogen, a C1~C8 alkyl, phenoxy optionally substituted by a substituent (the substituent is 1~3 same or different substituents selected from halogen, C1~C8 alkyl, C1~C8 haloalkyl, C3~C8 cycloalkyl and C1~C8 alkoxycarbonyl), 2,3-dihydro-1H-indenyloxy, and benzoyl optionally substituted by a substituent (the substituent is 1~3 same or different substituents selected from halogen, C1~C8 alkyl, C1~C8 haloalkyl, C1~C8 alkoxycarbonyl, nitro and C1~C8 alkylsulfonyl)}, phenyl, phenoxy, benzyloxy, phenylsulfanyl, benzylsulfanyl, wherein the phenyl, phenoxy, benzyloxy, phenylsulfanyl, or benzylsulfanyl is optionally substituted by a substituent (the substituent is 1~3 same or different substituents selected from halogen, C1~C8 alkyl, C1~C8 alkoxy, C1~C8 haloalkyl, and C1~C8 alkoxycarbonyl), and C1~C8 alkylsulfanyl], C3~C8cycloalkyl(thio)carbonyl, adamantyl(thio)carbonyl, C2~C8 alkenyl(thio)carbonyl optionally substituted by a substituent {the substituent is one or more same or different substituents selected from halogen, C1-C8 alkoxy, phenyl, phenylsulfanyl, and phenoxy, wherein the phenyl, phenylsulfanyl, or phenoxy is optionally substituted by a substituent (the substituent is 1~3 same or different substituents selected from halogen, C1~C8 alkyl, C1~C8 alkoxy, C1~C8 haloalkyl, and C1~C8 alkoxycarbonyl)}, C2~C8 alkynyl(thio)carbonyl, (thio)benzoyl, (thio)naphthoyl, wherein the (thio)benzoyl or (thio)naphthoyl is optionally substituted by a substitutent [the substituent is 1~3 same or different substituents selected from halogen atom, C1~C8 alkyl optionally substituted by a substituent (the substituent is one or more same or different substituents selected from halogen and phenyl), cyano, hydroxy, C1~C8 alkylcarbonyl, C1~C8 alkoxycarbonyl, C1~C8 alkylcarbonyloxy, C1~C8 alkylcarbonylamino, amino optionally substituted by a substituent (the substituent is 1~3 same or different substituents selected from C1~C8 alkyl, C1~C8 alkoxy, C1~C8 alkylcarbonyl, halogenated C1~C8 alkyl and phenyl), C2~C8 alkenyloxycarbonyl optionally substituted by a substituent {the substituent is 1~3 same or different substituents selected from C3~C8 cycloalkyl, cyano, and benzoyl optionally substituted by a substituent (the substituent is 1~3 same or different substituents selected from halogen, C1~C8 alkyl, C1~C8 haloalkyl, C1~C8 alkoxycarbonyl, nitro, and C1~C8 alkylsulfonyl)}, C3~C8 cycloalkenyloxycarbonyl optionally substituted by a substituent {the substituent is 1~2 same or different substituents selected from oxo, and benzoyl optionally substituted by a substituent (the substituent is 1~3 same or different substituents selected from halogen, C1~C8 alkyl, halogenated C1~C8 alkyl, C1~C8 alkoxycarbonyl, nitro, and C1~C8 alkylsulfonyl)}, phenyl, nitro, C1~C8 alkoxy optionally substituted by a substituent (the substituent is 1-3 same or different substituents selected from halogen and phenyl), phenoxy, 5- or 6-membered heterocyclyloxycarbonyl optionally substituted by a substituent {the ring of the heterocyclyl contains 1 nitrogen atom, oxygen atom or sulfur atom, and may further contain 1 to 2 nitrogen atoms, the substituent is 1~3 same or different substituents selected from halogen atom, C1~C8 alkyl, phenoxy optionally substituted by a substituent (the substituent is 1~3 same or different substituents selected from halogen, C1~C8 alkyl, halogenated C1~C8 alkyl, C3~C8 cycloalkyl, and C1~C8 alkoxycarbonyl), 2,3-dihydro-1H-indenyloxy, and benzoyl optionally substituted by a substituent (the substituent is 1~3 same or different substituents selected from halogen, C1~C8 alkyl, halogenated C1~C8 alkyl, C1~C8 alkoxycarbonyl, nitro, and C1~C8 alkylsulfonyl)}, and 5- or 6-membered heterocyclyloxysulfonyl optionally substituted by a substituent {the ring of the heterocyclyl contains 1 nitrogen atom, oxygen atom or sulfur atom, and may further contain 1 to 2 nitrogen atoms, the substituent is 1~3 same or different substituents selected from halogen, C1~C8 alkyl, phenoxy optionally substituted by a substituent (the substituent is 1~3 same or different substituents selected from halogen, C1~C8 alkyl, halogenated C1~C8 alkyl, C3~C8cycloalkyl, and C1~C8 alkoxycarbonyl), 2,3-dihydro-1H-indenyloxy, and benzoyl optionally substituted by a substituent (the substituent is 1~3 same or different substituents selected from halogen, C1~C8 alkyl, C1~C8 haloalkyl, C1~C8 alkoxycarbonyl, nitro, and C1~C8 alkylsulfonyl)}], halogen-substituted sulfhydryl formyl, 3- to 8-membered heterocyclyl (thio)carbonyl optionally substituted by a substituent {the ring of the heterocyclyl contains 1 nitrogen atom, oxygen atom or sulfur atom, and may further contain 1 to 2 nitrogen atoms, or may form a 5- to 6-membered spiro ring having 1 to 2 oxygen atoms in the heterocyclyl, the substituent is 1~3 same or different substituents selected from halogen, C1~C8 alkyl optionally substituted by a substituent (the substituent is one or more same or different substituents selected from halogen and phenyl), C1~C8 alkylcarbonyl, C1~C8 alkoxycarbonyl, phenyl optionally substituted by a substituent (the substituent is 1~3 same or different halogen), nitro, hydroxy, C1~C8 alkoxy, phenoxy, C1~C8 alkylsulfanyl, C2~C8 alkenylsulfanyl, and phenylsulfanyl}, fused 5- to 14-membered bicyclic or tricyclic heterocyclyl(thio)carbonyl optionally substituted by a substituent (the ring of the heterocyclyl contains 1 nitrogen atom, oxygen atom or sulfur atom, and may further contain 1 to 2 nitrogen atoms or oxygen atoms; the substituent is 1~3 same or different substituents selected from halogen atom and C1~C8 alkyl), 5- or 6-membered heterocyclyl(thio)carbonyl(thio)carbonyl (the ring of the heterocyclyl contains one nitrogen atom, oxygen atom or sulfur atom, and may further contain one or two nitrogen atoms), C1~C18 alkoxy(thio)carbonyl, C1~C18 alkylsulfanyl(thio)carbonyl, wherein the C1~C18 alkoxy(thio)carbonyl or C1-C18 alkylsulfanyl(thio)carbonyl is optionally substituted by a substituent (the substituent is one or more same or different substituents selected from halogen atom, C1~C8 alkoxy and phenyl), C2~C8 alkenyloxy(thio)carbonyl, C2~C8 alkenylsulfanyl(thio)carbonyl, C2~C8 chain alkynyloxy(thio)carbonyl, C2~C8 chain alkynylsulfanyl(thio)carbonyl, C3~C8 cycloalkyloxy(thio)carbonyl, C3~C8 cycloalkylsulfanyl(thio)carbonyl, phenoxy(thio)carbonyl, phenylsulfanyl(thio)carbonyl, phenyl C1~C8 alkyloxy(thio)carbonyl, phenyl C1~C8 alkylsulfanyl(thio)carbonyl, wherein the phenoxy(thio)carbonyl, phenylsulfanyl(thio) carbonyl, phenyl C1~C8 alkyloxy(thio)carbonyl or phenyl C1~C8 alkylsulfanyl(thio)carbonyl is optionally substituted by a substituent (the substituent is 1~3 same or different substituents selected from halogen, C1~C8 alkyl, cyano, C1~C8 alkylcarbonyl, C1~C8 alkoxycarbonyl, nitro, and C1~C8 alkoxy), fused polycyclicoxy(thio)carbonyl, fused polycyclicsulfanyl(thio)carbonyl, a group selected from 5- or 6-membered heterocyclyloxy(thio)carbonyl and 5- or 6-membered heterocyclylsulfanyl(thio)carbonyl, which is optionally substituted by a substituent {the ring of the heterocyclyl contains 1 nitrogen atom, oxygen atom or sulfur atom, and may further contain 1 to 2 nitrogen atoms, the substituent is 1~3 same or different substituents selected from halogen atom, C1~C8 alkyl, phenoxy optionally substituted by a substituent (the substituent is 1~3 same or different substituents selected from halogen, C1~C8 alkyl, C1~C8 haloalkyl, C3~C8 cycloalkyl, and C1~C8 alkoxycarbonyl), 2,3-dihydro-1H-indenyloxy, and benzoyl optionally substituted by a substituent (the substituent is 1~3 same or different substituents selected from halogen, C1~C8 alkyl, C1~C8 haloalkyl, C1~C8 alkoxycarbonyl, nitro, and C1~C8 alkylsulfonyl)}, amino(thio)formyl optionally substituted by a substituent {the substituent is 1~3 same or different substituents selected from C1~C8 alkyl optionally substituted by a substituent (the substituent is one or more same or different substituents selected from halogen, C1~C8 alkoxycarbonyl, cyano, phenyl, and C1~C8 alkoxy), C2~C8 alkenyl, phenyl, C1~C8 alkylcarbonyl, C1~C8 alkoxycarbonyl, and C1~C8 alkoxy},

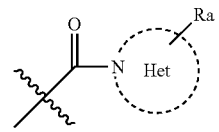

(Het is a 5- to 6-membered heterocyclyl, the heterocyclyl contains, besides C atoms and the 1-N, 0 to 3 atoms or radicals follows to form the ring: O, $NR_b$, C=O, $R_a$ and $R_b$ independently are hydrogen or C1~C8 alkyl), C1~C8 alkylsulfoxide, C1~C8 alkylsulfonyl, C2~C8 alkenylsulfonyl, C3~C8 cycloalkylsulfonyl, wherein the C1~C8 alkylsulfoxide, C1~C8 alkylsulfonyl, C2~C8 alkenylsulfonyl, or C3~C8 cycloalkylsulfonyl is optionally substituted by a substituent (the substituent is one or more same or different substituents selected from halogen and C1~C8 alkylsulfonyl), phenylsulfonyl, benzylsulfonyl, naphthylsulfonyl, wherein the phenylsulfonyl, benzylsulfonyl, or naphthylsulfonyl is optionally substituted by a substituent [the substituent is 1~3 same or different substituents selected from halogen, C1~C8 alkyl, halogenated C1~C8 alkyl, cyano, C1~C8 alkylcarbonyl, C1~C8 alkoxycarbonyl, nitro, C1~C8 alkoxy, halogenated C1~C8 alkoxy, C1~C8 alkylsulfonyl, aminoformyl optionally substituted by a substituent (the substituent is C1~C8 alkyl), phenoxy optionally substituted by a substituent (the substituent is 1~3 same or different substituents selected from halogen, C1~C8 alkyl, C1~C8 haloalkyl, C3~C8 cycloalkyl, and C1~C8 alkoxycarbonyl), C2~C8 alkenyloxysulfonyl optionally substituted by a substituent {the substituent is 1~3 same or different substituents selected from C3~C8 cycloalkyl, cyano, and benzoyl optionally substituted by a substituent (the substituent is 1~3 same or different substituents selected from halogen, C1~C8 alkyl, C1~C8 haloalkyl, C1~C8 alkoxycarbonyl, nitro, and C1~C8 alkylsulfonyl)}, C3~C8 cycloalkenyloxysulfonyl optionally substituted by a substituent {the substituent is 1-2 same or different substituents selected from oxo, and benzoyl optionally substituted by a substituent (the substituent is 1~3 same or different substituents selected from halogen, C1~C8 alkyl, C1~C8 haloalkyl, C1~C8 alkoxycarbonyl, nitro, and C1~C8 alkylsulfonyl)}, and 5- or 6-membered heterocyclyloxysulfonyl optionally substituted by a substituent {the ring of the heterocyclyl contains 1 nitrogen atom, oxygen atom or sulfur atom, and may further contain 1 to 2 nitrogen atoms, the substituent is 1~3 same or different substituents selected from halogen atom, C1~C8 alkyl, phenoxy optionally substituted by a substituent (the substituent is 1~3 same or different substituents selected from halogen atom, C1~C8 alkyl, C1~C8 haloalkyl, C3~C8 cycloalkyl, and C1~C8 alkoxycarbonyl), 2,3-dihydro-1H-indenyloxy, and benzoyl optionally substituted by a substituent (the substituent is 1~3 same or different substituents selected from halogen atom, C1~C8 alkyl, C1~C8 haloalkyl, C1~C8 alkoxycarbonyl, nitro, and C1~C8 alkylsulfonyl)}], 5- to 10-membered heteroarylsulfonyl, 5- to 10-membered heterocyclyloxysulfonyl, wherein the 5- to 10-membered heteroarylsulfonyl or 5- to 10-membered heterocyclyloxysulfonyl is optionally substituted by a substituent {the ring of the heterocyclyl contains 1 nitrogen atom, oxygen atom or sulfur atom, and may further contain 1 to 2 nitrogen atoms, the substituent is 1~3 same or different substituents selected from halogen atom, C1~C8 alkyl, phenoxy optionally substituted by a substituent (the substituent is 1~3 same or different substituents selected from halogen atom, C1~C8 alkyl, C1~C8 haloalkyl, C3~C8 cycloalkyl, and C1~C8 alkoxycarbonyl), 2,3-dihydro-1H-indenyloxy, and benzoyl optionally substituted by a substituent (the substituent is 1~3 same or different substituents selected from halogen atom, C1~C8 alkyl, C1~C8 haloalkyl, C1~C8 alkoxycarbonyl, nitro, and C1~C8 alkylsulfonyl)}, C1~C8 alkoxysulfonyl, C1~C8 alkylaminosulfonyl optionally substituted by a substituent (the substituent is one or more same or different substituents selected from halogen atom),

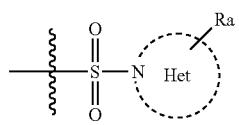

Het is a 5- to 6-membered heterocyclyl, and contains, besides C atoms and the 1-N, 0 to 3 atoms or radicals as follows to form the ring: O, $NR_b$, and C=O, $R_a$ and $R_b$ independently are hydrogen or C1~C8 alkyl), di(C1~C8 alkyl)phosphoryl, or di(C1~C8 alkyl)thiophosphoryl.

Preferably, the group may be C1~C10 alkyl(thio)carbonyl optionally substituted by a substituent {the substituent is one or more same or different substituents selected from fluorine, chlorine, bromine, C3~C6 cycloalkyl, C1~C6 alkoxy, C1~C6 alkylsulfanyl, C1~C6 alkoxycarbonyl, C1~C6 alkylcarbonyl, C1~C6 alkylcarbonyloxy, phenyl, phenylsulfanyl, phenoxy, and benzyloxy, wherein the phenyl, phenylsulfanyl, phenoxy or benzyloxy is optionally substituted by a substituent (the substituent is 1~3 same or different substituents selected from fluorine, chlorine, bromine, C1~C6 alkyl, and C1~C6 alkoxy)}, C3~C6 cycloalkyl(thio)carbonyl, C2~C6 alkenyl(thio)carbonyl optionally substituted by a substituent {the substituent is one or more same or different substituents selected from fluorine, chlorine, bromine, C1~C6 alkoxy, phenyl, phenylthio, and phenoxy, wherein the phenyl, phenylthio or phenoxy is optionally substituted by a substituent (the substituent is 1~3 same or different substituents selected from fluoride, chlorine, bromine, C1~C6 alkyl, and C1~C6 alkoxy)}, (thio)benzoyl, (thio)naphthoyl, wherein the (thio)benzoyl or (thio)naphthoyl is optionally substituted by a substituent {the substituent is 1~3 same or different substituents selected from fluorine, chlorine, bromine, C1~C6 alkyl, C1~C6 alkoxy, wherein the C1~C6 alkyl or C1~C6 alkoxy is optionally substituted by a substituent (the substituent is 1~3 same or different substituents selected from fluorine, chlorine, bromine, and phenyl), cyano, hydroxy, C1~C6 alkylcarbonyl, C1~C6 alkoxycarbonyl, C1~C6 alkylcarbonyloxy, C1~C6 alkylcarbonylamino, amino optionally substituted by a substituent (the substituent is 1~3 same or different substituents selected from C1~C6 alkyl, C1~C6 alkoxy, C1~C6 alkylcarbonyl, halogenated C1~C6 alkyl, and phenyl), phenyl, nitro, and phenoxy}, 3- to 8-membered heterocyclyl(thio)carbonyl optionally substituted by a substituent {the heterocyclyl is

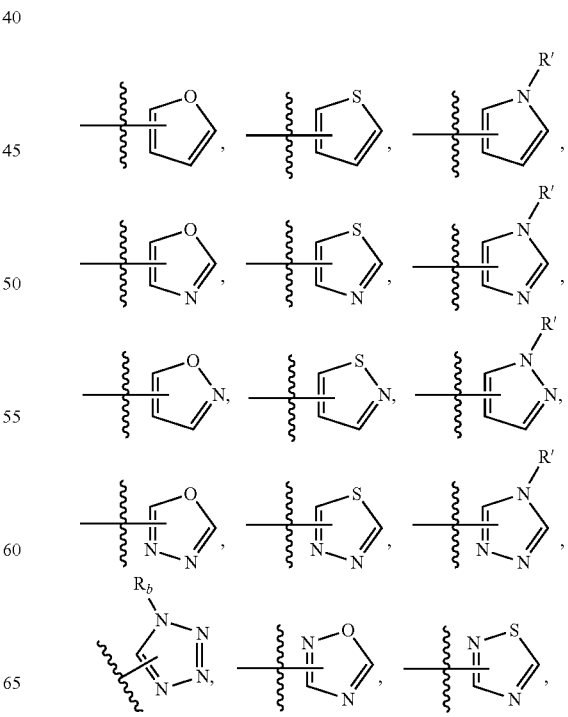

-continued

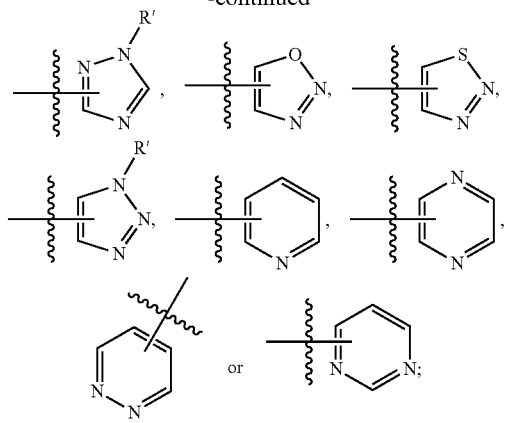

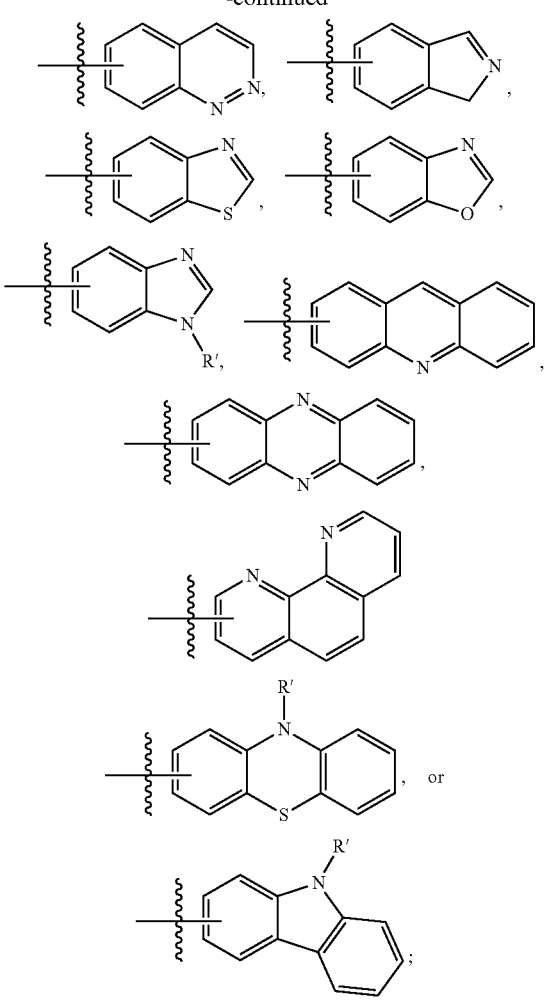

the substituent is 1~3 same or different substituents selected from fluorine, chlorine, bromine, C1~C6 alkyl optionally substituted by a substituent (the substituent is one or more same or different substituents selected from fluorine, chlorine, bromine, and phenyl), C1~C6 alkylcarbonyl, C1~C6 alkoxycarbonyl, phenyl optionally substituted by a substituent (the substituent is 1~3 same or different substituents selected from fluorine, chlorine, and bromine), nitro, hydroxy, C1~C6 alkoxy, phenoxy, C1~C6 alkylsulfanyl, C2~C6 alkenylsulfanyl, and phenylsulfanyl}, fused 5- to 14-membered bicyclic or tricyclic heterocyclyl(thio)carbonyl optionally substituted by a substituent (the heterocyclyl is

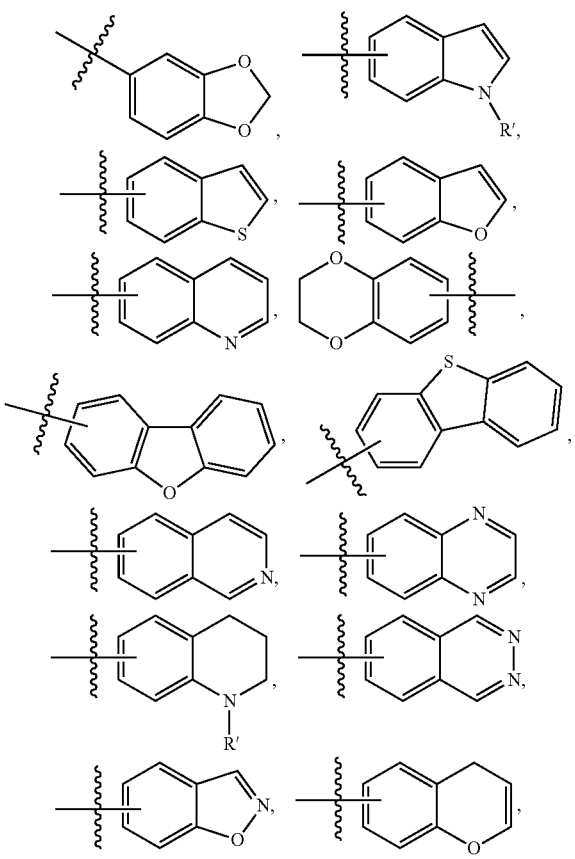

the substituent is 1~3 same or different substituents selected from fluorine, chlorine, bromine, and C1~C6 alkyl), C1~C10 alkoxy(thio)carbonyl, C1~C10 alkylsulfanyl(thio)carbonyl, wherein the C1~C10 alkoxy(thio)carbonyl or C1~C10 alkylsulfanyl(thio)carbonyl is optionally substituted by a substituent (the substituent is one or more same or different substituents selected from fluorine, chlorine, bromine, C1~C6 alkoxy, and phenyl), C3~C6 cycloalkyloxy(thio)carbonyl, C3~C6 cycloalkylsulfanyl(thio)carbonyl, phenoxy(thio)carbonyl, phenylsulfanyl(thio)carbonyl, phenyl-C1~C6 alkyloxy(thio)carbonyl, phenyl-C1~C6 alkylsulfanyl(thio)carbonyl, wherein the phenoxy(thio)carbonyl, phenylsulfanyl(thio)carbonyl, phenyl-C1~C6 alkyloxy(thio)carbonyl or phenyl-C1~C6 alkylsulfanyl(thio)carbonyl is optionally substituted by a substituent (the substituent is 1~3 same or different substituents selected from fluorine, chlorine, bromine, C1~C6 alkyl, cyano, C1~C6 alkylcarbonyl, C1~C6 alkoxycarbonyl, nitro, and C1~C6 alkoxy), amino(thio)formyl optionally substituted by a substituent {the substituent is 1~3 same or different substituents selected from C1~C6 alkyl optionally substituted by a substituent (the substituent is one or more same or different substituents selected from fluorine, chlorine, and bromine), C2~C6 alkenyl, phenyl, C1~C6 alkylcarbonyl, C1~C6 alkoxycarbonyl, and C1~C6 alkoxy)},

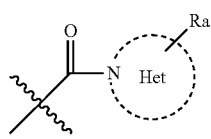

(Het is

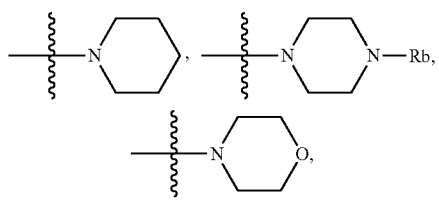

or

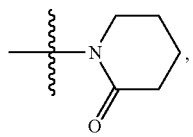 [SMILES: *N1CCCCC1=O]

$R_a$ and $R_b$ independently are hydrogen or C1~C6 alkyl), C1~C6 alkylsulfoxide, C1~C6 alkylsulfonyl, C2~C6 alkenylsulfonyl, C3~C6 cycloalkylsulfonyl, wherein the C1~C6 alkylsulfoxide, C1~C6 alkylsulfonyl, C2~C6 alkenylsulfonyl or C3~C6 cycloalkylsulfonyl is optionally substituted by a substituent (the substituent is one or more same or different substituents selected from fluorine, chlorine, bromine, and C1~C6 alkylsulfonyl), phenylsulfonyl, benzylsulfonyl, naphthylsulfonyl, wherein the phenylsulfonyl, benzylsulfonyl or naphthylsulfonyl is optionally substituted by a substituent {the substituent is 1~3 same or different substituents selected from fluorine, chlorine, bromine, C1~C6 alkyl, halogenated C1~C6 alkyl, cyano, C1~C6 alkanocarbonyl, C1~C6 alkoxycarbonyl, nitro, C1~C6 alkoxy, halogenated C1~C6 alkoxy, C1~C6 alkylsulfonyl, aminoformyl optionally substituted by a substituent (the substituent is C1~C6 alkyl), and phenoxy optionally substituted by a substituent (the substituent is 1~3 same or different substituents selected from fluorine, chlorine, bromine, C1~C6 alkyl, C1~C8 haloalkyl, C3~C6 cycloalkyl, and C1~C6 alkoxycarbonyl)}, 5- to 10-membered heteroarylsulfonyl optionally substituted by a substituent {the heterocyclyl is

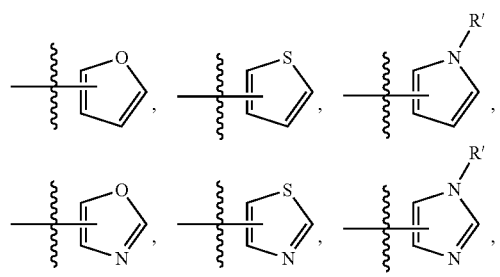

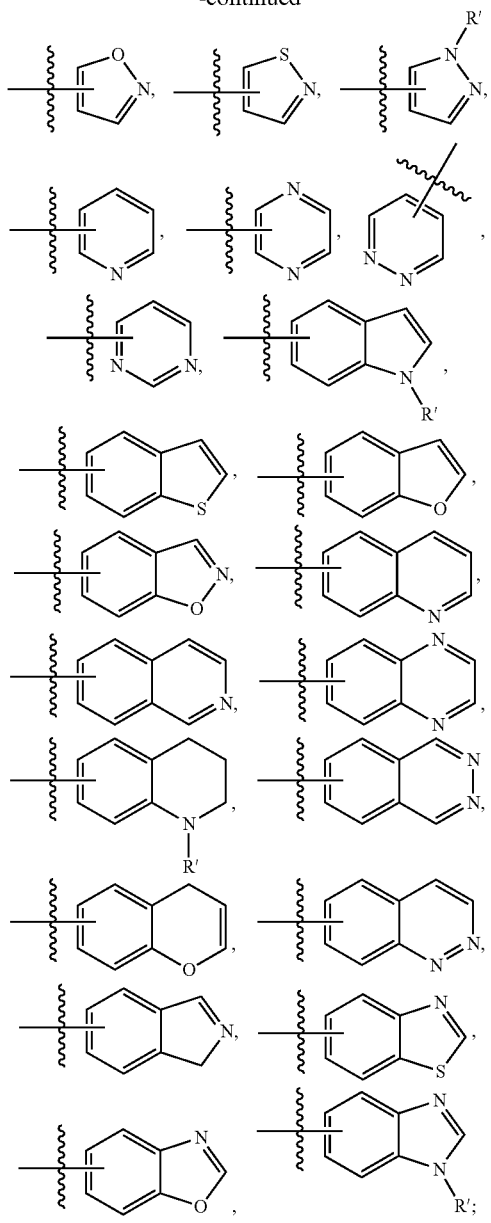

or

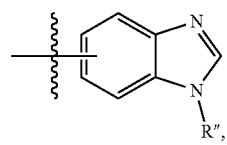

the substituent is 1~3 same or different substituents selected from fluorine, chlorine, bromine, C1~C6 alkyl, and phenoxy optionally substituted by a substituent (the substituent is 1~3 same or different substituents selected from fluorine, chlorine, bromine, C1~C6 alkyl, C1~C6 haloalkyl, C3~C6 cycloalkyl, and C1~C6 alkoxycarbonyl)}, C1~C6 alkylaminosulfonyl optionally substituted by a substituent (the substituent is one or more same or different substituents selected from fluorine, chlorine, and bromine),

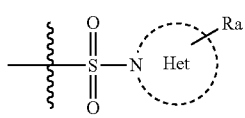

(Het is

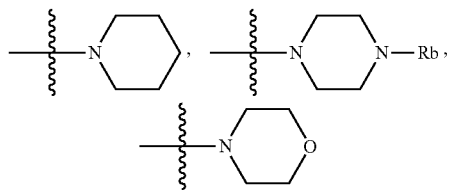

or

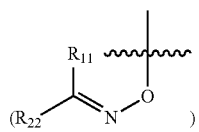

$R_a$ and $R_b$ independently are hydrogen or C1~C6 alkyl), di(C1~C6 alkyl)phosphoryl, or di(C1~C6 alkyl)thiophosphoryl.

The oxime derivative refers to a compound having an oxime group

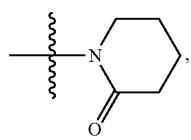

formed by bonding to the oxygen atom of the hydroxyl group at the 4-position of the pyridazine ring. For example, wherein $R_{11}$, $R_{22}$ separately and independently are hydrogen, C1~C18 alkyl, C2~C18 alkenyl, wherein the C1~C18 alkyl or C2~C18 alkenyl is optionally substituted with a substituent (the substituent is one or more same or different substituents selected from halogen atom, C1~C8 alkoxy, C1~C8 alkylsulfanyl, and C1~C8 alkylamino), phenyl, phenylcarbonyl, 5- to 6-membered heteroaryl, wherein the phenyl, phenylcarbonyl or 5- to 6-membered heteroaryl is optionally substituted with a substituent (the substituent is 1~3 same or different substituents selected from halogen atom, C1~C8 alkyl, C2~C8 alkenyl, C2~C8 alkynyl, C3~C8 cycloalkyl, C1~C8 haloalkyl, C1~C8 alkylcarbonyl, C1~C8 alkoxy, C1~C8 alkoxycarbonyl, C1~C8 alkylamino, hydroxy, carboxyl, sulfhydryl, amino, cyano, nitro, and C1~C8 alkylsulfonyl, the heteroaryl contains at least one oxygen, sulfur, or nitrogen, or other heteroatoms), or $R_{11}$, $R_{22}$ form a 5- to 6-membered saturated carbocyclic ring or 5- to 6-membered heterocyclic ring (containing at least one heteroatom such as oxygen, sulfur, nitrogen, etc.).

Preferably, $R_{11}$, $R_{22}$ independently are hydrogen, C1~C10 alkyl, C2~C10 alkenyl, the C1~C10 alkyl or C2~C10 alkenyl is optionally substituted with a substituent (the substituent is one or more same or different substituents selected from fluorine, chlorine, bromine, C1~C6 alkoxy, C1~C6 alkylsulfanyl, and C1~C6 alkylamino), phenyl, benzoyl, 5- to 6-membered heteroaryl, wherein the phenyl, benzoyl or 5- to 6-membered heteroaryl is optionally substituted with a substituent (the heteroaryl is

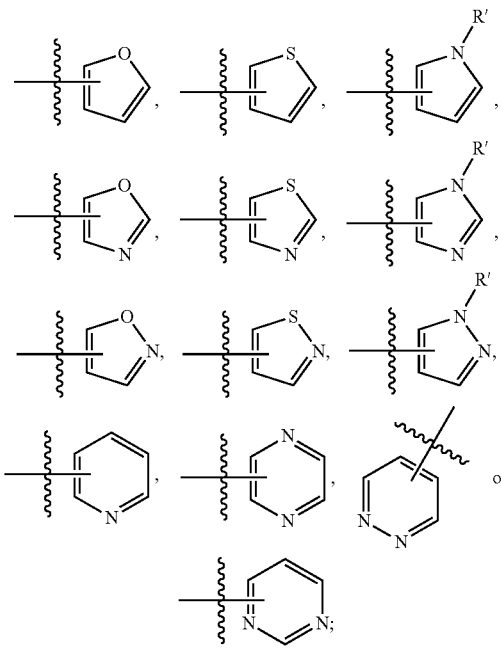

the substituent is 1~3 same or different substituents selected from fluorine, chlorine, bromine, C1~C6 alkyl, C3~C6 cycloalkyl, C1~C6 haloalkyl, C1~C6 alkylcarbonyl, C1~C6 alkoxy, C1~C6 alkoxycarbonyl, C1~C6 alkylamino, hydroxy, carboxyl, sulfhydryl, amino, cyano, nitro, and C1~C6 alkylsulfonyl), or $R_{11}$ and $R_{22}$ form a 5- to 6-membered saturated carbocyclic ring or a 5- to 6-membered heterocyclic ring (containing at least one heteroatom such as oxygen, sulfur, nitrogen, etc.).

The hydroxylamine derivative refers to a compound containing a hydroxylamine group

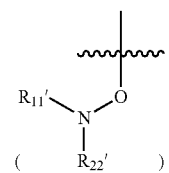

formed by bonding to the oxygen atom of the hydroxyl group at the 4-position of the pyridazine ring, for example, $R_{11}{}'$, $R_{22}{}'$ are independently hydrogen, C1~C18 alkyl, C2~C18 alkenyl, wherein the C1~C18 alkyl or C2~C18 alkenyl is optionally substituted with a substituent (the substituent is one or more same or different substituents selected from halogen atom, C1~C8 alkoxy, C1~C8 alkylsulfanyl, and C1~C8 alkylamino), phenyl optionally substituted with a substituent (the substituent is 1~3 same or different substituents selected from halogen atom, C1~C8 alkyl, C2~C8 alkenyl, C2~C8 alkynyl, C3~C8 cycloalkyl, C1~C8 haloalkyl, C1~C8 alkylcarbonyl, C1~C8 alkoxy, C1~C8 alkoxycarbonyl, C1~C8 alkylamino, hydroxy, carboxyl, sulfhydryl, amino, cyano, nitro, and C1~C8 alkylsulfonyl), C1~C18 alkoxycarbonyl, or benzoyl optionally substituent with a substituent [the substituent is 1~3 same or different substituents selected from halogen atom, C1~C8 alkyl, C2~C8 alkenyl, C2~C8 alkynyl, C3~C8 cycloalkyl, wherein the C1~C8 alkyl, C2~C8 alkenyl, C2~C8 alkynyl or C3~C8 cycloalkyl is optionally substituent with a substituent (the substituent is 1~3 same or different substituents selected from halogen and phenyl), cyano, C1~C8 alkylcarbonyl, C1~C8 alkoxycarbonyl, C1~C8 alkylsulfonyl, C2~C8 alkenyloxycarbonyl optionally substituent with a substituent {the substituent is 1~3 same or different substituents selected from C3~C8 cycloalkyl, cyano, and benzoyl optionally substituent with a substituent (the substituent is 1~3 same or different substituents selected from halogen atom, C1~C8 alkyl, C1~C8 haloalkyl, C1~C8 alkoxycarbonyl, nitro, and C1~C8 alkylsulfonyl)}, C3~C8 cycloalkenyloxycarbonyl optionally substituent with a substituent {the substituent is 1~2 same or different substituents selected from oxo, and benzoyl optionally substituent with a substituent (the substituent is 1~3 same or different substituents selected from halogen atom, C1~C8 alkyl, C1~C8 haloalkyl, C1~C8 alkoxycarbonyl, nitro, and C1~C8 alkylsulfonyl)}, hydroxy, carboxyl, sulfhydryl, amino, phenyl, nitro, C1~C8 alkoxy, C1~C8 alkylamino, C1~C8 alkylsulfanyl, wherein the C1~C8 alkoxy, C1~C8 alkylamino or C1~C8 alkylsulfanyl is optionally substituent with a substituent (the substituent is 1~3 same or different substituents selected from halogen and phenyl), phenoxy, 5- or 6-membered heterocyclyloxycarbonyl optionally substituent with a substituent {the ring of the heterocyclyl contains one nitrogen atom, oxygen atom or sulfur atom, may further contain 1 to 2 nitrogen atoms; the substituent is 1~3 same or different substituents selected from halogen atom, C1~C8 alkyl, phenoxy optionally substituent with a substituent (the substituent is 1~3 same or different substituents selected from halogen atom, C1~C8 alkyl, C1~C8 haloalkyl, C3~C8 cycloalkyl, and C1~C8 alkoxycarbonyl), 2,3-dihydro-1H-indenyloxy, and benzoyl optionally substituent with a substituent (the substituent is 1~3 same or different substituents selected from halogen atom, C1~C8 alkyl, C1~C8 haloalkyl, C1~C8 alkoxycarbonyl, nitro, and C1~C8 alkylsulfonyl)}, and 5- or 6-membered heterocycly-loxysulfonyl optionally substituent with a substituent {the ring in the heterocyclyl contains one nitrogen atom, oxygen atom or sulfur atom, and may further contain 1 or 2 nitrogen atoms; the substituent is 1~3 same or different substituents selected from halogen atom, C1~C8 alkyl, phenoxy optionally substituent with a substituent (the substituent is 1~3 same or different substituents selected from halogen atom, C1~C8 alkyl, C1~C8 haloalkyl, C3~C8 cycloalkyl, and C1~C8 alkoxycarbonyl), 2,3-dihydro-1H-indenyloxyl, and benzoyl optionally substituent with a substituent (the substituent is 1~3 same or different substitutions selected from halogen atom, C1~C8 alkyl, C1~C8 haloalkyl, C1~C8 alkoxycarbonyl, nitro, and C1~C8 alkylsulfonyl)}].

Preferably, $R_{11}'$, $R_{22}'$ are independently hydrogen, C1~C10 alkyl, C2~C10 alkenyl, wherein the C1~C10 alkyl or C2~C10 alkenyl is optionally substituent with a substituent (the substituent is one or more same or different substituents selected from fluorine, chlorine, bromine), C1~C10 alkoxycarbonyl, phenyl, or benzoyl, wherein the phenyl or benzoyl optionally substituent with a substituent (the substituent is 1~3 same or different substituents selected from fluorine, chlorine, bromine, C1~C6 alkyl, C2~C6 alkenyl, C2~C6 alkynyl, C3~C6 cycloalkyl, C1~C6 haloalkyl, C1~C6 alkylcarbonyl, C1~C6 alkoxy, C1~C6 alkoxycarbonyl, C1~C6 alkylamino, hydroxy, carboxyl, sulfhydryl, amino, cyano, nitro, and C1~C6 alkylsulfonyl).

The ether derivative refers to a compound formed by bonding the oxygen atom of the hydroxyl group at the 4-position of the pyridazine ring with a group as follows, for example, cyano, C1~C18 alkyl, C2~C18 alkenyl, wherein the C1~C18 alkyl or C2~C18 alkenyl is optionally substituted with a substituent (the substituent is one or more same or different substituents selected from halogen atom, C1~C8 alkoxy, C1~C8 alkylsulfanyl, C1~C8 alkylamino, di(C1~C8 alkyl)amino, C1~C8 alkoxycarbonyl, C1~C8 alkoxycarbonyloxy, C3~C8 cycloalkyloxy, C3~C8 cycloalkylsulfanyl, C3~C8 cycloalkylamino, di(C3~C8cycloalkyl)amino, C3~C8 cycloalkoxycarbonyl, and C3~C8 cycloalkoxycarbonyloxy), phenyl, benzyl, or benzoyl-C1~C8 alkyl, wherein the phenyl, benzyl or benzoyl-C1~C8 alkyl is optionally substituent with a substituent [the substituent is 1~3 same or different substituents selected from halogen atom, C1~C8 alkyl, C2~C8 alkenyl, C2~C8 alkynyl, C3~C8 cycloalkyl, wherein the C1~C8 alkyl, C2~C8 alkenyl, C2~C8 alkynyl or C3~C8 cycloalkyl is optionally substituent with a substituent (the substituent is 1~3 same or different substituents selected from halogen and phenyl), cyano, C1~C8 alkylcarbonyl, C1~C8 alkoxycarbonyl, C1~C8 alkylsulfonyl, C2~C8 alkenyloxycarbonyl optionally substituent with a substituent {the substituent is 1~3 same or different substituents selected from C3~C8 cycloalkyl, cyano, and benzoyl optionally substituent with a substituent (the substituent is 1~3 same or different substitutions selected from halogen atom, C1~C8 alkyl, C1~C8 haloalkyl, C1~C8 alkoxycarbonyl, nitro, and C1~C8 alkylsulfonyl)}, C3~C8 cycloalkenyloxycarbonyl optionally substituent with a substituent {the substituent is 1-2 same or different substituents selected from oxo, and benzoyl optionally substituent with a substituent (the substituent is 1~3 same or different substituents selected from halogen atom, C1~C8 alkyl, C1~C8 haloalkyl, C1~C8 alkoxycarbonyl, nitro, and C1~C8 alkylsulfonyl)}, hydroxy, carboxyl, sulfhydryl, amino, phenyl, nitro, C1~C8 alkoxy, C1~C8 alkylamino, C1~C8 alkylsufanyl, wherein the C1~C8 alkoxy, C1~C8 alkylamino or C1~C8 alkylsufanyl is optionally substituent with a substituent (the substituent is 1~3 same or different substituents selected from halogen and phenyl), phenoxy, 5- or 6-membered heterocyclyloxycarbonyl optionally substituent with a substituent {the ring of the heterocyclyl contains one nitrogen atom, oxygen atom or sulfur atom, and may further contain 1 to 2 nitrogen atoms; the substituent is 1~3 same or different substituents selected from halogen atom, C1~C8 alkyl, phenoxy optionally substituent with a substituent (the substituent is 1~3 same or different substituents selected from halogen atom, C1~C8 alkyl, C1~C8 haloalkyl, C3~C8 cycloalkyl, and C1~C8 alkoxycarbonyl), 2,3-dihydro-1H-indenyloxy, and benzoyl optionally substituent with a substituent (the substituent is 1~3 same or different substituents selected from halogen atom, C1~C8 alkyl, C1~C8 haloalkyl, C1~C8 alkoxycarbonyl, nitro, and C1~C8 alkylsulfonyl)}, and 5- or 6-membered heterocycly-loxysulfonyl optionally substituent with a substituent {the ring of the heterocyclyl contains one nitrogen atom, oxygen atom or sulfur atom, and may further contain 1 to 2 nitrogen atoms; the substituent is 1~3 same or different substituents selected from halogen atom, C1~C8 alkyl, C1~C8 haloalkyl, C3~C8 cycloalkyl, and C1~C8 alkoxycarbonyl), 2,3-dihydro-1H-indenyloxy, and benzoyl optionally substituent with a substituent (the substituent is 1~3 same or different substituents selected from halogen atom, C1~C8 alkyl, C1~C8 haloalkyl, C1~C8 alkoxycarbonyl, nitro, and C1~C8 alkylsulfonyl)}].

Preferably, C8~C18 alkyl, C8~C18 alkenyl, C1~C10 alkyl, C2~C10 alkenyl, wherein the C1~C10 alkyl or C2~C10 alkenyl is substituent with a substituent {the substituent is one or more same or different substituents selected from fluorine, chlorine, bromine, C1~C6 alkoxy, C1~C6 alkylsulfanyl, C1~C6 alkylamino, C1~C6 alkoxycarbonyl, C1~C6 alkoxycarbonyloxy, and C3~C6 cycloalkoxycarbonyloxy}, phenyl, benzyl, or benzoyl-C1~C6 alkyl, wherein the phenyl, benzyl or benzoyl-C1~C6 alkyl is optionally substituent with a substituent (the substituent is 1~3 same or different substituents selected from fluorine, chlorine, bromine, C1~C6 alkyl, C2~C6 alkenyl, C2~C6 alkynyl, C3~C6 cycloalkyl, C1~C6 haloalkyl, C1~C6 alkylcarbonyl, C1~C6 alkoxy, C1~C6 alkoxycarbonyl, C1~C6 alkylamino, hydroxy, carboxyl, sulfhydryl, amino, cyano, nitro, and C1~C6 alkylsulfonyl).

A method for preparing the pyridazinol compound, comprising the following steps:
(1) subjecting a compound of Formula II and a halogenating reagent to halogenation reaction to obtain a compound of Formula I';
(2) subjecting a compound of Formula I' to hydroxyl protection reaction to obtain a compound of Formula I-1';
(3) subjecting a compound of Formula I-1' to substitution reaction, deprotection reaction in sequence to obtain a compound of Formula I'';
the reaction route is as follows:

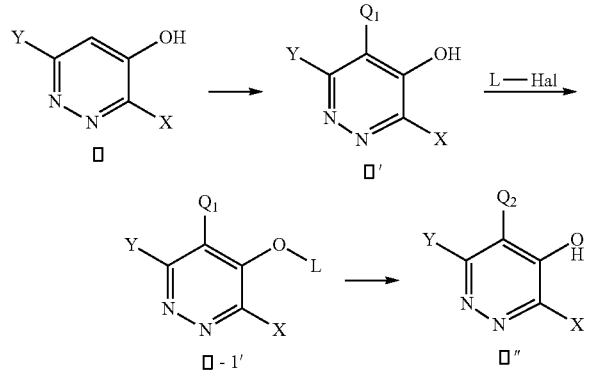

wherein Q₁ and Hal each independently represent halogen (such as F, Cl, Br, I); Q₂ represents a group other than halogen in the aforementioned substituent Z; L-represents TMS-, TBDMS-, TBDPS-, TBS-, PMB- or SEM-;

in the step (1), the halogenation reaction is carried out in the presence of an initiator and a solvent; the halogenation reagent is Cl₂, Br₂, I₂, NBS, NCS, NIS, dichlorohydantoin, dibromohydantoin, selective fluorine reagent or hexabromoethane, etc., the initiator is AIBN or BPO, etc., and the solvent is CCl₄, AcOH/HO₂, MeCN, DMF, NMP or AcOH, etc.;

the step (2) is carried out in the presence of a base and a solvent; the solvent is selected from at least one of MeCN, DMF, DMSO, dioxane, dichloromethane, dichloroethane and ethyl acetate, and the base is inorganic base (such as K₂CO₃, Na₂CO₃, Cs₂CO₃, NaHCO₃, KF, CsF, KOAc, NaOAc, K₃PO₄, t-BuONa, EtONa, NaOH, KOH, etc.) or organic base (such as pyrazole, triethylamine, DIEA, etc.);

in the step (3), the conventional substitution reaction type is selected according to the type of Q₂ substituent, such as Suzuki, Buchwald, copper-catalyzed or nucleophilic substitution, etc., and the deprotection reaction is carried out in the presence of reagents such as trifluoroacetic acid, hydrochloric acid, hydrobromic acid, hydroiodic acid, DDQ or H₂.

In addition, the compound II and the derivative I-1 can be prepared with reference to patents WO2019149260A1, WO2019148851A1, WO2019148850A1, etc.

A herbicidal composition, comprising (i) the pyridazinol compound of Formula I or derivative thereof;
preferably, further comprising (ii) one or more additional herbicides and/or safeners;
more preferably, further comprising (iii) an agriculturally acceptable formulation auxiliary.

A method for controlling a weed, comprising applying a herbicidally effective amount of at least one of the above mentioned pyridazinol compounds and derivatives thereof, or the herbicidal composition to a plant or a weed area.

Use of at least one of the pyridazinol compounds and derivatives thereof or the herbicidal composition for controlling a weed;
preferably, the pyridazinol compound or derivative thereof or the herbicidal composition being used for preventing and/or controlling a weed in a useful crop;
more preferably, the useful crop is a transgenic crop or a crop treated by gene editing technique.

The compound of Formula I and derivative thereof according to the invention have an outstanding herbicidal activity against a broad spectrum of economically important monocotyledonous and dicotyledonous weeds. The active compounds also act efficiently on perennial weeds which produce shoots from rhizomes, root stocks or other perennial organs and which are difficult to control. In this context, it is generally immaterial whether the substances are applied pre-sowing, pre-emergence or post-emergence. Specifically, examples may be mentioned of some representatives of the monocotyledonous and dicotyledonous weed flora which can be controlled by the compounds according to the invention, without these being a restriction to certain species. Examples of weed species on which the active compounds act efficiently are, from amongst the monocotyledons, *Avena, Lolium, Alopecurus, Phalaris, Echinochloa, Digitaria, Setaria* and also *Cyperus* species from the annual sector and from amongst the perennial species *Agropyron, Cynodon, Imperata* and *Sorghum*, and also perennial *Cyperus* species.

In the case of the dicotyledonous weed species, the spectrum of action extends to species such as, for example, *Galium, Viola, Veronica, Lamium, Stellaria, Amaranthus, Sinapis, Ipomoea, Sida, Matricaria* and *Abutilon* from amongst the annuals, and *Convolvulus, Cirsium, Rumex* and *Artemisia* in the case of the perennial weeds. The active compounds according to the invention also effect outstanding control of weeds which occur under the specific conditions of rice growing such as, for example, *Echinochloa, Sagittaria, Alisma, Eleocharis, Scirpus* and *Cyperus*. If the compounds according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely. In particular, the compounds according to the invention exhibit excellent activity against *Apera spica venti, Chenopodium album, Lamium*

*purpureum, Polygonum convulvulus, Stellaria media, Veronica hederifolia, Veronica persica, Viola tricolor* and against *Amaranthus, Galium* and *Kochia* species.

Although the compounds according to the invention have an excellent herbicidal activity against monocotyledonous and dicotyledonous weeds, crop plants of economically important crops such as, for example, wheat, barley, rye, rice, corn, sugarbeet, cotton and soya, are not damaged at all, or only to a negligible extent. In particular, they have excellent compatibility in cereals, such as wheat, barley and corn, in particular wheat. For these reasons, the present compounds are highly suitable for selectively controlling undesired plant growth in plantings for agricultural use or in plantings of ornamentals.

Owing to their herbicidal properties, these active compounds can also be employed for controlling weeds in crops of known or still to be developed genetically engineered plants. The transgenic plants generally have particularly advantageous properties, for example resistance to certain pesticides, in particular certain herbicides, resistance to plant diseases or causative organisms of plant diseases, such as certain insects or microorganisms such as fungi, bacteria or viruses. Other particular properties relate, for example, to the quantity, quality, storage-stability, composition and to specific ingredients of the harvested product. Thus, transgenic plants having an increased starch content or a modified quality of the starch or those having a different fatty acid composition of the harvested produce are known.

The use of the compound of Formula I according to the invention or derivative thereof in economically important transgenic crops of useful and ornamental plants, for example of cereal, such as wheat, barley, rye, oats, millet, rice, maniok and corn, or else in crops of sugarbeet, cotton, soya, rapeseed, potato, tomato, pea and other vegetable species is preferred. The compound of Formula I or derivative thereof can preferably be used as herbicides in crops of useful plants which are resistant or which have been made resistant by genetic engineering toward the phytotoxic effects of the herbicides.

Conventional ways for preparing novel plants which have modified properties compared to known plants comprise, for example, traditional breeding methods and the generation of mutants. Alternatively, novel plants having modified properties can be generated with the aid of genetic engineering methods (see, for example, EP-A 0 221 044, EP-A 0 131 624). For example, there have been described several cases:

genetically engineered changes in crop plants in order to modify the starch synthesized in the plants (for example WO 92/11376, WO 92/14827, WO 91/19806);

transgenic crop plants which are resistant to certain herbicides, for example, glufosinate (EP-A 0 242 236, EP-A 0 242 246), glyphosate-type (WO 92/00377), or sulfonylurea-type (EP-A 0 257 993, U.S. Pat. No. 5,013,659);

transgenic crop plants, for example cotton, having the ability to produce *Bacillus thuringiensis* toxins (Bt toxins) which impart resistance to certain pests to the plants (EP-A 0 142 924, EP-A 0 193 259);

transgenic crop plants having a modified fatty acid composition (WO 91/13972).

Numerous molecular biological techniques which allow the preparation of novel transgenic plants having modified properties are known in principle; see, for example, Sambrook et al., 1989, Molecular Cloning, A Laboratory Manual, 2nd ed. Cold Spring Harbor Laboratory Press, Cold Spring Harbor, N.Y.; or Winnacker "Gene und Klone" [Genes and Clones], VCH Weinheim, 2nd edition 1996, or Christou, "Trends in Plant Science" 1 (1996) 423-431). In order to carry out such genetic engineering manipulations, it is possible to introduce nucleic acid molecules into plasmids which allow a mutagenesis or a change in the sequence to occur by recombination of DNA sequences. Using the abovementioned standard processes it is possible, for example, to exchange bases, to remove partial sequences or to add natural or synthetic sequences. To link the DNA fragments with each other, it is possible to attach adaptors or linkers to the fragments.

Plant cells having a reduced activity of a gene product can be prepared, for example, by expressing at least one appropriate antisense-RNA, a sense-RNA to achieve a cosuppression effect, or by expressing at least one appropriately constructed ribozyme which specifically cleaves transcripts of the abovementioned gene product.

To this end it is possible to employ both DNA molecules which comprise the entire coding sequence of a gene product including any flanking sequences that may be present, and DNA molecules which comprise only parts of the coding sequence, it being necessary for these parts to be long enough to cause an antisense effect in the cells. It is also possible to use DNA sequences which have a high degree of homology to the coding sequences of a gene product but which are not entirely identical.

When expressing nucleic acid molecules in plants, the synthesized protein can be localized in any desired compartment of the plant cells. However, to achieve localization in a certain compartment, it is, for example, possible to link the coding region with DNA sequences which ensure localization in a certain compartment. Such sequences are known to the person skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated to whole plants using known techniques. The transgenic plants can in principle be plants of any desired plant species, i.e. both monocotyledonous and dicotyledonous plants. In this manner, it is possible to obtain transgenic plants which have modified properties by overexpression, suppression or inhibition of homologous (=natural) genes or gene sequences or by expression of heterologous (=foreign) genes or gene sequences.

When using the active compounds according to the invention in transgenic crops, in addition to the effects against weeds which can be observed in other crops, there are frequently effects which are specific for the application in the respective transgenic crop, for example a modified or specifically broadened spectrum of weeds which can be controlled, modified application rates which can be used for the application, preferably good combinability with the herbicides to which the transgenic crops are resistant, and an effect on the growth and the yield of the transgenic crop plants. The invention therefore also provides for the use of the compounds according to the invention as herbicides for controlling weeds in transgenic crop plants.

In addition, the substances according to the invention have outstanding growth-regulating properties in crop plants. They engage in the plant metabolism in a regulating manner and can this be employed for the targeted control of plant constituents and for facilitating harvesting, for example by provoking desiccation and stunted growth. Furthermore, they are also suitable for generally regulating and inhibiting undesirable vegetative growth, without destroying the plants in the process. Inhibition of vegetative growth plays an important role in many monocotyledon and dicotyledon crops because lodging can be reduced hereby, or prevented completely.

The compounds according to the invention can be applied in the customary formulations in the form of wettable powders, emulsifiable concentrates, sprayable solutions, dusts or granules. The invention therefore also provides herbicidal compositions comprising the compound of Formula I or derivative thereof. The compound of Formula I or derivative thereof can be formulated in various ways depending on the prevailing biological and/or chemico-physical parameters. Examples of suitable formulation options are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, dusts (DP), capsule suspensions (CS), seed-dressing compositions, granules for broadcasting and soil application, granules (GR) in the form of microgranules, spray granules, coating granules and adsorption granules, water-dispersible granules (WG), water-soluble granules (SG), ULV formulations, microcapsules and waxes. These individual formulation types are known in principle and are described, for example, in Winnacker-Kuhler, "Chemische Technologie" [Chemical Technology], Volume 7, C. Hauser Verlag Munich, 4th. Edition 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation auxiliaries, such as inert materials, surfactants, solvents and other additives, are likewise known and are described, for example, in Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzflchenaktive thylenoxidaddukte" [Surface-active ethylene oxide adducts], Wiss. Verlagsgesell, Stuttgart 1976; Winnacker-Kuchler, "Chemische Technologie" [Chemical Technology], Volume 7, C. Hauser Verlag Munich, 4th Edition 1986.

Wettable powders are preparations which are uniformly dispersible in water and which contain, in addition to the active compound and as well as a diluent or inert substance, surfactants of ionic and/or nonionic type (wetting agents, dispersants), for example polyethoxylated alkyl phenols, polyethoxylated fatty alcohols, polyethoxylated fatty amines, fatty alcohol polyglycol ethersulfates, alkanesulfonates, alkylbenzenesulfonates, sodium ligninsulfonate, sodium 2,2'-dinaphthylmethane-6,6'-disulfonate, sodium dibutyinaphthalenesulfona-te or else sodium oleoylmethyltaurinate. To prepare the wettable powders, the herbicidally active compounds are finely ground, for example in customary apparatus such as hammer mills, fan mills and air-jet mills, and are mixed simultaneously or subsequently with Formulation auxiliaries.

Emulsifiable concentrates are prepared by dissolving the active compound in an organic solvent, for example butanol, cyclohexanone, dimethylformamide, xylene or else relatively high-boiling aromatic compounds or hydrocarbons or mixtures of the solvents, with the addition of one or more surfactants of ionic and/or nonionic type (emulsifiers). Examples of emulsifiers which can be used are calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters or polyoxyethylene sorbitan esters, for example polyoxyethylene sorbitan fatty acid esters.

Dusts are obtained by grinding the active compound with finely divided solid substances, for example talc, natural clays, such as kaolin, bentonite and pyrophyllite, or diatomaceous earth. Suspension concentrates can be water- or oil-based. They can be prepared, for example, by wet milling using commercially customary bead mills, with or without the addition of surfactants as already mentioned above, for example, in the case of the other formulation types.

Emulsions, for example oil-in-water emulsions (EW), can be prepared for example by means of stirrers, colloid mills and/or static mixers using aqueous organic solvents and, if desired, surfactants as already mentioned above, for example, in the case of the other formulation types.

Granules can be prepared either by spraying the active compound onto adsorptive, granulated inert material or by applying active-compound concentrates to the surface of carriers such as sand, kaolinites or granulated inert material, by means of adhesive binders, for example polyvinyl alcohol, sodium polyacrylate or else mineral oils. Suitable active compounds can also be granulated in the manner which is customary for the preparation of fertilizer granules, if desired as a mixture with fertilizers. Water-dispersible granules are generally prepared by the customary processes, such as spray-drying, fluidized-bed granulation, disk granulation, mixing using high-speed mixers, and extrusion without solid inert material.

For the preparation of disk, fluidized-bed, extruder and spray granules, see for example processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th Ed., McGraw-Hill, New York 1973, pp. 8-57. For further details on the formulation of crop protection products, see for example G. C. Klingman, "Weed Control as a Science", John Wiley and Sons Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations generally contain from 0.1 to 99% by weight, in particular from 0.1 to 95% by weight, of active compound of Formula I or derivative thereof. In wettable powders the concentration of active compound is, for example, from about 10 to 99% by weight, the remainder to 100% by weight consisting of customary formulation constituents. In emulsifiable concentrates the concentration of active compound can be from about 1 to 90%, preferably from 5 to 80%, by weight. Formulations in the form of dusts contain from 1 to 30% by weight of active compound, preferably most commonly from 5 to 20% by weight of active compound, while sprayable solutions contain from about 0.05 to 80%, preferably from 2 to 50%, by weight of active compound. In the case of water-dispersible granules the content of active compound depends partly on whether the active compound is in liquid or solid form and on the granulation auxiliaries, fillers, etc. that are used. In water-dispersible granules the content of active compound, for example, is between 1 and 95% by weight, preferably between 10 and 80% by weight.

In addition, the formulations of active compound may comprise the tackifiers, wetting agents, dispersants, emulsifiers, penetrants, preservatives, antifreeze agents, solvents, fillers, carriers, colorants, antifoams, evaporation inhibitors and pH and viscosity regulators which are customary in each case.

Based on these formulations it is also possible to produce combinations with other pesticidally active substances, for example insecticides, acaricides, herbicides and fungicides, and also with safeners, fertilizers and/or growth regulators, for example in the form of a ready-mix or tank mix.

Suitable active compounds which can be combined with the active compounds according to the invention in mixed formulations or in a tank mix are, for example, known active compounds as described in for example World Herbicide New Product Technology Handbook, China Agricultural Science and Farming Techniques Press, 2010.9 and in the literature cited therein. For example the following active compounds may be mentioned as herbicides which can be combined with the compound of the formula I or derivative thereof (note: the compounds are either named by the "common name" in accordance with the International Organization for Standardization (ISO) or by the chemical names, if appropriate together with a customary code number): acetochlor, butachlor, alachlor, propisochlor, metolachlor, s-metolachlor, pretilachlor, propachlor, ethachlor, napropamide, R-left handed napropamide, propanil, mefenacet, diphenamid, diflufenican, ethaprochlor, beflubutamid, bromobutide, dimethenamid, dimethenamid-P, etobenzanid, flufenacet, thenylchlor, metazachlor, isoxaben, flamprop-M-methyl, flamprop-M-propyl, allidochlor, pethoxamid, chloranocryl, cyprazine, mefluidide, monalide, delachlor, prynachlor, terbuchlor, xylachlor, dimethachlor, cisanilide, trimexachlor, clomeprop, propyzamide, pentanochlor, carbetamide, benzoylprop-ethyl, cyprazole, butenachlor, tebutam, benzipram, mogrton, dichlofluanid, naproanilide, diethatyl-ethyl, naptalam, flufenacet, EL-177, benzadox, chlorthiamid, chlorophthalimide, isocarbamide, picolinafen, atrazine, simazine, prometryn, cyanatryn, simetryn, ametryn, propazine, dipropetryn, SSH-108, terbutryn, terbuthylazine, triaziflam, cyprazine, proglinazine, trietazine, prometon, simetone, aziprotryne, desmetryn, dimethametryn, procyazine, mesoprazine, sebuthylazine, secbumeton, terbumeton, methoprotryne, cyanatryn, ipazine, chlorazine, atraton, pendimethalin, eglinazine, cyanuric acid, indaziflam, chlorsulfuron, metsulfuron-methyl, bensulfuron methyl, chlorimuron-ethyl, tribenuron-methyl, thifensulfuron-methyl, pyrazosulfuron-ethyl, mesosulfuron, iodosulfuron-methyl sodium, foramsulfuron, cinosulfuron, triasulfuron, sulfometuron methyl, nicosulfuron, ethametsulfuron-methyl, amidosulfuron, ethoxysulfuron, cyclosulfamuron, rimsulfuron, azimsulfuron, flazasulfuron, monosulfuron, monosulfuron-ester, flucarbazone-sodium, flupyrsulfuron-methyl, halosulfuron-methyl, oxasulfuron, imazosulfuron, primisulfuron, propoxycarbazone, prosulfuron, sulfosulfuron, trifloxysulfuron, triflusulfuron-methyl, tritosulfuron, sodium metsulfuron methyl, flucetosulfuron, HNPC-C, orthosulfamuron, propyrisulfuron, metazosulfuron, acifluorfen, fomesafen, lactofen, fluoroglycofen, oxyfluorfen, chlornitrofen, aclonifen, ethoxyfen-ethyl, bifenox, nitrofluorfen, chlomethoxyfen, fluorodifen, fluoronitrofen, furyloxyfen, nitrofen, TOPE, DMNP, PPG1013, AKH-7088, halosafen, chlortoluron, isoproturon, linuron, diuron, dymron, fluometuron, benzthiazuron, methabenzthiazuron, cumyluron, ethidimuron, isouron, tebuthiuron, buturon, chlorbromuron, methyldymron, phenobenzuron, SK-85, metobromuron, metoxuron, afesin, monuron, siduron, fenuron, fluothiuron, neburon, chloroxuron, noruron, isonoruron, 3-cyclooctyl-1, thiazfluron, tebuthiuron, difenoxuron, parafluron, methylamine tribunil, karbutilate, trimeturon, dimefuron, monisouron, anisuron, methiuron, chloreturon, tetrafluron, phenmedipham, phenmedipham-ethyl, desmedipham, asulam, terbucarb, barban, propham, chlorpropham, rowmate, swep, chlorbufam, carboxazole, chlorprocarb, fenasulam, BCPC, CPPC, carbasulam, butylate, benthiocarb, vernolate, molinate, triallate, dimepiperate, esprocarb, pyributicarb, cycloate, avadex, EPTC, ethiolate, orbencarb, pebulate, prosulfocarb, tiocarbazil, CDEC, dimexano, isopolinate, methiobencarb, 2,4-D butyl ester, MCPA-Na, 2,4-D isooctyl ester, MCPA isooctyl ester, 2,4-D sodium salt, 2,4-D dimethyla mine salt, MCPA-thioethyl, MCPA, 2,4-D propionic acid, high 2,4-D propionic acid salt, 2,4-D butyric acid, MCPA propionic acid, MCPA propionic acid salt, MCPA butyric acid, 2,4,5-D, 2,4,5-D propionic acid, 2,4,5-D butyric acid, MCPA amine salt, dicamba, erbon, chlorfenac, saison, TBA, chloramben, methoxy-TBA, diclofop-methyl, fluazifop-butyl, fluazifop-p-butyl, haloxyfop-methyl, haloxyfop-P, quizalofop-ethyl, quizalofop-p-ethyl, fenoxaprop-ethy, fenoxaprop-p-ethyl, propaquizafop, cyhalofop-butyl, metamifop, clodinafop-propargyl, fenthiaprop-ethyl, chloroazifop-propynyl, poppenate-methyl, trifopsime, isoxapyrifop, paraquat, diquat, oryzalin, ethalfluralin, isopropalin, nitralin, profluralin, prodinamine, benfluralin, fluchloraline, dinitramina, dipropalin, chlornidine, methalpropalin, dinoprop, glyphosate, anilofos, glufosinate ammonium, amiprophos-methyl, sulphosate, piperophos, bialaphos-sodium, bensulide, butamifos, phocarb, 2,4-DEP, H-9201, zytron, imazapyr, imazethapyr, imazaquin, imazamox, imazamox ammonium salt, imazapic, imazamethabenz-methyl, fluroxypyr, fluroxypyr isooctyl ester, clopyralid, picloram, trichlopyr, dithiopyr, haloxydine, 3,5,6-trichloro-2-pyridinol, thiazopyr, fluridone, aminopyralid, diflufenzopyr, triclopyr-butotyl, Cliodinate, sethoxydim, clethodim, cycloxydim, alloxydim, clefoxydim, butroxydim, tralkoxydim, tepraloxydim, buthidazole, metribuzin, hexazinone, metamitron, ethiozin, ametridione, amibuzin, bromoxynil, bromoxynil octanoate, ioxynil octanoate, ioxynil, dichlobenil, diphenatrile, pyraclonil, chloroxynil, iodobonil, flumetsulam, florasulam, penoxsulam, metosulam, cloransulam-methyl, diclosulam, pyroxsulam, benfuresate, bispyribac-sodium, pyribenzoxim, pyriftalid, pyriminobac-methyl, pyrithiobac-sodium, benzobicylon, mesotrione, sulcotrione, tembotrione, tefuryltrione, bicyclopyrone, ketodpiradox, isoxaflutole, clomazone, fenoxasulfone, methiozolin, fluazolate, pyraflufen-ethyl, pyrazolynate, difenzoquat, pyrazoxyfen, benzofenap, nipyraclofen, pyrasulfotole, topramezone, pyroxasulfone, cafenstrole, flupoxam, aminotriazole, amicarbazone, azafenidin, carfentrazone-ethyl, sulfentrazone, bencarbazone, benzfendizone, butafenacil, bromacil, isocil, lenacil, terbacil, flupropacil, cinidon-ethyl, flumiclorac-pentyl, flumioxazin, propyzamide, MK-129, flumezin, pentachlorophenol, dinoseb, dinoterb, dinoterb acetate, dinosam, DNOC, chloronitrophene, medinoterb acetate, dinofenate, oxadiargyl, oxadiazon, pentoxazone, Flufenacet, fluthiacet-methyl, fentrazamide, flufenpyr-ethyl, pyrazon, brompyrazon, metflurazon, kusakira, dimidazon, oxapyrazon, norflurazon, pyridafol, quinclorac, quinmerac, bentazone, pyridate, oxaziclomefone, benazolin, clomazone, cinmethylin, ZJ0702, pyribambenz-propyl, indanofan, sodium chlorate, dalapon, trichloroacetic acid, monochloroacetic acid, hexachloroacetone, flupropanate, cyperquat, bromofenoxim, epronaz, methazole, flurtamone, benfuresate, ethofumesate, tioclorim, chlorthal, fluorochloridone, tavron, acrolein, bentranil, tridiphane, chlorfenpropmethyl, thidiarizonaimin, phenisopham, busoxinone, methoxyphenone, saflufenacil, clacyfos, chloropon, alorac, diethamquat, etnipromid, iprymidam, ipfencarbazone, thiencarbazone-methyl, pyrimisulfan, chlorflurazole, tripropindan, sulglycapin, prosulfalin, cambendichlor, aminocyclopyrachlor, rodethanil, benoxacor, fenclorim, flurazole, fenchlorazole-ethyl, cloquintocet-mexyl, oxabetrinil, MG/91, cyometrinil, DKA-24, mefenpyr-diethyl, furilazole, fluxofenim, isoxadifen-ethyl, dichlormid, halauxifen-methyl, DOW florpyrauxifen, UBH-509, D489, LS 82-556, KPP-300, NC-324, NC-330, KH-218, DPX-N8189, SC-0744, DOWCO535, DK-8910, V-53482, PP-600, MBH-001, KIH-9201, ET-751, KIH-6127 and KIH-2023.

For use, Formulations which are present in commercially available form are, if appropriate, diluted in the customary manner, for example using water in the case of wettable powders, emulsifiable concentrates, dispersions and water-dispersible granules. Products in the form of dusts, granules for soil application or broadcasting and sprayable solutions are usually not further diluted with other inert substances prior to use. The application rate of the compound of Formula I or derivative thereof required varies with the external conditions, such as temperature, humidity, the nature of the herbicide used and the like. It can vary within wide limits, for example between 0.001 and 2.0 kg/ha or more of active substance, but it is preferably between 0.005 and 1.20 kg/ha.

SPECIFIC MODE FOR CARRYING OUT THE INVENTION

The following embodiments are used to illustrate the present invention in detail and should not be taken as any limit to the present invention. The scope of the invention would be explained through the Claims.

In view of economics, variety and biological activity of a compound, we preferably synthesized several compounds, part of which are listed in the following table 1-3. The structure and information of a certain compound are shown in Table 1-3. The compounds in Table 1-3 are listed for further explication of the present invention, other than any limit therefor. The subject of the present invention should not be interpreted by those skilled in the art as being limited to the following compounds.

TABLE 1

Structures and $^1$HNMR data of Compounds I

| NO. | X | Y | Z | $^1$HNMR |
|---|---|---|---|---|
| 1 | 4-cyanophenyl | CF$_3$ | F | $^1$H NMR (500 MHz, DMSO-d$_6$) δ 14.50 (s, 1H), 7.97 (d, J = 7.5 Hz, 2H), 7.77 (d, J = 1.5 Hz, 2H). |
| 2 | 4-cyanophenyl | CF$_3$ | Cl | $^1$H NMR (500 MHz, DMSO-d$_6$ δ 14.42 (s, 1H), 8.25 (d, J = 7.5 Hz, 2H), 7.75 (d, J = 7.5 Hz, 2H). |
| 3 | 4-cyanophenyl | CF$_3$ | Br | $^1$H NMR (500 MHz, DMSO-d$_6$) δ 14.45 (s, 1H), 8.20 (d, J = 8.0 Hz, 2H), 7.94 (d, J = 8.0 Hz, 2H). |
| 4 | 4-cyanophenyl | CF$_3$ | I | $^1$H NMR (500 MHz, DMSO-d$_6$) δ 14.42 (s, 1H), 8.25 (d, J = 8.0 Hz, 2H), 7.95 (d, J = 8.0 Hz, 2H). |
| 5 | 4-cyanophenyl | CF$_3$ | Me | $^1$H NMR (500 MHz, DMSO-d$_6$) δ 14.40 (s, 1H), 8.25 (d, J = 8.0 Hz, 2H), 7.94 (d, J = 8.0 Hz, 2H), 2.15 (s, 3H). |

TABLE 1-continued

Structures and ¹HNMR data of Compounds I

| NO. | X | Y | Z | ¹HNMR |
|---|---|---|---|---|
| 6 | 4-CN-phenyl | $CF_3$ | Et | ¹H NMR (500 MHz, DMSO-$d_6$) δ 14.42 (s, 1H), 8.25 (d, J = 8.0 Hz, 2H), 7.95 (d, J = 8.0 Hz, 2H), 2.81 (q, J = 8.0 Hz, 2H), 1.30 (t, J = 8.0 Hz, 3H). |
| 7 | 4-CN-phenyl | $CF_3$ | cyclopropyl | ¹H NMR (500 MHz, DMSO-$d_6$) δ 14.49 (s, 1H), 8.16 (d, J = 7.5 Hz, 2H), 7.92 (d, J = 7.5 Hz, 2H), 1.70-1.67 (m, 1H), 1.35-1.32 (m, 2H), 0.89-0.85 (m, 2H). |
| 8 | 4-CN-phenyl | $CF_3$ | CN | ¹H NMR (500 MHz, DMSO-$d_6$) δ 14.42 (s, 1H), 8.25 (d, J = 8.0 Hz, 2H), 7.85 (d, J = 8.0 Hz, 2H). |
| 9 | 4-CN-phenyl | $CF_3$ | vinyl | ¹H NMR (500 MHz, DMSO-$d_6$) δ 14.43 (s, 1H), 8.20 (d, J = 8.0 Hz, 2H), 7.92 (d, J = 8.0 Hz, 2H), 6.91-6.78 (m, 1H), 6.62-6.56 (m, 1H), 5.77 (dd, 12.0, 2.5 Hz, 1H). |
| 10 | 4-CN-phenyl | $CF_3$ | isopropenyl | ¹H NMR (500 MHz, DMSO-$d_6$) δ 14.50 (s, 1H), 8.21 (d, J = 8.0 Hz, 2H), 7.92 (d, J = 8.0 Hz, 2H), 5.30 (s, 1H), 4.91 (s, 1H), 1.94 (s, 3H). |
| 11 | 4-CN-phenyl | $CF_3$ | ethynyl | ¹H NMR (500 MHz, DMSO-$d_6$) δ 14.42 (s, 1H), 8.20 (d, J = 8.0 Hz, 2H), 7.84 (d, J = 8.0 Hz, 2H), 3.56 (s, 1H). |
| 12 | 4-CN-phenyl | $CF_3$ | OMe | ¹H NMR (500 MHz, DMSO-$d_6$) δ 14.45 (s, 1H), 8.23 (d, J = 8.0 Hz, 2H), 7.97 (d, J = 8.0 Hz, 2H), 4.03 (s, 3H). |
| 13 | 4-CN-phenyl | $CF_3$ | OEt | ¹H NMR (500 MHz, DMSO-$d_6$) δ 14.45 (s, 1H), 8.24 (d, J = 8.0 Hz, 2H), 7.97 (d, J = 8.0 Hz, 2H), 4.29 (q, J = 7.5 Hz, 2H), 1.45 (t, J = 7.5 Hz, 3H). |
| 14 | 4-CN-phenyl | $CF_3$ | OCH$_2$CF$_3$ | ¹H NMR (500 MHz, DMSO-$d_6$) δ 14.43 (s, 1H), 8.23 (d, J = 8.0 Hz, 2H), 7.96 (d, J = 8.0 Hz, 2H), 4.89 (q, J = 8.0 Hz, 2H). |

TABLE 1-continued

Structures and ¹HNMR data of Compounds I

| NO. | X | Y | Z | ¹HNMR |
|---|---|---|---|---|
| 15 | 4-CN-C₆H₄- | CF₃ | OH | ¹H NMR (500 MHz, DMSO-d₆) δ 14.39 (s, 1H), 14.18 (s, 1H), 8.00 (d, J = 8.0 Hz, 2H), 7.92 (d, J = 8.0 Hz, 2H). |
| 16 | 4-CN-C₆H₄- | CF₃ | NH₂ | ¹H NMR (500 MHz, DMSO-d₆) δ 14.35 (s, 1H), 8.31 (d, J = 8.0 Hz, 2H), 7.94 (d, J = 8.0 Hz, 2H), 6.84 (s, 2H). |
| 17 | 4-CN-C₆H₄- | CF₃ | NHMe | ¹H NMR (500 MHz, DMSO-d₆) δ 14.50 (s, 1H), 7.99 (d, J = 7.5 Hz, 2H), 7.75 (d, J = 7.5 Hz, 2H), 5.95 (s, 1H), 2.72 (s, 3H). |
| 18 | 4-CN-C₆H₄- | CF₃ | N(Me)₂ | ¹H NMR (500 MHz, DMSO-d₆) δ 14.43 (s, 1H), 8.20 (d, J = 8.0 Hz, 2H), 7.96 (d, J = 8.0 Hz, 2H), 2.89 (s, 6H) |
| 19 | 4-CN-C₆H₄- | CF₃ | NHAc | ¹H NMR (500 MHz, DMSO-d₆) δ 14.45 (s, 1H), 9.94 (s, 1H), 8.20 (d, J = 8.0 Hz, 2H), 7.96 (d, J = 8.0 Hz, 2H), 2.07 (s, 3H) |
| 20 | 4-CN-C₆H₄- | CF₃ | NHC(O)N(Me)₂ | ¹H NMR (500 MHz, DMSO-d₆) δ Hz, 2H), 7.96 (d, J = 8.0 Hz, 2H), 2.95 (s, 6H) |
| 21 | 4-CN-C₆H₄- | CF₃ | NHPh | ¹H NMR (500 MHz, DMSO-d₆) δ 14.50 (s, 1H), 10.29 (s, 1H), 8.06 (d, J = 8.0 Hz, 2H), 7.74 (d, J = 8.0 Hz, 2H), 7.44-7.36 (m, 2H), 7.31-7.24 (m, 2H), 7.02 (tt, J = 7.5, 2.0 Hz, 1H). |
| 22 | 4-CN-C₆H₄- | CF₃ | 2-oxopyrrolidin-1-yl | ¹H NMR (500 MHz, DMSO-d₆) δ 14.43 (s, 1H), 8.22 (d, J = 8.0 Hz, 2H), 7.94 (d, J = 8.0 Hz, 2H), 3.91-3.86 (m, 2H), 2.48 (t, J = 5.5 Hz, 2H), 2.06-1.98 (m, 2H). |

TABLE 1-continued

Structures and ¹HNMR data of Compounds I

[Structure: pyridazine core with Y at position 6, Z at position 5, OH at position 4, X at position 3]

| NO. | X | Y | Z | ¹HNMR |
|---|---|---|---|---|
| 23 | 4-cyanophenyl | CF$_3$ | 2-oxopiperidin-1-yl | ¹H NMR (500 MHz, DMSO-d$_6$) δ 14.44 (s, 1H), 8.23 (d, J = 8.0 Hz, 2H), 7.92 (d, J = 8.0 Hz, 2H), 4.06 (t, J = 5.5 Hz, 2H), 2.46 (t, J = 6.5 Hz, 2H), 1.85-1.61 (m, 4H). |
| 24 | 4-cyanophenyl | CF$_3$ | 3,5-dimethyl-1H-pyrazol-1-yl | ¹H NMR (500 MHz, DMSO-d$_6$) δ 14.43 (s, 1H), 8.20 (d, J = 8.0 Hz, 2H), 7.96 (d, J = 8.0 Hz, 2H), 5.91 (s, 1H), 2.15 (s, 3H), 2.10 (s, 3H). |
| 25 | 4-cyanophenyl | CF$_3$ | 1H-pyrazol-1-yl | ¹H NMR (500 MHz, DMSO-d$_6$) δ 14.45 (s, 1H), 8.21 (d, J = 8.0 Hz, 2H), 7.96 (d, J = 8.0 Hz, 2H), 7.70 (d, J = 4.0 Hz, 1H), 7.53 (d, J = 2.5 Hz, 1H), 6.45 (dd, J = 4.0, 2.5 Hz, 1H). |
| 26 | 4-cyanophenyl | CF$_3$ | SMe | ¹H NMR (500 MHz, DMSO-d$_6$) δ 14.45 (s, 1H), 8.23 (d, J = 8.0 Hz, 2H), 7.97 (d, J = 8.0 Hz, 2H), 2.57 (s, 3H). |
| 27 | 4-cyanophenyl | CF$_3$ | SEt | ¹H NMR (500 MHz, DMSO-d$_6$) δ 14.46 (s, 1H), 8.24 (d, J = 8.0 Hz, 2H), 7.96 (d, J = 8.0 Hz, 2H), 3.07 (q, J = 7.5 Hz, 2H), 1.11 (t, J = 7.5 Hz, 3H). |
| 28 | 4-cyanophenyl | CF$_3$ | SOEt | ¹H NMR (500 MHz, DMSO-d$_6$) δ 14.45 (s, 1H), 7.96 (d, J = 8.0 Hz, 2H), 7.74 (d, J = 8.0 Hz, 2H), 2.61 (q, J = 8.0 Hz, 2H), 1.33 (t, J = 8.0 Hz, 3H). |
| 29 | 4-cyanophenyl | CF$_3$ | SO$_2$Et | ¹H NMR (500 MHz, DMSO-d$_6$) δ 14.50 (s, 1H), 8.25 (d, J = 8.0 Hz, 2H), 7.96 (d, J = 8.0 Hz, 2H), 3.57 (q, J = 7.5 Hz, 2H), 1.17 (t, J = 7.5 Hz, 3H). |
| 30 | 4-cyanophenyl | CF$_3$ | Ph | ¹H NMR (500 MHz, DMSO-d$_6$) δ 14.44 (s, 1H), 8.23 (d, J = 8.0 Hz, 2H), 7.92 (d, J = 8.0 Hz, 2H), 7.35-7.23 (m, 5H). |

TABLE 1-continued

Structures and ¹HNMR data of Compounds I

[Structure: pyridazine core with Y at position 6, Z at position 5, OH at position 4, X at position 3]

| NO. | X | Y | Z | ¹HNMR |
|---|---|---|---|---|
| 31 | 4-cyanophenyl | CF$_3$ | 4-fluorophenyl | ¹H NMR (500 MHz, DMSO-d$_6$) δ 14.54 (s, 1H), 8.23 (d, J = 8.0 Hz, 2H), 7.92 (d, J = 8.0 Hz, 2H), 7.35-7.23 (m, 4H). |
| 32 | 4-cyanophenyl | CF$_3$ | 4-cyanophenyl | ¹H NMR (500 MHz, DMSO-d$_6$) δ 14.46 (s, 1H), 8.24 (d, J = 8.0 Hz, 2H), 7.94 (d, J = 8.0 Hz, 2H), 7.91 (d, J = 8.0 Hz, 2H), 7.49 (d, J = 8.0 Hz, 2H). |
| 33 | 4-cyanophenyl | CF$_3$ | pyridin-2-yl | ¹H NMR (500 MHz, DMSO-d$_6$) δ 14.40 (s, 1H), 8.74-8.70 (m, 1H), 8.06-7.99 (m, 2H), 7.91-7.88 (m, 1H), 7.86-7.78 (m, 3H), 7.53-7.49 (m, 1H). |
| 34 | 4-cyanophenyl | CF$_3$ | pyridin-3-yl | ¹H NMR (500 MHz, DMSO-d$_6$) δ 14.44 (s, 1H), 8.64 (dd, J = 5.0, 1.5 Hz, 1H), 8.50 (d, J = 1.5 Hz, 1H), 8.28 (d, J = 8.0 Hz, 2H), 7.96 (d, J = 8.0 Hz, 2H), 7.78 (d, J = 8.0 Hz, 1H), 7.54 (dd, J = 8.0, 5.0 Hz, 1H). |
| 35 | 4-cyanophenyl | CF$_3$ | pyridin-4-yl | ¹H NMR (500 MHz, DMSO-d$_6$) δ 14.45 (s, 1H), 8.68 (d, J = 5.0 Hz, 2H), 8.08-8.01 (m, 2H), 7.75-7.73 (m, 4H). |
| 36 | 4-cyanophenyl | CF$_3$ | 1-methyl-1H-pyrazol-4-yl | ¹H NMR (500 MHz, DMSO-d$_6$) δ 14.45 (s, 1H), 8.68 (d, J = 5.0 Hz, 2H), 7.87-7.81 (m, 3H), 7.77 (s, 1H), 3.95 (s, 3H). |
| 37 | 4-cyanophenyl | CF$_3$ | thiophen-2-yl | ¹H NMR (500 MHz, DMSO-d$_6$) δ 14.45 (s, 1H), 8.23 (d, J = 8.0 Hz, 2H), 7.93 (d, J = 8.0 Hz, 2H), 7.78 (dd, J = 5.0, 2.0 Hz, 1H), 7.15-7.14 (m, 2H). |

TABLE 1-continued

Structures and ¹HNMR data of Compounds I

| NO. | X | Y | Z | ¹HNMR |
|---|---|---|---|---|
| 38 | 4-CN-phenyl | CF$_3$ | thiophen-3-yl | ¹H NMR (500 MHz, DMSO-d$_6$) δ 14.50 (s, 1H), 8.22 (d, J = 8.0 Hz, 2H), 7.93 (d, J = 8.0 Hz, 2H), 7.61-7.60 (m, 1H), 7.55 (s, 1H), 7.09 (d, J = 5.0 Hz, 1H). |
| 39 | 4-CN-phenyl | CF$_3$ | thiazol-5-yl | ¹H NMR (500 MHz, DMSO-d$_6$) δ 14.50 (s, 1H), 8.96 (s, 1H), 8.23 (s, 1H), 8.00-7.93 (m, 2H), 7.86-7.80 (m, 2H). |
| 40 | 4-CN-phenyl | CF$_3$ | furan-2-yl | ¹H NMR (500 MHz, DMSO-d$_6$) δ 14.46 (s, 1H), 8.04-7.98 (m, 2H), 7.86-7.80 (m, 3H), 6.97-6.95 (m, 1H), 6.66-6.62 (m, 1H). |
| 41 | 4-CN-phenyl | CF$_3$ | furan-3-yl | ¹H NMR (500 MHz, DMSO-d$_6$) δ 14.55 (s, 1H), 8.05 (d, J = 8.0 Hz, 2H), 7.74 (d, J = 8.0 Hz, 2H), 7.50 (d, J = 7.5 Hz, 2H), 6.49-6.47 (m, 1H). |
| 42 | 4-CN-phenyl | CF$_3$ | phenoxy | ¹H NMR (500 MHz, DMSO-d$_6$) δ 14.45 (s, 1H), 8.23 (d, J = 8.0 Hz, 2H), 7.92 (d, J = 8.0 Hz, 2H), 7.28 (t, J = 7.5 Hz, 2H), 7.06-7.02 (m, 1H), 7.00 (d, J = 8.0 Hz, 2H). |
| 43 | 4-CN-phenyl | CF$_3$ | (1-methyl-1H-pyrazol-5-yl)oxy | ¹H NMR (500 MHz, DMSO-d$_6$) δ 14.48 (s, 1H), 8.06 (d, J = 8.0 Hz, 2H), 7.74 (d, J = 8.0 Hz, 2H), 7.61 (d, J = 7.5 Hz, 1H), 6.14 (d, J = 7.5 Hz, 1H), 3.76 (s, 3H). |
| 44 | 1-(difluoromethyl)-1H-pyrazol-4-yl | CF$_3$ | F | ¹H NMR (500 MHz, DMSO-d$_6$) δ 14.49 (s, 1H), 7.96-7.68 (m, 2H), 7.09 (s, 1H). |
| 45 | 1-(difluoromethyl)-1H-pyrazol-4-yl | CF$_3$ | Cl | ¹H NMR (500 MHz. DMSO-d$_6$) δ 14.42 (s, 1H), 9.20 (s, 1H), 8.48 (s, 1H), 7.97 (t, J = 58.5 Hz, 1H). |

TABLE 1-continued

Structures and ¹HNMR data of Compounds I

| NO. | X | Y | Z | ¹HNMR |
|---|---|---|---|---|
| 46 | pyrazole-N-CHF₂ | $CF_3$ | Br | ¹H NMR (500 MHz, DMSO-d₆) δ 14.42 (s, 1H), 9.20 (s, 1H), 8.47 (s, 1H), 7.96 (t, J = 58.5 Hz, 1H). |
| 47 | pyrazole-N-CHF₂ | $CF_3$ | I | ¹H NMR (500 MHz, DMSO-d₆) δ 14.42 (s, 1H), 9.18 (s, 1H), 8.44 (s, 1H), 7.95 (t, J = 58.5 Hz, 1H). |
| 48 | pyrazole-N-CHF₂ | $CF_3$ | Me | ¹H NMR (500 MHz, DMSO-d₆) δ 14.24 (s, 1H), 9.12 (s, 1H), 8.41 (s, 1H), 7.94 (t, J = 58.5 Hz, 1H), 2.16 (s, 3H). |
| 49 | pyrazole-N-CHF₂ | $CF_3$ | Et | ¹H NMR (500 MHz, DMSO-d₆) δ 14.51 (s, 1H), 9.12 (s, 1H), 8.41 (s, 1H), 7.94 (t, J = 58.5 Hz, 1H), 2.70 (q, J = 8.0 Hz, 2H), 1.22 (t, J = 8.0 Hz, 3H). |
| 50 | pyrazole-N-CHF₂ | $CF_3$ | cyclopropyl | ¹H NMR (500 MHz, DMSO-d₆) δ 14.30 (s, 1H), 9.08 (s, 1H), 8.35 (s, 1H), 7.90 (t, J = 58.5 Hz, 1H), 1.69 (s, 1H), 1.50-1.28 (m, 2H), 0.88-0.85 (m, 2H). |
| 51 | pyrazole-N-CHF₂ | $CF_3$ | CN | ¹H NMR (500 MHz, DMSO-d6) δ 14.49 (s, 1H), 9.12 (s, 1H), 8.41 (s, 1H), 7.94 (t, J = 58.5 Hz, 1H). |
| 52 | pyrazole-N-CHF₂ | $CF_3$ | vinyl | ¹H NMR (500 MHz, DMSO-d6) δ 14.42 (s, 1H), 9.17 (s, 1H), 8.41 (s, 1H), 7.90 (t, J = 59.0 Hz, 1H), 7.06 (dd, J = 17.0, 3.5 Hz, 1H), 6.64-6.58 (m, 1H), 5.52 (dd, J = 17.0, 3.5 Hz, 1H). |
| 53 | pyrazole-N-CHF₂ | $CF_3$ | isopropenyl | ¹H NMR (500 MHz, DMSO-d₆) δ 14.38 (s, 1H), 9.10 (s, 1H), 8.40 (s, 1H), 7.93 (t, J = 58.5 Hz, 1H), 5.32 (s, 1H), 4.91 (s, 1H), 1.97 (s, 3H). |

TABLE 1-continued

Structures and ¹HNMR data of Compounds I

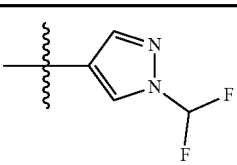

| NO. | X | Y | Z | ¹HNMR |
|---|---|---|---|---|
| 54 | 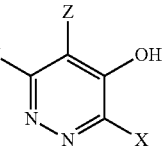 | CF₃ | 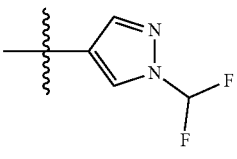 [SMILES: *c1cnn(C(F)F)c1] | ¹H NMR (500 MHz, DMSO-d6) δ 14.48 (s, 1H), 9.12 (s, 1H), 8.41 (s, 1H), 7.94 (t, J = 58.5 Hz, 1H), 4.43 (s, 1H). |
| 55 | 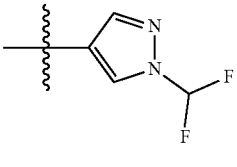 [SMILES: *c1cnn(C(F)F)c1] | CF₃ | OMe | ¹H NMR (500 MHz, DMSO-d6) δ 14.48 (s, 1H), 9.10 (s, 1H), 8.40 (s, 1H), 7.93 (t, J = 58.5 Hz, 1H), 3.86 (s, 3H). |
| 56 | 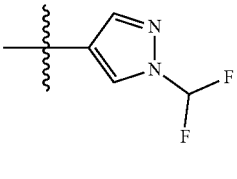 [SMILES: *c1cnn(C(F)F)c1] | CF₃ | OEt | ¹H NMR (500 MHz, DMSO-d6) δ 14.48 (s, 1H), 9.10 (s, 1H), 8.42 (s, 1H), 7.93 (t, J = 58.5 Hz, 1H), 4.10 (q, J = 8.0 Hz, 2H), 1.34 (t, J = 8.0 Hz, 3H). |
| 57 | 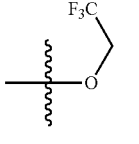 [SMILES: *OCC(F)(F)F] | CF₃ | 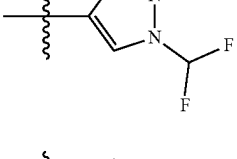 | ¹H NMR (500 MHz, DMSO-d6) δ 14.48 (s, 1H), 9.10 (s, 1H), 8.40 (s, 1H), 7.93 (t, J = 58.5 Hz, 1H), 5.05 (q, J = 8.0 Hz, 2H). |
| 58 | 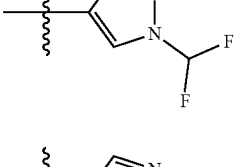 | CF₃ | OH | ¹H NMR (500 MHz, DMSO-d6) δ 14.43 (s, 1H), 14.48 (s, 1H), 9.10 (s, 1H), 8.40 (s, 1H), 7.93 (t, J = 58.5 Hz, 1H). |
| 59 | 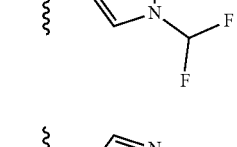 | CF₃ | NH₂ | ¹H NMR (500 MHz, DMSO-d6) δ 14.48 (s, 1H), 9.16 (s, 1H), 8.56 (s, 1H), 7.96 (t, J = 58.5 Hz, 1H), 6.88 (s, 2H). |
| 60 | 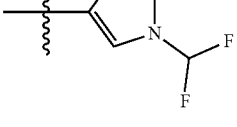 | CF₃ | NHMe | ¹H NMR (500 MHz, DMSO-d6) δ 14.42 (s, 1H), 9.14 (s, 1H), 8.56 (s, 1H), 7.96 (t, J = 58.5 Hz, 1H), 5.95 (s, 1H), 2.69 (s, 3H). |
| 61 | 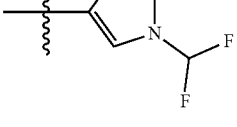 | CF₃ | N(Me)₂ | ¹H NMR (500 MHz, DMSO-d6) δ 14.50 (s, 1H). 9.10 (s, 1H), 8.36 (s, 1H), 7.93 (t, J = 58.5 Hz, 1H), 2.95 (s, 6H). |

TABLE 1-continued

Structures and ¹HNMR data of Compounds I

| NO. | X | Y | Z | ¹HNMR |
|---|---|---|---|---|
| 62 | pyrazole-CHF₂ | CF₃ | C(CH₃)₂NHAc | ¹H NMR (500 MHz, DMSO-d6) δ 14.42 (s, 1H), 9.61 (s, 1H), 9.09 (s, 1H), 8.48 (s, 1H), 7.97 (t, J = 59.0 Hz, 1H), 2.07 (s, 3H). |
| 63 | pyrazole-CHF₂ | CF₃ | C(CH₃)₂NHC(O)N(CH₃)₂ | ¹H NMR (500 MHz, DMSO-d6) δ 14.49 (s, 1H), 9.10 (s, 1H), 8.36 (s, 1H), 7.93 (t, J = 58.5 Hz, 1H), 7.08 (s, 1H), 3.18 (s, 6H). |
| 64 | pyrazole-CHF₂ | CF₃ | C(CH₃)₂NHPh | ¹H NMR (500 MHz, DMSO-d6) δ 14.49 (s, 1H), 10.29 (s, 1H), 9.10 (s, 1H), 8.36 (s, 1H), 7.93 (t, J = 58.5 Hz, 1H), 7.40-7.32 (m, 3H), 7.28-7.24 (m, 2H). |
| 65 | pyrazole-CHF₂ | CF₃ | 2-oxopyrrolidin-1-yl | ¹H NMR (500 MHz, DMSO-d6) δ 14.48 (s, 1H), 9.17 (s, 1H), 8.36 (s, 1H), 7.94 (t, J = 58.5 Hz, 1H), 3.55-3.52 (m, 2H), 2.19-2.02 (m, 2H), 1.86-1.83 (m, 2H). |
| 66 | pyrazole-CHF₂ | CF₃ | 2-oxopiperidin-1-yl | ¹H NMR (500 MHz, DMSO-d6) δ 14.48 (s, 1H), 9.13 (s, 1H), 8.34 (s, 1H), 7.89 (t, J = 58.5 Hz, 1H), 3.55-3.52 (m, 2H), 2.28-2.25 (m, 2H), 1.80-1.59 (m, 4H). |
| 67 | pyrazole-CHF₂ | CF₃ | 3,5-dimethylpyrazol-1-yl | ¹H NMR (500 MHz, DMSO-d6) δ 14.48 (s, 1H), 9.16 (s, 1H), 8.32 (s, 1H), 7.91 (t, J = 58.5 Hz, 1H), 5.85 (s, 1H), 2.20 (s, 3H), 1.96 (s, 3H). |
| 68 | pyrazole-CHF₂ | CF₃ | pyrazol-1-yl | ¹H NMR (500 MHz, DMSO-d6) δ 14.48 (s, 1H), 9.13 (s, 1H), 8.34 (s, 1H), 7.93 (t, J = 58.5 Hz, 1H) 7.85-7.63 (m, 2H), 7.13 (s, 1H). |
| 69 | pyrazole-CHF₂ | CF₃ | SMe | ¹H NMR (500 MHz, DMSO-d6) δ 14.48 (s, 1H), 9.17 (s, 1H), 8.39 (s, 1H), 7.91 (t, J = 58.5 Hz, 1H), 2.48 (s, 3H), |

TABLE 1-continued

Structures and ¹HNMR data of Compounds I

| NO. | X | Y | Z | ¹HNMR |
|---|---|---|---|---|
| 70 | pyrazole-CHF₂ | CF₃ | SEt | ¹H NMR (500 MHz, DMSO-d₆) δ 14.28 (s, 1H), 9.16 (s, 1H), 8.42 (s, 1H), 7.93 (t, J = 58.5 Hz, 1H), 3.06 (q, J = 7.5 Hz, 2H), 1.07 (t, J = 7.5 Hz, 3H). |
| 71 | pyrazole-CHF₂ | CF₃ | SOEt | ¹H NMR (500 MHz, DMSO-d6) δ 14.50 (s, 1H), 9.16 (s, 1H), 8.42 (s, 1H), 7.93 (t, J = 58.5 Hz, 1H), 2.61 (q, J = 8.0 Hz, 2H), 1.33 (t, J = 8.0 Hz, 3H). |
| 72 | pyrazole-CHF₂ | CF₃ | SO₂Et | ¹H NMR (500 MHz, DMSOd6) δ 14.49 (s, 1H), 9.16 (s, 1H), 8.42 (s, 1H), 7.93 (t, J = 58.5 Hz, 1H), 3.51 (q, J = 8.0 Hz, 2H), 1.32 (t, J = 8.0 Hz, 3H). |
| 73 | pyrazole-CHF₂ | CF₃ | Ph | ¹H NMR (500 MHz, DMSO-d6) δ 14.47 (s, 1H), 9.16 (s, 1H), 8.42 (s, 1H), 7.93 (t, J = 58.5 Hz, 1H), 7.57-7.53 (m, 2H), 7.46-7.35 (m, 3H). |
| 74 | pyrazole-CHF₂ | CF₃ | 4-F-C₆H₄ | ¹H NMR (500 MHz, DMSO-d6) δ 14.49 (s, 1H), 9.16 (s, 1H), 8.42 (s, 1H), 7.93 (t, J = 58.5 Hz, 1H), 7.48-7.39 (m, 2H), 7.23-7.13 (m, 2H). |
| 75 | pyrazole-CHF₂ | CF₃ | 4-NC-C₆H₄ | ¹H NMR (500 MHz, DMSO-d6) δ 14.43 (s, 1H), 9.16 (s, 1H), 8.42 (s, 1H), 7.93 (t, J = 58.5 Hz, 1H), 7.55-7.49 (m, 2H), 7.33-7.26 (m, 2H). |
| 76 | pyrazole-CHF₂ | CF₃ | 2-pyridyl | ¹H NMR (500 MHz, DMSO-d6) δ 14.48 (s, 1H), 9.16 (s, 1H), 8.59-8.55 (m, 1H), 8.42 (s, 1H), 7.92-7.71 (m, 3H), 7.40-7.35 (m, 1H), |
| 77 | pyrazole-CHF₂ | CF₃ | 3-pyridyl | ¹H NMR (500 MHz, DMSO-d6) δ 14.45 (s, 1H), 9.16 (s, 1H), 8.79 (s, 1H), 8.59-8.55 (m, 2H), 8.42 (s, 1H), 7.93 (t, J = 58.5 Hz, 1H), 7.48-7.45 (m, 1H). |

TABLE 1-continued

Structures and ¹HNMR data of Compounds I

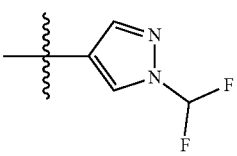 [SMILES: *c1cnn(C(F)F)c1]

| NO. | X | Y | Z | ¹HNMR |
|---|---|---|---|---|
| 78 | 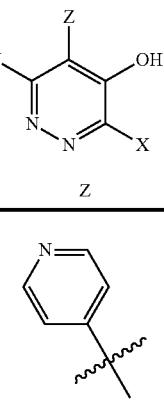 | CF₃ | 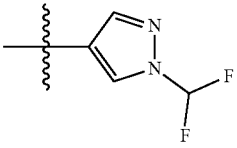 [SMILES: *c1cnn(C(F)F)c1] | ¹H NMR (500 MHz, DMSO-d6) δ 14.48 (s, 1H), 9.16 (s, 1H), 8.68 (d, J = 5.0 Hz, 2H), 8.43 (s, 1H), 7.93 (t, J = 58.5 Hz, 1H), 7.66 (d, J = 5.0 Hz, 2H), |
| 79 | 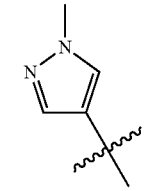 | CF₃ | 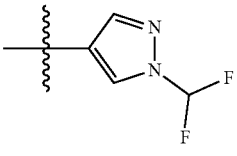 [SMILES: *c1cnn(C(F)F)c1] | ¹H NMR (500 MHz, DMSO-d6) δ 14.49 (s, 1H), 9.17 (s, 1H), 8.42 (s, 1H), 7.93 (t, J = 58.5 Hz, 1H), 7.89 (s, 1H), 6.85 (s, 1H), 3.92 (s, 3H). |
| 80 | 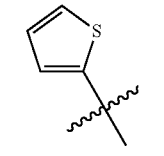 [SMILES: *c1cccs1] | CF₃ | 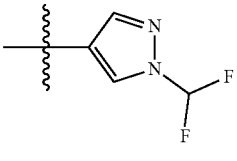 [SMILES: *c1cnn(C(F)F)c1] | ¹H NMR (500 MHz, DMSO-d6) δ 14.46 (s, 1H), 9.14 (s, 1H), 8.41 (s, 1H), 7.98-7.66 (m, 2H), 7.39-7.36 (m, 1H), 7.13-7.10 (m, 1H). |
| 81 | 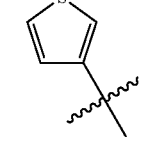 | CF₃ | 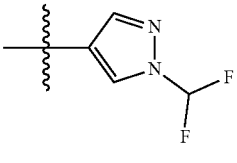 [SMILES: *c1cnn(C(F)F)c1] | ¹H NMR (500 MHz, DMSO-d6) δ 14.49 (s, 1H), 9.16 (s, 1H), 8.40 (s, 1H), 7.92 (t, J = 58.5 Hz, 1H), 7.78-7.71 (m, 1H), 7.65 (s, 1H), 7.25-7.20 (m, 1H). |
| 82 | 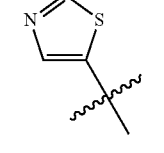 | CF₃ | 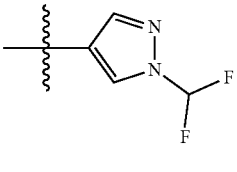 [SMILES: *c1cnn(C(F)F)c1] | ¹H NMR (500 MHz, DMSO-d6) δ 14.46 (s, 1H), 9.16 (s, 1H), 9.10 (s, 1H), 8.40 (s, 1H), 7.93 (t, J = 58.5 Hz, 1H), 7.78 (s, 1H). |
| 83 | 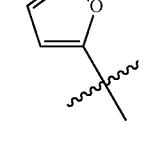 | CF₃ | 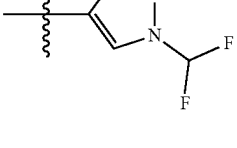 | ¹H NMR (500 MHz, DMSO-d6) δ 14.48 (s, 1H), 9.17 (s, 1H), 8.42 (s, 1H), 7.97-7.68 (m, 2H), 6.94-6.90 (m, 1H), 6.61-6.58 (m, 1H). |
| 84 | 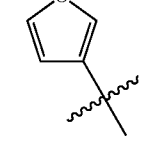 | CF₃ | 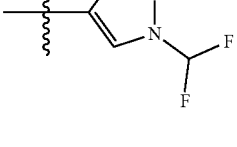 | ¹H NMR (500 MHz, DMSO-d6) δ 14.46 (s, 1H), 9.16 (s, 1H), 8.40 (s, 1H), 7.92 (t, J = 58.5 Hz, 1H), 7.55-7.44 (m, 2H), 6.47-6.43 (m, 1H). |
| 85 | 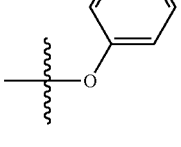 | CF₃ |  | ¹H NMR (500 MHz, DMSO-d6) δ 14.48 (s, 1H), 9.18 (s, 1H), 8.42 (s, 1H), 7.94 (t, J = 58.5 Hz, 1H), 7.32-7.12 (m, 3H), 7.04-6.84 (m, 2H). |

TABLE 1-continued

Structures and ¹HNMR data of Compounds I

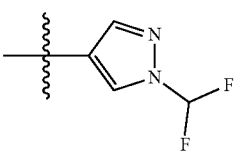 [SMILES: *c1cnn(C(F)F)c1]

| NO. | X | Y | Z | ¹HNMR |
|---|---|---|---|---|
| 86 | 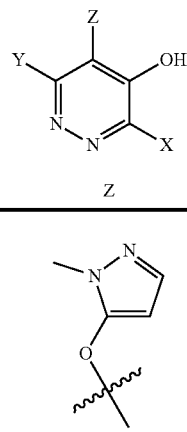 | CF₃ | 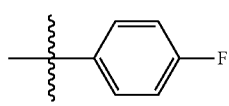 [SMILES: *c1ccc(F)cc1] | ¹H NMR (500 MHz, DMSO-d6) δ 14.49 (s, 1H), 9.16 (s, 1H), 8.40 (s, 1H), 7.92 (t, J = 58.5 Hz, 1H), 7.29 (d, J = 5.5 Hz, 1H), 6.25 (d, J = 5.5 Hz, 1H), 3.76 (s, 3H). |
| 87 | 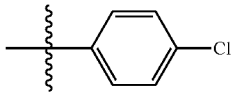 | CF₃ | Me | ¹H NMR (500 MHz, DMSO-d6) δ 14.45 (s, 1H), 7.97-7.91 (m, 2H), 7.38-7.28 (m, 2H), 2.16 (s, 3H). |
| 88 | 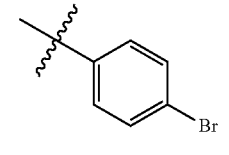 [SMILES: *c1ccc(Br)cc1] | CF₃ | Me | ¹H NMR (500 MHz, DMSO-d6) δ 14.42 (s. 1H), 7.76 (d, J = 7.5 Hz, 2H), 7.51 (d, J = 7.5 Hz, 2H), 2.15 (s, 3H). |
| 89 | 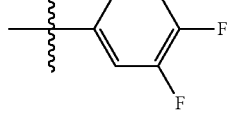 | CF₃ | Me | ¹H NMR (500 MHz, DMSO-d6) δ 14.50 (s, 1H), 7.72 (d, J = 7.5 Hz, 2H), 7.45 (d, J = 7.5 Hz, 2H), 2.25 (s, 3H). |
| 90 | 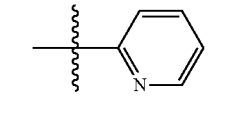 | CF₃ | Me | ¹H NMR (500 MHz, DMSO-d6) δ 14.49 (s, 1H), 7.58-7.45 (m, 2H), 7.38-7.35 (m, 1H), 2.12 (s, 3H). |
| 91 | 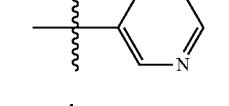 | CF₃ | Me | ¹H NMR (500 MHz, DMSO-d6) δ 14.42 (s, 1H), 8.74 (d, J = 5.0 Hz, 1H), 8.20 (d, J = 8.0 Hz, 1H), 8.02-7.99 (m, 1H), 7.62-7.56 (m, 1H), 2.16 (s, 3H). |
| 92 | 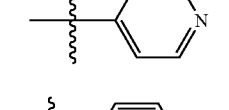 | CF₃ | Me | ¹H NMR (500 MHz, DMSO-d6) δ 14.42 (s, 1H), 8.75 (s, 1H), 8.51 (d, J = 5.0 Hz, 1H), 8.33 (d, J = 5.0 Hz, 1H), 7.57-7.52 (m, 1H), 2.17 (s, 3H). |
| 93 | 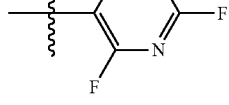 | CF₃ | Me | ¹H NMR (500 MHz, DMSO) δ 14.51 (s, 1H), 8.51 (d, J = 6.0 Hz, 2H), 8.45 (d, J = 6.0 Hz, 2H), 2.05 (s, 3H). |
| 94 | 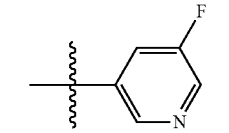 | CF₃ | Me | ¹H NMR (500 MHz, DMSO-d6) δ 14.50 (s, 1H), 8.23-8.19 (m, 1H), 7.13-7.09 (m, 1H), 2.17 (s, 3H). |
| 95 |  | CF₃ | Me | ¹H NMR (500 MHz, DMSO-d6) δ 14.49 (s, 1H), 8.67 (s, 1H), 8.46-8.42 (m, 1H), 8.24-8.20 (m, 1H), 2.15 (s,3H). |

TABLE 1-continued

Structures and ¹HNMR data of Compounds I

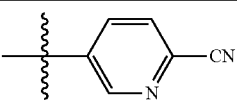

| NO. | X | Y | Z | ¹HNMR |
|---|---|---|---|---|
| 96 | 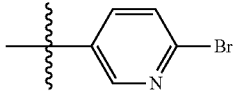 | CF$_3$ | Me | ¹H NMR (500 MHz, DMSO-d6) δ 14.53 (s, 1H), 8.78 (s, 1H), 8.11 (d, J = 8.0. 1H), 7.83 (d, J = 8.0 Hz, 1H), 2.18 (s, 3H). |
| 97 | 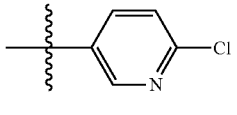 | CF$_3$ | Me | ¹H NMR (500 MHz, DMSO-d6) δ 14.46 (s, 1H), 8.58 (s, 1H), 7.80 (d, J = 8.0,1H), 7.71 (d, J = 8.0 Hz, 1H), 2.20 (s, 3H). |
| 98 | 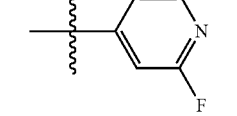 | CF$_3$ | Me | ¹H NMR (500 MHz, DMSO-d6) δ 14.45 (s, 1H), 8.53 (s, 1H), 7.89 (d, J = 8.0 Hz, 1H), 7.51 (d, J = 8.0 Hz, 1H), 2.15 (s, 3H). |
| 99 | 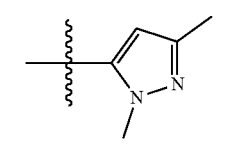 [SMILES: *c1cc(C)nn1C] | CF$_3$ | Me | ¹H NMR (500 MHz, DMSO-d$_6$) δ 14.43 (s, 1H), 8.43-8.40 (m 1H), 7.81-7.78 (m, 1H), 7.69 (d, J = 5.0 Hz, 1H), 2.13 (s, 3H). |
| 100 | 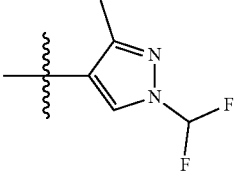 [SMILES: *c1cn(C(F)F)nc1C] | CF$_3$ | Me | ¹H NMR (500 MHz, DMSO-d6) δ 14.53 (s, 1H), 6.60 (s, 1H), 3.87 (s, 3H), 2.39 (s, 3H), 2.20 (s, 3H). |
| 101 | 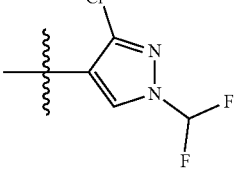 | CF$_3$ | Me | ¹H NMR (500 MHz, DMSO-d6) δ 14.45 (s, 1H), 7.84 (t, J = 57.0 Hz, 1H), 7.00 (s, 1H), 2.39 (s, 3H), 2.35 (s, 3H). |
| 102 | 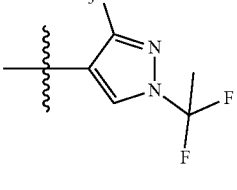 | CF$_3$ | Me | ¹H NMR (500 MHz, DMSO-d6) δ 14.48 (s, 1H), 7.86 (t, J = 57.5 Hz, 1H), 7.10 (s, 1H), 2.34 (s, 3H). |
| 103 | 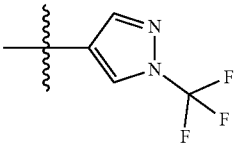 [SMILES: *c1cnn(C(F)(F)F)c1] | CF$_3$ | Me | ¹H NMR (500 MHz, DMSO-d6) δ 14.49 (s, 1H), 7.06 (s, 1H), 2.35 (s, 3H), 1.87 (s, 3H). |
| 104 |  | CF$_3$ | Me | ¹H NMR (500 MHz, DMSO-d6) δ 14.48 (s, 1H), 7.87 (s, 1H), 7.20 (s, 1H), 2.13 (s, 3H). |

TABLE 1-continued

Structures and ¹HNMR data of Compounds I

| NO. | X | Y | Z | ¹HNMR |
|---|---|---|---|---|
| 105 | (4-(1-(trifluoromethyl)-3-fluoro-1H-pyrazol-4-yl)) | CF₃ | Me | ¹H NMR (500 MHz, DMSO-d6) δ 14.48 (s, 1H), 7.84 (t, J = 57.5 Hz, 1H), 7.64 (d, J = 7.5 Hz, 1H), 6.66 (d, J = 7.5 Hz, 1H), 2.34 (s, 3H). |
| 106 | (4-(1-(difluoromethyl)-3-fluoro-1H-pyrazol-4-yl)) | CF₃ | Me | ¹H NMR (500 MHz, DMSO-d6) δ 14.46 (s, 1H), 7.97 (s, 1H), 2.37 (s, 3H), 2.32 (s, 3H). |
| 107 | (2-methylthiazol-5-yl) | CF₃ | Me | ¹H NMR (500 MHz, DMSO-d6) δ 14.44 (s, 1H), 9.20 (s, 1H), 8.10 (s, 1H), 2.34 (s, 3H). |
| 108 | (thiazol-4-yl) | CF₃ | Me | ¹H NMR (500 MHz, DMSO-d6) δ 14.52 (s, 1H), 8.43 (dd, J = 7.0, 5.0 Hz, 1H), 8.02-7.98 (m, 1H), 7.75 (dd, J = 8.0, 7.0 Hz, 1H), 2.16 (s, 3H). |
| 109 | (2-fluoropyridin-3-yl) | CF₃ | Me | ¹H NMR (500 MHz, DMSO-d₆) δ 14.49 (s, 1H), 8.44 (d, J = 5.0 Hz, 1H), 8.23 (s, 1H), 7.82 (d, J = 5.0 Hz, 1H), 2.25 (s, 3H). |
| 110 | (2-chloropyridin-4-yl) | CF₃ | Me | ¹H NMR (500 MHz, DMSO-d6) δ 14.46 (s, 1H), 8.83 (d, J = 2.5 Hz, 1H), 8.71 (d, J = 2.5 Hz, 1H), 8.06-8.02 (m, 1H), 2.25 (s, 3H). |
| 111 | (5-chloropyridin-3-yl) | CF₃ | Me | ¹H NMR (500 MHz, DMSO-d₆) δ 14.47 (s, 1H), 8.47 (dd, J = 5.0, 2.5 Hz, 1H), 7.90-7.80 (m, 2H), 2.24 (s, 3H). |
| 112 | (2-chloropyridin-3-yl) | CF₃ | Me | ¹H NMR (500 MHz, DMSO-d6) δ 14.46 (s, 1H), 8.14-8.08 (m, 1H), 7.53-7.48 (m, 1H), 2.27 (s, 3H). |
| 113 | (6-chloro-2-fluoropyridin-3-yl) | CF₃ | Me | ¹H NMR (500 MHz, DMSO-d6) δ 14.46 (s, 1H), 8.14-8.08 (m, 1H), 7.53-7.48 (m, 1H), 2.27 (s, 3H). |

TABLE 1-continued

Structures and ¹HNMR data of Compounds I

| NO. | X | Y | Z | ¹HNMR |
|---|---|---|---|---|
| 114 | 5-chloro-2-fluoropyridin-3-yl | CF$_3$ | Me | ¹H NMR (500 MHz, DMSO-d6) δ 14.49 (s, 1H), 8.60 (d, J = 7.0 Hz, 1H), 8.33 (dd, J = 7.0, 2.5 Hz, 1H), 2.27 (s, 3H). |
| 115 | 4-fluorophenyl | CF$_3$ | cyclopropyl | ¹H NMR (500 MHz, DMSO-d6) δ 14.46 (s, 1H), 7.81-7.76 (m, 2H), 7.35-7.27 (m, 2H), 1.70-1.67 (m, 1H), 1.35-1.32 (m, 2H), 0.89-0.85 (m, 2H). |
| 116 | 4-chlorophenyl | CF$_3$ | cyclopropyl | ¹H NMR (500 MHz, DMSO-d6) δ 14.49 (s, 1H), 7.75 (d, J = 7.5 Hz, 2H), 7.50 (d, J = 7.5 Hz, 2H), 1.70-1.66 (m, 1H), 1.34-1.31 (m, 2H), 0.89-0.85 (m, 2H). |
| 117 | 3,4-difluorophenyl | CF$_3$ | cyclopropyl | ¹H NMR (500 MHz, DMSO-d6) δ 14.48 (s, 1H), 7.55-7.45 (m, 2H), 7.38-7.32 (m, 1H), 1.70-1.67 (m, 1H), 1.35-1.32 (m, 2H), 0.87-0.83 (m, 2H). |
| 118 | pyridin-2-yl | CF$_3$ | cyclopropyl | ¹H NMR (500 MHz, DMSO-d6) δ 14.42 (s, 1H), 8.74 (d, J = 5.0, 1H), 8.20 (d, J = 8.0 Hz, 1H), 8.02-7.99 (m, 1H), 7.62-7.56 (m, 1H), 1.70-1.66 (m, 1H), 1.34-1.31 (m, 2H), 0.89-0.85 (m, 2H). |
| 119 | pyridin-3-yl | CF$_3$ | cyclopropyl | ¹H NMR (500 MHz, DMSO-d6) δ 14.45 (s, 1H), 8.82 (s, 1H), 8.41 (d, J = 5.0, 1H), 8.05 (d, J = 7.5, 1H), 7.46 (dd, J = 7.0, 5.0 Hz, 1H), 1.70-1.66 (m, 1H), 1.34-1.31 (m, 2H), 0.89-0.85 (m, 2H). |
| 120 | pyridin-4-yl | CF$_3$ | cyclopropyl | ¹H NMR (500 MHz. DMSO-d6) δ 14.51 (s, 1H). 8.66 (d, J = 5.0 Hz, 2H), 7.86 (d, J = 5.0 Hz, 2H), 1.69-1.64 (m, 1H), 1.34-1.31 (m, 2H), 0.89-0.85 (m, 2H). |
| 121 | 2,6-difluoropyridin-3-yl | CF$_3$ | cyclopropyl | ¹H NMR (500 MHz, DMSO-d6) δ 14.50 (s, 1H), 8.23-8.19 (m, 1H), 7.13-7.09 (m, 1H), 1.70-1.66 (m, 1H), 1.34-1.31 (m, 2H), 0.85-0.82 (m, 2H). |
| 122 | 5-fluoropyridin-3-yl | CF$_3$ | cyclopropyl | ¹H NMR (500 MHz, DMSO-d6) δ 14.48 (s, 1H), 8.67 (s, 1H), 8.44-8.40 (m, 1H), 8.24-8.20 (m, 1H), 1.70-1.66 (m, 1H), 1.33-1.30 (m, 2H), 0.85-0.83 (m, 2H). |

TABLE 1-continued

Structures and ¹HNMR data of Compounds I

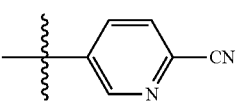 [SMILES: *c1ccc(C#N)nc1]

| NO. | X | Y | Z | ¹HNMR |
|---|---|---|---|---|
| 123 | 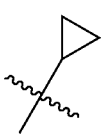 | CF₃ | 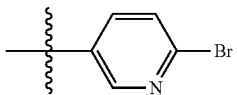 [SMILES: *c1ccc(Br)nc1] | ¹H NMR (500 MHz. DMSO-d₆) δ 14.52 (s, 1H), 9.14 (s, 1H), 8.11 (d, J = 6.5 Hz, 1H), 7.83 (d, J = 8.0 Hz, 1H), 1.70-1.66 (m, 1H), 1.34-1.31 (m, 2H), 0.90-0.85 (m, 2H). |
| 124 |  | CF₃ | 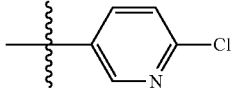 [SMILES: *c1ccc(Cl)nc1] | ¹H NMR (500 MHz, DMSO-d6) δ 14.49 (s, 1H), 8.75 (s, 1H), 7.82 (d, J = 6.5 Hz, 1H), 7.70 (d, J = 8.0 Hz, 1H), 1.70-1.65 (m, 1H), 1.33-1.29 (m, 2H), 0.85-0.82 (m, 2H). |
| 125 |  | CF₃ | 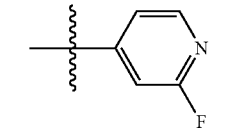 | ¹H NMR (500 MHz, DMSO-d6) δ 14.46 (s, 1H), 8.82 (s, 1H), 7.89 (d, J = 8.0 Hz, 1H), 7.51 (d, J = 6.5 Hz, 1H), 1.70-1.66 (m, 1H), 1.34-1.31 (m, 2H), 0.85-0.82 (m, 2H). |
| 126 |  | CF₃ | 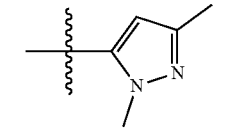 [SMILES: *c1cc(C)nn1C] | ¹H NMR (500 MHz, DMSO-d₆) δ 14.52 (s, 1H), 8.45-8.40 (m, 1H), 7.80 (d, J = 8.0 Hz, 1H), 7.69 (d, J = 5.0 Hz, 1H), 1.70-1.67 (m, 1H), 1.35-1.32 (m, 2H), 0.87-0.83 (m, 2H). |
| 127 | 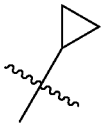 | CF₃ | 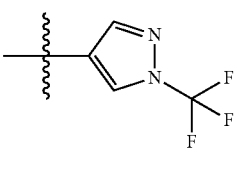 [SMILES: *c1cnn(C(F)(F)F)c1] | ¹H NMR (500 MHz, DMSO-d6) δ 14.53 (s, 1H), 6.60 (s, 1H), 3.87 (s, 3H), 2.39 (s, 3H), 1.70-1.67 (m, 1H), 1.35-1.32 (m, 2H), 0.87-0.83 (m, 2H) |
| 128 | 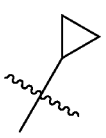 [SMILES: *C1CC1] | CF₃ | 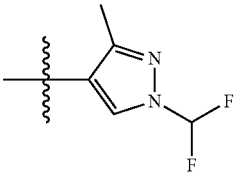 [SMILES: *c1cn(C(F)F)nc1C] | ¹H NMR (500 MHz, DMSO-d6) δ 14.50 (s, 1H). 7.87 (s, 1H), 7.22 (s, 1H), 1.70-1.67 (m, 1H), 1.35-1.32 (m, 2H), 0.88-0.83 (m, 2H) |
| 129 |  | CF₃ | 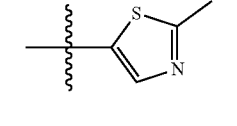 [SMILES: *c1cnc(C)s1] | ¹H NMR (500 MHz, DMSO-d6) δ 14.49 (s, 1H), 7.84 (t, J = 57.5 Hz, 1H), 7.12 (s, 1H), 2.40 (s, 3H), 2.23-2.18 (m, 1H), 1.02-0.98 (m, 2H), 0.77-0.73 (m, 2H). |
| 130 | 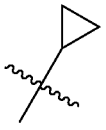 [SMILES: *C1CC1] | CF₃ | 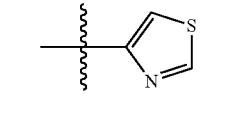 [SMILES: *c1cscn1] | ¹H NMR (500 MHz, DMSO-d6) δ 14.49 (s, 1H), 7.98 (s, 1H), 2.37 (s, 3H), 1.70-1.66 (m, 1H), 1.35-1.31 (m, 2H), 0.87-0.83 (m, 2H). |
| 131 |  | CF₃ | | ¹H NMR (500 MHz, DMSO-d6) δ 14.44 (s, 1H), 9.20 (s, 1H), 8.10 (s, 1H), 1.70-1.67 (m, 1H), 1.35-1.32 (m, 2H), 0.87-0.83 (m, 2H) |

TABLE 1-continued

Structures and ¹HNMR data of Compounds I

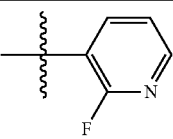

| NO. | X | Y | Z | ¹HNMR |
|---|---|---|---|---|
| 132 | 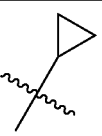 | CF₃ | 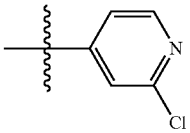 [SMILES: *c1ccnc(Cl)c1] | ¹H NMR (500 MHz, DMSO-d6) δ 14.52 (s, 1H), 8.40 (dd, J = 7.0, 5.0 Hz, 1H), 8.00-7.96 (m, 1H), 7.60 (dd, J = 7.0, 5.0 Hz, 1H), 1.70-1.65 (m, 1H), 1.35-1.32 (m, 2H), 0.87-0.84 (m, 2H). |
| 133 | 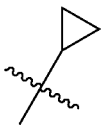 [SMILES: *C1CC1] | CF₃ | 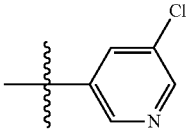 [SMILES: *c1cncc(Cl)c1] | ¹H NMR (500 MHz, DMSO-d6) δ 14.46 (s, 1H), 8.34 (d, J = 5.0 Hz, 1H), 8.22 (s, 1H), 7.80 (d, J = 5.0 Hz, 1H), 1.70-1.67 (m, 1H), 1.35-1.32 (m, 2H), 0.87-0.83 (m, 2H). |
| 134 | 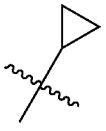 | CF₃ | 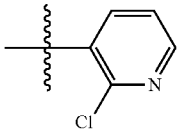 [SMILES: *c1cccnc1Cl] | ¹H NMR (500 MHz, DMSO-d₆) δ 14.46 (s, 1H), 8.83 (d, J = 2.5 Hz, 1H), 8.71 (d, J = 2.5 Hz, 1H), 8.06-8.02 (m, 1H), 1.70-1.67 (m, 1H), 1.35-1.32 (m, 2H), 0.87-0.83 (m, 2H). |
| 135 |  | CF₃ | 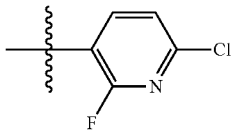 [SMILES: *c1ccc(Cl)nc1F] | ¹H NMR (500 MHz, DMSO-d6) δ 14.49 (s, 1H), 8.45 (dd, J = 5.0, 2.5 Hz, 1H), 7.90-7.85 (m, 2H), 1.70-1.67 (m, 1H), 1.35-1.32 (m, 2H), 0.87-0.83 (m, 2H). |
| 136 |  | CF₃ | 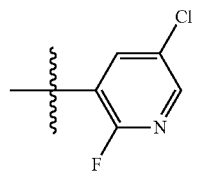 | ¹H NMR (500 MHz, DMSO-d6) δ 14.53 (s, 1H), 8.22 (dd, J = 7.0, 5.0 Hz, 1H), 7.45 (d, J = 8.0 Hz, 1H), 1.70-1.67 (m, 1H), 1.35-1.30 (m, 2H), 0.87-0.83 (m, 2H) |
| 137 |  | CF₃ | 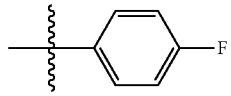 [SMILES: *c1ccc(F)cc1] | ¹H NMR (500 MHz, DMSO-d6) δ 14.52 (s, 1H), 8.60 (d, J = 7.0 Hz, 1H), 8.33 (dd, J = 7.0, 2.5 Hz, 1H), 1.70-1.67 (m, 1H), 1.35-1.32 (m, 2H), 0.87-0.83 (m, 2H). |
| 138 | 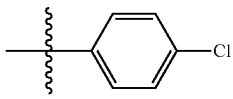 [SMILES: *c1ccc(Cl)cc1] | CF₃ | SEt | ¹H NMR (500 MHz, DMSO-d6) δ 14.53 (s, 1H), 7.91-7.83 (m, 2H), 7.35-7.27 (m, 2H), 3.07 (q, J = 8.0 Hz, 2H), 1.11 (t, J = 8.0 Hz, 3H). |
| 139 | 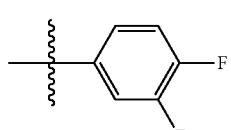 | CF₃ | SEt | ¹H NMR (500 MHz, DMSO-d6) δ 14.46 (s, 1H), 7.85-7.78 (m, 2H), 7.51-7.45 (m, 2H), 3.05 (q, J = 8.0 Hz, 2H), 1.21 (t, J = 8.0 Hz, 3H). |
| 140 | 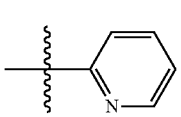 [SMILES: *c1ccccn1] | CF₃ | SEt | ¹H NMR (500 MHz, DMSO-d6) δ 14.46 (s, 1H), 7.64-7.60 (m, 1H), 7.53-7.48 (m, 1H), 7.39-7.35 (m, 1H), 3.03 (q, J = 8.0 Hz, 2H), 1.12 (t, J = 8.0 Hz, 3H). |
| 141 |  | CF₃ | SEt | ¹H NMR (500 MHz, DMSO-d6) δ 14.48 (s, 1H), 8.74 (d, J = 5.0 Hz, 1H), 8.23-8.18 (m, 1H), 8.02-7.99 (m, 1H), 7.62-7.56 (m, 1H), 3.00 (q, J = 8.0 Hz, 2H), 1.11 (t, J = 8.0 Hz, 3H). |

TABLE 1-continued

Structures and ¹HNMR data of Compounds I

| NO. | X | Y | Z | ¹HNMR |
|---|---|---|---|---|
| 142 | 3-pyridyl | CF$_3$ | SEt | ¹H NMR (500 MHz, DMSO-d6) δ 14.45 (s, 1H), 8.82 (s, 1H), 8.41 (d, J = 5.0, 1H), 8.08-8.02 (m, 1H), 7.49-7.44 (m, 1H), 3.02 (q, J = 8.0 Hz, 2H), 1.12 (t, J = 8.0 Hz, 3H). |
| 143 | 4-pyridyl | CF$_3$ | SEt | ¹H NMR (500 MHz, DMSO-d6) δ 14.51 (s, 1H), 8.66 (d, J = 5.0 Hz, 2H), 7.86 (d, J = 5.0 Hz, 2H), 3.08 (q, J = 8.0 Hz, 2H), 1.21 (t, J = 8.0 Hz, 3H). |
| 144 | 2,6-difluoropyridin-3-yl | CF$_3$ | SEt | ¹H NMR (500 MHz, DMSO-d6) δ 14.50 (s, 1H), 8.23-8.19 (m, 1H), 7.13-7.09 (m, 1H), 3.04 (q, J = 8.0 Hz, 2H), 1.11 (t, J = 8.0 Hz, 3H). |
| 145 | 5-fluoropyridin-3-yl | CF$_3$ | SEt | ¹H NMR (500 MHz, DMSO-d6) δ 14.51 (s, 1H), 8.67 (s, 1H), 8.46-8.42 (m, 1H), 8.24-8.20 (m, 1H), 3.05 (q, J = 8.0 Hz, 2H), 1.12 (t, J = 8.0 Hz, 3H) |
| 146 | 6-cyanopyridin-3-yl | CF$_3$ | SEt | ¹H NMR (500 MHz, DMSO-d6) δ 14.53 (s, 1H), 9.14 (s, 1H), 8.11 (d, J = 5.0 Hz, 1H), 7.83 (d, J = 8.0 Hz, 1H), 3.04 (q, J = 5.0 Hz, 2H), 1.12 (t, J = 8.0 Hz, 3H) |
| 147 | 6-bromopyridin-3-yl | CF$_3$ | SEt | ¹H NMR (500 MHz, DMSO-d6) δ 14.45 (s, 1H), 8.73 (s, 1H), 7.78 (d, J = 5.0 Hz, 1H), 7.71 (d, J = 5.0 Hz, 1H), 3.04 (q, J = 8.0 Hz, 2H), 1.13 (t, J = 8.0 Hz, 3H) |
| 148 | 6-chloropyridin-3-yl | CF$_3$ | SEt | ¹H NMR (500 MHz, DMSO-d6) δ 14.48 (s, 1H), 8.83 (s, 1H), 7.88 (d, J = 8.0 Hz, 1H), 7.51 (d, J = 8.0 Hz, 1H), 3.04 (q, J = 6.5 Hz, 2H), 1.11 (t, J = 8.0 Hz, 3H) |
| 149 | 2-fluoropyridin-4-yl | CF$_3$ | SEt | ¹H NMR (500 MHz, DMSO-d6) δ 14.50 (s, 1H), 8.45-8.40 (m, 1H), 7.80 (d, J = 8.0 Hz, 1H), 7.69 (d, J = 5.0 Hz, 1H), 3.06 (q, J = 8.0 Hz, 2H), 1.12 (t, J = 8.0 Hz, 3H) |
| 150 | 1,3-dimethyl-1H-pyrazol-5-yl | CF$_3$ | SEt | ¹H NMR (500 MHz, DMSO-d6) δ 14.45 (s, 1H), 6.60 (s, 1H), 3.87 (s, 3H), 2.38 (s, 3H), 3.05 (q, J = 8.0 Hz, 2H), 1.11 (t, J = 8.0 Hz, 3H) |
| 151 | 1-(trifluoromethyl)-1H-pyrazol-4-yl | CF$_3$ | SEt | ¹H NMR (500 MHz, DMSO-d6) δ 14.48 (s, 1H), 7.87 (s, 1H), 7.21 (s, 1H), 3.04 (q, J = 8.0 Hz, 2H), 1.11 (t, J = 8.0 Hz, 3H) |

TABLE 1-continued

Structures and ¹HNMR data of Compounds I

| NO. | X | Y | Z | ¹HNMR |
|---|---|---|---|---|
| 152 | 3-methyl-1-(difluoromethyl)-1H-pyrazol-4-yl | CF₃ | SEt | ¹H NMR (500 MHz, DMSO-d6) δ 14.50 (s, 1H), 7.84 (t, J = 57.5 Hz, 1H), 7.05 (s, 1H), 3.00 (q, J = 8.0 Hz, 2H), 2.42 (s, 3H), 1.31 (t, J = 8.0 Hz, 3H). |
| 153 | 2-methylthiazol-5-yl | CF₃ | SEt | ¹H NMR (500 MHz. DMSO-d6) δ 14.49 (s, 1H), 7.97 (s, 1H), 2.35 (s, 3H), 3.03 (q, J = 8.0 Hz, 2H), 1.11 (t, J = 8.0 Hz, 3H) |
| 154 | thiazol-4-yl | CF₃ | SEt | ¹H NMR (500 MHz, DMSO-d6) δ 14.54 (s, 1H), 9.20 (s, 1H), 8.10 (s, 1H), 3.04 (q, J = 8.0 Hz, 2H), 1.11 (t, J = 8.0 Hz, 3H) |
| 155 | 2-fluoropyridin-3-yl | CF₃ | SEt | ¹H NMR (500 MHz, DMSO-d6) δ 14.52 (s, 1H), 8.40 (dd, J = 7.0, 5.0 Hz, 1H), 8.00-7.96 (m, 1H), 7.60 (dd, J = 8.0, 5.0 Hz. 1H), 3.03 (q, J = 8.0 Hz, 2H), 1.11 (t, J = 8.0 Hz, 3H) |
| 156 | 4-fluorophenyl | CF₃ | isopropenyl | ¹H NMR (500 MHz, DMSO-d6) δ 14.46 (s, 1H), 7.89-7.81 (m, 2H), 7.35-7.27 (m, 2H), 5.30 (s, 1H), 4.90 (s, 1H), 2.06 (s, 3H). |
| 157 | 4-chlorophenyl | CF₃ | isopropenyl | ¹H NMR (500 MHz, DMSO-d₆) δ 14.48 (s, 1H), 7.82 (d, J = 7.5 Hz, 2H), 7.50 (d, J = 7.5 Hz, 2H), 5.29 (s, 1H), 4.91 (s, 1H), 2.03 (s, 3H). |
| 158 | 3,4-difluorophenyl | CF₃ | isopropenyl | ¹H NMR (500 MHz, DMSO-d₆) δ 14.49 (s, 1H), 7.74-7.70 (m, 1H), 7.53-7.48 (m, 1H), 7.39-7.35 (m, 1H), 5.29 (s, 1H), 4.91 (s, 1H), 1.93 (s, 3H). |
| 159 | pyridin-2-yl | CF₃ | isopropenyl | ¹H NMR (500 MHz, DMSO-d₆) δ 14.48 (s, 1H), 8.74 (d, J = 5.0 Hz, 1H), 8.23-8.18 (m, 1H), 8.02-7.99 (m, 1H), 7.62-7.56 (m, 1H), 5.31 (s, 1H), 4.92 (s, 1H), 1.93 (s, 3H). |
| 160 | pyridazin-4-yl | CF₃ | isopropenyl | ¹H NMR (500 MHz, DMSO-d₆) δ 14.49 (s, 1H), 8.82 (s, 1H), 8.41 (d, J = 5.0 Hz, 1H), 8.05 (d, J = 7.5 Hz, 1H), 7.46 (d, J = 5.0 Hz, 1H), 5.31 (s, 1H). 4.91 (s, 1H), 1.94 (s, 3H). |
| 161 | pyridin-4-yl | CF₃ | isopropenyl | ¹H NMR (500 MHz, DMSO-d₆) δ 14.49 (s, 1H), 8.66 (d, J = 5.0 Hz, 2H), 7.86 (d, J = 5.0 Hz, 2H), 5.29 (s, 1H), 4.91 (s, 1H), 1.95 (s, 3H). |

TABLE 1-continued

Structures and ¹HNMR data of Compounds I

| NO. | X | Y | Z | ¹HNMR |
|---|---|---|---|---|
| 162 | 2,6-difluoropyridin-3-yl | $CF_3$ | isopropenyl | ¹H NMR (500 MHz, DMSO-$d_6$) δ 14.48 (s, 1H), 8.23-8.19 (m, 1H), 7.13-7.09 (m, 1H), 5.29 (s, 1H), 4.91 (s, 1H), 1.93 (s, 3H). |
| 163 | 5-fluoropyridin-3-yl | $CF_3$ | isopropenyl | ¹H NMR (500 MHz, DMSO-$d_6$) δ 14.49 (s, 1H), 8.66 (s, 1H), 8.46-8.42 (m, 1H), 8.24-8.20 (m, 1H), 5.29 (s, 1H), 4.91 (s, 1H), 1.95 (s, 3H). |
| 164 | 6-cyanopyridin-3-yl | $CF_3$ | isopropenyl | ¹H NMR (500 MHz, DMSO-$d_6$)) δ 14.53 (s, 1H), 9.14 (s, 1H), 8.10 (d, J = 5.0 Hz, 1H), 7.82 (d, J = 8.0 Hz, 1H), 5.31 (s, 1H), 4.90 (s, 1H), 1.93 (s, my |
| 165 | 6-bromopyridin-3-yl | $CF_3$ | isopropenyl | ¹H NMR (500 MHz, DMSO-$d_6$) δ 14.49 (s, 1H), 8.73 (s, 1H), 7.78 (d, J = 5.0 Hz, 1H), 7.71 (d, J = 8.0 Hz, 1H), 5.29 (s, 1H), 4.91 (s, 1H), 1.93 (s, 3H). |
| 166 | 6-chloropyridin-3-yl | $CF_3$ | isopropenyl | ¹H NMR (500 MHz, DMSO-$d_6$) δ 14.50 (s, 1H), 8.82 (s, 1H), 7.87 (d, J = 8.0 Hz, 1H), 7.51 (d, J = 5.0 Hz, 1H), 5.30 (s, 1H), 4.91 (s, 1H), 1.93 (s, 3H). |
| 167 | 2-fluoropyridin-4-yl | $CF_3$ | isopropenyl | ¹H NMR (500 MHz, DMSO-$d_6$) δ 14.48 (s, 1H), 8.45-8.40 (m, 1H), 7.80 (d, J = 8.0 Hz, 1H), 7.69 (d, J = 5.0 Hz, 1H), 5.29 (s, 1H), 4.91 (s, 1H), 1.93 (s, 3H). |
| 168 | 1,3-dimethyl-1H-pyrazol-5-yl | $CF_3$ | isopropenyl | ¹H NMR (500 MHz, DMSO-$d_6$) δ 14.45 (s, 1H), 6.60 (s, 1H), 3.87 (s, 3H), 2.38 (s, 3H), 5.30 (s, 1H), 4.91 (s, 1H), 1.94 (s, 3H). |
| 169 | 1-(trifluoromethyl)-1H-pyrazol-4-yl | $CF_3$ | isopropenyl | ¹H NMR (500 MHz, DMSO-$d_6$) δ 14.49 (s, 1H), 7.87 (s, 1H), 7.21 (s, 1H), 5.29 (s, 1H), 4.91 (s, 1H), 1.93 (s,3H). |
| 170 | 1-(difluoromethyl)-3-methyl-1H-pyrazol-4-yl | $CF_3$ | isopropenyl | ¹H NMR (500 MHz, DMSO-$d_6$) δ 14.51 (s, 1H), 7.84 (t, J = 57.5 Hz, 1H), 7.04 (s, 1H), 5.18 (s, 1H), 4.87 (s, 1H), 2.41 (s, 3H), 2.06 (s, 3H). |

TABLE 1-continued

Structures and ¹HNMR data of Compounds I

| NO. | X | Y | Z | ¹HNMR |
|---|---|---|---|---|
| 171 | 2-methyl-thiazol-5-yl | CF₃ | isopropenyl | ¹H NMR (500 MHz, DMSO-d₆) δ 14.46 (s, 1H), 7.97 (s, 1H), 5.30 (s, 1H), 4.91 (s, 1H), 2.35 (s, 3H), 1.94 (s, 3H). |
| 172 | thiazol-4-yl | CF₃ | isopropenyl | ¹H NMR (500 MHz, DMSO-d₆) δ 14.44 (s, 1H), 9.21 (s, 1H), 8.10 (s, 1H), 5.29 (s, 1H), 4.90 (s, 1H), 1.93 (s, 3H). |
| 173 | 2-fluoropyridin-3-yl | CF₃ | isopropenyl | ¹H NMR (500 MHz, DMSO-d₆) δ 14.52 (s, 1H), 8.40 (dd, J = 7.0, 5.0 Hz, 1H), 8.00-7.96 (m, 1H), 7.60 (dd, J = 8.0, 5.0 Hz, 1H), 5.30 (s, 1H), 4.91 (s, 1H), 1.93 (s, 3H). |
| 174 | 4-fluorophenyl | CF₃ | NH₂ | ¹H NMR (500 MHz, DMSO-d₆) δ 14.51 (s, 1H), 7.82-7.74 (m, 2H), 7.35-7.27 (m, 2H), 6.84 (s, 2H). |
| 175 | 4-chlorophenyl | CF₃ | NH₂ | ¹H NMR (500 MHz, DMSO-d₆) δ 1451 (s, 1H). 7.75 (d, J = 7.5 Hz, 2H), 7.50 (d, J = 7.5 Hz, 2H), 6.84 (s, 2H). |
| 176 | 3,4-difluorophenyl | CF₃ | NH₂ | ¹H NMR (500 MHz, DMSO-d₆) δ 14.48 (s, 1H), 7.58-7.50 (m, 2H), 7.38-7.35 (m, 1H), 6.84 (s, 2H). |
| 177 | pyridin-2-yl | CF₃ | NH₂ | ¹H NMR (500 MHz, DMSO-d₆) δ 14.52 (s, 1H), 8.73 (d, J = 5.0 Hz, 1H), 8.20 (d, J = 8.0 Hz, 1H), 8.02-7.99 (m, 1H), 7.62-7.56 (m, 1H), 6.84 (s, 2H) |
| 178 | pyridin-3-yl | CF₃ | NH₂ | ¹H NMR (500 MHz, DMSO-d₆) δ 14.45 (s, 1H), 8.80 (s, 1H), 8.40 (d, J = 5.0 Hz, 1H), 8.03 (d, J = 5.0 Hz. 1H), 7.49-7.45 (m, 1H), 6.83 (s, 2H). |
| 179 | pyridin-4-yl | CF₃ | NH₂ | ¹H NMR (500 MHz, DMSO-d₆) δ 14.48 (s, 1H), 8.65 (d, J = 5.0 Hz, 2H), 7.80 (d, J = 5.0 Hz, 2H), 6.85 (s, 2H). |
| 180 | 2,6-difluoropyridin-3-yl | CF₃ | NH₂ | ¹H NMR (500 MHz, DMSO-d₆) δ 14.49 (s, 1H), 8.22-8.19 (m, 1H), 7.13-7.09 (m, 1H), 6.85 (s, 2H). |
| 181 | 5-fluoropyridin-3-yl | CF₃ | NH₂ | ¹H NMR (500 MHz, DMSO-d₆) δ 14.52 (s, 1H), 8.65 (s, 1H), 8.46-8.42 (m, 1H), 8.25-8.21 (m, 1H), 6.84 (s, 2H). |

TABLE 1-continued

Structures and ¹HNMR data of Compounds I

[Structure: pyridazine core with substituents Y, Z, X and OH, where Z and OH are on adjacent carbons, Y is adjacent to one ring nitrogen, X is adjacent to the other ring nitrogen]

| NO. | X | Y | Z | ¹HNMR |
|---|---|---|---|---|
| 182 | 5-(2-cyanopyridinyl) | $CF_3$ | $NH_2$ | ¹H NMR (500 MHz, DMSO-$d_6$) δ 14.48 (s, 1H), 9.15 (s, 1H), 8.11 (d, J = 8.0 Hz, 1H), 7.82 (d, J = 5.0 Hz, 1H), 6.86 (s, 2H). |
| 183 | 5-(2-bromopyridinyl) | $CF_3$ | $NH_2$ | ¹H NMR (500 MHz, DMSO-$d_6$) δ 14.46 (s, 1H), 8.73 (s, 1H), 7.80 (d, J = 8.0 Hz, 1H), 7.71 (d, J = 8.0 Hz, 1H), 6.83 (s, 2H). |
| 184 | 5-(2-chloropyridinyl) | $CF_3$ | $NH_2$ | ¹H NMR (500 MHz, DMSO-$d_6$) δ 14.45 (s, 1H), 8.83 (s, 1H), 7.89 (d, J = 8.0 Hz, 1H), 7.51 (d, J = 8.0 Hz, 1H), 6.84 (s, 2H). |
| 185 | 4-(2-fluoropyridinyl) | $CF_3$ | $NH_2$ | ¹H NMR (500 MHz, DMSO-$d_6$) δ 14.53 (s, 1H), 8.43-8.40 (m 1H), 7.80 (d, J = 8.0 Hz, 1H), 7.69 (d, J = 5.0 Hz, 1H), 6.84 (s, 2H). |
| 186 | 1,3-dimethyl-1H-pyrazol-4-yl | $CF_3$ | $NH_2$ | ¹H NMR (500 MHz, DMSO-$d_6$) δ 14.48 (s, 1H), 6.84 (s, 2H), 6.60 (s, 1H), 3.87 (s, 3H), 2.39 (s, 3H). |
| 187 | 1-(trifluoromethyl)-1H-pyrazol-4-yl | $CF_3$ | $NH_2$ | ¹H NMR (500 MHz, DMSO-$d_6$) δ 14.48 (s, 1H), 7.87 (s, 1H), 7.20 (s, 1H), 6.84 (s, 2H). |
| 188 | 1-(difluoromethyl)-3-methyl-1H-pyrazol-4-yl | $CF_3$ | $NH_2$ | ¹H NMR (500 MHz, DMSO-$d_6$) δ 14.51 (s, 1H), 7.84 (t, J = 57.5 Hz, 1H), 7.04 (s, 1H), 6.86 (s, 2H), 2.41 (s, 3H), |
| 189 | 2-methylthiazol-5-yl | $CF_3$ | $NH_2$ | ¹H NMR (500 MHz, DMSO-$d_6$) δ 14.46 (s, 1H), 7.97 (s, 1H), 6.86 (s, 2H), 2.37 (s, 3H). |
| 190 | thiazol-5-yl | $CF_3$ | $NH_2$ | ¹H NMR (500 MHz, DMSO-$d_6$) δ 14.44 (s, 1H), 9.20 (s, 1H), 8.10 (s, 1H), 6.84 (s, 2H) |
| 191 | 3-(2-fluoropyridinyl) | $CF_3$ | $NH_2$ | ¹H NMR (500 MHz, DMSO-$d_6$) δ 14.52 (s, 1H), 8.43 (dd, J = 7.0, 5.0 Hz, 1H), 8.02-7.98 (m, 1H), 7.79-7.75 (m, 1H), 6.86 (s, 2H). |

TABLE 1-continued

Structures and ¹HNMR data of Compounds I

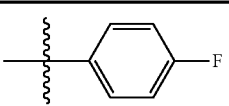

| NO. | X | Y | Z | ¹HNMR |
|---|---|---|---|---|
| 192 | 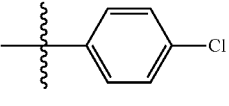 | CF$_3$ | NHMe | ¹H NMR (500 MHz, DMSO-d$_6$) δ 14.52 (s, 1H), 7.92-7.84 (m, 2H), 7.35-7.27 (m, 2H), 5.95 (s, 1H), 2.71 (s, 3H). |
| 193 | 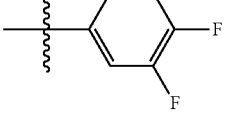 | CF$_3$ | NHMe | ¹H NMR (500 MHz, DMSO-d$_6$) δ 14.48 (s, 1H), 7.86-7.80 (m, 2H), 7.51-7.45 (m, 2H), 5.93 (s, 1H), 2.70 (s, 3H). |
| 194 | 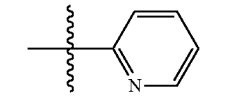 | CF$_3$ | NHMe | ¹H NMR (500 MHz, DMSO-d$_6$) δ 14.49 (s, 1H), 7.65-7.61 (m, 1H), 7.55-7.51 (m, 1H), 7.39-7.35 (m, 1H), 5.93 (s, 1H), 2.71 (s, 3H). |
| 195 | 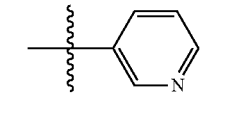 | CF$_3$ | NHMe | ¹H NMR (500 MHz, DMSO-d$_6$) δ 14.48 (s, 1H), 8.74-8.71 (m, 1H), 8.20 (d, J = 8.0 Hz, 1H), 8.02-7.98 (m, 1H), 7.62-7.56 (m, 1H), 5.96 (s, 1H), 2.72 (s, 3H). |
| 196 | 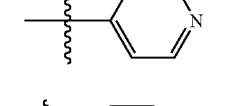 | CF$_3$ | NHMe | ¹H NMR (500 MHz, DMSO-d$_6$) δ 1 4.49 (s, 1H), 8.91 (s, 1H), 8.41-8.38 (m, 1H), 8.13-8.10 (m, 1H), 7.46-7.42 (m, 1H), 5.93 (s, 1H), 2.70 (s, 3H). |
| 197 | 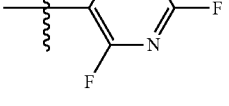 | CF$_3$ | NHMe | ¹H NMR (500 MHz, DMSO-d$_6$) δ 14.45 (s, 1H), 8.66 (d, J = 5.0 Hz, 2H), 7.92 (d, J = 5.0 Hz, 2H), 5.95 (s, 1H), 2.70 (s, 3H). |
| 198 | 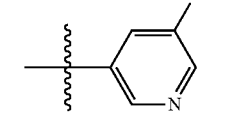 | CF$_3$ | NHMe | ¹H NMR (500 MHz, DMSO-d$_6$) δ 14.49 (s, 1H), 8.20-8.15 (m, 1H), 7.12-7.09 (m, 1H), 5.93 (s, 1H), 2.69(s, 3H). |
| 199 | 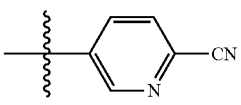 [SMILES: *c1ccc(C#N)nc1] | CF$_3$ | NHMe | ¹H NMR (500 MHz, DMSO-d$_6$) δ 14.49 (s, 1H), 8.67 (s, 1H), 8.45-8.40 (m, 1H), 8.25-8.21 (m, 1H), 5.95 (s, 1H), 2.71 (s, 3H). |
| 200 | 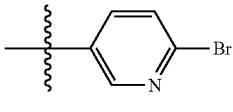 | CF$_3$ | NHMe | ¹H NMR (500 MHz, DMSO-d$_6$) δ 14.49 (s, 1H), 9.16 (s, 1H), 8.13-8.09 (m, 1H), 7.83 (d, J = 8.0 Hz. 1H), 5.95 (s, 1H), 2.70 (s, 3H). |
| 201 | 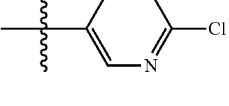 | CF$_3$ | NHMe | ¹H NMR (500 MHz, DMSO-d$_6$) δ 14.50 (s, 1H), 8.80 (s, 1H), 7.87-7.84 (m, 1H), 7.72 (d, J = 8.0 Hz, 1H), 5.93 (s, 1H), 2.72 (s, 3H). |
| 202 |  | CF$_3$ | NHMe | ¹H NMR (500 MHz, DMSO-d$_6$) δ 14.39 (s, 1H), 8.94 (s, 1H), 7.96-7.92 (m, 1H), 7.52 (d, J = 50 Hz, 1H), 5.93 (s, 1H), 2.70 (s, 3H). |

TABLE 1-continued

Structures and ¹HNMR data of Compounds I

| NO. | X | Y | Z | ¹HNMR |
|---|---|---|---|---|
| 203 | 2-fluoropyridin-4-yl | $CF_3$ | NHMe | ¹H NMR (500 MHz, DMSO-$d_6$) δ 14.46 (s, 1H), 8.43 (d, J = 5.0 Hz, 1H), 7.92-7.87 (m, 1H), 7.82-7.76 (m, 1H), 5.95 (s, 1H), 2.71 (s, 3H). |
| 204 | 1,3-dimethyl-1H-pyrazol-5-yl | $CF_3$ | NHMe | ¹H NMR (500 MHz, DMSO-$d_6$) δ 14.46 (s, 1H), 6.62 (s, 1H), 5.95 (s, 1H), 3.87 (s, 3H), 2.70 (s, 3H), 2.39 (s, 3H). |
| 205 | 1-(trifluoromethyl)-1H-pyrazol-4-yl | $CF_3$ | NHMe | ¹H NMR (500 MHz, DMSO-$d_6$) δ 14.46 (s, 1H), 7.94 (s, 1H), 7.25 (s, 1H), 5.95 (s, 1H), 2.70 (s, 3H). |
| 206 | 1-(difluoromethyl)-3-methyl-1H-pyrazol-4-yl | $CF_3$ | NHMe | ¹H NMR (500 MHz, DMSO-$d_6$) δ 14.48 (s, 1H), 7.84 (t, J = 57.5 Hz, 1H), 6.99 (s, 1H), 5.95 (s, 1H), 2.78 (s, 3H), 2.40 (s, 3H). |
| 207 | 2-methylthiazol-5-yl | $CF_3$ | NHMe | ¹H NMR (500 MHz, DMSO-$d_6$) δ 14.46 (s, 1H), 7.96 (s, 1H), 5.93 (s, 1H), 2.71 (s, 3H), 2.34 (s, 3H). |
| 208 | thiazol-4-yl | $CF_3$ | NHMe | ¹H NMR (500 MHz, DMSO-$d_6$) δ 14.46 (s, 1H), 9.20 (s, 1H), 8.07 (s, 1H), 5.95 (s, 1H), 2.79 (s, 3H). |
| 209 | 2-fluoropyridin-3-yl | $CF_3$ | NHMe | ¹H NMR (500 MHz. DMSO-$d_6$) δ 14.49 (s, 1H), 8.43-8.40 (m, 1H), 7.99-7.94 (m, 1H), 7.74-7.70 (m, 1H), 5.95 (s, 1H), 2.70 (s, 3H). |
| 210 | 4-fluorophenyl | $CF_3$ | NHAc | ¹H NMR (500 MHz, DMSO-$d_6$) δ 14.40 (s, 1H), 9.94 (s, 1H), 7.89-7.81 (m, 2H), 7.35-7.27 (m, 2H), 2.07 (s, 3H). |
| 211 | 4-chlorophenyl | $CF_3$ | NHAc | ¹H NMR (500 MHz, DMSO-$d_6$) δ 14.51 (s, 1H), 9.94 (s, 1H), 7.75 (d, J = 7.5 Hz, 2H), 7.50 (d, J = 7.5 Hz, 2H), 2.07 (s, 3H). |

TABLE 1-continued

Structures and ¹HNMR data of Compounds I

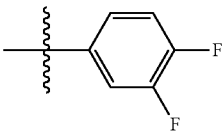 [SMILES: *c1ccc(F)c(F)c1]

| NO. | X | Y | Z | ¹HNMR |
|---|---|---|---|---|
| 212 | 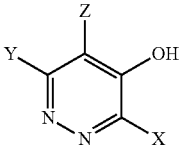 | $CF_3$ | 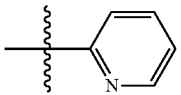 [SMILES: *c1ccccn1] Ac | ¹H NMR (500 MHz, DMSO-$d_6$) δ 14.48 (s, 1H), 9.93 (s, 1H), 7.58-7.50 (m, 2H), 7.36-7.34 (m, 1H), 2.07 (s, 3H). |
| 213 | 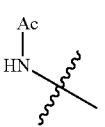 | $CF_3$ | 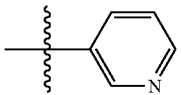 [SMILES: *c1cccnc1] Ac | ¹H NMR (500 MHz, DMSO-$d_6$) δ 14.52 (s, 1H), 9.94 (s, 1H), 8.73 (d, J = 5.0 Hz, 1H), 8.19 (d, J = 8.0 Hz, 1H), 8.02-7.99 (m, 1H), 7.62-7.56 (m, 1H), 2.07 (s, 3H). |
| 214 | 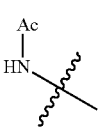 | $CF_3$ | 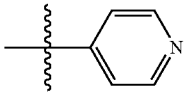 [SMILES: *c1ccncc1] Ac | ¹H NMR (500 MHz, DMSO-$d_6$) δ 14.45 (s, 1H), 9.94 (s, 1H), 8.80 (s, 1H), 8.38 (d, J = 5.0 Hz, 1H), 8.03 (d, J = 5.0 Hz, 1H), 7.49-7.45 (m, 1H), 2.07 (s, 3H). |
| 215 | 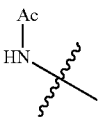 | $CF_3$ | 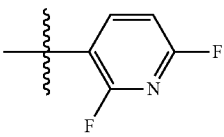 [SMILES: *c1ccc(F)nc1F] Ac | ¹H NMR (500 MHz, DMSO-$d_6$) δ 14.48 (s, 1H), 9.94 (s, 1H), 8.64 (d, J = 5.0 Hz, 2H), 7.80 (d, J = 5.0 Hz, 2H), 2.07 (s, 3H). |
| 216 | 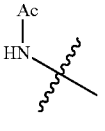 | $CF_3$ | 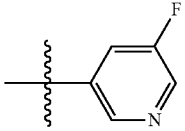 [SMILES: *c1cncc(F)c1] Ac | ¹H NMR (500 MHz, DMSO-$d_6$) δ 14.49 (s, 1H), 9.92 (s, 1H), 8.22-8.19 (m, 1H), 7.13-7.09 (m, 1H), 2.06 (s, 3H). |
| 217 | 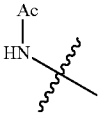 | $CF_3$ | 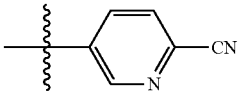 Ac | ¹H NMR (500 MHz, DMSO-$d_6$) δ 14.52 (s, 1H), 9.94 (s, 1H), 8.65 (s, 1H), 8.46-8.42 (m, 1H), 8.25-8.21 (m, 1H), 2.06 (s, 3H). |
| 218 | 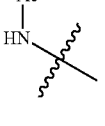 | $CF_3$ | 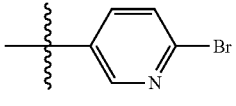 Ac | ¹H NMR (500 MHz, DMSO-$d_6$) δ 14.48 (s, 1H), 9.94 (s, 1H), 9.15 (s, 1H), 8.10 (d, J = 8.0 Hz, 1H), 7.82 (d, J = 8.0 Hz, 1H), 2.07 (s, 3H). |
| 219 | 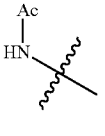 | $CF_3$ | 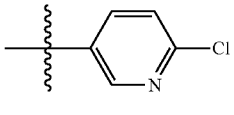 Ac | ¹H NMR (500 MHz, DMSO-$d_6$) δ 14.46 (s, 1H), 9.94 (s, 1H), 8.73 (s, 1H), 7.78 (d, J = 8.0 Hz, 1H), 7.71 (d, J = 8.0 Hz, 1H), 2.07 (s, 3H). |
| 220 | 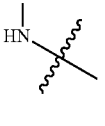 | $CF_3$ | 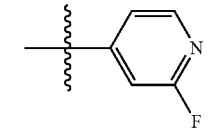 [SMILES: *c1ccnc(F)c1] Ac | ¹H NMR (500 MHz, DMSO-$d_6$) δ 14.45 (s, 1H), 9.94 (s, 1H), 8.83 (s, 1H), 7.89 (d, J = 8.0 Hz, 1H), 7.51 (d, J = 8.0 Hz, 1H), 2.07 (s, 3H) |
| 221 | 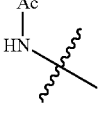 | $CF_3$ | Ac | ¹H NMR (500 MHz, DMSO-$d_6$) δ 14.53 (s, 1H), 9.92 (s, 1H), 8.43-8.40 (m 1H), 7.80 (d, J = 8.0 Hz, 1H), 7.69 (d, J = 5.0 Hz, 1H), 2.08 (s, 3H). |

TABLE 1-continued

Structures and ¹HNMR data of Compounds I

| NO. | X | Y | Z | ¹HNMR |
|---|---|---|---|---|
| 222 | 1,3-dimethylpyrazol-5-yl | $CF_3$ | AcHN- | ¹H NMR (500 MHz, DMSO-$d_6$) δ 14.43 (s, 1H), 9.94 (s, 1H), 6.60 (s, 1H), 3.87 (s, 3H), 2.39 (s, 3H), 2.07 (s, 3H). |
| 223 | 1-(trifluoromethyl)pyrazol-4-yl | $CF_3$ | AcHN- | ¹H NMR (500 MHz, DMSO-$d_6$) δ 14.48 (s, 1H), 9.94 (s, 1H), 7.87 (s, 1H), 7.20 (s, 1H), 2.07 (s, 3H). |
| 224 | 1-(difluoromethyl)-3-methylpyrazol-4-yl | $CF_3$ | AcHN- | ¹H NMR (500 MHz, DMSO-$d_6$) δ 14.49 (s, 1H), 9.54 (s, 1H), 7.85 (t, J = 57.5 Hz, 1H), 7.03 (s, 1H), 2.44 (s, 3H), 2.07 (s, 3H). |
| 225 | 2-methylthiazol-5-yl | $CF_3$ | AcHN- | ¹H NMR (500 MHz, DMSO-$d_6$) δ 14.46 (s, 1H), 9.94 (s, 1H), 7.97 (s, 1H), 2.37 (s, 3H), 2.07 (s, 3H), |
| 226 | thiazol-4-yl | $CF_3$ | AcHN- | ¹H NMR (500 MHz, DMSO-$d_6$) δ 14.44 (s, 1H), 9.94 (s, 1H), 9.20 (s, 1H), 8.10 (s, 1H), 2.07 (s, 3H). |
| 227 | 2-fluoropyridin-3-yl | $CF_3$ | AcHN- | ¹H NMR (500 MHz, DMSO-$d_6$) δ 14.52 (s, 1H), 9.94 (s, 1H), 8.42 (dd, J = 7.0, 5.0 Hz, 1H), 8.02-7.98 (m, 1H), 7.77-7.73 (m, 1H), 2.07 (s, 3H). |
| 228 | 4-cyanophenyl | $CF_3$ | Me | ¹H NMR (500 MHz, DMSO-$d_6$) δ 14.49 (s, 1H), 7.98 (d, J = 7.5 Hz, 2H), 7.75 (d, J = 7.5 Hz, 2H), 2.28 (s, 3H). |
| 229 | 1-(difluoromethyl)pyrazol-4-yl | $CF_3$ | Me | ¹H NMR (500 MHz, DMSO-$d_6$) δ 14.50 (s, 1H), 8.07-7.55 (m, 2H), 7.10 (s, 1H), 2.34 (s, 3H). |
| 230 | phenyl | $CF_3$ | Me | |

TABLE 1-continued
Structures and ¹HNMR data of Compounds I
| NO. | X | Y | Z | ¹HNMR |
|---|---|---|---|---|
| 231 | 2-methylphenyl | CF$_3$ | Me | |
| 232 | 3-methylphenyl | CF$_3$ | Me | |
| 233 | 4-methylphenyl | CF$_3$ | Me | |
| 234 | 2-vinylphenyl | CF$_3$ | Me | |
| 235 | 3-ethynylphenyl | CF$_3$ | Me | |
| 236 | 4-cyclopropylphenyl | CF$_3$ | Me | |
| 237 | 2-fluorophenyl | CF$_3$ | Me | |
| 238 | 3-fluorophenyl | CF$_3$ | Me | |

TABLE 1-continued

Structures and ¹HNMR data of Compounds I

[Structure: pyridazine ring with Y at position 6, Z at position 5, OH at position 4, X at position 3]

| NO. | X | Y | Z | ¹HNMR |
|---|---|---|---|---|
| 239 | 2-Cl-phenyl | CF$_3$ | Me | |
| 240 | 3-Cl-phenyl | CF$_3$ | Me | |
| 241 | 2-Br-phenyl | CF$_3$ | Me | |
| 242 | 3-Br-phenyl | CF$_3$ | Me | |
| 243 | 3-I-phenyl | CF$_3$ | Me | |
| 244 | 4-I-phenyl | CF$_3$ | Me | |
| 245 | 3-CF$_3$-phenyl | CF$_3$ | Me | |
| 246 | 3-NC-phenyl | CF$_3$ | Me | |
| 247 | 4-NO$_2$-phenyl | CF$_3$ | Me | |

TABLE 1-continued
Structures and ¹HNMR data of Compounds I
| NO. | X | Y | Z | ¹HNMR |
|-----|---|---|---|-------|
| 248 | 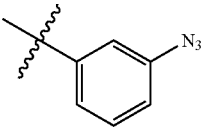 [SMILES: *c1cccc(N=[N+]=[N-])c1] | CF$_3$ | Me | |
| 249 | 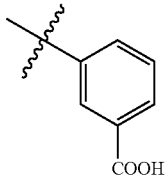 [SMILES: *c1cccc(C(=O)O)c1] | CF$_3$ | Me | |
| 250 | 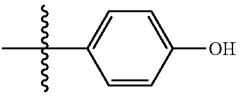 [SMILES: *c1ccc(O)cc1] | CF$_3$ | Me | |
| 251 | 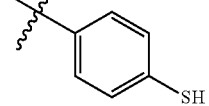 | CF$_3$ | Me | |
| 252 | 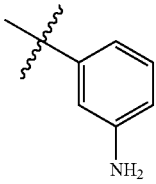 | CF$_3$ | Me | |
| 253 | 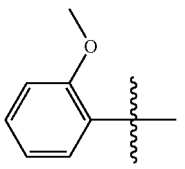 [SMILES: *c1ccccc1OC] | CF$_3$ | Me | |
| 254 | 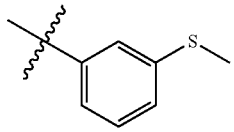 [SMILES: *c1cccc(SC)c1] | CF$_3$ | Me | |
| 255 | 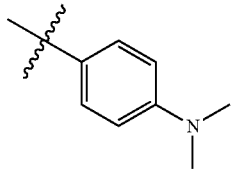 [SMILES: *c1ccc(N(C)C)cc1] | CF$_3$ | Me | |

TABLE 1-continued
Structures and $^1$HNMR data of Compounds I
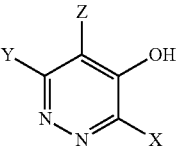
| NO. | X | Y | Z | $^1$HNMR |
|---|---|---|---|---|
| 256 | 4-(OCF$_3$)phenyl | CF$_3$ | Me | |
| 257 | 3-(phenoxy)phenyl | CF$_3$ | Me | |
| 258 | 3-(N-methyl-N-phenylamino)phenyl | CF$_3$ | Me | |
| 259 | 4-(COOMe)phenyl | CF$_3$ | Me | |
| 260 | 4-(SO$_2$Me)phenyl | CF$_3$ | Me | |
| 261 | 4-(OC(O)Me)phenyl | CF$_3$ | Me | |
| 262 | 4-(NHC(O)Me)phenyl | CF$_3$ | Me | |

TABLE 1-continued

Structures and ¹HNMR data of Compounds I

| NO. | X | Y | Z | ¹HNMR |
|---|---|---|---|---|
| 263 | 4-acetylphenyl | CF$_3$ | Me | |
| 264 | 4-biphenyl | CF$_3$ | Me | |
| 265 | 4-(methylsulfonyloxy)phenyl | CF$_3$ | Me | |
| 266 | 3-(carboxymethoxy)phenyl | CF$_3$ | Me | |
| 267 | 2-methyl-3-(methoxymethoxy)phenyl | CF$_3$ | Me | |
| 268 | 3-(methoxycarbonylamino)phenyl | CF$_3$ | Me | |
| 269 | 3-(methylsulfonylmethylamino)phenyl | CF$_3$ | Me | |
| 270 | 3-(methylsulfonylamino)phenyl | CF$_3$ | Me | |

TABLE 1-continued

Structures and ¹HNMR data of Compounds I

| NO. | X | Y | Z | ¹HNMR |
|---|---|---|---|---|
| 271 | 3-(ethoxymethyl)phenyl | CF₃ | Me | |
| 272 | 4-(2-oxobutyl)phenyl | CF₃ | Me | |
| 273 | 4-(diethoxyphosphoryl)phenyl | CF₃ | Me | |
| 274 | 4-(trimethylsilyl)phenyl | CF₃ | Me | |
| 275 | 2,4-dimethylphenyl | CF₃ | Me | |
| 276 | 2,6-dimethylphenyl | CF₃ | Me | |
| 277 | 3,5-dimethylphenyl | CF₃ | Me | |
| 278 | 3,4-dimethylphenyl | CF₃ | Me | |

TABLE 1-continued
Structures and ¹HNMR data of Compounds I
| NO. | X | Y | Z | ¹HNMR |
|---|---|---|---|---|
| 279 | 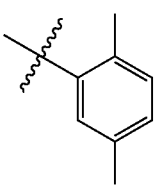 [SMILES: *c1cc(C)ccc1C] | CF₃ | Me | |
| 280 | 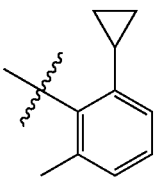 [SMILES: *c1c(C)cccc1C1CC1] | CF₃ | Me | |
| 281 | 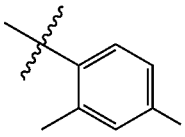 | CF₃ | Me | |
| 282 | 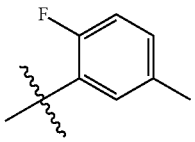 [SMILES: *c1cc(C)ccc1F] | CF₃ | Me | |
| 283 | 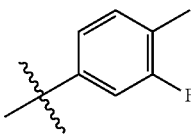 | CF₃ | Me | |
| 284 | 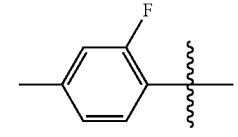 [SMILES: *c1ccc(C)cc1F] | CF₃ | Me | |
| 285 | 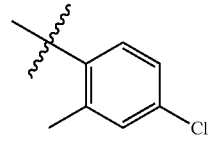 [SMILES: *c1ccc(Cl)cc1C] | CF₃ | Me | |
| 286 | 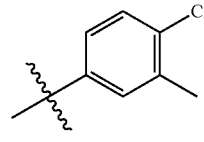 | CF₃ | Me | |

TABLE 1-continued

Structures and ¹HNMR data of Compounds I

| NO. | X | Y | Z | ¹HNMR |
|---|---|---|---|---|
| 287 | 3-Cl-5-Me-phenyl | CF$_3$ | Me | |
| 288 | 3-Cl-4-Me-phenyl | CF$_3$ | Me | |
| 289 | 2-Me-4-OMe-phenyl | CF$_3$ | Me | |
| 290 | 2-NO$_2$-4-Me-phenyl | CF$_3$ | Me | |
| 291 | 2,5-difluorophenyl | CF$_3$ | Me | |
| 292 | 3,5-difluorophenyl | CF$_3$ | Me | |
| 293 | 2,6-difluorophenyl | CF$_3$ | Me | |
| 294 | 2,5-dichlorophenyl | CF$_3$ | Me | |

TABLE 1-continued
Structures and ¹HNMR data of Compounds I
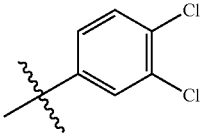 [SMILES: *c1ccc(Cl)c(Cl)c1]
| NO. | X | Y | Z | ¹HNMR |
|---|---|---|---|---|
| 295 | 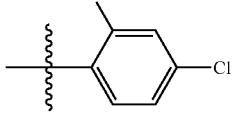 3,4-diCl-phenyl | CF₃ | Me | |
| 296 | 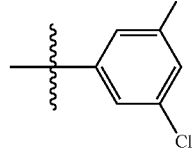 2,4-diCl-phenyl | CF₃ | Me | |
| 297 | 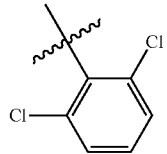 [SMILES: *c1c(Cl)cccc1Cl] 3,5-diCl-phenyl | CF₃ | Me | |
| 298 | 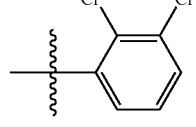 2,6-diCl-phenyl | CF₃ | Me | |
| 299 | 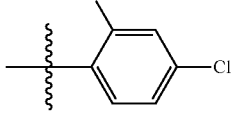 2,3-diCl-phenyl | CF₃ | Me | |
| 300 | 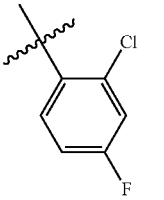 [SMILES: *c1ccc(F)cc1Cl] 2-F-4-Cl-phenyl | CF₃ | Me | |
| 301 | 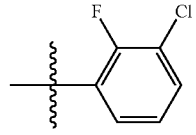 [SMILES: *c1cccc(Cl)c1F] 2-Cl-4-F-phenyl | CF₃ | Me | ¹H NMR (500 MHz, Chloroform-d) δ 14.38 (s, 1H), 7.57 (d, J = 8.0 Hz, 1H), 7.53 (dd, J = 8.5, 6.0 Hz, 1H), 7.39-7.32 (m, 1H), 2.17 (s, 3H). |
| 302 | 2-F-3-Cl-phenyl | CF₃ | Me | |

TABLE 1-continued
Structures and ¹HNMR data of Compounds I
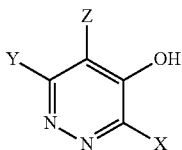
| NO. | X | Y | Z | ¹HNMR |
|-----|---|---|---|-------|
| 303 | 3-Cl, 5-F phenyl | CF₃ | Me | |
| 304 | 3-Cl, 4-F phenyl | CF₃ | Me | |
| 305 | 4-Cl, 3-F phenyl | CF₃ | Me | |
| 306 | 2-Br, 6-F phenyl | CF₃ | Me | |
| 307 | 2-F, 3-Br phenyl | CF₃ | Me | |
| 308 | 3-F, 5-Br phenyl | CF₃ | Me | |
| 309 | 2-F, 5-CF₃ phenyl | CF₃ | Me | |
| 310 | 2-F, 4-CF₃ phenyl | CF₃ | Me | |

TABLE 1-continued
Structures and ¹HNMR data of Compounds I
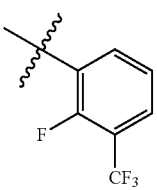 [SMILES: *c1cccc(C(F)(F)F)c1F]
| NO. | X | Y | Z | ¹HNMR |
|---|---|---|---|---|
| 311 | 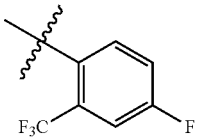 | CF₃ | Me | |
| 312 | 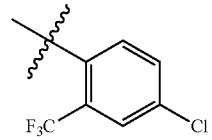 [SMILES: *c1ccc(Cl)cc1C(F)(F)F] | CF₃ | Me | |
| 313 | 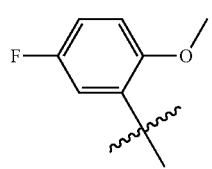 [SMILES: *c1cc(F)ccc1OC] | CF₃ | Me | ¹H NMR (500 MHz, DMSO-d₆) δ 14.54 (s, 1H), 7.97 (s, 1H), 7.88 (d, J = 8.0 Hz, 1H), 7.58 (d, J = 8.0 Hz, 1H), 2.17 (5.3H). |
| 314 | 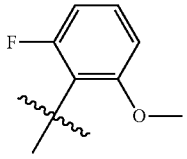 | CF₃ | Me | |
| 315 | 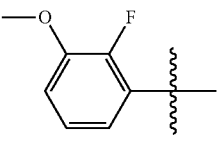 | CF₃ | Me | |
| 316 | 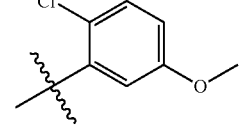 | CF₃ | Me | |
| 317 | 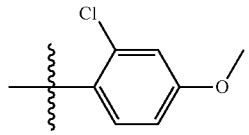 | CF₃ | Me | |
| 318 |  | CF₃ | Me | |

TABLE 1-continued

Structures and ¹HNMR data of Compounds I

| NO. | X | Y | Z | ¹HNMR |
|---|---|---|---|---|
| 319 | 4-CHO-2-F-phenyl | CF₃ | Me | |
| 320 | 3-F-4-CHO-phenyl | CF₃ | Me | |
| 321 | 4-F-2-CHO-phenyl | CF₃ | Me | |
| 322 | 2-CHO-6-F-phenyl | CF₃ | Me | |
| 323 | 3-NO₂-4-F-phenyl | CF₃ | Me | |
| 324 | 2-F-5-NO₂-phenyl | CF₃ | Me | |
| 325 | 3-NO₂-4-Cl-phenyl | CF₃ | Me | |
| 326 | 4-Cl-3-NO₂-phenyl | CF₃ | Me | |

TABLE 1-continued

Structures and ¹HNMR data of Compounds I

| NO. | X | Y | Z | ¹HNMR |
|---|---|---|---|---|
| 327 | 5-methyl-2-methoxy-4-(dimethylamino)phenyl | CF$_3$ | Me | |
| 328 | 2,6-dimethyl-4-chlorophenyl | CF$_3$ | Me | |
| 329 | 2-methyl-3,6-dichlorophenyl | CF$_3$ | Me | |
| 330 | 2-fluoro-3-methoxy-4-chloro-6-(F)phenyl | CF$_3$ | Me | |
| 331 | 2,3,4-trichlorophenyl | CF$_3$ | Me | |
| 332 | 4,6-dichloro-3-hydroxyphenyl | CF$_3$ | Me | |
| 333 | 2,3,5-trifluorophenyl | CF$_3$ | Me | |

TABLE 1-continued

Structures and ¹HNMR data of Compounds I

![Structure: pyridazine core with Y at position 6, Z at position 5, OH at position 4, X at position 3, N-N in ring]

| NO. | X | Y | Z | ¹HNMR |
|-----|---|-----|-----|-------|
| 334 | 3,4,5-trifluorophenyl | $CF_3$ | Me | ¹H NMR (500 MHz, DMSO-$d_6$) δ 14.42 (s, 1H) 8.09-8.06 (m, 2H), 2.15 (s, 3H). |
| 335 | 2,3,6-trifluorophenyl | $CF_3$ | Me | |
| 336 | pentafluorophenyl | $CF_3$ | Me | |
| 337 | 1-methyl-pyrrol-2-yl | $CF_3$ | Me | |
| 338 | furan-3-yl | $CF_3$ | Me | |
| 339 | furan-2-yl | $CF_3$ | Me | |
| 340 | thiophen-2-yl | $CF_3$ | Me | |
| 341 | thiophen-3-yl | $CF_3$ | Me | |

TABLE 1-continued

Structures and ¹HNMR data of Compounds I

| NO. | X | Y | Z | ¹HNMR |
|---|---|---|---|---|
| 342 | oxazol-5-yl | CF$_3$ | Me | |
| 343 | 1-methyl-imidazol-2-yl | CF$_3$ | Me | |
| 344 | isoxazol-3-yl | CF$_3$ | Me | |
| 345 | isothiazol-5-yl | CF$_3$ | Me | |
| 346 | 5-methyl-1,3,4-oxadiazol-2-yl | CF$_3$ | Me | |
| 347 | 1,3,4-thiadiazol-2-yl | CF$_3$ | Me | |
| 348 | 4-methyl-1,2,4-triazol-3-yl | CF$_3$ | Me | |
| 349 | 1,2,4-oxadiazol-3-yl | CF$_3$ | Me | |
| 350 | 1,3,4-thiadiazol-2-yl | CF$_3$ | Me | |

TABLE 1-continued

Structures and ¹HNMR data of Compounds I

| NO. | X | Y | Z | ¹HNMR |
|---|---|---|---|---|
| 351 | 1H-1,2,4-triazol-3-yl | CF$_3$ | Me | |
| 352 | 1,2,3-oxadiazol-4-yl | CF$_3$ | Me | |
| 353 | 1,2,3-thiadiazol-5-yl | CF$_3$ | Me | |
| 354 | 1H-1,2,3-triazol-4-yl | CF$_3$ | Me | |
| 355 | 1-methyl-1H-tetrazol-5-yl | CF$_3$ | Me | |
| 356 | pyrazin-2-yl | CF$_3$ | Me | |
| 357 | pyrimidin-5-yl | CF$_3$ | Me | |
| 358 | pyridazin-4-yl | CF$_3$ | Me | |

TABLE 1-continued

Structures and ¹HNMR data of Compounds I

| NO. | X | Y | Z | ¹HNMR |
|---|---|---|---|---|
| 359 | 1,3,5-triazin-2-yl | CF₃ | Me | |
| 360 | 1-methylindol-5-yl | CF₃ | Me | |
| 361 | benzo[b]thiophen-2-yl | CF₃ | Me | |
| 362 | benzofuran-5-yl | CF₃ | Me | |
| 363 | benzo[d]thiazol-5-yl | CF₃ | Me | |
| 364 | benzo[d]oxazol-6-yl | CF₃ | Me | |
| 365 | 1-ethylbenzimidazol-6-yl | CF₃ | Me | |
| 366 | 1-methylbenzotriazol-5-yl | CF₃ | Me | |
| 367 | isoquinolin-6-yl | CF₃ | Me | |

TABLE 1-continued

Structures and ¹HNMR data of Compounds I

| NO. | X | Y | Z | ¹HNMR |
|---|---|---|---|---|
| 368 | quinoxalin-2-yl | CF₃ | Me | |
| 369 | phthalazin-1-yl | CF₃ | Me | |
| 370 | cinnolin-4-yl | CF₃ | Me | |
| 371 | quinolin-4-yl | CF₃ | Me | |
| 372 | pteridin-6-yl | CF₃ | Me | |
| 373 | 9H-purin-8-yl | CF₃ | Me | |
| 374 | [1,2,4]triazolo[1,5-a]pyrimidin-6-yl | CF₃ | Me | |
| 375 | [1,2,4]triazolo[1,5-a]pyrimidin-6-yl isomer | CF₃ | Me | |

TABLE 1-continued

Structures and ¹HNMR data of Compounds I

| NO. | X | Y | Z | ¹HNMR |
|---|---|---|---|---|
| 376 | imidazo[1,2-b]pyridazin-6-yl | CF₃ | Me | |
| 377 | naphthalen-2-yl | CF₃ | Me | |
| 378 | anthracen-2-yl | CF₃ | Me | |
| 379 | phenanthren-2-yl | CF₃ | Me | |
| 380 | 2,3-dihydrobenzo[b][1,4]dioxin-6-yl | CF₃ | Me | |
| 381 | acridin-2-yl | CF₃ | Me | |
| 382 | phenazin-2-yl | CF₃ | Me | |
| 383 | 1,10-phenanthrolin-3-yl | CF₃ | Me | |

TABLE 1-continued

Structures and ¹HNMR data of Compounds I

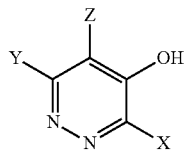

| NO. | X | Y | Z | ¹HNMR |
|---|---|---|---|---|
| 384 | (2-phenothiazinyl) | CF₃ | Me | |
| 385 | (2-carbazolyl) | CF₃ | Me | |
| 386 | (dibenzofuranyl) | CF₃ | Me | |
| 387 | (dibenzothiophenyl) | CF₃ | Me | |
| 388 | (1-(difluoromethyl)pyrazol-4-yl) | CF₃ | CHF₂ | ¹H NMR (500 MHz, DMSO-d6) δ 14.42 (s, 1H), 9.16 (s, 1H), 8.45 (s, 1H), 7.94 (t, J = 59.0 Hz, 1H), 7.25 (t, J = 54.5 Hz, 1H). |
| 389 | (1-(difluoromethyl)pyrazol-4-yl) | CF₃ | CF₃ | ¹H NMR (500 MHz, DMSO-d6) δ 14.32 (s, 1H), 9.12 (s, 1H), 8.44 (s, 1H), 7.91 (t, J = 59.1 Hz, 1H). |
| 390 | (1-(difluoromethyl)pyrazol-4-yl) | CF₃ | CHO | ¹H NMR (500 MHz, DMSO-d6) δ 14.37 (s, 1H), 10.32 (s, 1H), 9.24 (s, 1H), 8.46 (s, 1H), 7.97 (t, J = 58.5 Hz, 1H). |
| 391 | (1-(difluoromethyl)pyrazol-4-yl) | CF₃ | NHC(O)OEt | ¹H NMR (500 MHz, DMSO-d6) δ 14.32 (s, 1H), 9.13 (s, 1H), 8.46 (s, 1H), 7.96 (t, J = 59.0 Hz, 1H), 6.62 (s, 1H), 4.09 (q, J = 7.0 Hz, 2H), 1.21 (t, J = 7.0 Hz, 3H). |

TABLE 1-continued

Structures and ¹HNMR data of Compounds I

| NO. | X | Y | Z | ¹HNMR |
|-----|---|---|---|-------|
| 392 | 4-(difluoromethyl)pyrazol-1-yl linker | CF₃ | propyl carbamate | ¹H NMR (500 MHz, DMSO-d6) δ 14.32 (s, 1H), 9.12 (s, 1H), 8.45 (s, 1H), 7.96 (t, J = 59.0 Hz, 1H), 6.62 (s, 1H), 3.99 (t, J = 6.5 Hz, 2H), 1.63-1.56 (m, 2H), 0.89 (t, J = 7.5 Hz, 3H). |
| 393 | 4-(difluoromethyl)pyrazol-1-yl linker | CF₃ | isopropyl carbamate | ¹H NMR (500 MHz, DMSO-d6) δ 14.32 (s, 1H), 9.16 (s, 1H), 8.59 (s, 1H), 7.96 (t, J = 59.0 Hz, 1H), 6.62 (s, 1H), 4.27-4.16 (m, 1H), 1.19 (s, 6H). |
| 394 | 4-(difluoromethyl)pyrazol-1-yl linker | CF₃ | cyclohexyl carbamate | ¹H NMR (500 MHz, DMSO-d6) δ 14.32 (s, 1H), 9.12 (s, 1H), 8.45 (s, 1H), 7.96 (t, J = 59.0 Hz, 1H), 6.62 (s, 1H), 4.57-4.51 (m, 1H), 2.14-1.07 (m, 10H). |
| 395 | 4-(difluoromethyl)pyrazol-1-yl linker | CF₃ | ethylsulfonamide | ¹H NMR (500 MHz, DMSO-d6) δ 14.32 (s, 1H), 9.12 (s, 1H), 8.49 (s, 1H), 7.96 (t, J = 59.0 Hz, 1H), 6.62 (s, 1H), 3.86 (q, J = 7.0 Hz, 2H), 1.37 (t, J = 7.5 Hz, 3H). |
| 396 | 4-(difluoromethyl)pyrazol-1-yl linker | CF₃ | pyrrolidin-1-yl | ¹H NMR (500 MHz, DMSO-d6) δ 14.39 (s, 1H), 9.12 (s, 1H), 8.49 (s, 1H), 7.96 (t, J = 59.0 Hz, 1H), 3.39-3.36 (m, 4H), 1.97-1.93 (m, 4H). |
| 397 | 4-fluorophenyl | CF₃ | F | ¹H NMR (500 MHz, DMSO-d₆) δ 14.38 (s, 1H), 7.92-7.88 (dd, J = 9.0, 5.5 Hz, 2H), 7.38-7.28 (m, 2H). |

TABLE 1-continued

Structures and ¹HNMR data of Compounds I

| NO. | X | Y | Z | ¹HNMR |
|---|---|---|---|---|
| 398 | 4-F-phenyl | $CF_3$ | 4-methoxybenzyl-NH-C(CH₃)- | ¹H NMR (500 MHz, DMSO-$d_6$) δ 14.33 (s, 1H), 7.89-7.79 (m, 2H), 7.34-7.28 (m, 2H), 7.26-7.23 (m, 2H), 6.91-6.87 (m, 2H), 6.22 (s, 1H), 4.32 (s, 2H), 3.79 (s, 3H). |
| 399 | 4-cyano-3-methylphenyl | $CF_3$ | Me | ¹H NMR (500 MHz, DMSO-$d_6$) δ 14.41 (s, 1H), 7.81 (d, J = 2.0 Hz, 1H), 7.71 (d, J = 7.5 Hz, 1H), 7.61 (dd, J = 7.5, 2.0 Hz, 1H), 2.41 (s, 3H), 2.34 (s, 3H). |
| 400 | 4-cyano-3-methylphenyl | $CF_3$ | cyclopropyl | ¹H NMR (500 MHz, DMSO-$d_6$) δ 14.39 (s, 1H), 7.43 (d, J = 7.5 Hz, 1H), 7.13-7.05 (m, 2H), 2.31 (s, 3H), 2.20-2.16 (m, 1H), 1.01-0.96 (m, 2H), 0.78-0.74 (m, 2H). |
| 401 | 2-Cl-4-F-phenyl | $CF_3$ | isopropenyl | ¹H NMR (500 MHz, DMSO-$d_6$) δ 14.38 (br, 1H), 7.62-7.55 (m, 2H), 7.39-7.32 (m, 1H), 5.35 (s, 1H), 4.96 (s, 1H), 1.96 (s, 3H). |
| 402 | 2-Cl-4-F-phenyl | $CF_3$ | cyclopropyl | ¹H NMR (500 MHz, DMSO-$d_6$) δ 14.36 (br, 1H), 7.56 (d, J = 8.0 Hz, 1H), 7.52 (dd, J = 8.5, 6.0 Hz, 1H), 7.39-7.32 (m, 1H), 1.73 (s, 1H), 1.32 (m, 2H), 0.92-0.80 (m, 2H). |
| 403 | 4-Cl-2-CF₃-phenyl | $CF_3$ | isopropenyl | ¹H NMR (500 MHz. DMSO-$d_6$) δ 14.34 (br, 1H), 7.97 (d, J = 2.0 Hz, 1H), 7.88 (dd, J = 8.5, 2.0 Hz, 1H), 7.62 (d, J = 8.5 Hz, 1H), 5.34 (s, 1H), 4.94 (s, 1H), 1.94 (s, 3H). |
| 404 | 4-Cl-2-CF₃-phenyl | $CF_3$ | cyclopropyl | ¹H NMR (500 MHz, DMSO-$d_6$) δ 14.38 (br, 1H), 7.95 (d, J = 2.0 Hz, 1H), 7.88-7.83 (m, 1H), 7.56 (d, J = 8.5 Hz, 1H), 1.76-1.68 (m, 1H), 1.35-1.20 (m, 2H), 0.94-0.84 (m, 2H). |

TABLE 1-continued

Structures and ¹HNMR data of Compounds I

| NO. | X | Y | Z | ¹HNMR |
|---|---|---|---|---|
| 405 | (2-fluoro-3-cyanophenyl) | $CF_3$ | cyclopropyl | ¹H NMR (500 MHz, DMSO-d6) δ 14.37 (br, 1H), 8.79 (d, J = 7.5 Hz, 1H), 8.37 (d, J = 7.5 Hz, 1H), 7.81 (t, J = 7.5 Hz, 1H), 2.31-2.28 (m, 1H), 1.62-1.56 (m, 2H), 1.42-1.35 (m, 2H). |
| 406 | (3,4,5-trifluorophenyl) | $CF_3$ | isopropenyl | ¹H NMR (500 MHz, DMSO-d₆) δ 14.29 (s, 1H), 8.07-8.03 (m, 2H), 5.33 (s, 1H), 4.93 (s, 1H), 1.96 (s, 3H). |
| 407 | (3,4,5-trifluorophenyl) | $CF_3$ | cyclopropyl | ¹H NMR (500 MHz, DMSO-d₆) δ 14.36 (s, 1H), 7.35-7.27 (m, 2H), 2.17-2.11 (m, 1H), 0.99-0.95 (m, 2H), 0.75-0.71 (m, 2H). |
| 408 | (2,2-difluorobenzo[d][1,3]dioxol-5-yl) | $CF_3$ | Me | ¹H NMR (500 MHz, Chloroform-d) δ 14.37 (br, 1H), 8.09 (s, 1H), 8.0 (d, J = 8.5 Hz, 1H), 7.5 (d, J = 8.5 Hz, 1H), 2.18 (s, 3H). |
| 409 | (2,2-difluorobenzo[d][1,3]dioxol-5-yl) | $CF_3$ | isopropenyl | ¹H NMR (500 MHz, DMSO-d₆) δ 14.44 (s, 1H), 8.01 (s, 1H), 7.90 (d, J = 8.5 Hz, 1H), 7.68 (d, J = 8.5 Hz, 1H), 5.35 (s, 1H), 4.96 (s, 1H), 1.99 (s, 3H). |
| 410 | (2,2-difluorobenzo[d][1,3]dioxol-5-yl) | $CF_3$ | cyclopropyl | ¹H NMR (500 MHz, Chloroform-d) δ 14.43 (br, 1H), 8.01 (s, 1H), 7.90 (d, J = 8.5 Hz, 1H), 7.53 (d, J = 8.5 Hz, 1H), 1.11 (m, 1H), 1.36 (m, 2H), 0.91 (m, 2H). |
| 411 | (2-chloropyridin-4-yl) | $CF_3$ | isopropenyl | ¹H NMR (500 MHz, DMSO-d₆) δ 14.34 (s, 1H), 8.57 (d, J = 5.0 Hz, 1H), 8.24 (s, 1H), 8.07 (dd, J = 5.0, 1.5 Hz, 1H), 5.35 (s, 1H), 4.96 (s, 1H), 1.99 (s, 3H). |

TABLE 1-continued

Structures and ¹HNMR data of Compounds I

| NO. | X | Y | Z | ¹HNMR |
|---|---|---|---|---|
| 412 | 5-chloropyridin-3-yl | CF₃ | isopropenyl | ¹H NMR (500 MHz, DMSO-d6) δ 14.38 (s, 1H), 9.41 (s, 1H), 8.88 (d, J = 2.5 Hz, 1H), 8.56 (d, J = 2.5 Hz, 1H), 5.14 (s, 1H), 4.73 (s, 1H), 1.95 (s, 3H). |
| 413 | 6-isopropylpyridin-3-yl | CF₃ | isopropenyl | ¹H NMR (500 MHz, DMSO-d₆) δ 14.39 (s, 1H), 9.54 (s, 1H), 8.98 (s, 1H), 7.80 (d, J = 8.0 Hz, 1H), 7.62 (d, J = 8.0 Hz, 1H), 5.69 (s, 1H), 5.17 (s, 1H), 5.09 (s, 1H), 4.86 (s, 1H), 2.06 (s, 3H), 2.01 (s, 3H). |
| 414 | 2,6-difluoropyridin-3-yl | CF₃ | Br | ¹H NMR (500 MHz, DMSO-d₆) δ 14.36 (s, 1H), 8.19-8.16 (m, 1H), 7.13-7.10 (m, 1H). |

TABLE 2

The structures of the group M in the derivative compounds I-1 (X, Y, Z groups are shown in Table 1)

| NO. | M |
|---|---|
| M-1 | acetyl (−C(O)CH₃) |
| M-2 | propanoyl (−C(O)CH₂CH₃) |
| M-3 | butanoyl (−C(O)CH₂CH₂CH₃) |
| M-4 | isobutanoyl (−C(O)CH(CH₃)₂) |
| M-5 | pentanoyl (−C(O)CH₂CH₂CH₂CH₃) |
| M-6 | 3-methylbutanoyl (−C(O)CH₂CH(CH₃)₂) |
| M-7 | pivaloyl (−C(O)C(CH₃)₃) |
| M-8 | hexanoyl (−C(O)CH₂CH₂CH₂CH₂CH₃) |

TABLE 2-continued
The structures of the group M in the derivative compounds I-1
(X, Y, Z groups are shown in Table 1)
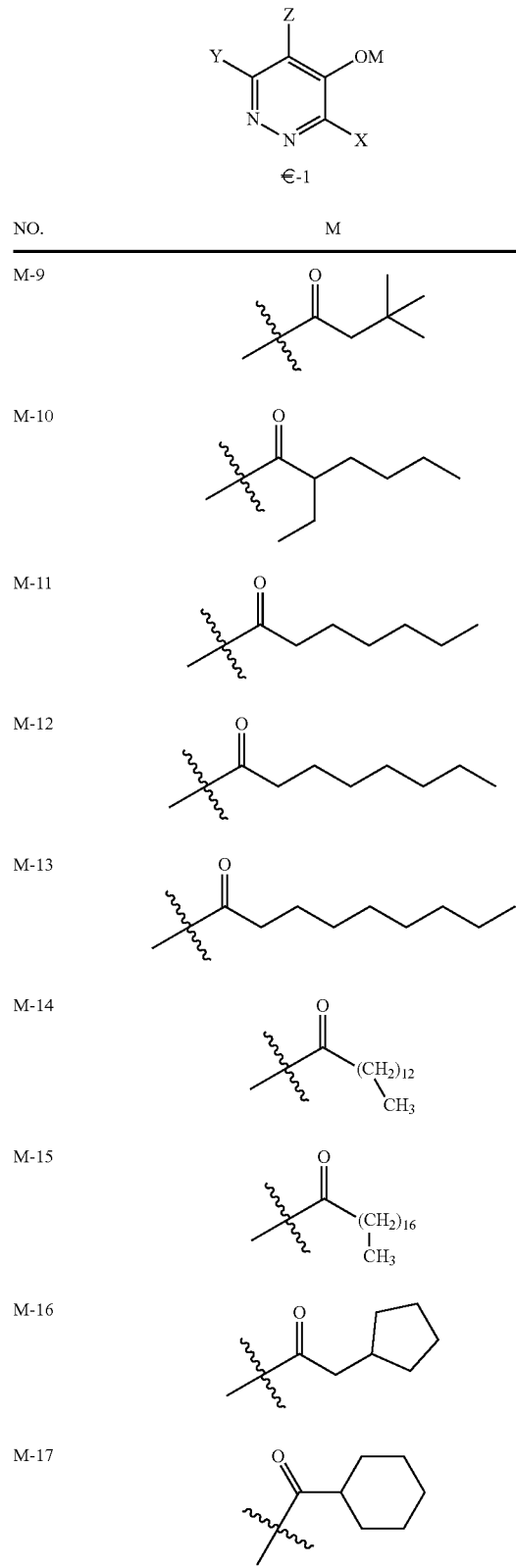
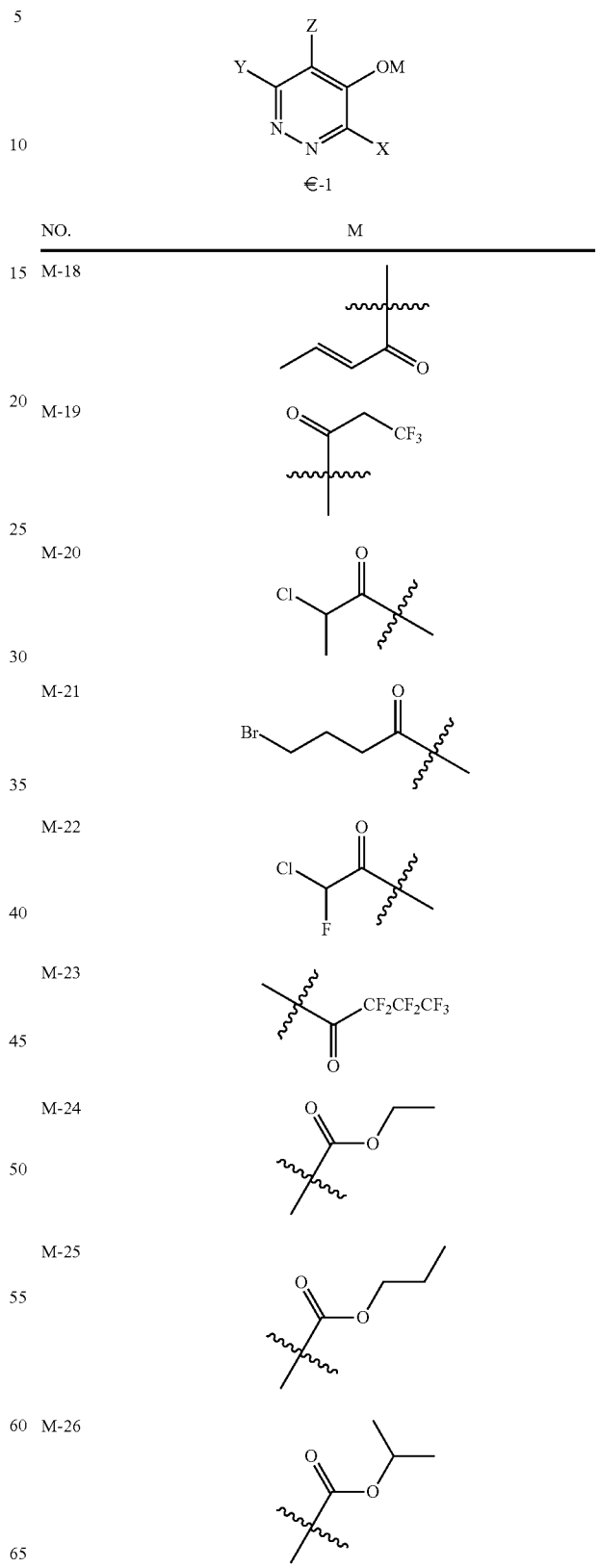

TABLE 2-continued
The structures of the group M in the derivative compounds I-1
(X, Y, Z groups are shown in Table 1)
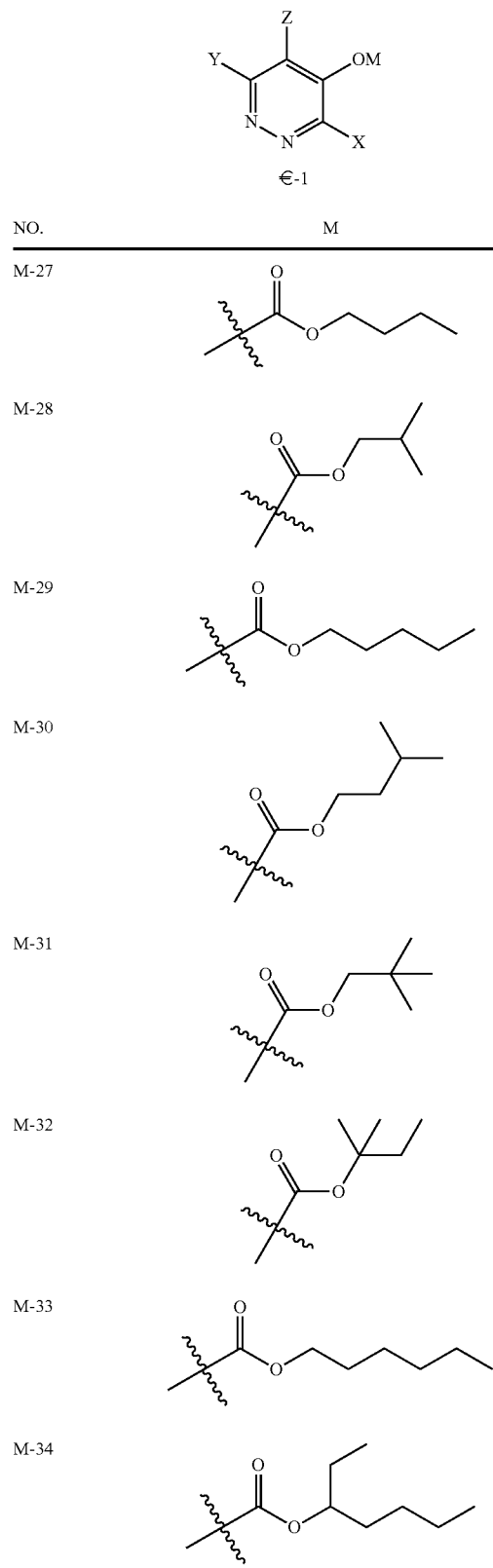
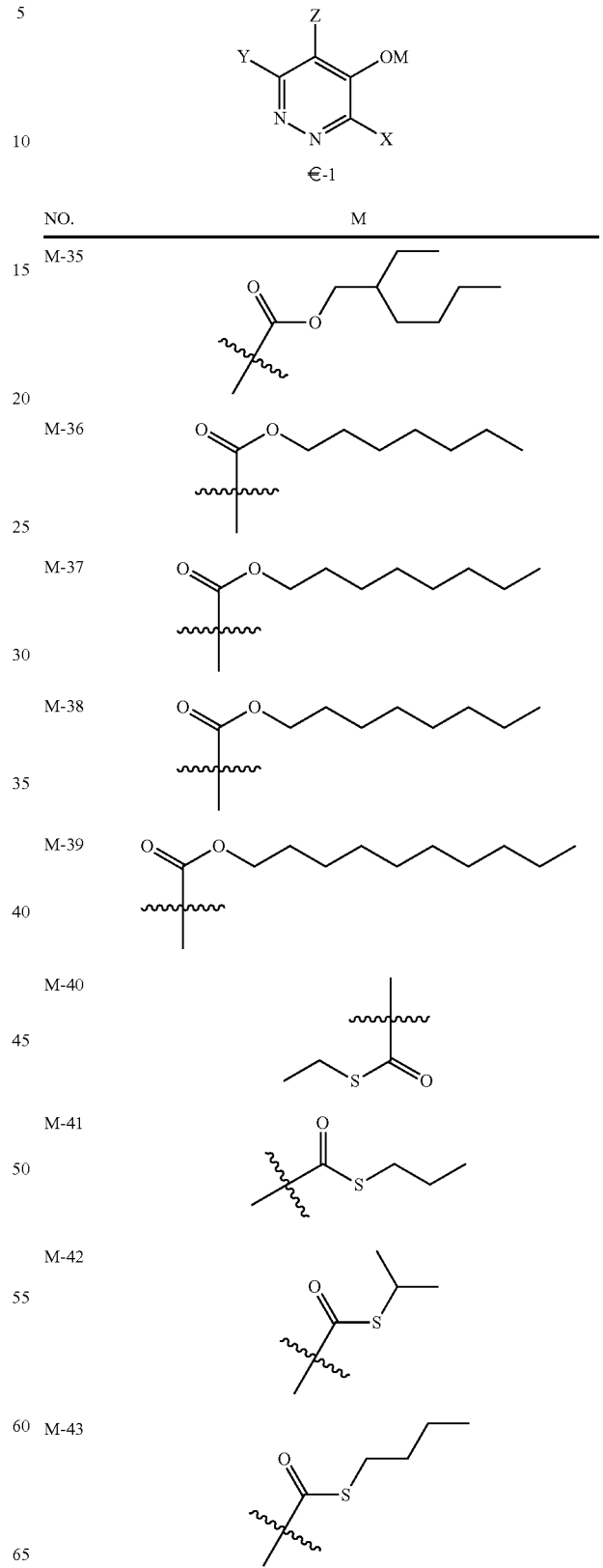

TABLE 2-continued
The structures of the group M in the derivative compounds I-1
(X, Y, Z groups are shown in Table 1)
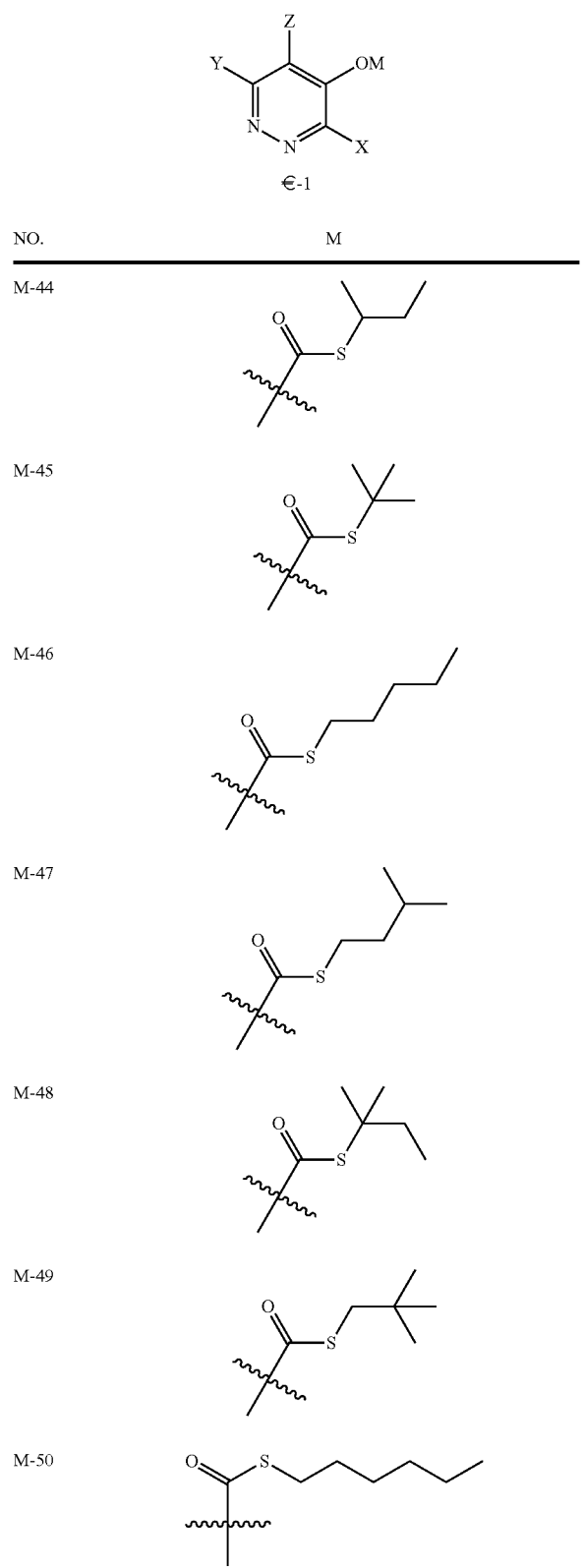
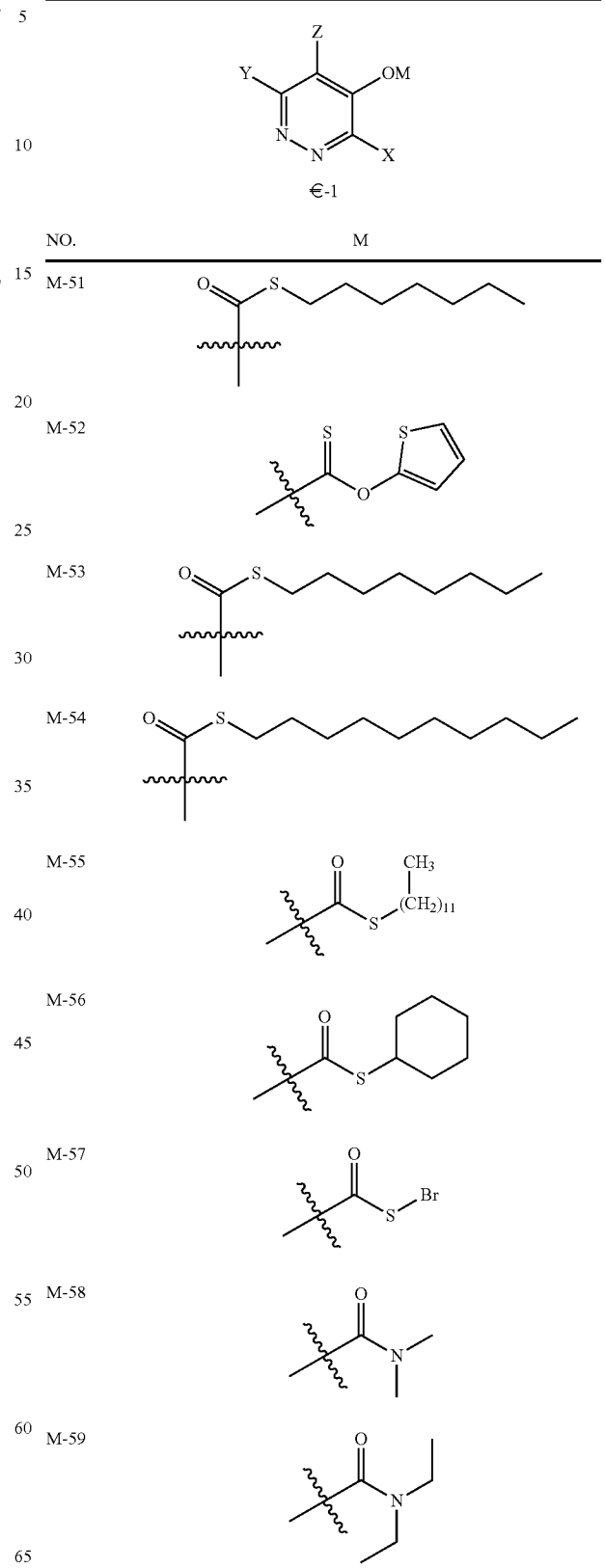

TABLE 2-continued
The structures of the group M in the derivative compounds I-1
(X, Y, Z groups are shown in Table 1)
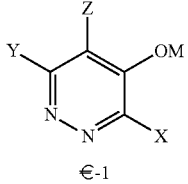
| NO. | M |
|---|---|
| M-60 | 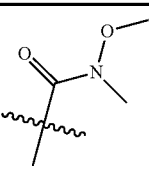 |
| M-61 | 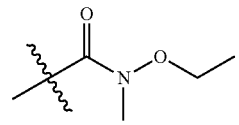 [SMILES: *C(=O)N(C)OCC] |
| M-62 | 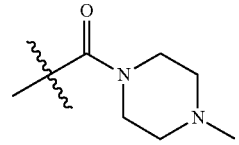 [SMILES: *C(=O)N1CCN(C)CC1] |
| M-63 | 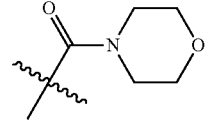 [SMILES: *C(=O)N1CCOCC1] |
| M-64 | 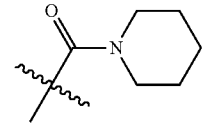 |
| M-65 | 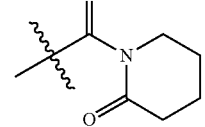 |
| M-66 | 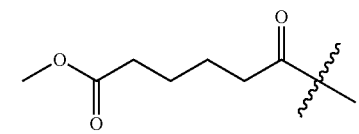 [SMILES: *C(=O)CCCCC(=O)OC] |
| M-67 | 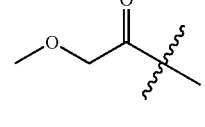 |
| M-68 | 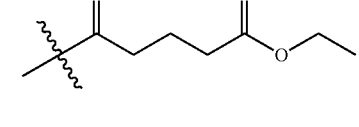 |
TABLE 2-continued
The structures of the group M in the derivative compounds I-1
(X, Y, Z groups are shown in Table 1)
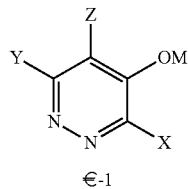
| NO. | M |
|---|---|
| M-69 | 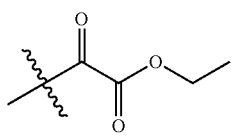 [SMILES: *C(=O)C(=O)OCC] |
| M-70 | 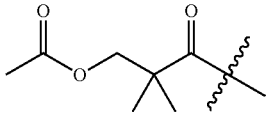 [SMILES: *C(=O)C(C)(C)COC(C)=O] |
| M-71 | 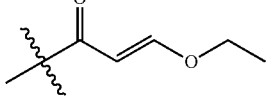 |
| M-72 | 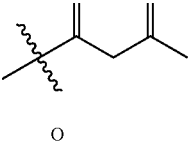 |
| M-73 | 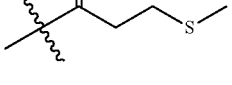 |
| M-74 | 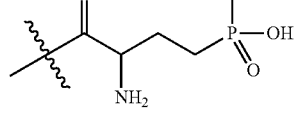 |
| M-75 | 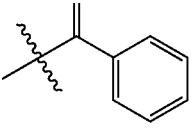 |
| M-76 | 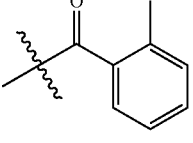 |
| M-77 | 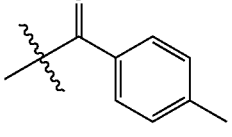 |

TABLE 2-continued
The structures of the group M in the derivative compounds I-1
(X, Y, Z groups are shown in Table 1)
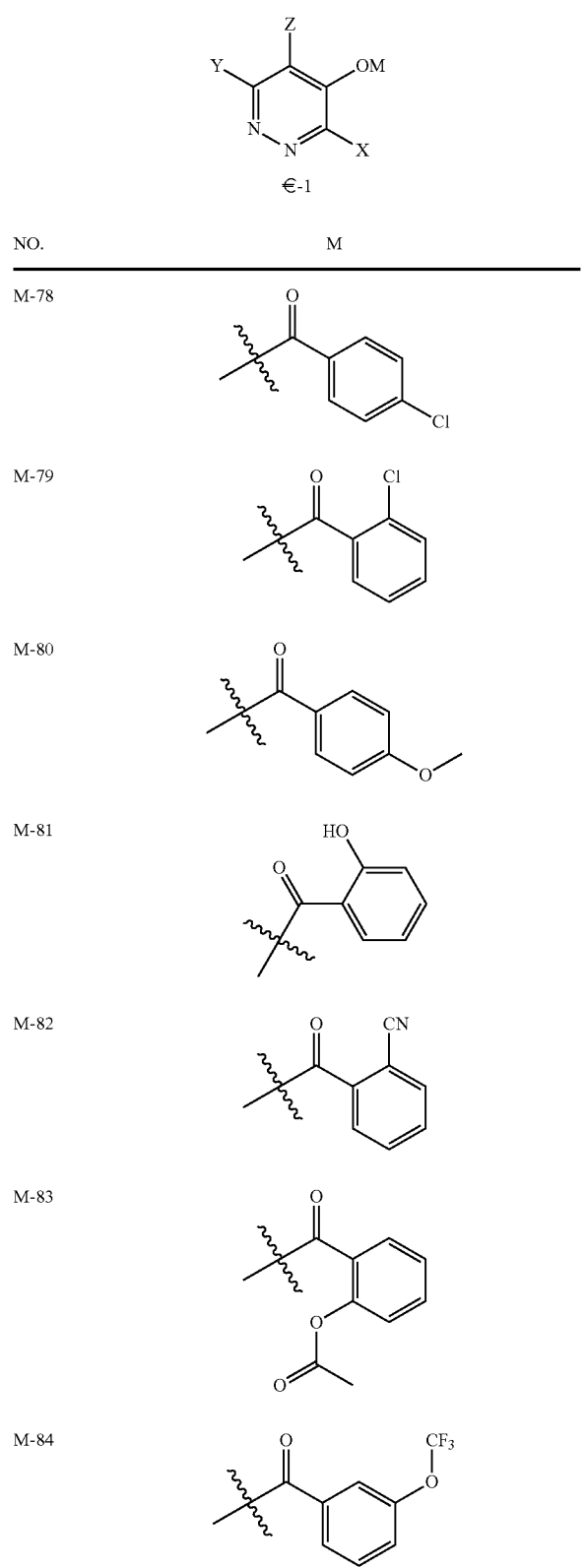
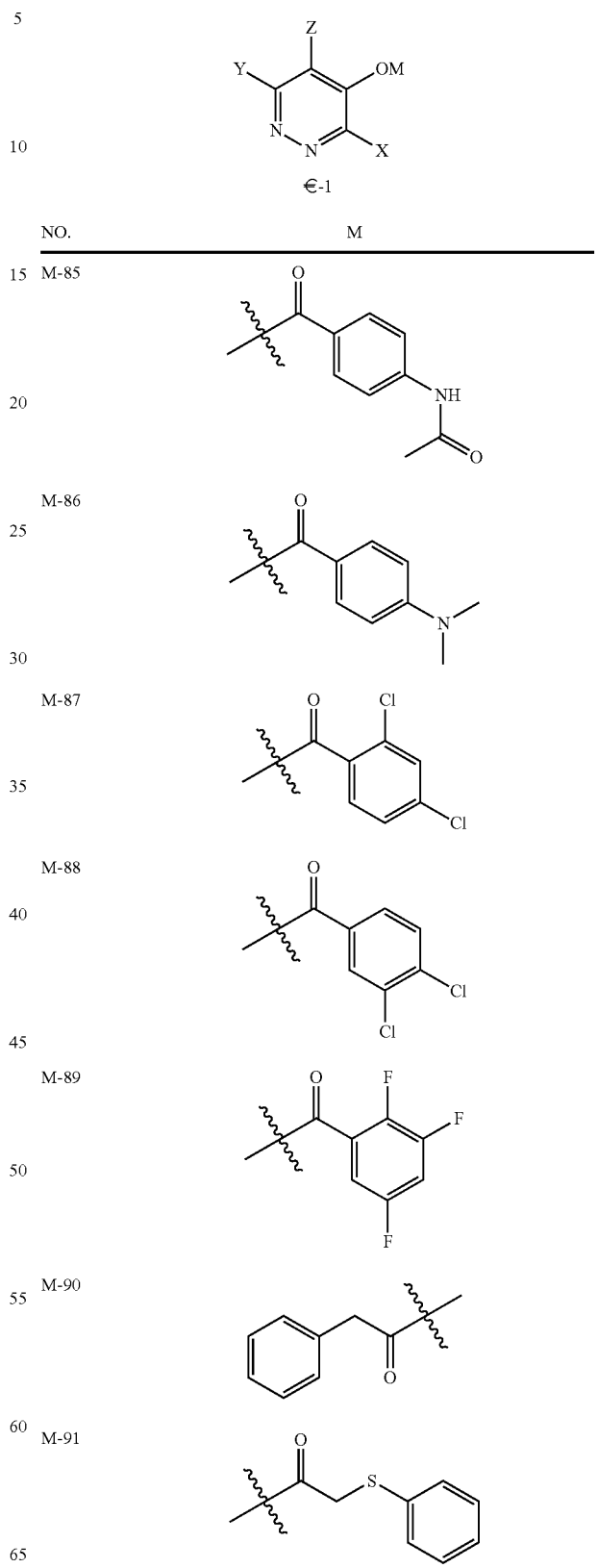

TABLE 2-continued
The structures of the group M in the derivative compounds I-1
(X, Y, Z groups are shown in Table 1)
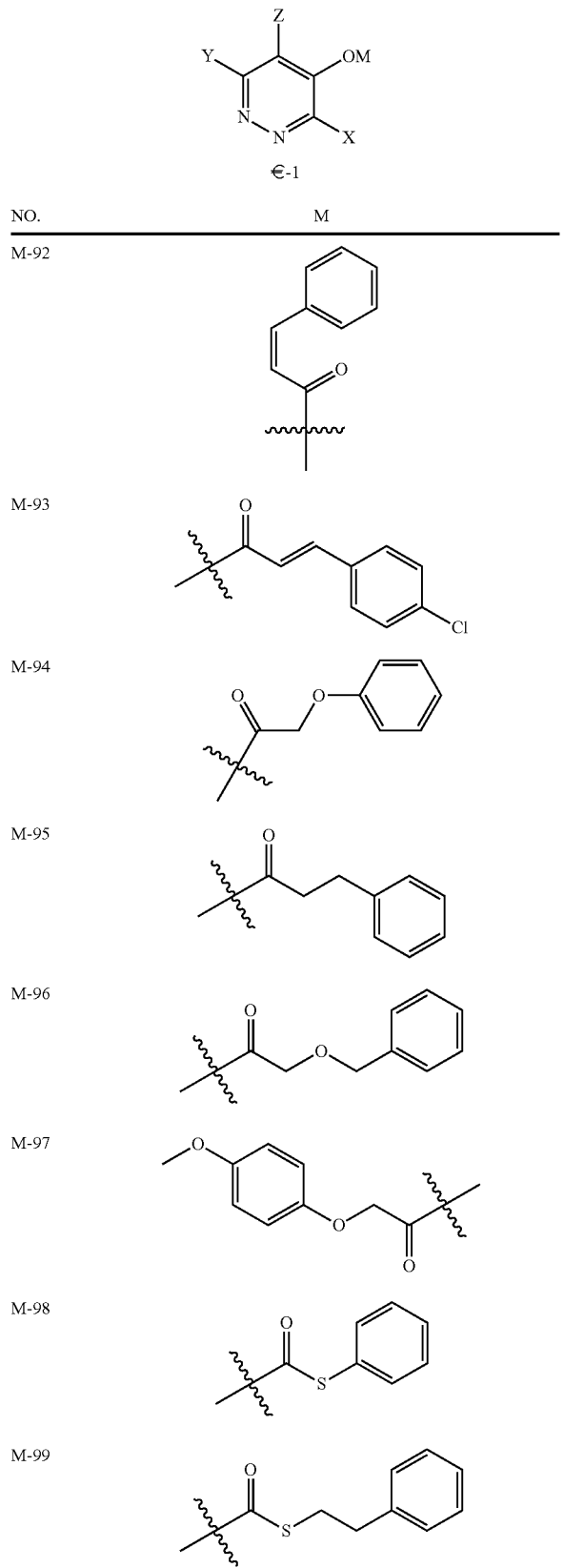
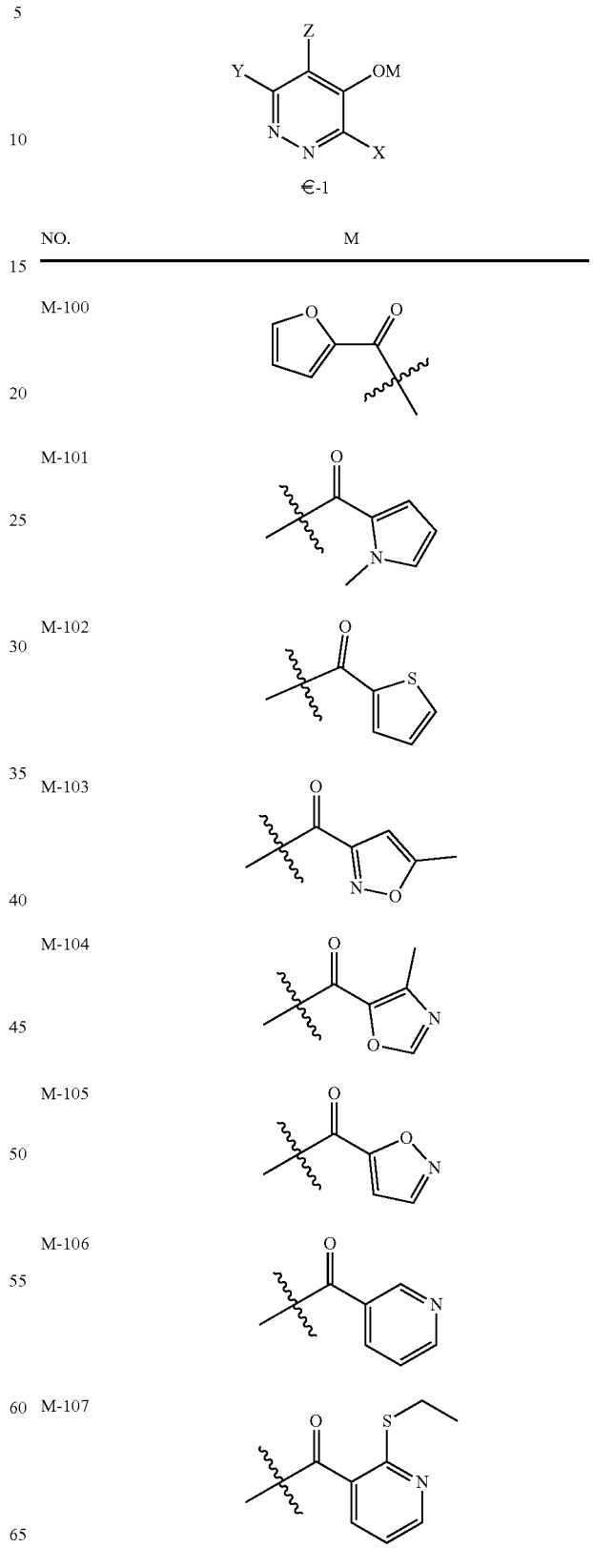

TABLE 2-continued

The structures of the group M in the derivative compounds I-1
(X, Y, Z groups are shown in Table 1)

€-1

| NO. | M |
|---|---|
| M-108 | 6-chloropyridin-3-yl carbonyl |
| M-109 | 2,6-dichloropyrimidin-4-yl carbonyl |
| M-110 | pyrazin-2-yl carbonyl |
| M-111 | naphthalen-2-yl carbonyl |
| M-112 | 1H-indol-5-yl carbonyl |
| M-113 | quinolin-2-yl carbonyl |
| M-114 | benzofuran-5-yl carbonyl |
| M-115 | benzo[d][1,3]dioxol-4-yl carbonyl |
| M-116 | benzo[b]thiophen-7-yl carbonyl |
| M-117 | benzofuran-2-yl carbonyl |
| M-118 | ethylsulfonyl |
| M-119 | cyclopropylsulfonyl |
| M-120 | (methylsulfonyl)methylsulfonyl |
| M-121 | N-(3-chloropropyl)sulfamoyl |
| M-122 | (4-methylpiperazin-1-yl)sulfonyl |
| M-123 | piperidin-1-ylsulfonyl |
| M-124 | (2-fluoro-4-chlorophenyl)sulfonyl |
| M-125 | (4-(trifluoromethyl)phenyl)sulfonyl |

TABLE 2-continued
The structures of the group M in the derivative compounds I-1
(X, Y, Z groups are shown in Table 1)
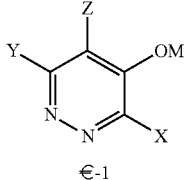
| NO. | M |
|---|---|
| M-126 | 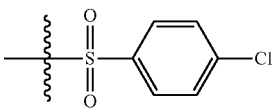 [SMILES: *S(=O)(=O)c1ccc(Cl)cc1] |
| M-127 | 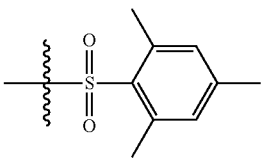 [SMILES: *S(=O)(=O)c1c(C)cc(C)cc1C] |
| M-128 | 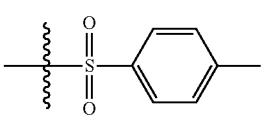 |
| M-129 | 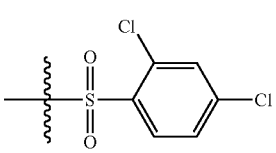 |
| M-130 | 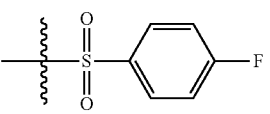 [SMILES: *S(=O)(=O)c1ccc(F)cc1] |
| M-131 | 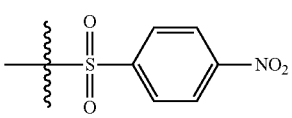 |
| M-132 | 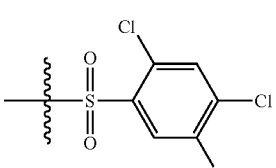 |
| M-133 | 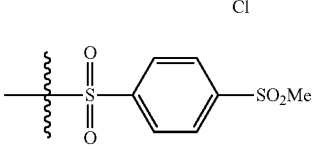 |
| M-134 | 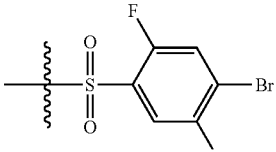 |
TABLE 2-continued
The structures of the group M in the derivative compounds I-1
(X, Y, Z groups are shown in Table 1)
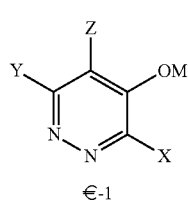
| NO. | M |
|---|---|
| M-135 | 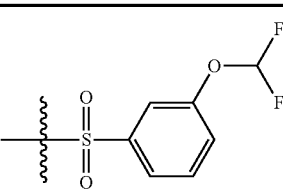 |
| M-136 | 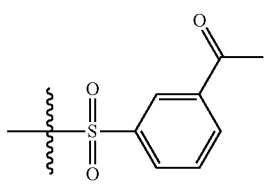 [SMILES: *S(=O)(=O)c1cccc(C(C)=O)c1] |
| M-137 | 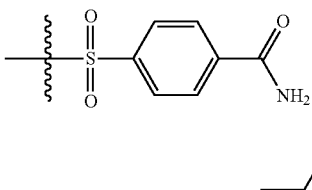 |
| M-138 | 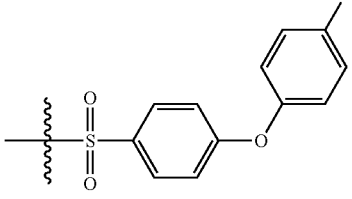 |
| M-139 | 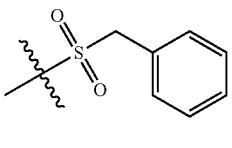 [SMILES: *S(=O)(=O)Cc1ccccc1] |
| M-140 | 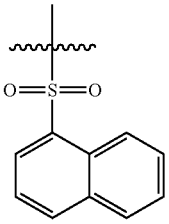 |
| M-141 | 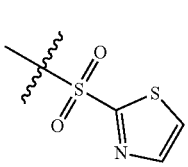 [SMILES: *S(=O)(=O)c1nccs1] |

TABLE 2-continued
The structures of the group M in the derivative compounds I-1
(X, Y, Z groups are shown in Table 1)
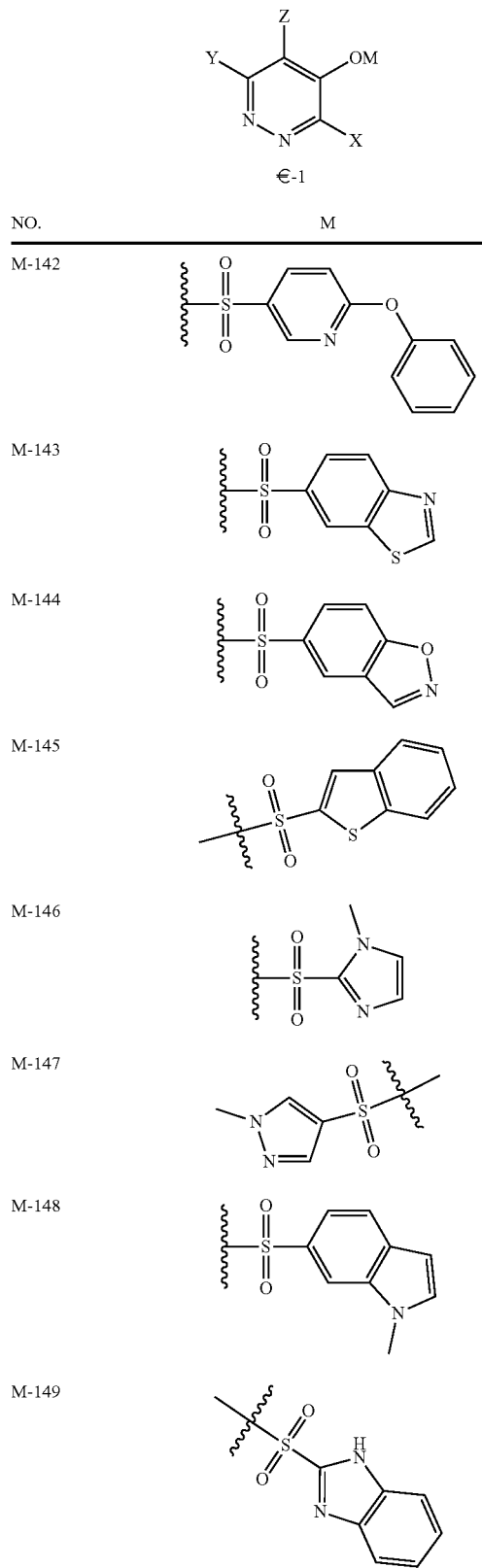
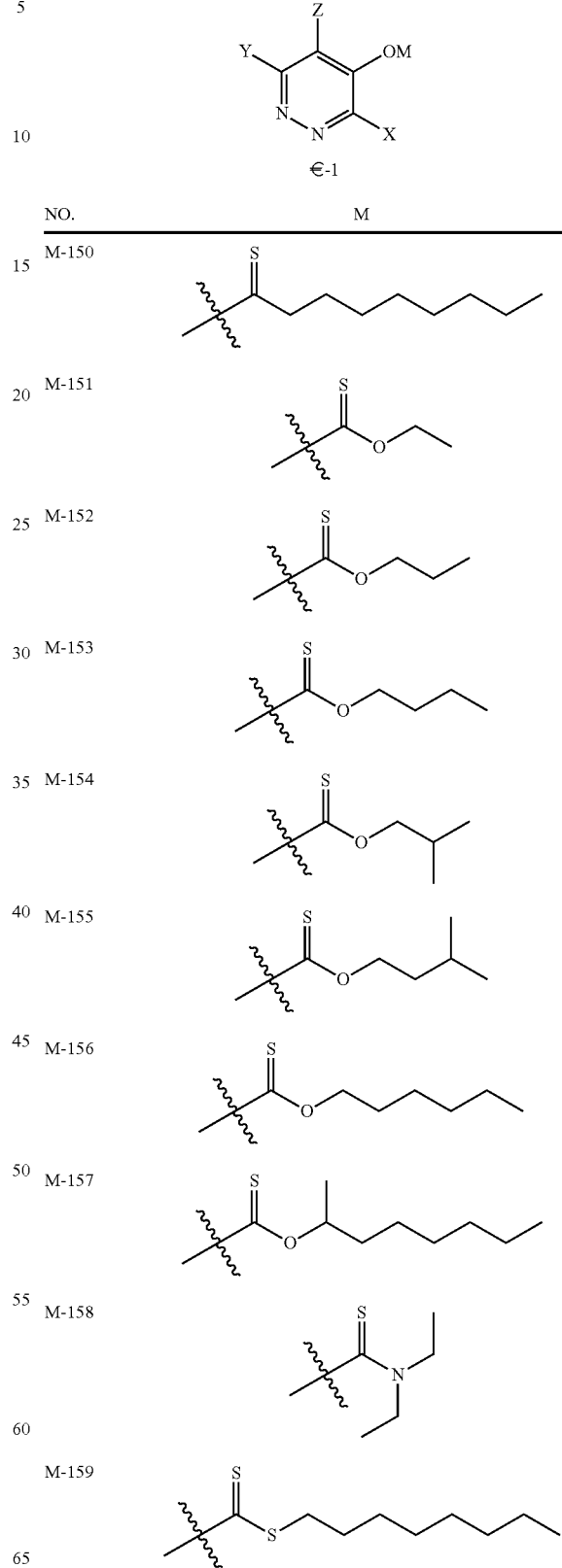

TABLE 2-continued

The structures of the group M in the derivative compounds I-1
(X, Y, Z groups are shown in Table 1)

| NO. | M |
|---|---|
| M-160 | (phenyl-S-C(=S)-) |
| M-161 | ethyl sulfoxide |
| M-162 | -S(=O)-CF₃ |
| M-163 | (MeO)₂P(=O)- |
| M-164 | (EtO)₂P(=S)- |
| M-165 | -C(CH₃)=N- |
| M-166 | -C(Et)=N- |
| M-167 | -C(CH₃)=N- (with ethyl) |
| M-168 | -CH=N-CH₂CH₂CH₃ |
| M-169 | -C(CH₃)=N-CH₂CH(CH₃)₂ |
| M-170 | -C(CH₃)=N-C(CH₃)₃ |
| M-171 | -C(CH₃)=N- n-propyl |
| M-172 | -C(CH₃)=N- n-pentyl |
| M-173 | -C(Et)=N- n-pentyl |
| M-174 | -C(n-Bu)=N- n-butyl |
| M-175 | -C(Et)=N-CH₂CH(Et)CH₃ |
| M-176 | -C(iBu)=N-iBu |

TABLE 2-continued

The structures of the group M in the derivative compounds I-1
(X, Y, Z groups are shown in Table 1)

| NO. | M |
|---|---|
| M-177 | |
| M-178 | |
| M-179 | |
| M-180 | |
| M-181 | |
| M-182 | |
| M-183 | |
| M-184 | |
| M-185 | |
| M-186 | |
| M-187 | |
| M-188 | |
| M-189 | |
| M-190 | |
| M-191 | |
| M-192 | |
| M-193 | |

TABLE 2-continued
The structures of the group M in the derivative compounds I-1
(X, Y, Z groups are shown in Table 1)
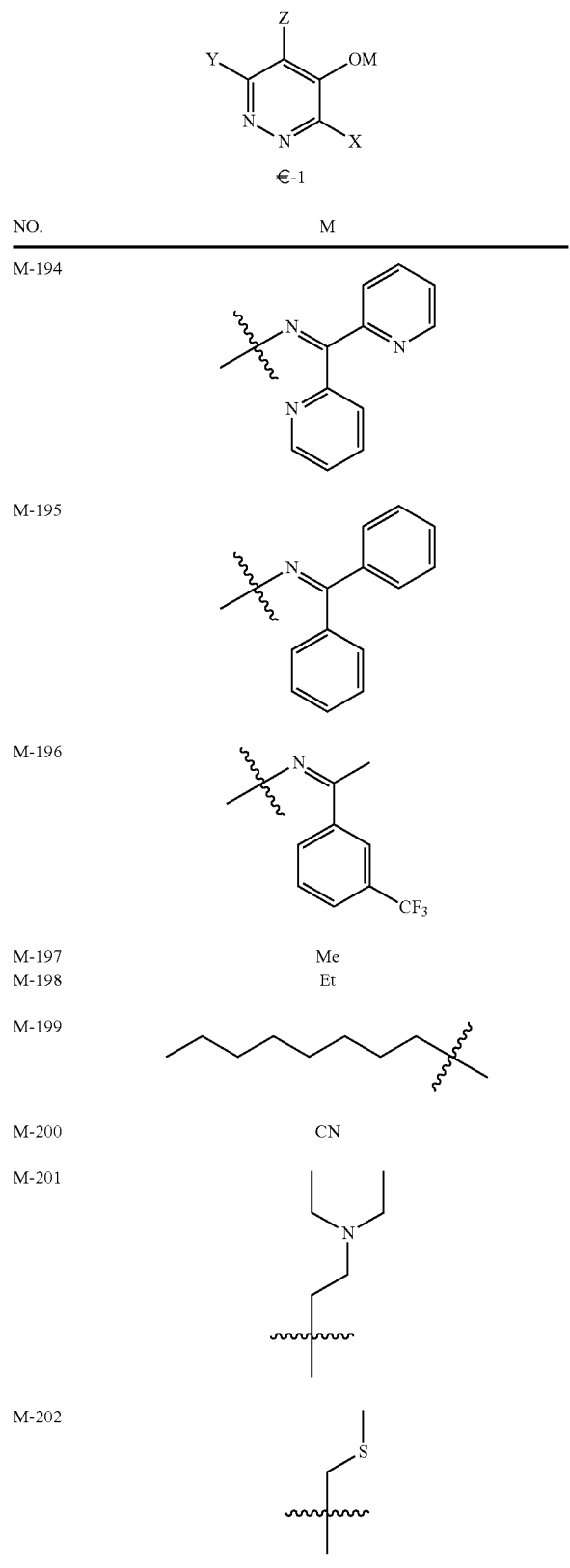
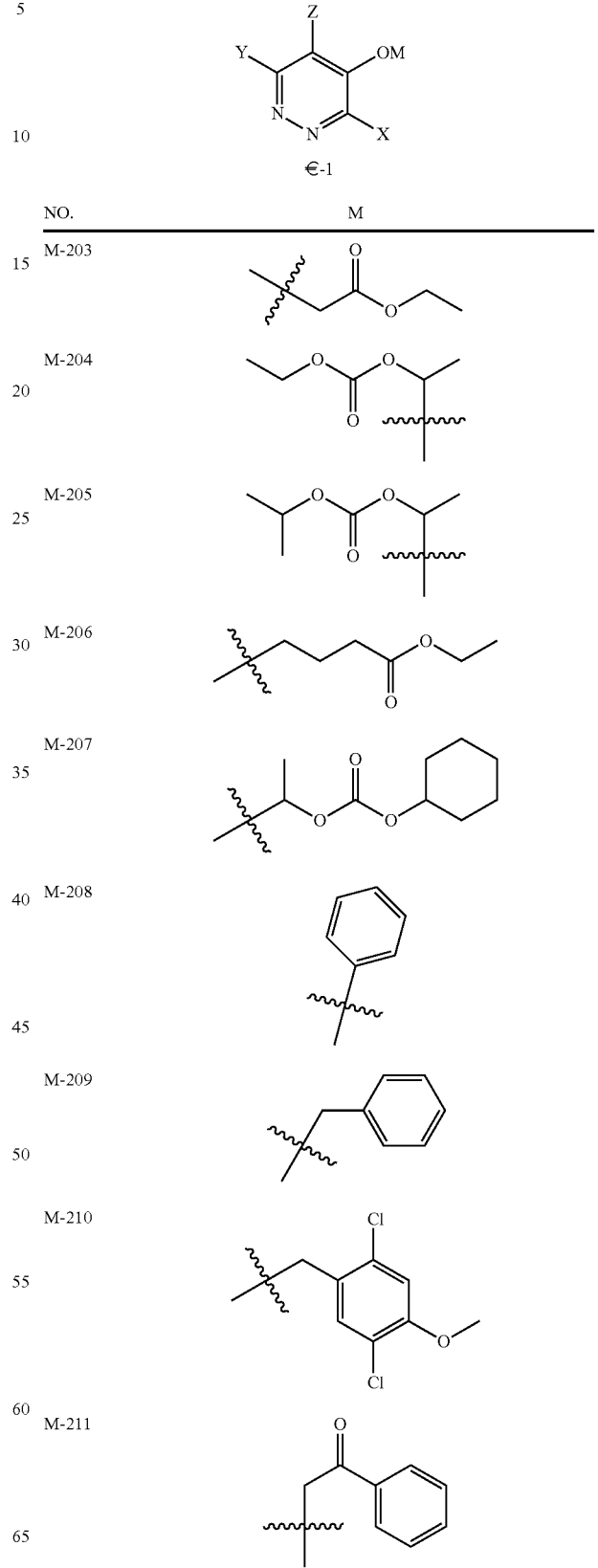

TABLE 2-continued

The structures of the group M in the derivative compounds I-1
(X, Y, Z groups are shown in Table 1)

| NO. | M |
|---|---|
| M-212 | –C(CH₃)₂–N(CH₃)₂ |
| M-213 | –C(CH₃)₂–N(CH₂CH₃)₂ |
| M-214 | –C(CH₃)₂–NH–C(=O)–C₆H₅ |
| M-215 | –NH–C(=O)–O–CH₂CH₃ |
| M-216 | –C(CH₃)₂–N(CH₃)(CH₂CH₃) |
| M-217 | –CH₂–C₆H₄–OCH₃ (para) |

TABLE 3

Structures of some derivative compounds I-1

| NO. | X | Y | Z | M | ¹HNMR |
|---|---|---|---|---|---|
| 1-1 | 4-CN-C₆H₄– | CF₃ | Me | M-1 | |
| 1-2 | 4-CN-C₆H₄– | CF₃ | Me | M-2 | |
| 1-3 | 4-CN-C₆H₄– | CF₃ | Me | M-7 | |
| 1-4 | 4-CN-C₆H₄– | CF₃ | Me | M-12 | |

TABLE 3-continued

Structures of some derivative compounds I-1

| NO. | X | Y | Z | M | ¹HNMR |
|---|---|---|---|---|---|
| 1-5 | 4-CN-C₆H₄- | CF₃ | Me | M-24 | |
| 1-6 | 4-CN-C₆H₄- | CF₃ | Me | M-27 | |
| 1-7 | 4-CN-C₆H₄- | CF₃ | Me | M-29 | |
| 1-8 | 4-CN-C₆H₄- | CF₃ | Me | M-37 | |
| 1-9 | 4-CN-C₆H₄- | CF₃ | Me | M-40 | |
| 1-10 | 4-CN-C₆H₄- | CF₃ | Me | M-52 | |
| 1-11 | 4-CN-C₆H₄- | CF₃ | Me | M-53 | |
| 1-12 | 4-CN-C₆H₄- | CF₃ | Me | M-54 | |
| 1-13 | 4-CN-C₆H₄- | CF₃ | Me | M-58 | |
| 1-14 | 4-CN-C₆H₄- | CF₃ | Me | M-60 | |

TABLE 3-continued

Structures of some derivative compounds I-1

| NO. | X | Y | Z | M | ¹HNMR |
|---|---|---|---|---|---|
| 1-15 | 4-CN-C6H4 | CF₃ | Me | M-63 | |
| 1-16 | 4-CN-C6H4 | CF₃ | Me | M-77 | |
| 1-17 | 4-CN-C6H4 | CF₃ | Me | M-79 | |
| 1-18 | 4-CN-C6H4 | CF₃ | Me | M-88 | |
| 1-19 | 4-CN-C6H4 | CF₃ | Me | M-92 | |
| 1-20 | 4-CN-C6H4 | CF₃ | Me | M-104 | |
| 1-21 | 4-CN-C6H4 | CF₃ | Me | M-108 | |
| 1-22 | 4-CN-C6H4 | CF₃ | Me | M-119 | |
| 1-23 | 4-CN-C6H4 | CF₃ | Me | M-120 | |
| 1-24 | 4-CN-C6H4 | CF₃ | Me | M-121 | |

TABLE 3-continued

Structures of some derivative compounds I-1

| NO. | X | Y | Z | M | ¹HNMR |
|-----|---|---|---|---|-------|
| 1-25 | 4-CN-phenyl | CF$_3$ | Me | M-123 | |
| 1-26 | 4-CN-phenyl | CF$_3$ | Me | M-125 | |
| 1-27 | 4-CN-phenyl | CF$_3$ | Me | M-126 | |
| 1-28 | 4-CN-phenyl | CF$_3$ | Me | M-127 | |
| 1-29 | 4-CN-phenyl | CF$_3$ | Me | M-128 | |
| 1-30 | 4-CN-phenyl | CF$_3$ | Me | M-131 | |
| 1-31 | 4-CN-phenyl | CF$_3$ | Me | M-132 | |
| 1-32 | 4-CN-phenyl | CF$_3$ | Me | M-150 | |
| 1-33 | 4-CN-phenyl | CF$_3$ | Me | M-156 | |
| 1-34 | 4-CN-phenyl | CF$_3$ | Me | M-160 | |

TABLE 3-continued

Structures of some derivative compounds I-1

| NO. | X | Y | Z | M | ¹HNMR |
|---|---|---|---|---|---|
| 1-35 | 4-CN-C₆H₄ | CF₃ | Me | M-162 | |
| 1-36 | 4-CN-C₆H₄ | CF₃ | Me | M-165 | |
| 1-37 | 4-CN-C₆H₄ | CF₃ | Me | M-168 | |
| 1-38 | 4-CN-C₆H₄ | CF₃ | Me | M-198 | |
| 1-39 | 4-CN-C₆H₄ | CF₃ | Me | M-199 | |
| 1-40 | 4-CN-C₆H₄ | CF₃ | Me | M-200 | |
| 1-41 | 4-CN-C₆H₄ | CF₃ | Me | M-203 | |
| 1-42 | 4-CN-C₆H₄ | CF₃ | Me | M-204 | |
| 1-43 | 4-CN-C₆H₄ | CF₃ | Me | M-205 | |
| 1-44 | 4-CN-C₆H₄ | CF₃ | Me | M-207 | |

TABLE 3-continued

Structures of some derivative compounds I-1

| NO. | X | Y | Z | M | ¹HNMR |
|---|---|---|---|---|---|
| 1-45 | 4-CN-phenyl | CF$_3$ | Me | M-208 | |
| 1-46 | 4-CN-phenyl | CF$_3$ | Me | M-209 | |
| 1-47 | 4-CN-phenyl | CF$_3$ | Me | M-211 | |
| 1-48 | 4-CN-phenyl | CF$_3$ | Me | M-212 | |
| 1-49 | 4-CN-phenyl | CF$_3$ | Me | M-216 | |
| 1-50 | 1-(CHF$_2$)-pyrazol-4-yl | CF$_3$ | Me | M-1 | |
| 1-51 | 1-(CHF$_2$)-pyrazol-4-yl | CF$_3$ | Me | M-2 | |
| 1-52 | 1-(CHF$_2$)-pyrazol-4-yl | CF$_3$ | Me | M-7 | |
| 1-53 | 1-(CHF$_2$)-pyrazol-4-yl | CF$_3$ | Me | M-12 | |
| 1-54 | 1-(CHF$_2$)-pyrazol-4-yl | CF$_3$ | Me | M-24 | |

TABLE 3-continued

Structures of some derivative compounds I-1

| NO. | X | Y | Z | M | ¹HNMR |
|-----|---|---|---|---|-------|
| 1-55 | pyrazole-CHF₂ | CF₃ | Me | M-27 | |
| 1-56 | pyrazole-CHF₂ | CF₃ | Me | M-29 | |
| 1-57 | pyrazole-CHF₂ | CF₃ | Me | M-37 | |
| 1-58 | pyrazole-CHF₂ | CF₃ | Me | M-40 | |
| 1-59 | pyrazole-CHF₂ | CF₃ | Me | M-52 | |
| 1-60 | pyrazole-CHF₂ | CF₃ | Me | M-53 | |
| 1-61 | pyrazole-CHF₂ | CF₃ | Me | M-54 | |
| 1-62 | pyrazole-CHF₂ | CF₃ | Me | M-58 | |
| 1-63 | pyrazole-CHF₂ | CF₃ | Me | M-60 | |

TABLE 3-continued
Structures of some derivative compounds I-1
| NO. | X | Y | Z | M | ¹HNMR |
|---|---|---|---|---|---|
| 1-64 | 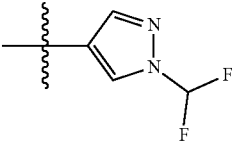 [SMILES: *c1cnn(C(F)F)c1] | CF$_3$ | Me | M-63 | |
| 1-65 | 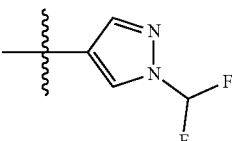 | CF$_3$ | Me | M-77 | |
| 1-66 | 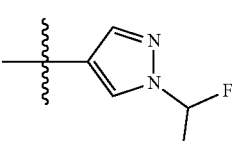 | CF$_3$ | Me | M-79 | |
| 1-67 | 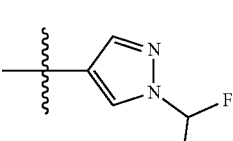 | CF$_3$ | Me | M-88 | |
| 1-68 | 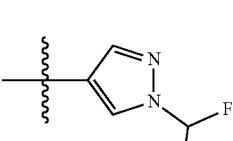 | CF$_3$ | Me | M-92 | |
| 1-69 | 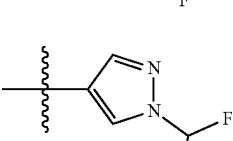 | CF$_3$ | Me | M-104 | |
| 1-70 | 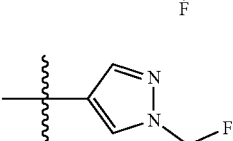 | CF$_3$ | Me | M-108 | |
| 1-71 | 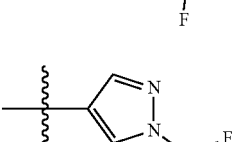 | CF$_3$ | Me | M-119 | |
| 1-72 | 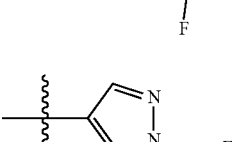 | CF$_3$ | Me | M-120 | |

TABLE 3-continued
Structures of some derivative compounds I-1
| NO. | X | Y | Z | M | ¹HNMR |
|---|---|---|---|---|---|
| 1-73 | 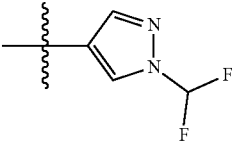 [SMILES: *c1cnn(C(F)F)c1] | CF₃ | Me | M-121 | |
| 1-74 | 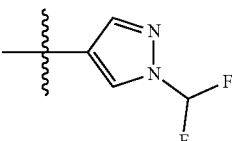 | CF₃ | Me | M-123 | |
| 1-75 | 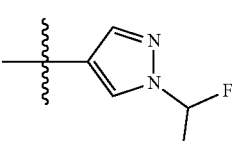 | CF₃ | Me | M-125 | |
| 1-76 | 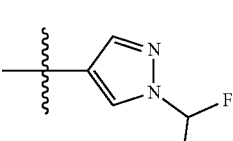 | CF₃ | Me | M-126 | |
| 1-77 | 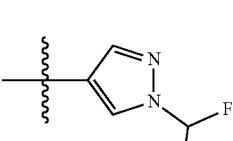 | CF₃ | Me | M-127 | |
| 1-78 | 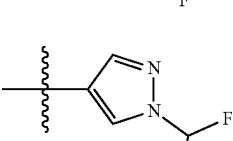 | CF₃ | Me | M-128 | |
| 1-79 | 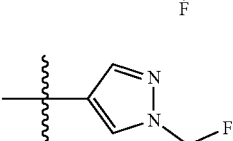 | CF₃ | Me | M-131 | |
| 1-80 | 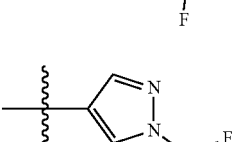 | CF₃ | Me | M-132 | |
| 1-81 | 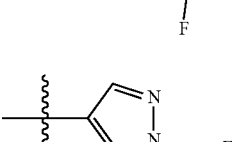 | CF₃ | Me | M-150 | |

TABLE 3-continued

Structures of some derivative compounds I-1

| NO. | X | Y | Z | M | ¹HNMR |
|---|---|---|---|---|---|
| 1-82 | pyrazole-CHF₂ | CF₃ | Me | M-156 | |
| 1-83 | pyrazole-CHF₂ | CF₃ | Me | M-160 | |
| 1-84 | pyrazole-CHF₂ | CF₃ | Me | M-162 | |
| 1-85 | pyrazole-CHF₂ | CF₃ | Me | M-165 | |
| 1-86 | pyrazole-CHF₂ | CF₃ | Me | M-168 | |
| 1-87 | pyrazole-CHF₂ | CF₃ | Me | M-198 | |
| 1-88 | pyrazole-CHF₂ | CF₃ | Me | M-199 | |
| 1-89 | pyrazole-CHF₂ | CF₃ | Me | M-200 | |
| 1-90 | pyrazole-CHF₂ | CF₃ | Me | M-203 | |

TABLE 3-continued

Structures of some derivative compounds I-1

| NO. | X | Y | Z | M | $^1$HNMR |
|---|---|---|---|---|---|
| 1-91 | pyrazole-CHF$_2$ | CF$_3$ | Me | M-204 | |
| 1-92 | pyrazole-CHF$_2$ | CF$_3$ | Me | M-205 | |
| 1-93 | pyrazole-CHF$_2$ | CF$_3$ | Me | M-207 | |
| 1-94 | pyrazole-CHF$_2$ | CF$_3$ | Me | M-208 | |
| 1-95 | pyrazole-CHF$_2$ | CF$_3$ | Me | M-209 | |
| 1-96 | pyrazole-CHF$_2$ | CF$_3$ | Me | M-211 | |
| 1-97 | pyrazole-CHF$_2$ | CF$_3$ | Me | M-212 | |
| 1-98 | pyrazole-CHF$_2$ | CF$_3$ | Me | M-216 | |
| 1-99 | 4-F-C$_6$H$_4$ | CF$_3$ | Me | M-7 | |
| 1-100 | 4-Cl-C$_6$H$_4$ | CF$_3$ | Me | M-58 | |

TABLE 3-continued

Structures of some derivative compounds I-1

| NO. | X | Y | Z | M | $^1$HNMR |
|---|---|---|---|---|---|
| 1-101 | (4-bromophenyl) | CF$_3$ | Me | M-123 | |
| 1-102 | (3-methyl-1-(difluoromethyl)pyrazol-4-yl) | CF$_3$ | Me | M-125 | |
| 1-103 | (3-chloro-1-(difluoromethyl)pyrazol-4-yl) | CF$_3$ | Me | M-160 | |
| 1-104 | (3-trifluoromethyl-1-(difluoromethyl)pyrazol-4-yl) | CF$_3$ | Me | M-165 | |
| 1-105 | (3-fluoro-1-(difluoromethyl)pyrazol-4-yl) | CF$_3$ | Me | M-205 | |
| 1-106 | (1-(difluoromethyl)pyrazol-4-yl) | CF$_3$ | (N-methylcarbamoyl-N-methyl) | M-217 | $^1$H NMR (500 MHz, DMSO-d6) δ 9.04 (s, 1H), 8.36 (s, 1H), 7.96 (t, J = 59.0 Hz, 1H), 7.88 (s, 1H), 7.32 (d, J = 8.5 Hz, 2H), 6.98-6.93 (m, 2H), 5.50 (s, 2H), 3.74 (s, 3H), 2.96 (s, 6H). |

The method for preparing the compound of the invention will be explained in detail in the following program and embodiment. The material is commercial available or prepared through known method reported in the literature or shown in the route. Those skilled in the art should understand that the compound of the invention can also be synthesized by other synthetic route. Although the detailed material and reaction condition in the synthetic route have been explicated in the following text, it is still easy to be replaced by other similar material and condition. Isomer of the compound, for example, that produced with the variation of the preparation method of the present invention is included in the scope of the present invention. In addition, the following preparation method can be further modified according to the disclosures of the present invention by using common chemical method known to those skilled in the art, for example, protection of suitable group in the process of the reaction, etc.

The following method of application can be used to improve further understanding of the preparation method of the present invention. The specific material, class and condition have been determined to be further explication of the present invention, not to be any limit of the reasonable scope thereof. Reagents of the following synthetic compound showed in the table can either be purchased from the market or easily prepared by those skilled in the art.

Examples of representative compounds are as follows, and the synthesis methods of other compounds are similar, and the detailed description is omitted here.

1. Synthesis of Intermediate a (1) Compound a-1 (1 g, 4.69 mmol), Compound a-2 (1.0 g, 7.0 mmol), and potassium carbonate (1.9 g, 14.0 mmol) were placed in the round bottom flask, added with 1,4-dioxane (10 mL)/water (2 mL) and then subjected to replacement with nitrogen for three times, added with Pd(dppf)Cl$_2$CH$_2$Cl$_2$ (0.16 g) quickly and subjected to replacement with nitrogen for three times, then the reaction solution was subjected to replacement with nitrogen for three times again, and finally the reaction was carried out at 100° C. for 16 hours. The completion of the reaction was determined by HPLC, then the reaction system was concentrated, and separated by column chromatography to obtain 0.88 g (3.1 mmol, yield: 67%) of Compound a-3 (white solid).

(2) Compound a-3 (0.88 g, 3.1 mmol) was placed in the round bottom flask, added with 8 mL of water and sodium hydroxide (0.37 g, 9.3 mmol), and the reaction was carried out at 100° C. for 12 h. After the reaction, the temperature of the reaction system was reduced to room temperature. The reaction solution was extracted with 30 mL of dichloromethane for three times, the aqueous phase was adjusted to pH 2 with 1N HCl solution, and a white solid was precipitated. A filter cake was obtained by filtration, and then dried to obtain 0.65 g (2.4 mmol, yield 79%) of Compound a.

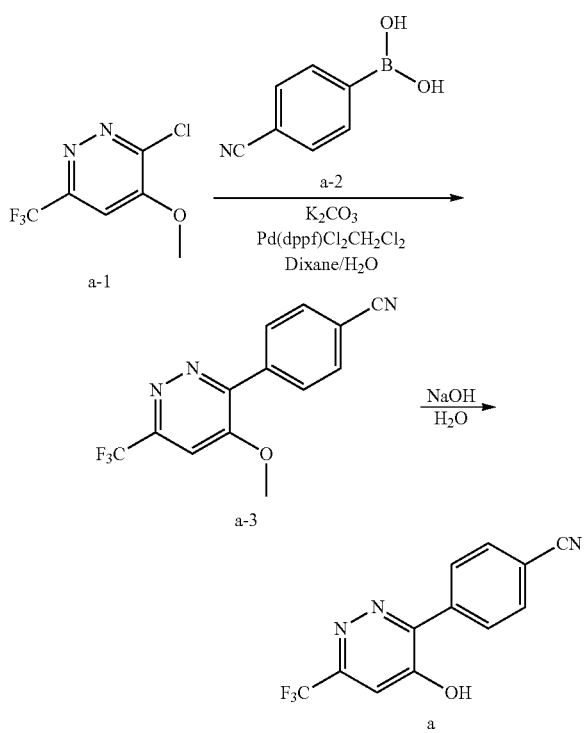

2. Synthesis of Compound 2

1 g of Compound a was dissolved in 10 mL of CCl$_4$, NCS (1.5 eq) and AIBN (0.05 eq) were added respectively. The temperature was raised to 70° C. for overnight reaction. The completion of the reaction was determined by LCMS. The post processing was: the reaction solution was concentrated to remove the solvent, the crude product was dispersed with water by stirring for 15 minutes, then a filter cake was obtained by filtration and dried to obtain Product 2 (0.75 g, yield: 67%).

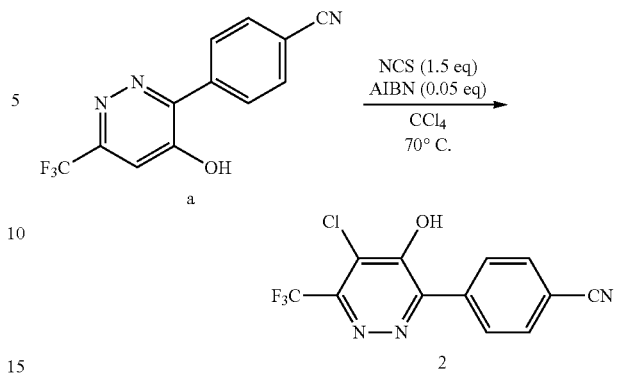

3. Synthesis of Compound 3

50 g (1.0 eq) of Compound a was placed into the reactor, added with 500 mL of AcOH/H$_2$O (5:1) as a solvent, and added dropwise with Br$_2$ (2.5 eq) at room temperature, then stirred overnight at room temperature. The completion of the reaction was determined by LCMS, the reaction solution was concentrated to obtain a solid, the solid was dispersed fully with water by stirring for half an hour, then a filter cake was obtained by filtration, and dried to obtain white solid 3 (55 g, yield: 83%).

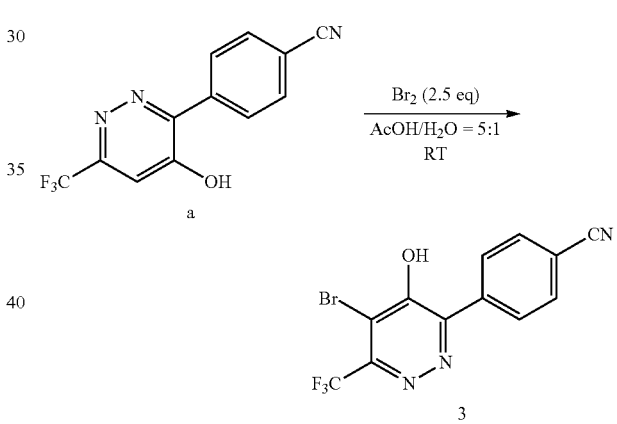

4. Synthesis of Compound 4

1 g of Compound a was dissolved in 10 mL of CCl$_4$, NCS (1.5 eq) and AIBN (0.05 eq) were added respectively. The temperature was raised to 70° C. for overnight reaction. The completion of the reaction was determined by LCMS. The post processing was: the reaction solution was concentrated to remove the solvent, the crude product was dispersed with water by stirring for 15 minutes, a filter cake was obtained by filtration and dried to obtain Product 4 (0.8 g, yield: 59%).

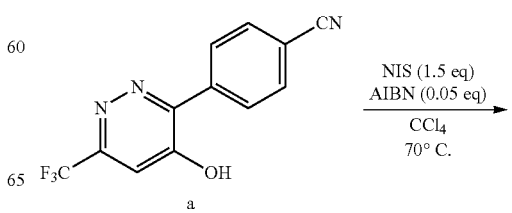

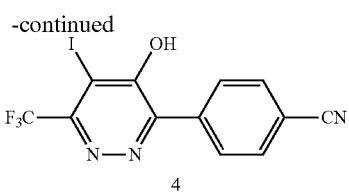

5. Synthesis of Compound 5

55 g of Compound 3 was added to 500 mL of MeCN, $K_2CO_3$ (2.5 eq) and b-1 (1.5 eq) were added. The temperature was raised to 70° C. for overnight reaction. The consumption of raw materials was detected by LCMS. The post processing was: the reaction solution was cooled and filtered, the mother liquor was concentrated, mixed and subjected to column chromatography to obtain Product b (41 g, yield: 57%).

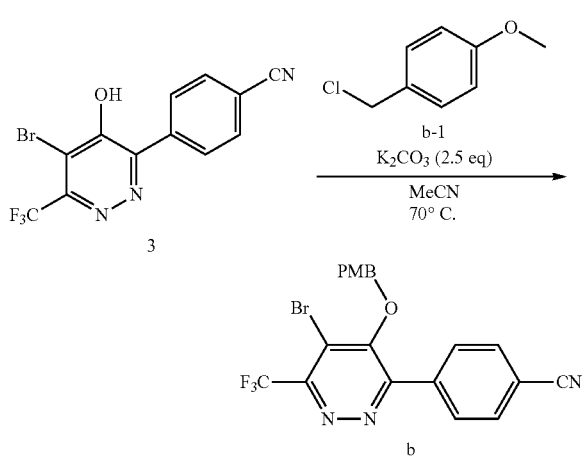

0.6 g of Compound b (1 eq), 5-1 (1.5 eq), and $K_2CO_3$ (3 eq) were dissolved in dioxane/$H_2O$=10:1 (6 mL), subjected to replacement with nitrogen for three times quickly, added with Pd(dppf)$Cl_2$—$CH_2Cl_2$ (0.05 eq), then subjected to replacement with nitrogen for three times again. The temperature was raised to 120° C. for overnight reaction. The consumption of raw materials was detected by LCMS. The reaction solution was concentrated, mixed and subjected to column chromatography to obtain Product 5-2 (0.18 g, yield: 37.5%).

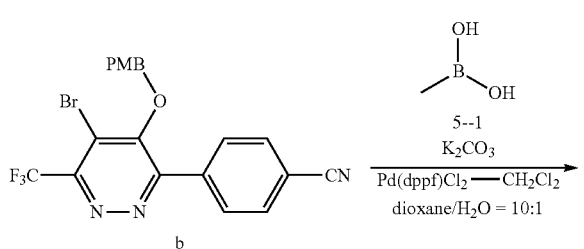

0.18 g of Compound 5-2 was dissolved in TFA (2.0 mL). The temperature was raised to 50° C. for overnight reaction. The completion of the reaction was determined by LCMS. The reaction solution was concentrated, dispersed with water by stirring, and filtered to obtain a filter cake, and the filter cake was dissolved in DMSO, and Product 5 (0.075 g, yield: 59.7%) was obtained by Preparative reversed-phase HPLC.

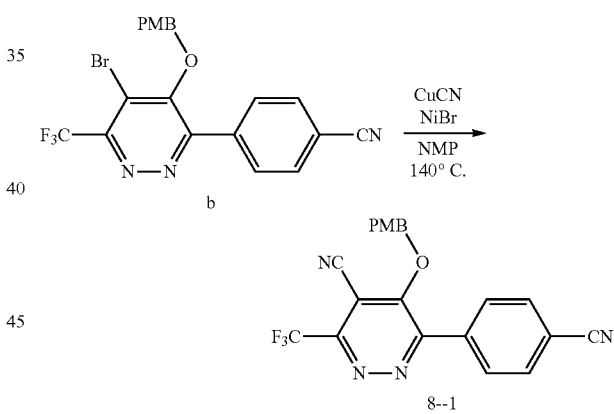

6. Synthesis of Compound 8

0.6 g of Compound b (1 eq), CuCN (1.5 eq), and NiBr (0.1 eq) were dissolved in NMP (6 mL) and reacted under microwave condition at 140° C. for 3 hours. The consumption of raw materials was detected, then the reaction solution was filtered, and Product 8-1 (0.13 g, yield: 25%) was obtained from the mother liquor through Preparative reversed-phase HPLC.

0.13 g of Compound 8-1 was dissolved in TFA (2 mL), heated to 50° C. for overnight reaction. The completion of the reaction was determined by LCMS, then the reaction solution was concentrated, dispersed with water by stirring, then filtered to obtain a filter cake. The filter cake was dissolved in DMSO, and Product 8 (0.08 g, yield: 87%) was obtained by Preparative reversed-phase HPLC.

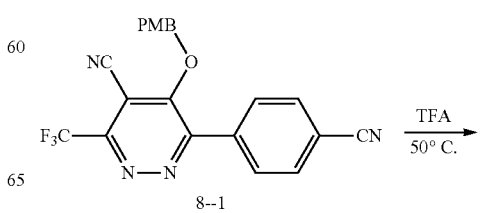

-continued

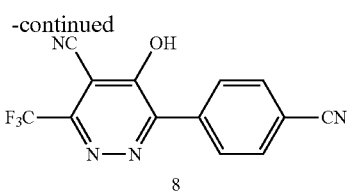

8

7. Synthesis of Compound 12

(1) 1 equivalent of Compound b was dissolved in 5 volumes of methanol, then 10 equivalents of sodium methoxide solution was added, the temperature was raised to 60° C. and reacted for 3 hours. After the completion of the In-Process Control, the temperature was reduced, the methanol in the reaction solution was removed by rotary-evaporation, 5 volumes of water was added, extracted twice with 10 volumes of ethyl acetate, the organic phases were combined and Product 12-1 was obtained with a yield of 89% by rotary evaporation of the organic phase.

(2) The obtained Product 12-1 was dissolved in 5 volumes of trifluoroacetic acid, the temperature was raised to 50° C. for 10 hours' reaction. After the completion of the In-Process Control, the temperature was reduced to room temperature, the trifluoroacetic acid in the system was removed by vacuum, then 5 volumes of water was added dropwise to the system slowly, stirred continually for 15 minutes after a solid precipitation appeared, filtered to obtain a solid, and the solid was dried to obtain Product 12 with a yield of 78%.

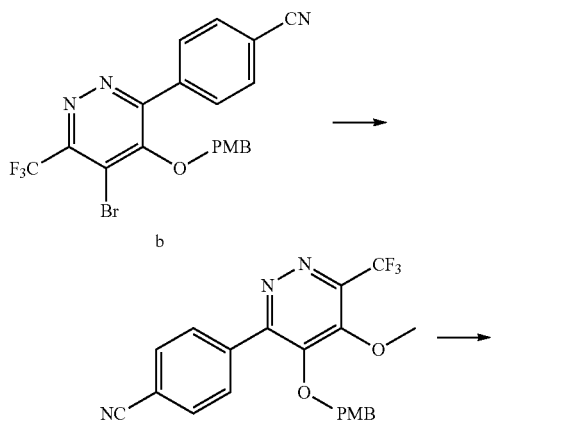

8. Synthesis of Compound 16

(1) 1 equivalent of Compound b was dissolved in 10 volumes of dioxane solution, 1.5 equivalents of p-methoxybenzylamine, 2.0 equivalents of cesium carbonate and 0.05 equivalents of BINAP were added, then subjected to replacement with nitrogen for three times, added with 5% mass of Pd$_2$(dba)$_3$, heated to 120° C. under nitrogen protection and reacted for 16 hours at 120° C., finally the reaction was terminated after the completion of the In-Process Control. The temperature was reduced to room temperature, the reaction solution was filtered to remove the insoluble solids, the dioxane solution was removed by vacuum, then 5 volumes of water was added, extracted twice with 10 volumes of ethyl acetate, the organic phases were combined, rotary-evaporated, mixed with silica gel, and purified by column chromatography to obtain Product 16-1 with a yield of 62%.

(2) The obtained Product 16-1 was dissolved in 5 volumes of trifluoroacetic acid, the temperature was raised to 50° C. and reacted for 5 hours. After the completion of the In-Process Control, the temperature was reduced to room temperature. Trifluoroacetic acid in the system was removed by vacuum, and 5 volumes of water was added dropwise to the system slowly, stirred continually for 20 minutes after a solid precipitation appeared, then filtered to obtain a solid, the solid was purified by Preparative reversed-phase HPLC to obtain Product 16 with a yield of 80%.

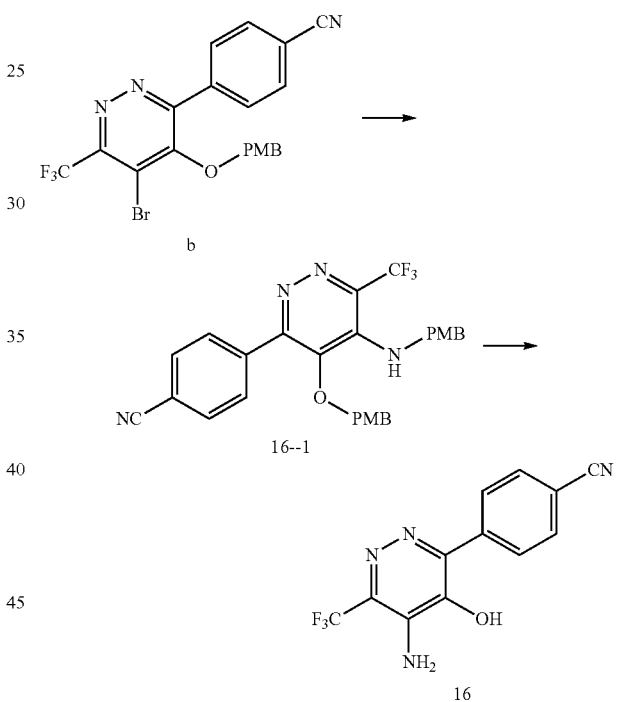

9. Synthesis of Compound 25

(1) Compound 25-1 was prepared by referring to the synthetic method of compound b, then 1 equivalent of Compound 25-1 was dissolved in 10 volumes of dioxane solution, 2.0 equivalents of pyrazole was added, then 3.0 equivalents of N,N-Diisopropylethylamine and 0.05 equivalents of Xantphos were added. The above reaction system was subjected to replacement with nitrogen for three times, then added with 5% mass Pd$_2$(dba)$_3$, heated to 120° C. under nitrogen protection and reacted for 20 hours at 120° C., finally the reaction was terminated after the completion of the In-Process Control. The temperature was reduced to room temperature, the insoluble solids in the reaction solution were removed by filtration, the dioxane solution was removed by vacuum, 5 volumes of water was added, extracted twice with 10 volumes of ethyl acetate, the organic phases were combined, rotary-evaporated, mixed with silica gel, and purified by column chromatography to obtain Product 25-2 with a yield of 54%.

(2) The obtained Product 25-2 was dissolved in 5 volumes of trifluoroacetic acid, the temperature was raised to 50° C. and reacted for 16 hours. After the completion of the In-Process Control, the temperature was reduced to room temperature. Trifluoroacetic acid in the system was removed by vacuum, and 5 volumes of water was added dropwise to the system slowly, stirred continually for 30 minutes after a solid precipitation appeared, then filtered to obtain a solid, and the solid was purified by Preparative reversed-phase HPLC to obtain Product 25 with a yield of 85%.

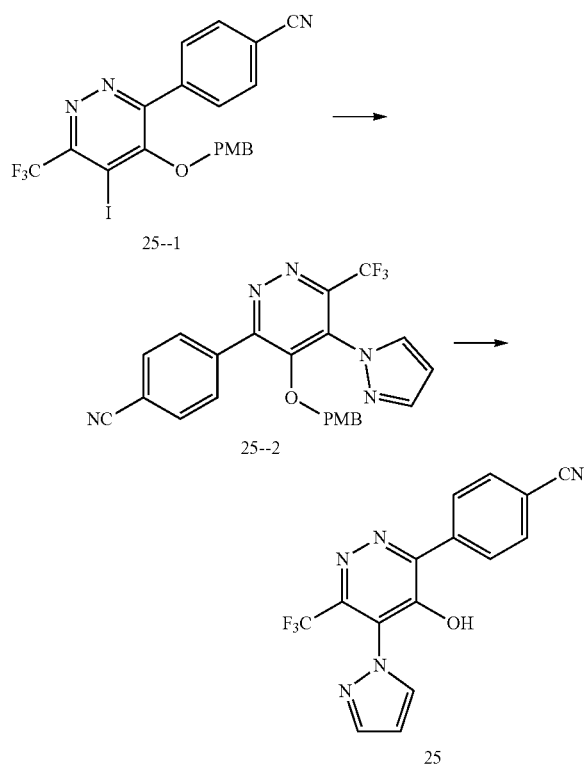

10. Synthesis of Compound 27

0.6 g of compound b (1 eq), DIPEA (3 eq), Xantphos (0.05 eq) and Pd$_2$(dba)$_3$ (0.05 eq) were dissolved in dioxane (6 mL), subjected to replacement with nitrogen for three times, then added with compound 27-1 (2 eq) quickly, heated to 120° C. for overnight reaction. After the completion of the reaction was determined, the reaction solution was concentrated, mixed with silica gel, and subjected to column chromatography to obtain Product 27-2 (0.32 g, yield: 59%).

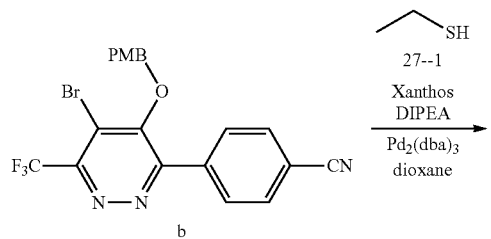

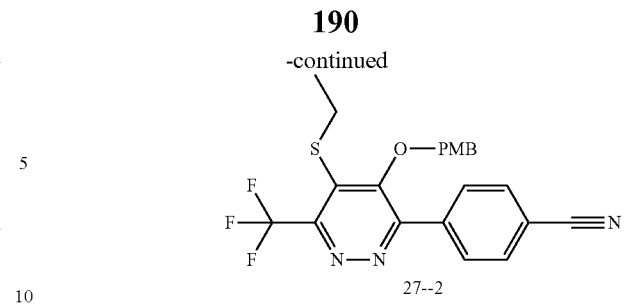

0.32 g of Product 27-2 was dissolved in TFA (4 mL), heated to 50° C. for overnight reaction. After the completion of the reaction was determined by LCMS, the reaction solution was concentrated, dispersed with water by stirring, filtered to obtain a filter cake, and the filter cake was dissolved in DMSO. Product 27 (0.13 g, yield: 56%) was obtained by Preparative reversed-phase HPLC.

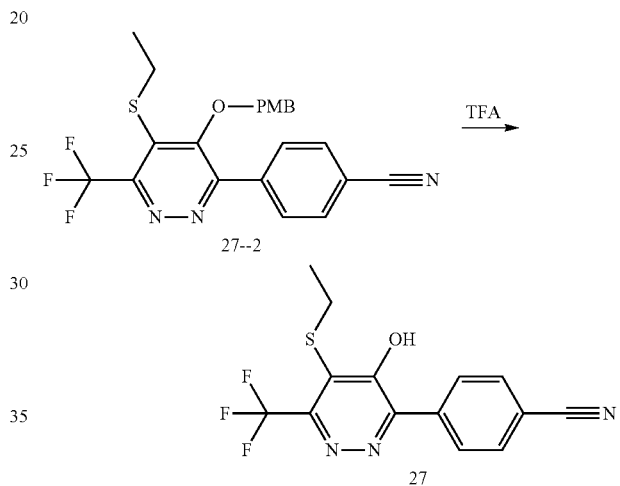

11. Synthesis of Compound 31

0.6 g of Compound b (1 eq), 31-1 (1.5 eq) and K$_2$CO$_3$ (3 eq) were dissolved in dioxane/H$_2$O=5:1 (6 mL), and subjected to replacement with nitrogen for three times quickly, added with Pd(dppf)Cl$_2$—CH$_2$Cl$_2$ (0.05 eq), then the reaction solution was subjected to replacement with nitrogen for three times again, and finally heated to 120° C. for overnight reaction. The consumption of raw materials was detected by LCMS, the reaction solution was concentrated, mixed with silica gel, and subjected to column chromatography to obtain Product 31-2 (0.42 g, yield: 92%).

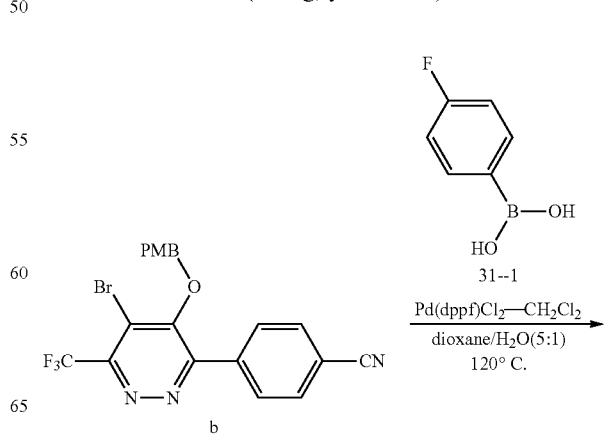

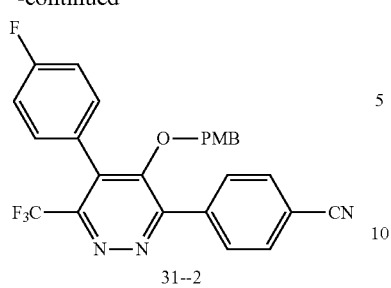

0.42 g of Compound 31-2 was dissolved in TFA (5 mL), heated to 50° C. for overnight reaction. After the completion of the reaction was determined by LCMS, the reaction solution was concentrated, dispersed with water by stirring, filtered to obtain a filter cake, and the filter cake was dissolved in DMSO, Product 31 (0.31 g, yield: 78%) was obtained by Preparative reversed-phase HPLC.

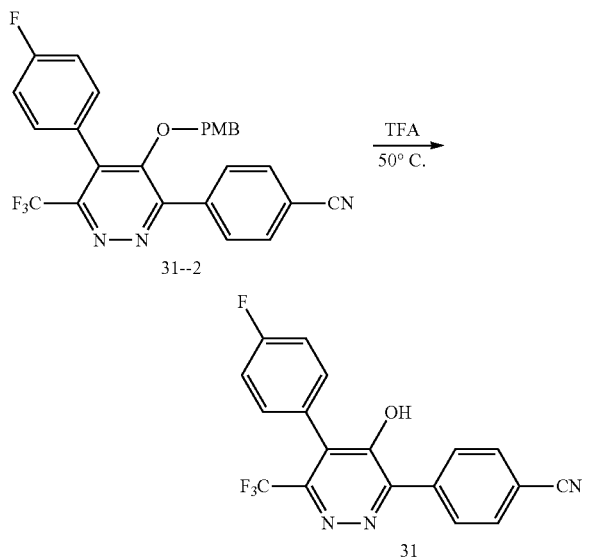

12. Synthesis of Intermediate c

Raw material c-1 was added to 10 volumes of DMF, c-2 (1.5 eq) and cesium carbonate (2 eq) were added, the temperature was raised to 120° C. for 2 hours' reaction, and C02 was generated during the reaction. After the completion of the reaction was determined by HPLC, the temperature was reduced to room temperature, cesium carbonate was removed by filtration, and the mother liquor was used directly in the next step.

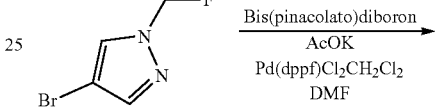

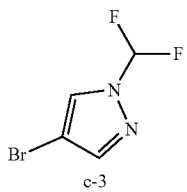

Bis(pinacolato)diboron (1.2 eq) and potassium acetate (1.5 eq) were added to the mother liquor of the previous step, subjected to replacement with nitrogen, then palladium catalyst (5%) was added under nitrogens protection, the temperature was raised to 100° C. and reacted for 16 hours. After the completion of the reaction was determined by HPLC, the temperature was reduced to room temperature, and the reaction solution was used directly in the next step.

1 volume of water was added to the reaction solution of the previous step, then intermediate c-5 and potassium carbonate (3 eq) were added, subjected to replacement of nitrogen, then palladium catalyst (5%) was added under nitrogen protection, the temperature was raised to 120° C. and reacted for 18 hours. After the completion of the reaction was determined by HPLC, 20 volumes of water was added to the reaction solution, extracted with ethyl acetate until no product was present in the aqueous phase, the organic phase was concentrated, mixed with silica gel, and purified by column chromatography (petroleum ether:ethyl acetate=5:1) to obtain Product c-6.

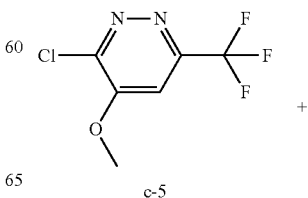

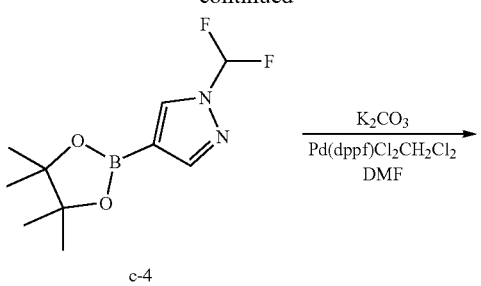

c-4

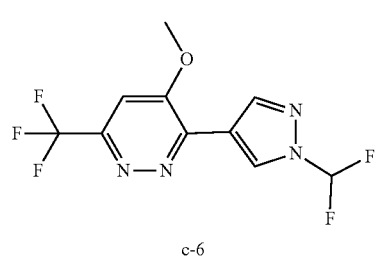

c-6

Compound c-6 was dissolved in 10 volumes of DMSO, potassium acetate (5 eq) was added, then the reaction system was raised to 120° C. and reacted for 16 hours. After the completion of the reaction was determined by HPLC, the temperature was reduced to room temperature, then 20 volumes of water was poured, extracted three times with DCM, the aqueous phase was adjusted to pH=4 with 1M hydrochloric acid, a large amount of solids were precipitated, and the reaction system was stirred continually for 30 minutes, filtered to give a filter cake, and the filter cake was dried to obtain Product c.

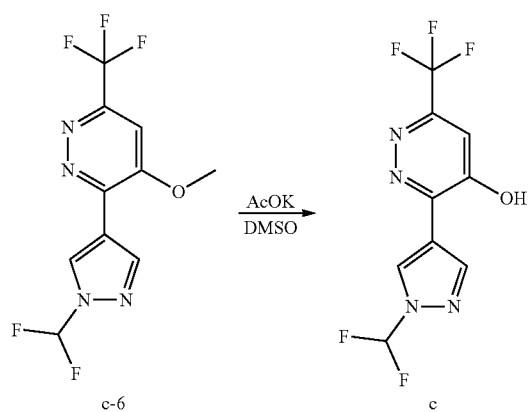 [SMILES: "AcOK" ; COc1cc(C(F)(F)F)nnc1-c1cnn(C(F)F)c1 ; Oc1cc(C(F)(F)F)nnc1-c1cnn(C(F)F)c1]

13. Synthesis of Compound 46

1 g of Compound c was dissolved in 10 mL of CCl$_4$, NBS (1.5 eq) and AIBN (0.05 eq) were added respectively. The temperature was raised to 80° C. for overnight reaction. The completion of the reaction was determined by LCMS. The post processing was: the reaction solution was concentrated to remove the solvent, the crude product was dispersed with water by stirring for 15 minutes, a filter cake was obtained by filtration and dried to obtain Product 46 (1 g, yield: 78%).

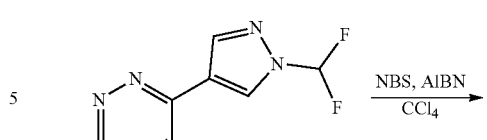

c

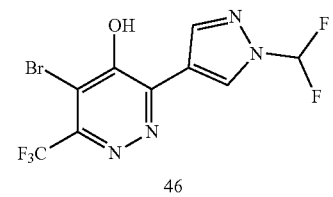

46

14. Synthesis of Compound 48

10 g of Compound 46 was added to 500 mL of MeCN, K$_2$CO$_3$ (2.5 eq) and b-1 (1.5 eq) were added and the temperature was raised to 70° C. for overnight reaction. The consumption of raw materials was detected by LCMS. The post processing was: the temperature of the reaction solution was reduced, the reaction solution was filtered to obtain a mother liquor, and the mother liquor was concentrated, mixed with silica gel, and subjected to column chromatography to obtain Product d (9.8 g, yield: 73%).

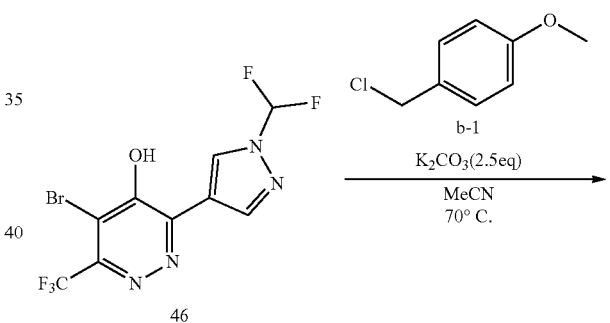

46

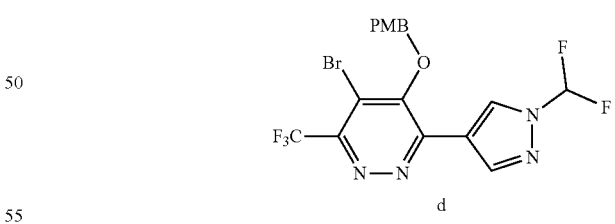

d 0.6 g of Compound d (1 eq), 48-1 (1.5 eq) and NaOH (3 eq) were dissolved in dioxane/H$_2$O=10:1 (6 mL), subjected to replacement with nitrogen for three times quickly, then added with Pd(dppf)Cl$_2$—CH$_2$Cl$_2$ (0.05 eq), and the reaction solution was subjected to replacement with nitrogen for three times again, finally heated to 120° C. and reacted for 24 hours. The consumption of raw materials was detected by LCMS, the reaction solution was concentrated, mixed with silica gel, and subjected to column chromatography to obtain Product 48-2 (0.2 g, yield: 38.6%).

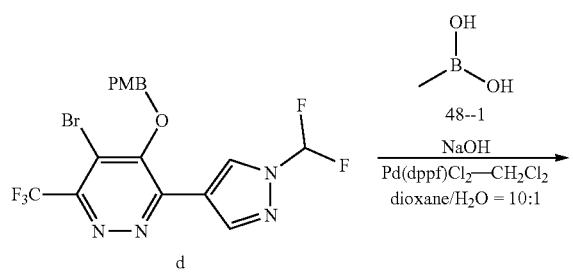

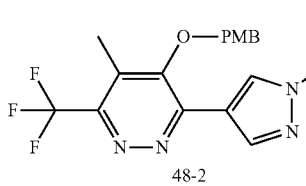

0.2 g of Compound 48-2 was dissolved in TFA (2 mL), heated to 50° C. for overnight reaction. The completion of the reaction was determined by LCMS, then the reaction solution was concentrated, dispersed with water by stirring, filtered to obtain a filter cake, and the filter cake was dissolved in DMSO, Product 48 (0.08 g, yield: 57%) was obtained by Preparative reversed-phase HPLC.

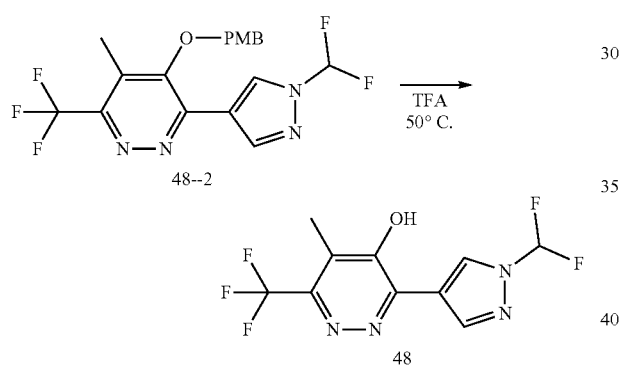

Evaluation of Biological Activity:

The activity level standard of plant destruction (i.e. growth inhibition rate) is as follows:

Level 5: growth control rate is above 85%;
Level 4: growth control rate is greater than or equal to 60% and less than 85%;
Level 3: growth control rate is greater than or equal to 40% and less than 60%;
Level 2: growth control rate is greater than or equal to 20% and less than 40%;
Level 1: growth control rate is greater than or equal to 5% and less than 20%;
Level 0: growth control rate is less than 5%.

The above described growth inhibition rates are fresh weight inhibition rates.

Experiment of post-emergence test: monocotyledonous and dicotyledonous weed seeds as well as main crop seeds (i.e., wheat, corn, rice, soybean, cotton, oilseed rape, millet and *sorghum*) were put into a plastic pot loaded with soil, then covered with 0.5-2 cm of soil, and the seeds were allowed to grow in good greenhouse environment. The test plants were treated at 2-3 leaf stage 2-3 weeks after sowing. The test compounds of the invention were dissolved in acetone respectively, then added with Tween-80 and diluted by a certain amount of water to give solutions with certain concentrations, and added with 80% vegetable oil methyl ester synergist at 1500 g/ha. The solution was sprayed to the plants with a sprayer. The plants were cultured in the greenhouse. The experiment results of weed controlling effect after 3 weeks were listed in Table 4.

TABLE 4

Experiment on weed control effect of compounds of Formula I in Post-emergence stage (1200 g/ha)

| Compound NO. | *Descurainia sophia* | *Capsella bursa-pastoris* | *Sinapis arvensis* |
|---|---|---|---|
| 5 | 5 | 5 | 5 |
| 6 | 5 | 5 | 5 |
| 7 | 5 | 5 | 5 |
| 9 | 5 | 5 | 5 |
| 10 | 5 | 5 | 5 |
| 12 | 5 | 4 | 5 |
| 16 | 4 | 4 | 4 |
| 17 | 4 | 3 | 4 |
| 18 | 3 | 3 | 4 |
| 45 | 5 | 5 | 5 |
| 46 | 5 | 3 | 5 |
| 47 | 5 | N | 5 |
| 48 | 5 | 5 | 5 |
| 49 | 5 | 5 | 5 |
| 50 | 5 | 5 | 5 |
| 52 | 3 | 3 | 5 |
| 53 | 5 | 5 | 5 |
| 59 | 5 | 5 | 5 |
| 60 | N | N | 3 |
| 70 | N | 3 | 5 |
| 87 | 5 | 5 | 5 |
| 88 | 5 | 5 | 5 |
| 89 | 5 | 5 | 5 |
| 90 | 5 | 5 | 5 |
| 91 | 5 | 5 | 5 |
| 92 | 5 | 5 | 5 |
| 93 | 5 | 5 | 5 |
| 94 | 5 | 5 | 5 |
| 95 | 5 | 5 | 5 |
| 96 | 5 | 5 | 5 |
| 97 | 5 | 5 | 5 |
| 98 | 5 | 5 | 5 |
| 99 | 5 | 5 | 5 |
| 109 | 5 | 5 | 5 |
| 110 | 5 | 5 | 5 |
| 111 | 5 | 5 | 5 |
| 112 | 5 | 5 | 5 |
| 113 | 5 | 5 | 5 |
| 114 | 5 | 5 | 5 |
| 115 | 5 | 5 | 5 |
| 116 | 5 | 5 | 5 |
| 117 | 5 | 5 | 5 |
| 118 | 5 | 5 | 5 |
| 119 | 5 | 5 | 5 |
| 120 | 5 | 5 | 5 |
| 121 | 5 | 5 | 5 |
| 122 | 5 | 5 | 5 |
| 123 | 5 | 5 | 5 |
| 124 | 5 | 5 | 5 |
| 125 | 5 | 5 | 5 |
| 126 | 5 | 5 | 5 |
| 132 | 5 | 5 | 5 |
| 133 | 5 | 5 | 5 |
| 134 | 5 | 5 | 5 |
| 135 | 5 | 5 | 5 |
| 136 | 5 | 5 | 5 |
| 137 | 5 | 5 | 5 |
| 138 | 3 | 3 | 5 |
| 156 | 5 | 5 | 5 |
| 157 | 5 | 5 | 5 |
| 158 | 5 | 5 | 5 |
| 159 | 5 | 5 | 5 |
| 160 | 5 | 5 | 5 |
| 161 | 5 | 5 | 5 |
| 162 | 5 | 5 | 5 |

TABLE 4-continued

Experiment on weed control effect of compounds of Formula I in Post-emergence stage (1200 g/ha)

| Compound NO. | Descurainia sophia | Capsella bursa-pastoris | Sinapis arvensis |
|---|---|---|---|
| 163 | 5 | 5 | 5 |
| 164 | 5 | 5 | 5 |
| 165 | 5 | 5 | 5 |
| 166 | 5 | 5 | 5 |
| 167 | 5 | 5 | 5 |
| 168 | 5 | 5 | 5 |
| 169 | 5 | 5 | 5 |
| 171 | 5 | 5 | 5 |
| 172 | 5 | 5 | 5 |
| 173 | 5 | 5 | 5 |
| 228 | 5 | 5 | 5 |
| 301 | 5 | 3 | 5 |
| 313 | 5 | 5 | 5 |
| 334 | 5 | 5 | 5 |
| 388 | 4 | 3 | 5 |
| 389 | N | 3 | 5 |
| 393 | N | N | 3 |
| 395 | N | N | 3 |
| 399 | 5 | 5 | 5 |
| 400 | 5 | 5 | 5 |
| 401 | 5 | 4 | 5 |
| 402 | 5 | 5 | 5 |
| 403 | 3 | 5 | 5 |
| 404 | 5 | 5 | 5 |
| 406 | N | N | 5 |
| 407 | 5 | 5 | 5 |
| 408 | N | N | 5 |
| 409 | 3 | 3 | 5 |
| 410 | 5 | 3 | 5 |
| 411 | N | 3 | 5 |
| 412 | N | 3 | 5 |
| 414 | 3 | N | 5 |

Note:
N means no data.

Experiment of Pre-Emergence Test:

Seeds of monocotyledonous and dicotyledonous weeds and main crops (e.g. wheat, corn, rice, soybean, cotton, oilseed rape, millet and *sorghum*) were put into a plastic pot loaded with soil and covered with 0.5-2 cm of soil. The test compounds of the present invention was dissolved with acetone, then added with Tween-80, diluted by a certain amount of water to reach a certain concentration, and sprayed immediately after sowing. The obtained seeds were incubated for 4 weeks in the greenhouse after spraying and the test results were observed. It was observed that the herbicides of the present invention mostly had excellent effect at dose of 250 g/ha, especially to weeds such as *Echinochloa crusgalli*, *Digitaria sanguinalis* and *Abutilon theophrasti*, etc., and many compounds had good selectivity for corn, wheat, rice, soybean, oilseed rape, etc.

It is found in the experiment that the compounds of the present invention generally have good weed control efficacy, especially for major broadleaf weeds such as *Abutilon theophrasti* and *Bidens bipinnata*, etc., which are widely occurred in corn, rice and wheat fields, and have excellent commercial value. Above all, it is noted that the compound of the invention have extremely high activity to broadleaf weeds, which are resistant to ALS inhibitor, like *Lithospermum arvense*, *Galium spurium* and *Stellaria media*, etc.

Transplanted rice safety evaluation and weed control effect evaluation in rice field:

Rice field soil was loaded into a 1/1,000,000 ha pot. The seeds of *Echinochloa crusgalli*, *Scirpus juncoides* and *Bidens tripartite* were sowed and gently covered with soil, then left to stand still in greenhouse in the state of 0.5-1 cm of water storage. The tuber of *Sagittaria trifolia* L. was planted in the next day or 2 days later. It was kept at 3-4 cm of water storage thereafter. The weeds were treated by dripping the WP or SC water diluents prepared according to the common preparation method of the compounds of the present invention with pipette homogeneously to achieve specified effective amount when *Echinochloa crusgalli*, *Scirpus juncoides* and *Bidens tripartite* reached 0.5 leaf stage and *Sagittaria trifolia* L. reached the time point of primary leaf stage.

In addition, the rice field soil that loaded into the 1/1,000,000 ha pot was leveled to keep water storage at 3-4 cm depth. The 3 leaf stage rice (japonica rice) was transplanted at 3 cm of transplanting depth the next day. The compound of the present invention was treated by the same way after 5 days of transplantation.

The fertility condition of *Echinochloa crusgalli*, *Scirpus juncoides*, *Bidens tripartite* and *Sagittaria trifolia* L. 14 days after the treatment of the compound of the invention and the fertility condition of rice 21 days after the treatment of the compound of the invention respectively with the naked eye. Evaluate the weed control effect with 0-5 activity standard level. It has been found that many of the compounds of the present invention have excellent activity and selectivity.

Note: The seeds of *Echinochloa crusgalli*, *Scirpus juncoides* and *Bidens tripartite* were collected from Heilongjiang Province of China. Tests indicated that the weeds were resistant to common rate of pyrazosulfuron-ethyl.

At the same time, the compounds and the compositions of the present invention have good selectivity to many gramineae grasses such as *Zoysia japonica*, bermuda grass, tall fescue, bluegrass, ryegrass and seashore paspalum, etc., and are able to control many important grass weeds and broadleaf weeds. The compounds also show excellent selectivity and commercial value in the tests on wheat, corn, rice, sorghum, millet, sugarcane, soybean, cotton, oil sunflower, potato, fruit trees, and vegetables in different herbicide application methods (such as pre-emergence and post-emergence).

The invention claimed is:

1. A pyridazinol compound of Formula I or a derivative thereof:

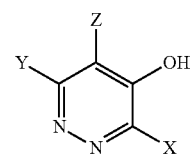

wherein, X represents

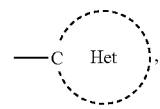

and the ring is an aryl or heterocyclyl containing a carbon atom at the 1-position;

Y represents haloalkyl;

Z represents halogen, cyano, hydroxy, formyl, aryl, heterocyclyl; alkyl, alkenyl, alkynyl, cycloalkyl, OR", SR", SOR" or $SO_2R"$ with or without halogen; or amino which is unsubstituted or substituted by one or two groups selected from R", COR", $CON(R")_2$, COOR", SO₂R", -alkyl-SO₂R" and OR", wherein each of the group contains or does not contain a halogen;

the "aryl", "heterocyclyl", "aryloxy" and "heterocyclyloxy" are respectively unsubstituted or substituted by at least one of the following groups: halogen, nitro, cyano, thiocyano, cyanoalkyl, sulfhydryl, hydroxy, hydroxyalkyl, carboxyl, carboxyalkyloxy, formyl, azide, trialkylsilyl, dialkylphosphono; heterocyclyl, heterocyclylalkyl, aryl or arylalkyl, each of which is unsubstituted or substituted; alkyl, alkenyl, alkynyl, cycloalkyl, cycloalkenyl, cycloalkylalkyl, cycloalkenylalkyl, alkyl-substituted cycloalkyl, OR", SR", -alkyl-OR", —O-alkyl-OR", -alkyl-SR", COR", -alkyl-COR", —O-alkyl-COR", COOR", -alkyl-COOR", —O-alkyl-COOR", COSR", SOR", SO₂R", —O—SO₂R", -alkyl-SO₂R", OCOR", -alkyl-OCOR" or SCOR" with or without halogen; amino, aminocarbonyl, aminocarbonylalkyl or aminosulfonyl, each of which is unsubstituted or substituted by one or two groups selected from R", COR", CON(R")₂, COOR", SO₂R", -alkyl-SO₂R" and OR", wherein each of the group contains or does not contain a halogen; or any two adjacent carbon atoms in the ring are connected with —CH₂CH₂CH₂—, —OCH₂CH₂—, —OCH₂O—, —OCH₂CH₂O— or —CH=CH—CH=CH— group to form a fused ring, wherein each of the group contains or does not contain a halogen;

R" each independently represents alkyl, alkenyl, alkynyl, cycloalkyl, cycloalkylalkyl, cycloalkenyl, cycloalkenylalkyl; or heterocyclyl, heterocyclylalkyl, aryl or arylalkyl, each of which is unsubstituted or substituted.

2. The pyridazinol compound or derivative thereof according to claim 1, wherein

X represents

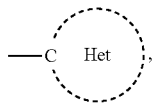

and the ring is an aryl or heterocyclyl group containing a carbon atom at the 1-position;

Y represents halo C1-C8 alkyl;

Z represents halogen, cyano, hydroxy, formyl, aryl, heterocyclyl; C1-C8 alkyl, C2-C8 alkenyl, C2-C8 alkynyl, C3-C8 cycloalkyl, OR", SR", SOR" or SO₂R" with or without halogen; or amino which is unsubstituted or substituted by one or two groups selected from R", COR", CON(R")₂, COOR", SO₂R", —(C1-C8)alkyl-SO₂R" and OR", wherein each of the group contains or does not contain a halogen;

the "aryl", "heterocyclyl", "aryloxy" and "heterocyclyloxy" are respectively unsubstituted or substituted by at least one of the following groups: halogen, nitro, cyano, thiocyano, cyano C1-C8 alkyl, sulfhydryl, hydroxy, hydroxy C1-C8 alkyl, carboxyl, carboxyalkyloxy, formyl, azide, tri-C1-C8 alkylsilyl, di-C1-C8 alkylphosphono; heterocyclyl, heterocyclyl C1-C8 alkyl, aryl or aryl C1-C8 alkyl, each of which is unsubstituted or substituted; C1-C8 alkyl, C2-C8 alkenyl, C2-C8 alkynyl, C3-C8 cycloalkyl, C3-C8 cycloalkenyl, C3-C8 cycloalkyl C1-C8 alkyl, C1-C8 alkyl-substituted C3-C8 cycloalkyl, OR", SR", —(C1-C8)alkyl-OR", —O—(C1-C8)alkyl-OR", —(C1-C8)alkyl-SR", COR", —(C1-C8)alkyl-COR", —O—(C1-C8)alkyl-COR", COOR", —(C1-C8)alkyl-COOR", —O—(C1-C8)alkyl-COOR", COSR", SOR", SO₂R", —O—SO₂R", —(C1-C8)alkyl-SO₂R", OCOR", —(C1-C8)alkyl-OCOR" or SCOR" with or without halogen; amino, aminocarbonyl, aminocarbonyl C1-C8 alkyl or aminosulfonyl, each of which is unsubstituted or substituted by one or two groups selected from R", COR", CON(R")₂, COOR", SO₂R", —(C1-C8)alkyl-SO₂R" and OR", wherein each of the group contains or does not contain a halogen; or any two adjacent carbon atoms in the ring are connected with —CH₂CH₂CH₂—, —OCH₂CH₂—, —OCH₂O—, —OCH₂CH₂O— or —CH=CH—CH=CH— group to form a fused ring, wherein each of the group contains or does not contain a halogen;

R" each independently represents C1-C8 alkyl, C2-C8 alkenyl, C2-C8 alkynyl, C3-C8 cycloalkyl, C3-C8 cycloalkyl C1-C8 alkyl, C3-C8 cycloalkenyl, C3-C8 cycloalkenyl C1-C8 alkyl; or heterocyclyl, heterocyclyl C1-C8 alkyl, aryl or aryl C1-C8 alkyl, each of which is unsubstituted or substituted by at least one group selected from halogen, cyano, C1-C8 alkyl, halo C1-C8 alkyl, C2-C8 alkenyl and C1-C8 alkoxy;

the derivative refers to an agriculturally acceptable derivative of the hydroxyl group at the 4-position of the pyridazine ring in the general formula I.

3. The pyridazinol compound or derivative thereof according to claim 1, wherein

X represents

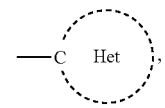

and the ring is an aryl or heterocyclyl group containing a carbon atom at the 1-position;

Y represents halo C1-C6 alkyl;

Z represents halogen, cyano, hydroxy, formyl, aryl, heterocyclyl; C1-C6 alkyl, C2-C6 alkenyl, C2-C6 alkynyl, C3-C6 cycloalkyl, OR", SR", SOR" or SO₂R" with or without halogen; or amino which is unsubstituted or substituted by one or two groups selected from R", COR", CON(R")₂, COOR", SO₂R", —(C1-C6)alkyl-SO₂R" and OR", wherein each of the group contains or does not contain a halogen;

the "aryl", "heterocyclyl", "aryloxy" and "heterocyclyloxy" are respectively unsubstituted or substituted by 1-5 of the following groups: halogen, nitro, cyano, thiocyano, cyano C1-C6 alkyl, sulfhydryl, hydroxy, hydroxy C1-C6 alkyl, carboxyl, carboxyalkyloxy, formyl, azide, tri-C1-C6 alkylsilyl, di-C1-C6 alkylphosphono; heterocyclyl, heterocyclyl C1-C6 alkyl, aryl or aryl C1-C6 alkyl, each of which is unsubstituted or substituted; C1-C6 alkyl, C2-C6 alkenyl, C2-C6 alkynyl, C3-C6 cycloalkyl, C3-C6 cycloalkenyl, C3-C6 cycloalkyl C1-C6 alkyl, C3-C6 cycloalkenyl C1-C6 alkyl, C1-C6 alkyl-substituted C3-C6 cycloalkyl, OR", SR", —(C1-C6)alkyl-OR", —O—(C1-C6)alkyl-OR", —(C1-C6)alkyl-SR", COR", —(C1-C6)alkyl-COR", —O—(C1-C6)alkyl-COR", COOR", —(C1-C6)alkyl-COOR", —O—(C1-C6)alkyl-COOR", COSR", SOR", SO₂R", —O—SO₂R", —(C1-C6)alkyl-SO₂R", OCOR", —(C1-C6)alkyl-OCOR" or SCOR" with or without halogen; amino, aminocarbonyl, aminocarbonyl C1-C6 alkyl or aminosulfonyl, each of which is unsubstituted or substituted by one or two groups selected from R", COR", CON(R")$_2$, COOR", SO$_2$R", —(C1-C6)alkyl-SO$_2$R" and OR", wherein each of the group contains or does not contain a halogen; or any two adjacent carbon atoms in the ring are connected with —CH$_2$CH$_2$CH$_2$—, —OCH$_2$CH$_2$—, —OCH$_2$O—, —OCH$_2$CH$_2$O— or —CH═CH—CH═CH— group to form a fused ring, wherein each of the group contains or does not contain a halogen;

R" each independently represents C1-C6 alkyl, C2-C6 alkenyl, C2-C6 alkynyl, C3-C6 cycloalkyl, C3-C6 cycloalkyl C1-C6 alkyl, C3-C6 cycloalkenyl, C3-C6 cycloalkenyl C1-C6 alkyl; or heterocyclyl, heterocyclyl C1-C6 alkyl, aryl or aryl C1-C6 alkyl, each of which is unsubstituted or substituted by 1-5 groups selected from halogen, cyano, C1-C6 alkyl, halo C1-C6 alkyl, C2-C6 alkenyl and C1-C6 alkoxy;

the derivative refers to an agriculturally acceptable derivative of the hydroxyl group at the 4-position of the pyridazine ring in the general formula I, including a salt, an ester, an oxime, a hydroxylamine and an ether derivative.

4. The pyridazinol compound or derivative thereof according to claim 1, wherein

X represents

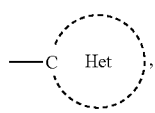

the ring is phenyl,

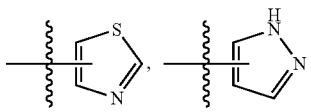

or

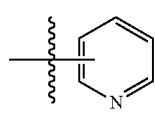

containing a carbon atom at the 1-position, which is respectively unsubstituted or substituted by 1-3 groups selected from fluorine, chlorine, bromine, cyano, C1-C6 alkyl, C2-C6 alkenyl, halo C1-C6 alkyl, or any two adjacent carbon atoms in the ring are connected with —OCH$_2$O— group to form a fused ring, wherein the —OCH$_2$O— group contains or does not contain a halogen;

Y represents trifluoromethyl or pentafluoroethyl;

Z represents halogen, cyano, hydroxy, formyl, aryl, heterocyclyl, C1-C6 alkyl, halo C1-C6 alkyl, C2-C6 alkenyl, C2-C6 alkynyl, C3-C6 cycloalkyl, C1-C6 alkoxy, halo C1-C6 alkoxy, aryloxy, heterocyclyloxy, C1-C6 alkylsulfanyl, C1-C6 alkylsulfoxide, C1-C6 alkylsulfonyl; or amino which is unsubstituted or substituted by one or two groups selected from C1-C6 alkyl, C1-C6 alkylcarbonyl, C1-C6 alkylaminocarbonyl, C1-C6 alkoxycarbonyl, C3-C6 cycloalkyloxycarbonyl, C1-C6 alkylsulfonyl, aryl and aryl C1-C2 alkyl;

the "aryl" is phenyl which is unsubstituted or substituted by 1-3 groups selected from fluorine, cyano and C1-C6 alkoxy; the "heterocyclyl" is

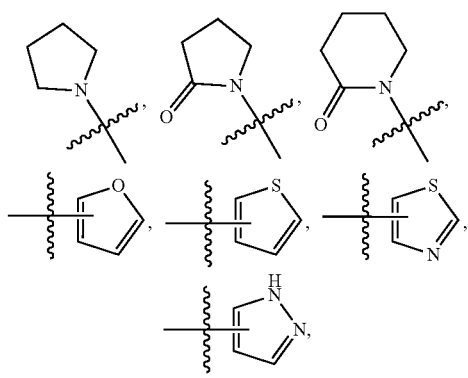

or

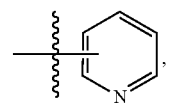

each of which is unsubstituted or substituted by 1-3 groups selected from C1-C6 alkyl.

5. The pyridazinol compound or derivative thereof according to claim 1, which is selected from:

TABLE 1

| NO. | X | Y | Z |
|---|---|---|---|
| 1 | ![4-cyanophenyl] | CF$_3$ | F |
| 2 | ![4-cyanophenyl] | CF$_3$ | Cl |
| 3 | ![4-cyanophenyl] | CF$_3$ | Br |

TABLE 1-continued
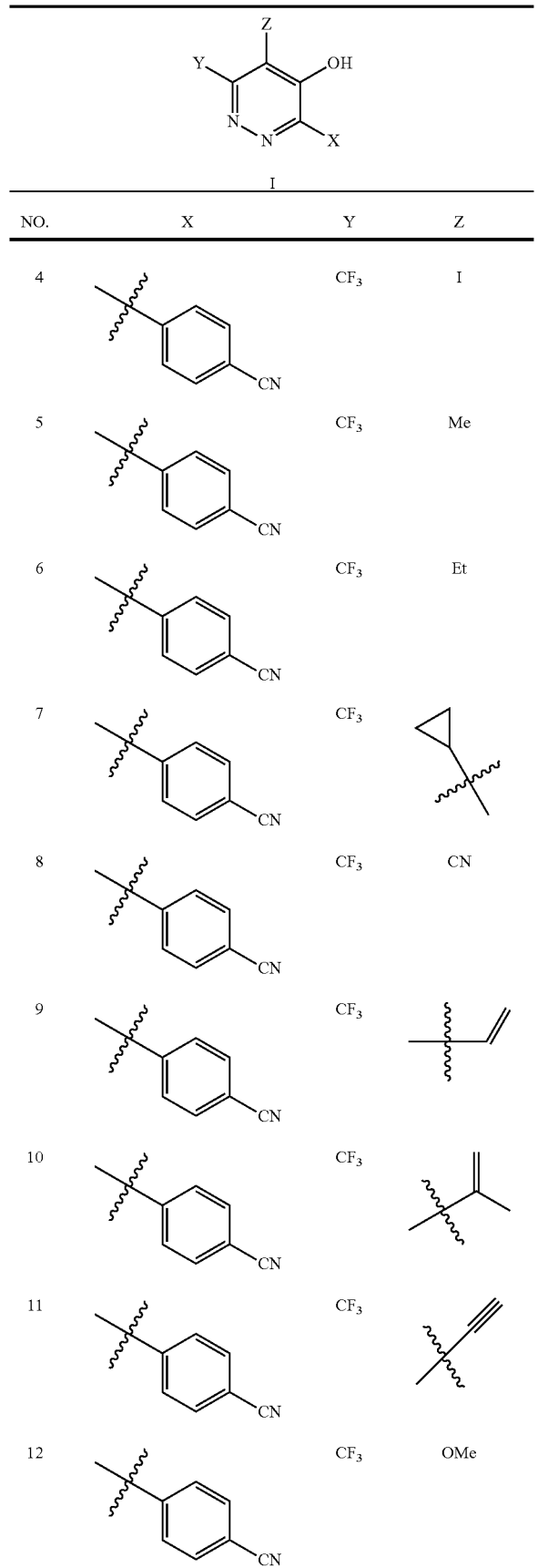
I
| NO. | X | Y | Z |
|---|---|---|---|
| 4 | 4-CN-C6H4- | CF3 | I |
| 5 | 4-CN-C6H4- | CF3 | Me |
| 6 | 4-CN-C6H4- | CF3 | Et |
| 7 | 4-CN-C6H4- | CF3 | cyclopropyl |
| 8 | 4-CN-C6H4- | CF3 | CN |
| 9 | 4-CN-C6H4- | CF3 | vinyl |
| 10 | 4-CN-C6H4- | CF3 | isopropenyl |
| 11 | 4-CN-C6H4- | CF3 | ethynyl |
| 12 | 4-CN-C6H4- | CF3 | OMe |
TABLE 1-continued
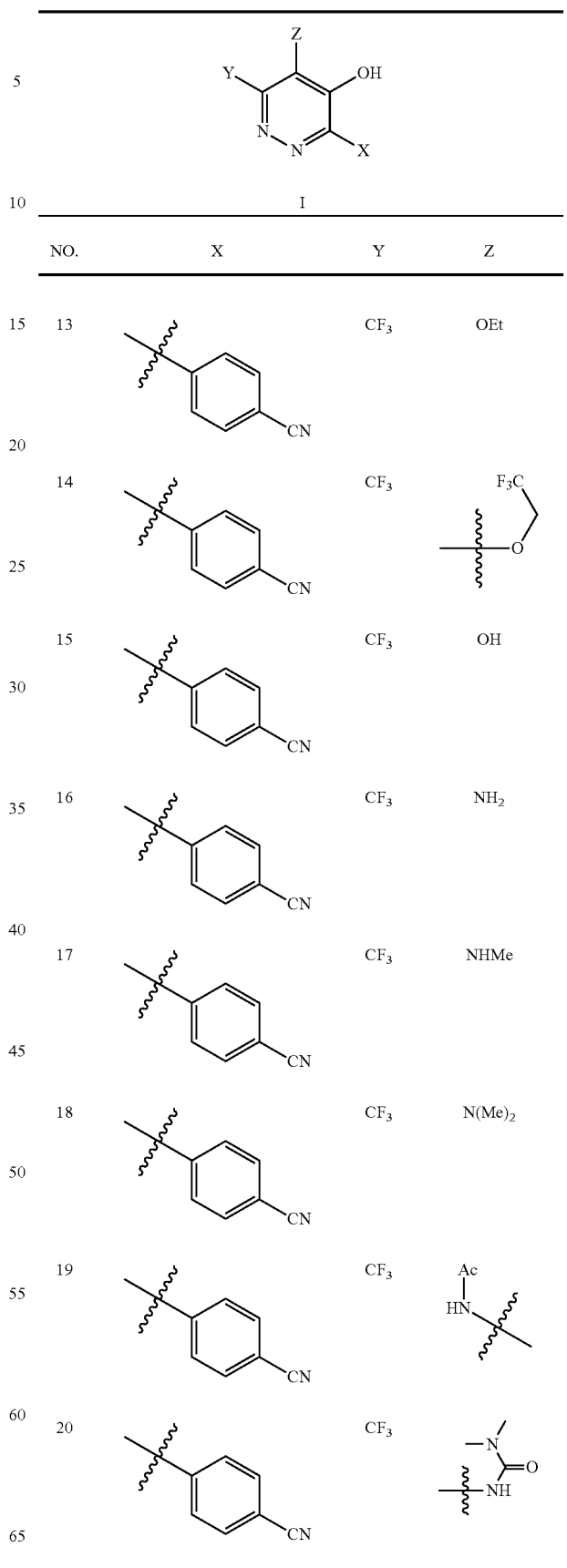
I
| NO. | X | Y | Z |
|---|---|---|---|
| 13 | 4-CN-C6H4- | CF3 | OEt |
| 14 | 4-CN-C6H4- | CF3 | OCH2CF3 |
| 15 | 4-CN-C6H4- | CF3 | OH |
| 16 | 4-CN-C6H4- | CF3 | NH2 |
| 17 | 4-CN-C6H4- | CF3 | NHMe |
| 18 | 4-CN-C6H4- | CF3 | N(Me)2 |
| 19 | 4-CN-C6H4- | CF3 | NHAc |
| 20 | 4-CN-C6H4- | CF3 | NHC(O)N(Me)2 |

TABLE 1-continued

Structure I: pyridazine with Y, Z, OH, X substituents

| NO. | X | Y | Z |
|---|---|---|---|
| 21 | 4-CN-C6H4- | CF3 | NHPh (via CH) |
| 22 | 4-CN-C6H4- | CF3 | 2-oxopyrrolidin-1-yl (via CH) |
| 23 | 4-CN-C6H4- | CF3 | 2-oxopiperidin-1-yl (via CH) |
| 24 | 4-CN-C6H4- | CF3 | 3,5-dimethylpyrazol-1-yl (via CH) |
| 25 | 4-CN-C6H4- | CF3 | pyrazol-1-yl (via CH) |
| 26 | 4-CN-C6H4- | CF3 | SMe |
| 27 | 4-CN-C6H4- | CF3 | SEt |
| 28 | 4-CN-C6H4- | CF3 | SOEt |
| 29 | 4-CN-C6H4- | CF3 | SO2Et |
| 30 | 4-CN-C6H4- | CF3 | Ph |
| 31 | 4-CN-C6H4- | CF3 | 4-F-C6H4- |
| 32 | 4-CN-C6H4- | CF3 | 4-NC-C6H4- |
| 33 | 4-CN-C6H4- | CF3 | pyridin-2-yl |
| 34 | 4-CN-C6H4- | CF3 | pyridin-3-yl |
| 35 | 4-CN-C6H4- | CF3 | pyridin-4-yl |

TABLE 1-continued
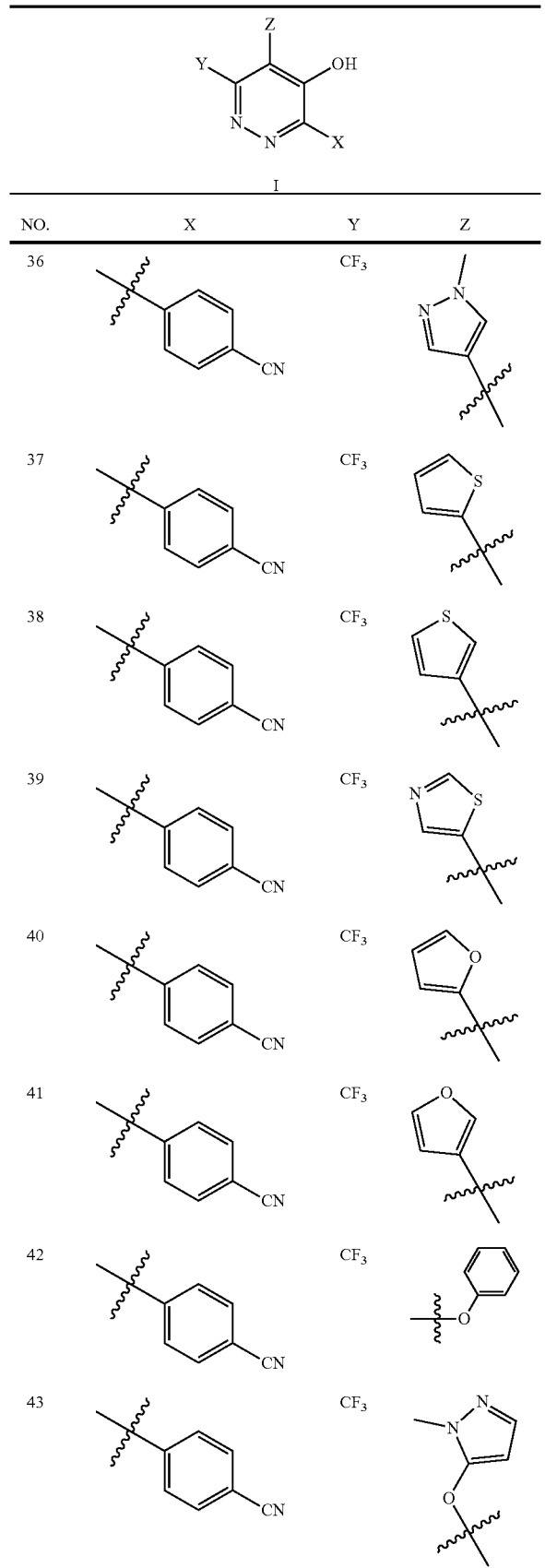
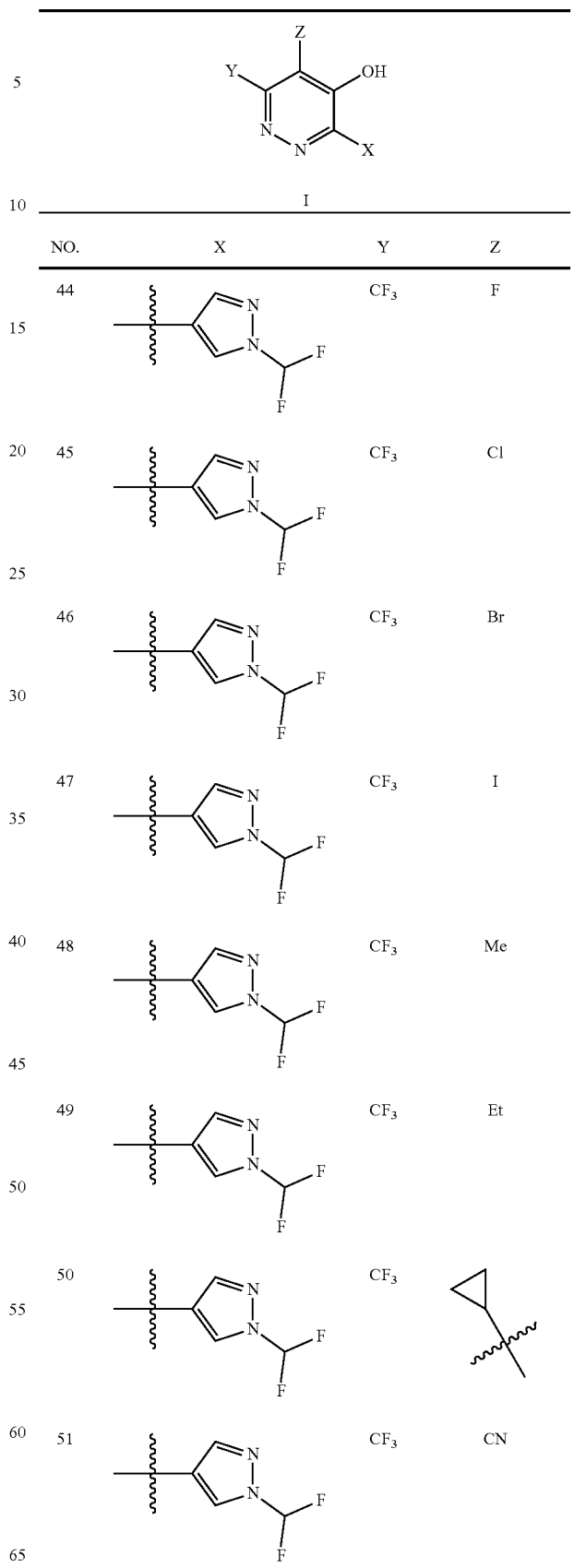

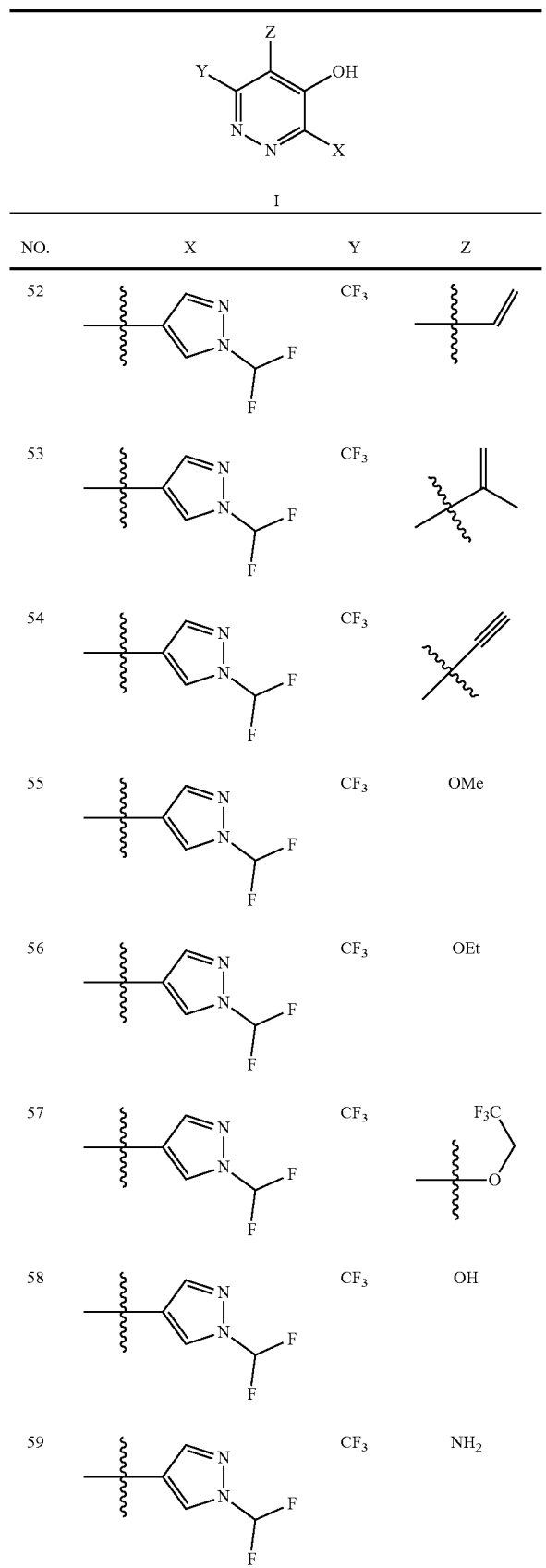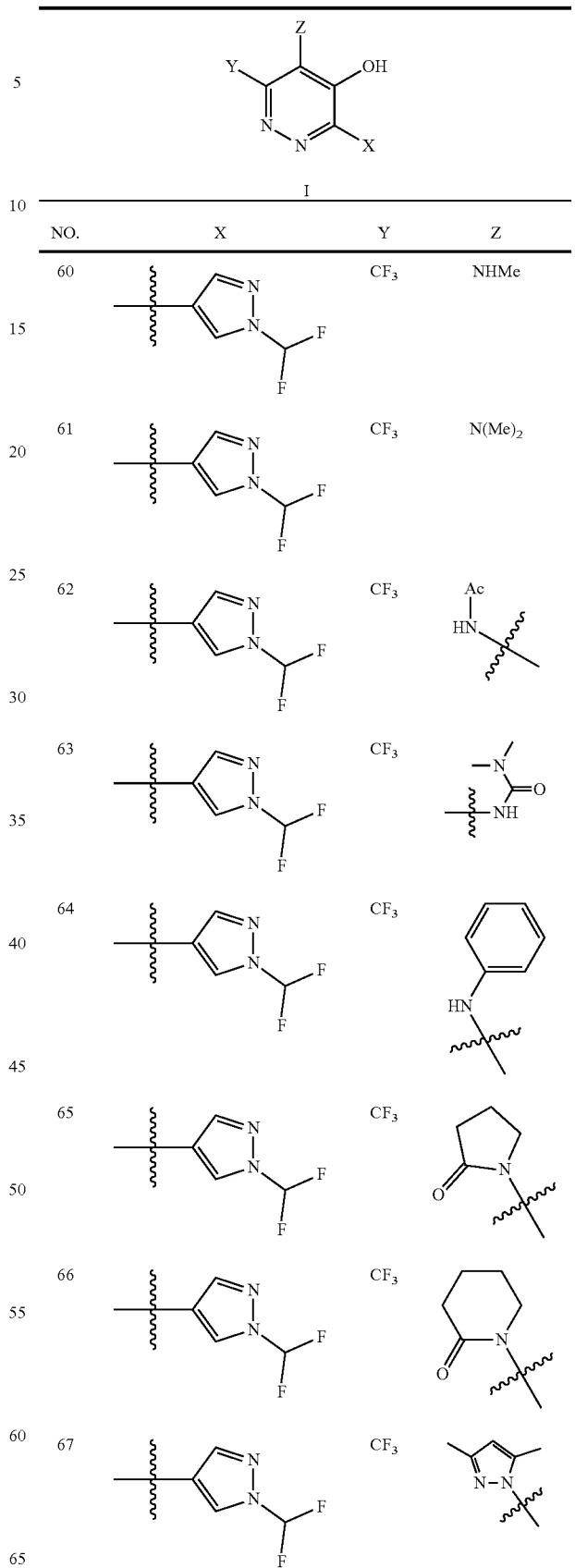

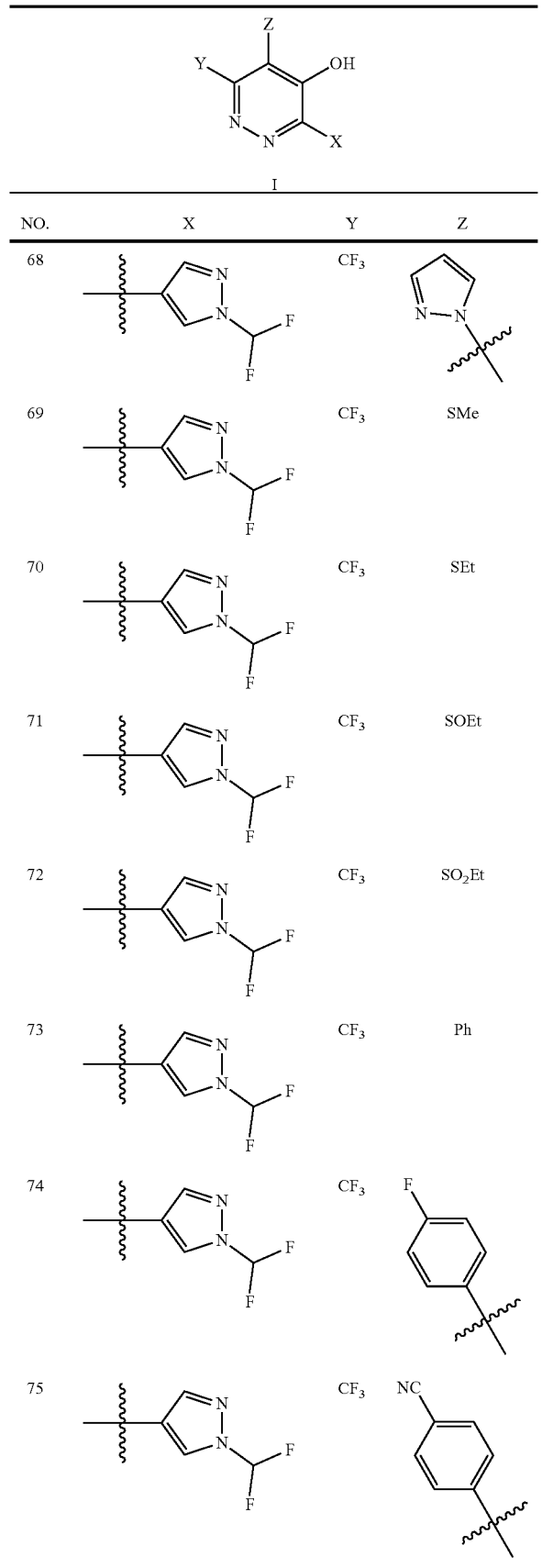
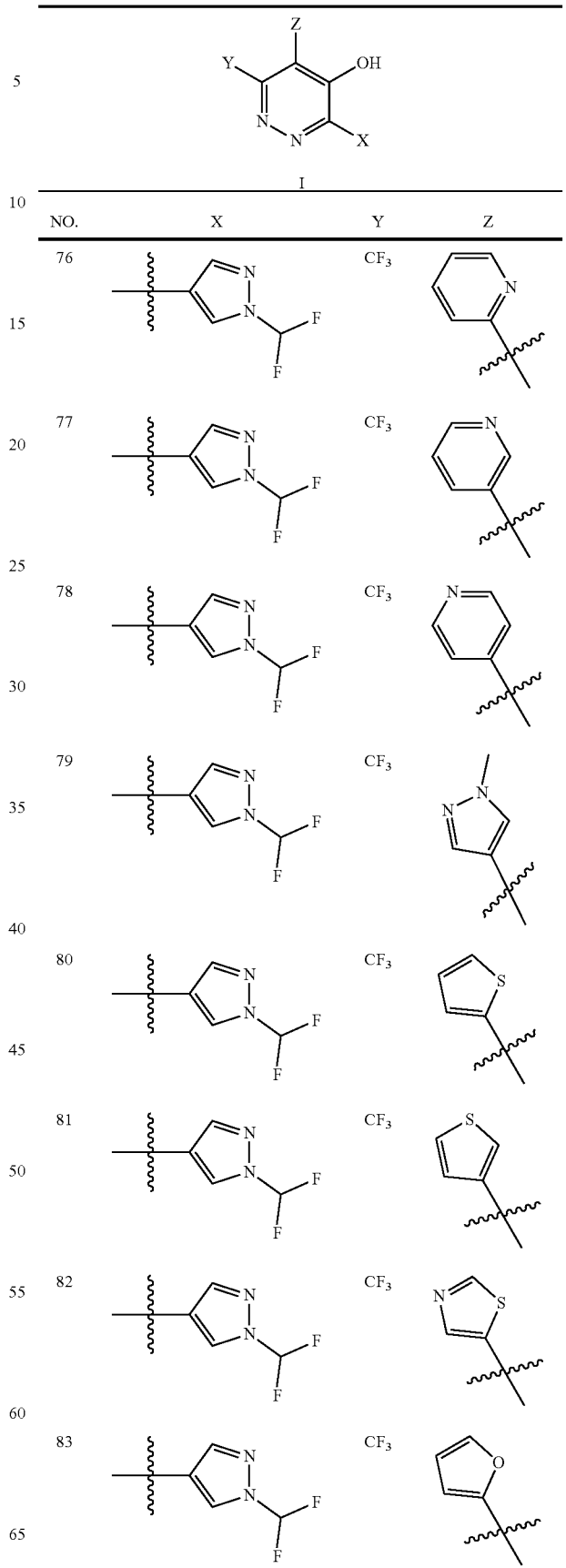

TABLE 1-continued
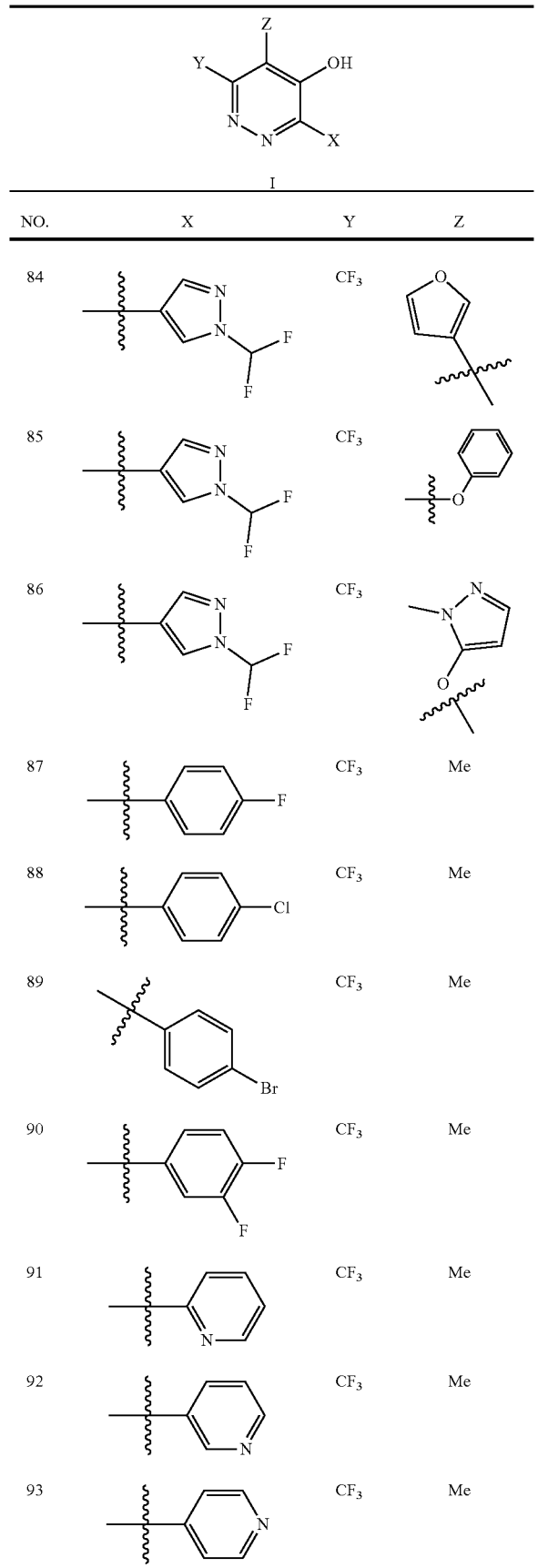
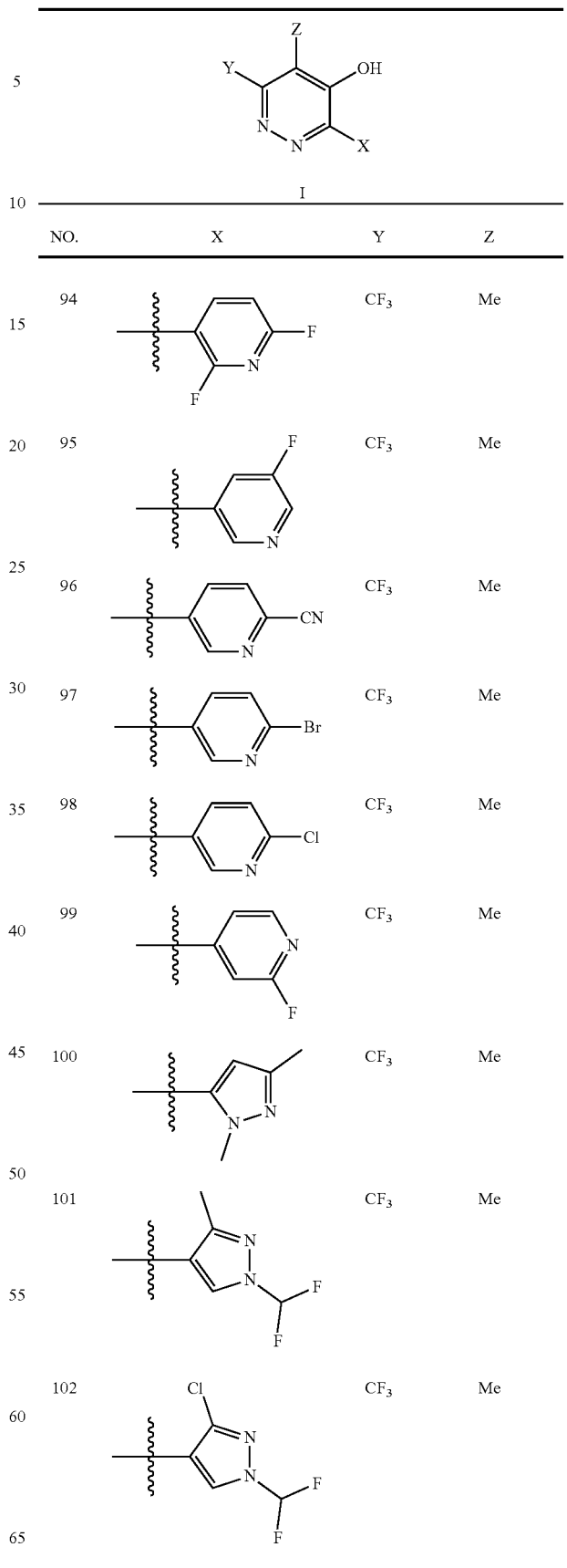

TABLE 1-continued

I

| NO. | X | Y | Z |
|-----|---|---|---|
| 103 | 3-Cl, 1-CHF₂-pyrazol-4-yl | CF₃ | Me |
| 104 | 1-CF₃-pyrazol-4-yl | CF₃ | Me |
| 105 | 3-F, 1-CF₃-pyrazol-4-yl | CF₃ | Me |
| 106 | 1-CHF₂-pyrazol-3-yl | CF₃ | Me |
| 107 | 2-Me-thiazol-5-yl | CF₃ | Me |
| 108 | thiazol-4-yl | CF₃ | Me |
| 109 | 2-F-pyridin-3-yl | CF₃ | Me |
| 110 | 2-Cl-pyridin-4-yl | CF₃ | Me |
| 111 | 5-Cl-pyridin-3-yl | CF₃ | Me |
| 112 | 2-Cl-pyridin-3-yl | CF₃ | Me |
| 113 | 2-Cl, 6-F-pyridin-3-yl | CF₃ | Me |
| 114 | 2-F, 5-Cl-pyridin-3-yl | CF₃ | Me |
| 115 | 4-F-phenyl | CF₃ | cyclopropyl |
| 116 | 4-Cl-phenyl | CF₃ | cyclopropyl |
| 117 | 3,4-di-F-phenyl | CF₃ | cyclopropyl |
| 118 | pyridin-2-yl | CF₃ | cyclopropyl |
| 119 | pyridin-3-yl | CF₃ | cyclopropyl |

TABLE 1-continued

![Structure I: pyridazine with Z, Y, OH, X, N, N substituents]

I

| NO. | X | Y | Z |
|-----|---|---|---|
| 120 | 4-pyridyl | CF₃ | cyclopropyl |
| 121 | 2,6-difluoropyridin-3-yl | CF₃ | cyclopropyl |
| 122 | 5-fluoropyridin-3-yl | CF₃ | cyclopropyl |
| 123 | 6-cyanopyridin-3-yl | CF₃ | cyclopropyl |
| 124 | 6-bromopyridin-3-yl | CF₃ | cyclopropyl |
| 125 | 6-chloropyridin-3-yl | CF₃ | cyclopropyl |
| 126 | 2-fluoropyridin-4-yl | CF₃ | cyclopropyl |
| 127 | 1,3-dimethyl-1H-pyrazol-5-yl | CF₃ | cyclopropyl |
| 128 | 1-(trifluoromethyl)-1H-pyrazol-4-yl | CF₃ | cyclopropyl |
| 129 | 1-(difluoromethyl)-3-methyl-1H-pyrazol-4-yl | CF₃ | cyclopropyl |
| 130 | 2-methylthiazol-5-yl | CF₃ | cyclopropyl |
| 131 | thiazol-4-yl | CF₃ | cyclopropyl |
| 132 | 2-fluoropyridin-3-yl | CF₃ | cyclopropyl |
| 133 | 2-chloropyridin-4-yl | CF₃ | cyclopropyl |
| 134 | 5-chloropyridin-3-yl | CF₃ | cyclopropyl |
| 135 | 2-chloropyridin-3-yl | CF₃ | cyclopropyl |
| 136 | 6-chloro-2-fluoropyridin-3-yl | CF₃ | cyclopropyl |
| 137 | 5-chloro-2-fluoropyridin-3-yl | CF₃ | cyclopropyl |

TABLE 1-continued structure I: pyridazine with Z, Y, OH, X substituents

| NO. | X | Y | Z |
|---|---|---|---|
| 138 | 4-F-phenyl | CF₃ | SEt |
| 139 | 4-Cl-phenyl | CF₃ | SEt |
| 140 | 3,4-diF-phenyl | CF₃ | SEt |
| 141 | pyridin-2-yl | CF₃ | SEt |
| 142 | pyridin-3-yl | CF₃ | SEt |
| 143 | pyridin-4-yl | CF₃ | SEt |
| 144 | 2,6-diF-pyridin-3-yl | CF₃ | SEt |
| 145 | 5-F-pyridin-3-yl | CF₃ | SEt |
| 146 | 6-CN-pyridin-3-yl | CF₃ | SEt |
| 147 | 6-Br-pyridin-3-yl | CF₃ | SEt |
| 148 | 6-Cl-pyridin-3-yl | CF₃ | SEt |
| 149 | 2-F-pyridin-4-yl | CF₃ | SEt |
| 150 | 1,3-dimethyl-pyrazol-5-yl | CF₃ | SEt |
| 151 | 1-(CF₃)-pyrazol-4-yl | CF₃ | SEt |
| 152 | 3-methyl-1-(CHF₂)-pyrazol-4-yl | CF₃ | SEt |
| 153 | 2-methyl-thiazol-5-yl | CF₃ | SEt |
| 154 | thiazol-4-yl | CF₃ | SEt |
| 155 | 2-F-pyridin-3-yl | CF₃ | SEt |
| 156 | 4-F-phenyl | CF₃ | isobutenyl |
| 157 | 4-Cl-phenyl | CF₃ | isobutenyl |
| 158 | 3,4-diF-phenyl | CF₃ | isobutenyl |

TABLE 1-continued structure I: pyridazine with Z, Y, OH, X, N, N substituents

| NO. | X | Y | Z |
|-----|---|---|---|
| 159 | 2-pyridyl | CF₃ | isopropenyl |
| 160 | 3-pyridyl | CF₃ | isopropenyl |
| 161 | 4-pyridyl | CF₃ | isopropenyl |
| 162 | 2,6-difluoropyridin-3-yl | CF₃ | isopropenyl |
| 163 | 5-fluoropyridin-3-yl | CF₃ | isopropenyl |
| 164 | 6-cyanopyridin-3-yl | CF₃ | isopropenyl |
| 165 | 6-bromopyridin-3-yl | CF₃ | isopropenyl |
| 166 | 6-chloropyridin-3-yl | CF₃ | isopropenyl |
| 167 | 2-fluoropyridin-4-yl | CF₃ | isopropenyl |
| 168 | 1,3-dimethyl-1H-pyrazol-5-yl | CF₃ | isopropenyl |

TABLE 1-continued structure I: pyridazine with Z, Y, OH, X, N, N substituents

| NO. | X | Y | Z |
|-----|---|---|---|
| 169 | 1-(trifluoromethyl)-1H-pyrazol-4-yl | CF₃ | isopropenyl |
| 170 | 1-(difluoromethyl)-3-methyl-1H-pyrazol-4-yl | CF₃ | isopropenyl |
| 171 | 2-methylthiazol-5-yl | CF₃ | isopropenyl |
| 172 | thiazol-4-yl | CF₃ | isopropenyl |
| 173 | 2-fluoropyridin-3-yl | CF₃ | isopropenyl |
| 174 | 4-fluorophenyl | CF₃ | NH₂ |
| 175 | 4-chlorophenyl | CF₃ | NH₂ |
| 176 | 3,4-difluorophenyl | CF₃ | NH₂ |
| 177 | 2-pyridyl | CF₃ | NH₂ |
| 178 | 3-pyridyl | CF₃ | NH₂ |

TABLE 1-continued structure I: pyridazine with Y, Z, OH, X, N-N

| NO. | X | Y | Z |
|---|---|---|---|
| 179 | 4-pyridyl | CF₃ | NH₂ |
| 180 | 2,6-difluoropyridin-3-yl | CF₃ | NH₂ |
| 181 | 5-fluoropyridin-3-yl | CF₃ | NH₂ |
| 182 | 6-cyanopyridin-3-yl | CF₃ | NH₂ |
| 183 | 6-bromopyridin-3-yl | CF₃ | NH₂ |
| 184 | 6-chloropyridin-3-yl | CF₃ | NH₂ |
| 185 | 2-fluoropyridin-4-yl | CF₃ | NH₂ |
| 186 | 1,3-dimethyl-1H-pyrazol-5-yl | CF₃ | NH₂ |
| 187 | 1-(trifluoromethyl)-1H-pyrazol-4-yl | CF₃ | NH₂ |
| 188 | 1-(difluoromethyl)-3-methyl-1H-pyrazol-4-yl | CF₃ | NH₂ |

TABLE 1-continued

| NO. | X | Y | Z |
|---|---|---|---|
| 189 | 2-methylthiazol-5-yl | CF₃ | NH₂ |
| 190 | thiazol-5-yl | CF₃ | NH₂ |
| 191 | 2-fluoropyridin-3-yl | CF₃ | NH₂ |
| 192 | 4-fluorophenyl | CF₃ | NHMe |
| 193 | 4-chlorophenyl | CF₃ | NHMe |
| 194 | 3,4-difluorophenyl | CF₃ | NHMe |
| 195 | 2-pyridyl | CF₃ | NHMe |
| 196 | 3-pyridyl | CF₃ | NHMe |
| 197 | 4-pyridyl | CF₃ | NHMe |
| 198 | 2,6-difluoropyridin-3-yl | CF₃ | NHMe |
| 199 | 5-fluoropyridin-3-yl | CF₃ | NHMe |

TABLE 1-continued

I

| NO. | X | Y | Z |
|---|---|---|---|
| 200 | 5-(2-cyanopyridinyl) | CF₃ | NHMe |
| 201 | 5-(2-bromopyridinyl) | CF₃ | NHMe |
| 202 | 5-(2-chloropyridinyl) | CF₃ | NHMe |
| 203 | 4-(2-fluoropyridinyl) | CF₃ | NHMe |
| 204 | 1,3-dimethylpyrazol-5-yl | CF₃ | NHMe |
| 205 | 1-(trifluoromethyl)pyrazol-4-yl | CF₃ | NHMe |
| 206 | 1-(difluoromethyl)-3-methylpyrazol-4-yl | CF₃ | NHMe |
| 207 | 2-methylthiazol-5-yl | CF₃ | NHMe |
| 208 | thiazol-5-yl | CF₃ | NHMe |
| 209 | 2-fluoropyridin-3-yl | CF₃ | NHMe |

TABLE 1-continued

I

| NO. | X | Y | Z |
|---|---|---|---|
| 210 | 4-fluorophenyl | CF₃ | Ac-HN- |
| 211 | 4-chlorophenyl | CF₃ | Ac-HN- |
| 212 | 3,4-difluorophenyl | CF₃ | Ac-HN- |
| 213 | pyridin-2-yl | CF₃ | Ac-HN- |
| 214 | pyridin-3-yl | CF₃ | Ac-HN- |
| 215 | pyridin-4-yl | CF₃ | Ac-HN- |
| 216 | 2,6-difluoropyridin-3-yl | CF₃ | Ac-HN- |
| 217 | 5-fluoropyridin-3-yl | CF₃ | Ac-HN- |
| 218 | 5-(2-cyanopyridinyl) | CF₃ | Ac-HN- |
| 219 | 5-(2-bromopyridinyl) | CF₃ | Ac-HN- |

TABLE 1-continued

| NO. | X | Y | Z |
|---|---|---|---|
| 220 | 5-(2-chloropyridin-5-yl) | CF₃ | Ac-HN- |
| 221 | 4-(2-fluoropyridin-4-yl) | CF₃ | Ac-HN- |
| 222 | 1,3-dimethylpyrazol-5-yl | CF₃ | Ac-HN- |
| 223 | 1-(trifluoromethyl)pyrazol-4-yl | CF₃ | Ac-HN- |
| 224 | 1-(difluoromethyl)-3-methylpyrazol-4-yl | CF₃ | Ac-HN- |
| 225 | 2-methylthiazol-5-yl | CF₃ | Ac-HN- |
| 226 | thiazol-5-yl | CF₃ | Ac-HN- |
| 227 | 2-fluoropyridin-3-yl | CF₃ | Ac-HN- |
| 228 | 4-cyanophenyl | CF₂CF₃ | Me |
| 229 | 1-(difluoromethyl)pyrazol-4-yl | CF₂CF₃ | Me |
| 230 | phenyl | CF₃ | Me |
| 231 | 2-methylphenyl | CF₃ | Me |
| 232 | 3-methylphenyl | CF₃ | Me |
| 233 | 4-methylphenyl | CF₃ | Me |
| 234 | 2-vinylphenyl | CF₃ | Me |
| 235 | 3-ethynylphenyl | CF₃ | Me |
| 236 | 4-cyclopropylphenyl | CF₃ | Me |

TABLE 1-continued

I

| NO. | X | Y | Z |
|---|---|---|---|
| 237 | 2-fluorophenyl | CF$_3$ | Me |
| 238 | 3-fluorophenyl | CF$_3$ | Me |
| 239 | 2-chlorophenyl | CF$_3$ | Me |
| 240 | 3-chlorophenyl | CF$_3$ | Me |
| 241 | 2-bromophenyl | CF$_3$ | Me |
| 242 | 3-bromophenyl | CF$_3$ | Me |
| 243 | 3-iodophenyl | CF$_3$ | Me |
| 244 | 4-iodophenyl | CF$_3$ | Me |
| 245 | 3-(trifluoromethyl)phenyl | CF$_3$ | Me |
| 246 | 3-cyanophenyl | CF$_3$ | Me |
| 247 | 4-nitrophenyl | CF$_3$ | Me |
| 248 | 3-azidophenyl | CF$_3$ | Me |
| 249 | 3-carboxyphenyl | CF$_3$ | Me |
| 250 | 4-hydroxyphenyl | CF$_3$ | Me |
| 251 | 4-mercaptophenyl | CF$_3$ | Me |
| 252 | 3-aminophenyl | CF$_3$ | Me |
| 253 | 2-methoxyphenyl | CF$_3$ | Me |

TABLE 1-continued

I

| NO. | X | Y | Z |
|---|---|---|---|
| 254 | 3-(methylthio)phenyl | CF₃ | Me |
| 255 | 4-(dimethylamino)phenyl | CF₃ | Me |
| 256 | 4-(trifluoromethoxy)phenyl | CF₃ | Me |
| 257 | 3-phenoxyphenyl | CF₃ | Me |
| 258 | 3-(N-methyl-N-phenylamino)phenyl | CF₃ | Me |
| 259 | 4-(methoxycarbonyl)phenyl | CF₃ | Me |
| 260 | 4-(methylsulfonyl)phenyl | CF₃ | Me |
| 261 | 4-acetoxyphenyl | CF₃ | Me |
| 262 | 4-acetamidophenyl | CF₃ | Me |
| 263 | 4-acetylphenyl | CF₃ | Me |
| 264 | biphenyl-4-yl | CF₃ | Me |
| 265 | 4-(methylsulfonyloxy)phenyl | CF₃ | Me |
| 266 | 3-(carboxymethoxy)phenyl | CF₃ | Me |
| 267 | 2-methyl-3-(methoxymethoxy)phenyl | CF₃ | Me |
| 268 | 3-(methoxycarbonylamino)phenyl | CF₃ | Me |
| 269 | 3-((methylsulfonyl)methylamino)phenyl | CF₃ | Me |
| 270 | 3-(methylsulfonylamino)phenyl | CF₃ | Me |

TABLE 1-continued

Structure I: pyridazine with Y, Z, OH, X substituents

| NO. | X | Y | Z |
|---|---|---|---|
| 271 | 3-(ethoxymethyl)phenyl | CF₃ | Me |
| 272 | 4-(2-oxobutyl)phenyl | CF₃ | Me |
| 273 | 4-(diethoxyphosphoryl)phenyl | CF₃ | Me |
| 274 | 4-(trimethylsilyl)phenyl | CF₃ | Me |
| 275 | 3,4-dimethylphenyl | CF₃ | Me |
| 276 | 2,6-dimethylphenyl | CF₃ | Me |
| 277 | 3,5-dimethylphenyl | CF₃ | Me |
| 278 | 3,4-dimethylphenyl | CF₃ | Me |
| 279 | 2,5-dimethylphenyl | CF₃ | Me |
| 280 | 2-cyclopropyl-6-methylphenyl | CF₃ | Me |
| 281 | 4-fluoro-2-methylphenyl | CF₃ | Me |
| 282 | 2-fluoro-5-methylphenyl | CF₃ | Me |
| 283 | 3-fluoro-4-methylphenyl | CF₃ | Me |
| 284 | 3-fluoro-4-methylphenyl | CF₃ | Me |
| 285 | 4-chloro-2-methylphenyl | CF₃ | Me |
| 286 | 4-chloro-3-methylphenyl | CF₃ | Me |

TABLE 1-continued structure I (pyridazine with Y, Z, OH, X substituents)

| NO. | X | Y | Z |
|---|---|---|---|
| 287 | 3-methyl-5-chlorophenyl | CF₃ | Me |
| 288 | 3-chloro-4-methylphenyl | CF₃ | Me |
| 289 | 2-methyl-4-methoxyphenyl | CF₃ | Me |
| 290 | 2-nitro-4-methylphenyl | CF₃ | Me |
| 291 | 2,5-difluorophenyl | CF₃ | Me |
| 292 | 3,5-difluorophenyl | CF₃ | Me |
| 293 | 2,6-difluorophenyl | CF₃ | Me |
| 294 | 2,5-dichlorophenyl | CF₃ | Me |
| 295 | 3,4-dichlorophenyl | CF₃ | Me |
| 296 | 2,4-dichlorophenyl | CF₃ | Me |
| 297 | 3,5-dichlorophenyl | CF₃ | Me |
| 298 | 2,6-dichlorophenyl | CF₃ | Me |
| 299 | 2,3-dichlorophenyl | CF₃ | Me |
| 300 | 2-fluoro-4-chlorophenyl | CF₃ | Me |
| 301 | 2-chloro-4-fluorophenyl | CF₃ | Me |
| 302 | 2-fluoro-3-chlorophenyl | CF₃ | Me |

TABLE 1-continued

I

| NO. | X | Y | Z |
|-----|---|---|---|
| 303 | 3-Cl, 5-F phenyl | CF₃ | Me |
| 304 | 3-Cl, 4-F phenyl | CF₃ | Me |
| 305 | 4-Cl, 3-F phenyl | CF₃ | Me |
| 306 | 2-Br, 6-F phenyl | CF₃ | Me |
| 307 | 3-Br, 2-F phenyl | CF₃ | Me |
| 308 | 3-F, 5-Br phenyl | CF₃ | Me |
| 309 | 2-F, 5-CF₃ phenyl | CF₃ | Me |
| 310 | 2-F, 4-CF₃ phenyl | CF₃ | Me |
| 311 | 2-F, 3-CF₃ phenyl | CF₃ | Me |
| 312 | 2-CF₃, 4-F phenyl | CF₃ | Me |
| 313 | 2-CF₃, 4-Cl phenyl | CF₃ | Me |
| 314 | 5-F, 2-OMe phenyl | CF₃ | Me |
| 315 | 3-F, 2-OMe phenyl | CF₃ | Me |
| 316 | 3-OMe, 2-F phenyl | CF₃ | Me |
| 317 | 2-Cl, 5-OMe phenyl | CF₃ | Me |
| 318 | 2-Cl, 4-OMe phenyl | CF₃ | Me |

TABLE 1-continued

I

| NO. | X | Y | Z |
|-----|---|-----|----|
| 319 | 3-fluoro-4-formylphenyl | CF$_3$ | Me |
| 320 | 3-fluoro-4-formylphenyl (alt) | CF$_3$ | Me |
| 321 | 4-fluoro-2-formylphenyl | CF$_3$ | Me |
| 322 | 2-fluoro-6-formylphenyl | CF$_3$ | Me |
| 323 | 3-nitro-4-fluorophenyl | CF$_3$ | Me |
| 324 | 4-fluoro-3-nitrophenyl | CF$_3$ | Me |
| 325 | 4-chloro-3-nitrophenyl | CF$_3$ | Me |
| 326 | 4-chloro-3-nitrophenyl (alt) | CF$_3$ | Me |
| 327 | 2-methyl-4-methoxy-5-(dimethylamino)phenyl | CF$_3$ | Me |
| 328 | 2,6-dimethyl-4-chlorophenyl | CF$_3$ | Me |
| 329 | 2-methyl-3,6-dichlorophenyl | CF$_3$ | Me |
| 330 | 2-fluoro-3-methoxy-4-chlorophenyl | CF$_3$ | Me |
| 331 | 2,3,4-trichlorophenyl | CF$_3$ | Me |
| 332 | 2,5-dichloro-4-hydroxyphenyl | CF$_3$ | Me |
| 333 | 2,3,5-trifluorophenyl | CF$_3$ | Me |

TABLE 1-continued

I

| NO. | X | Y | Z |
|---|---|---|---|
| 334 | 3,4,5-trifluorophenyl | CF$_3$ | Me |
| 335 | 2,3,6-trifluorophenyl | CF$_3$ | Me |
| 336 | pentafluorophenyl | CF$_3$ | Me |
| 337 | 1-methyl-pyrrol-2-yl | CF$_3$ | Me |
| 338 | furan-3-yl | CF$_3$ | Me |
| 339 | furan-2-yl | CF$_3$ | Me |
| 340 | thiophen-2-yl | CF$_3$ | Me |
| 341 | thiophen-3-yl | CF$_3$ | Me |
| 342 | oxazol-5-yl | CF$_3$ | Me |
| 343 | 1-methyl-imidazol-2-yl | CF$_3$ | Me |
| 344 | isoxazol-3-yl | CF$_3$ | Me |
| 345 | isothiazol-5-yl | CF$_3$ | Me |
| 346 | 5-methyl-1,3,4-oxadiazol-2-yl | CF$_3$ | Me |
| 347 | 1,3,4-thiadiazol-2-yl | CF$_3$ | Me |
| 348 | 4-methyl-4H-1,2,4-triazol-3-yl | CF$_3$ | Me |
| 349 | 1,2,4-oxadiazol-3-yl | CF$_3$ | Me |
| 350 | 1,3,4-thiadiazol-2-yl | CF$_3$ | Me |

TABLE 1-continued

Structure I: pyridazine core with Z, Y, OH, X, N, N substituents

| NO. | X | Y | Z |
|---|---|---|---|
| 351 | 1H-1,2,4-triazol-3-yl | CF₃ | Me |
| 352 | 1,2,3-oxadiazol-4-yl | CF₃ | Me |
| 353 | 1,2,3-thiadiazol-5-yl | CF₃ | Me |
| 354 | 1H-1,2,3-triazol-4-yl | CF₃ | Me |
| 355 | 1-methyl-1H-tetrazol-5-yl | CF₃ | Me |
| 356 | pyrazin-2-yl | CF₃ | Me |
| 357 | pyrimidin-5-yl | CF₃ | Me |
| 358 | pyridazin-4-yl | CF₃ | Me |
| 359 | 1,3,5-triazin-2-yl | CF₃ | Me |
| 360 | 1-methyl-1H-indol-5-yl | CF₃ | Me |
| 361 | benzo[b]thiophen-2-yl | CF₃ | Me |
| 362 | benzofuran-5-yl | CF₃ | Me |
| 363 | benzo[d]thiazol-5-yl | CF₃ | Me |
| 364 | benzo[d]oxazol-6-yl | CF₃ | Me |
| 365 | 1-ethyl-1H-benzo[d]imidazol-6-yl | CF₃ | Me |
| 366 | 1-methyl-1H-benzo[d][1,2,3]triazol-5-yl | CF₃ | Me |
| 367 | isoquinolin-6-yl | CF₃ | Me |

TABLE 1-continued

![Structure I: pyridazine with Z, OH, Y, X substituents]

I

| NO. | X | Y | Z |
|-----|---|---|---|
| 368 | quinoxalin-2-yl | CF₃ | Me |
| 369 | phthalazin-5-yl | CF₃ | Me |
| 370 | cinnolin-4-yl | CF₃ | Me |
| 371 | quinolin-4-yl | CF₃ | Me |
| 372 | pteridin-6-yl | CF₃ | Me |
| 373 | 9H-purin-8-yl | CF₃ | Me |
| 374 | [1,2,4]triazolo[1,5-a]pyrimidin-6-yl | CF₃ | Me |
| 375 | [1,2,4]triazolo[1,5-c]pyrimidin-7-yl | CF₃ | Me |
| 376 | imidazo[1,2-b]pyridazin-6-yl | CF₃ | Me |
| 377 | naphthalen-2-yl | CF₃ | Me |
| 378 | anthracen-2-yl | CF₃ | Me |
| 379 | phenanthren-2-yl | CF₃ | Me |
| 380 | 2,3-dihydrobenzo[b][1,4]dioxin-6-yl | CF₃ | Me |
| 381 | acridin-2-yl | CF₃ | Me |
| 382 | phenazin-2-yl | CF₃ | Me |
| 383 | 1,10-phenanthrolin-3-yl | CF₃ | Me |
| 384 | 10H-phenothiazin-2-yl | CF₃ | Me |
| 385 | 9H-carbazol-3-yl | CF₃ | Me |

TABLE 1-continued structure I: pyridazine with Y, Z, OH, X, N-N substituents

| NO. | X | Y | Z |
|---|---|---|---|
| 386 | dibenzofuran-yl | CF₃ | Me |
| 387 | dibenzothiophen-yl | CF₃ | Me |
| 388 | 1-(difluoromethyl)-1H-pyrazol-4-yl | CF₃ | CHF₂ |
| 389 | 1-(difluoromethyl)-1H-pyrazol-4-yl | CF | CF₃ |
| 390 | 1-(difluoromethyl)-1H-pyrazol-4-yl | CF₃ | CHO |
| 391 | 1-(difluoromethyl)-1H-pyrazol-4-yl | CF₃ | NH-C(O)-O-ethyl |
| 392 | 1-(difluoromethyl)-1H-pyrazol-4-yl | CF₃ | NH-C(O)-O-propyl |
| 393 | 1-(difluoromethyl)-1H-pyrazol-4-yl | CF₃ | NH-C(O)-O-isopropyl |
| 394 | 1-(difluoromethyl)-1H-pyrazol-4-yl | CF₃ | NH-C(O)-O-cyclohexyl |
| 395 | 1-(difluoromethyl)-1H-pyrazol-4-yl | CF₃ | NH-S(O)₂-ethyl |
| 396 | 1-(difluoromethyl)-1H-pyrazol-4-yl | CF₃ | pyrrolidin-1-yl |
| 397 | 4-fluorophenyl | CF₃ | F |
| 398 | 4-fluorophenyl | CF₃ | NH-CH₂-(4-methoxyphenyl) |
| 399 | 4-cyano-2-methylphenyl | CF₃ | Me |
| 400 | 4-cyano-2-methylphenyl | CF₃ | cyclopropyl |
| 401 | 2-chloro-4-fluorophenyl | CF₃ | isopropenyl |

TABLE 1-continued

| NO. | X | Y | Z |
|-----|---|---|---|
| 402 | 2-Cl-4-F-phenyl | CF₃ | cyclopropyl |
| 403 | 4-Cl-2-CF₃-phenyl | CF₃ | isopropenyl |
| 404 | 4-Cl-3-CF₃-phenyl | CF₃ | cyclopropyl |
| 405 | 2-F-3-CN-phenyl | CF₃ | cyclopropyl |
| 406 | 3,4,5-trifluorophenyl | CF₃ | isopropenyl |
| 407 | 3,4,5-trifluorophenyl | CF₃ | cyclopropyl |
| 408 | 2,2-difluoro-benzo[1,3]dioxol-5-yl | CF₃ | Me |
| 409 | 2,2-difluoro-benzo[1,3]dioxol-5-yl | CF₃ | isopropenyl |
| 410 | 2,2-difluoro-benzo[1,3]dioxol-5-yl | CF₃ | cyclopropyl |
| 411 | 2-chloropyridin-4-yl | CF₃ | isopropenyl |
| 412 | 5-chloropyridin-3-yl | CF₃ | isopropenyl |
| 413 | 6-isopropenyl-pyridin-3-yl | CF₃ | isopropenyl |
| 414 | 2,6-difluoropyridin-3-yl | CF₃ | Br |

6. A method for preparing the pyridazinol compound or derivative thereof according to claim 1, comprising the following steps:

(1) subjecting a compound of Formula II and a halogenating reagent to halogenation reaction to obtain a compound of Formula I';

(2) subjecting a compound of Formula I' to hydroxyl protection reaction to obtain a compound of Formula I-1';

(3) subjecting a compound of Formula I-1' to substitution reaction, deprotection reaction in sequence to obtain a compound of Formula I";

the reaction route is as follows:

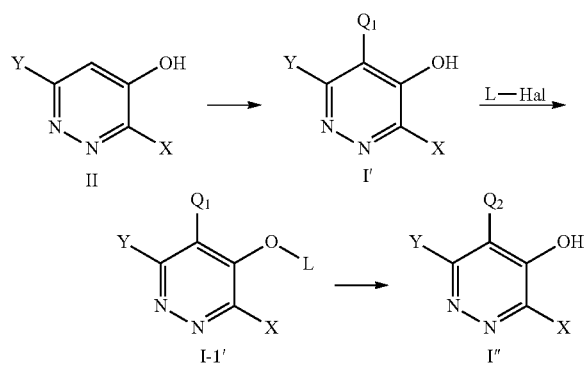

wherein $Q_1$ and Hal each independently represent halogen; $Q_2$ represents a group other than halogen in the substituent Z according to claim 1; X and Y are described in claim 1; L-represents TMS-, TBDMS-, TBDPS-, TBS-, PMB- or SEM-.

7. The method for preparing the pyridazinol compound or derivative thereof according to claim 6, wherein in the step (1), the halogenation reaction is carried out in the presence of an initiator and a solvent;
the step (2) is carried out in the presence of a base and a solvent;
in the step (3), the type of substitution reaction is Suzuki, Buchwald, copper-catalyzed or nucleophilic substitution, and the deprotection reaction is carried out in the presence of trifluoroacetic acid, hydrochloric acid, hydrobromic acid, hydroiodic acid, DDQ or $H_2$.

8. A herbicidal composition comprising (i) the pyridazinol compound of Formula I or derivative thereof according to claim 1, and (iii) an agriculturally acceptable formulation auxiliary.

9. A method for controlling a weed comprising applying a herbicidally effective amount of at least one of the pyridazinol compounds and derivatives thereof according to claim 1 to a plant or a weed area.

10. A method for controlling a weed comprising applying a herbicidally effective amount of at least one of the pyridazinol compounds and derivatives thereof according to claim 1 to a useful crop, wherein the useful crop is a transgenic crop or a crop treated by gene editing technique.

11. The method for preparing the pyridazinol compound or derivative thereof according to claim 6, wherein $Q_1$ and Hal each independently represent F, Cl, Br or I.

12. The method for preparing the pyridazinol compound or derivative thereof according to claim 7, wherein in the step (1), the halogenation reagent is $Cl_2$, $Br_2$, $I_2$, NBS, NCS, NIS, dichlorohydantoin, dibromohydantoin, selective fluorine reagent or hexabromoethane, the initiator is AIBN or BPO, and the solvent is $CCl_4$, $AcOH/H_2O$, MeCN, DMF, NMP or AcOH.

13. The method for preparing the pyridazinol compound or derivative thereof according to claim 7, wherein in the step (2), the solvent is selected from at least one of MeCN, DMF, DMSO, dioxane, dichloromethane, dichloroethane and ethyl acetate, and the base is inorganic base or organic base.

14. The herbicidal composition according to claim 8, further comprising (ii) one or more additional herbicides and/or safeners.

15. A method for controlling a weed comprising applying a herbicidally effective amount of the herbicidal composition according to claim 8 to a plant or a weed area.

16. A method for controlling a weed comprising applying a herbicidally effective amount of the herbicidal composition according to claim 8 to a useful crop, wherein the useful crop is a transgenic crop or a crop treated by gene editing technique.

* * * * *